US012715876B2

(12) United States Patent
Mondal et al.

(10) Patent No.: US 12,715,876 B2
(45) Date of Patent: Aug. 25, 2026

(54) CYCLIC COMPOUNDS AND METHODS OF USING SAME

(71) Applicant: SCHRÖDINGER, INC., New York, NY (US)

(72) Inventors: Sayan Mondal, La Jolla, CA (US); Haifeng Tang, Metuchen, NJ (US); Xianhai Huang, Warren, NJ (US); Adam Marc Levinson, Bronx, NY (US); Leah Frye, Portland, OR (US); Sathesh Bhat, New York, NY (US); Pieter Harm Bos, New York, NY (US); Zef Konst, San Francisco, CA (US); Phani Ghanakota, Edison, NJ (US); Jeremy Robert Greenwood, Brooklyn, NY (US)

(73) Assignee: SCHRÖDINGER, INC., New York, NY (US)

( * ) Notice: Subject to any disclaimer, the term of this patent is extended or adjusted under 35 U.S.C. 154(b) by 352 days.

(21) Appl. No.: 18/282,318

(22) PCT Filed: Mar. 17, 2022

(86) PCT No.: PCT/US2022/020712

§ 371 (c)(1),
(2) Date: Sep. 15, 2023

(87) PCT Pub. No.: WO2022/197898

PCT Pub. Date: Sep. 22, 2022

(65) Prior Publication Data

US 2024/0199634 A1 Jun. 20, 2024

Related U.S. Application Data

(60) Provisional application No. 63/297,058, filed on Jan. 6, 2022, provisional application No. 63/162,711, filed on Mar. 18, 2021.

(51) Int. Cl.

| | |
|---|---|
| ***C07D 495/04*** | (2006.01) |
| ***A61K 31/4365*** | (2006.01) |
| ***A61K 31/4375*** | (2006.01) |
| ***A61K 31/4743*** | (2006.01) |
| ***A61K 31/5377*** | (2006.01) |
| ***C07D 495/14*** | (2006.01) |

(52) U.S. Cl.

CPC ........ *C07D 495/04* (2013.01); *A61K 31/4365* (2013.01); *A61K 31/4375* (2013.01); *A61K 31/4743* (2013.01); *A61K 31/5377* (2013.01); *C07D 495/14* (2013.01)

(58) Field of Classification Search

CPC . C07D 495/04; C07D 495/14; A61K 31/4365

See application file for complete search history.

(56) References Cited

U.S. PATENT DOCUMENTS

| | | | | |
|---|---|---|---|---|
| 4,939,137 | A | 7/1990 | Russell et al. | |
| 7,514,446 | B2 | 4/2009 | Davis-Ward et al. | |
| 7,863,289 | B2 | 1/2011 | Spevak et al. | |
| 8,026,247 | B2 | 9/2011 | Bold et al. | |
| 8,501,756 | B2 | 8/2013 | Artman, III et al. | |
| 8,552,002 | B2 | 10/2013 | Ding et al. | |
| 8,568,998 | B2 | 10/2013 | Mani et al. | |
| 8,722,660 | B2 * | 5/2014 | Homma .............. | C07D 495/04 514/210.21 |
| 8,815,901 | B2 | 8/2014 | Furet et al. | |
| 8,912,204 | B2 | 12/2014 | Ibrahim et al. | |
| 9,260,437 | B2 | 2/2016 | Ibrahim et al. | |
| 9,273,051 | B2 | 3/2016 | Chen et al. | |
| 2007/0191344 | A1 | 8/2007 | Choidas et al. | |
| 2013/0029925 | A1 | 1/2013 | Vandier et al. | |
| 2014/0121231 | A1 | 5/2014 | Bolin et al. | |
| 2015/0018336 | A1 | 1/2015 | Chen et al. | |
| 2016/0163999 | A1 | 6/2016 | Kim et al. | |
| 2017/0117491 | A1 | 4/2017 | Sasada et al. | |
| 2017/0244043 | A1 | 8/2017 | Kim et al. | |
| 2017/0294489 | A1 | 10/2017 | Lim et al. | |
| 2018/0047912 | A1 | 2/2018 | Kwong et al. | |
| 2018/0159043 | A1 | 6/2018 | Fukuzaki et al. | |
| 2019/0214577 | A1 | 7/2019 | Pan et al. | |
| 2019/0233451 | A1 | 8/2019 | Ji et al. | |
| 2019/0278176 | A1 | 9/2019 | Baek et al. | |
| 2019/0312209 | A1 | 10/2019 | Jeon et al. | |
| 2019/0330226 | A1 | 10/2019 | Lindsley et al. | |
| 2020/0194694 | A1 | 6/2020 | Han et al. | |
| 2021/0111353 | A1 | 4/2021 | Choi et al. | |

FOREIGN PATENT DOCUMENTS

| | | |
|---|---|---|
| CN | 101965351 A | 2/2011 |
| CN | 103951676 A | 7/2014 |

(Continued)

OTHER PUBLICATIONS

Wang (J.Org. Chem vol. 79 pp. 9628-9638. Published 2014) (Year: 2014).*

Menichincheri (J. Med. Chem vol. 52 pp. 293-307 published 2009) (Year: 2009).*

Russell, Ronald et al. "Thiophene systems. 11. The synthesis of novel thieno[4,3,2-de]tricyclic ring systems." Journal of Heterocyclic Chemistry (1990), 27(6), 1761-70.

Im, Jun-Sub, et al.,. "ATR-dependent activation of p38 MAP kinase is responsible for apoptotic cell death in cells depleted of Cdc7." Journal of Biological Chemistry 283.37 (2008): 25171-25177.

Irie, Takayuki et al: "CDC7 kinase inhibitors: a survey of recent patent literature (2017-2022)", Expert Opinion on Therapeutic Patents, vol. 33, No. 7-8 (Nov. 6, 2023), p. 493-501.

(Continued)

*Primary Examiner* — George W Kosturko

(74) *Attorney, Agent, or Firm* — Barnes & Thornburg LLP; Steven M. Sturlis; William Bourdreaux

(57) ABSTRACT

The present application relates to compounds of Formula (I), as defined herein, and pharmaceutically acceptable salts thereof. The present application also describes pharmaceutical composition comprising a compound of Formula (I), and pharmaceutically acceptable salts thereof, and methods of using the compounds and compositions for inhibiting kinase activity, and for treating cancer.

94 Claims, No Drawings

(56) References Cited

FOREIGN PATENT DOCUMENTS

| | | | |
|---|---|---|---|
| CN | 105777666 A | 7/2016 | |
| CN | 104478900 B | 5/2017 | |
| CN | 104610178 B | 1/2018 | |
| CN | 108218887 A | 6/2018 | |
| CN | 110117290 A | 8/2019 | |
| CN | 112457326 B | 2/2022 | |
| CN | 111057048 B | 3/2022 | |
| EP | 2540728 B1 | 4/2019 | |
| EP | 3229290 B1 | 5/2024 | |
| WO | 1999067238 A2 | 12/1999 | |
| WO | 2000023451 A1 | 4/2000 | |
| WO | 2004001058 A2 | 12/2003 | |
| WO | 2004065351 A1 | 8/2004 | |
| WO | 2004113330 A1 | 12/2004 | |
| WO | 2005014537 A2 | 2/2005 | |
| WO | 2005037843 A1 | 4/2005 | |
| WO | 2005082841 A1 | 9/2005 | |
| WO | 2005121138 A2 | 12/2005 | |
| WO | 2006014135 A1 | 2/2006 | |
| WO | 2006102097 A2 | 9/2006 | |
| WO | 2007000246 A1 | 1/2007 | |
| WO | 2007000248 A1 | 1/2007 | |
| WO | 2007002325 A1 | 1/2007 | |
| WO | 2007002433 A1 | 1/2007 | |
| WO | 2007047604 A2 | 4/2007 | |
| WO | 2007070201 A1 | 6/2007 | |
| WO | 2007084451 A1 | 7/2007 | |
| WO | 2007084455 A1 | 7/2007 | |
| WO | 2007110344 A1 | 10/2007 | |
| WO | 2007143523 A2 | 12/2007 | |
| WO | 2008070908 A1 | 6/2008 | |
| WO | 2008079903 A1 | 7/2008 | |
| WO | 2008079906 A1 | 7/2008 | |
| WO | 2008079909 A1 | 7/2008 | |
| WO | 2008080001 A2 | 7/2008 | |
| WO | 2008080015 A2 | 7/2008 | |
| WO | 2009007748 A2 | 1/2009 | |
| WO | 2009012283 A1 | 1/2009 | |
| WO | 2009014637 A2 | 1/2009 | |
| WO | 2009071480 A2 | 6/2009 | |
| WO | 2009071890 A1 | 6/2009 | |
| WO | 2009071895 A1 | 6/2009 | |
| WO | 2009086264 A1 | 7/2009 | |
| WO | 2009118411 A2 | 10/2009 | |
| WO | 2009143018 A2 | 11/2009 | |
| WO | 2009143024 A2 | 11/2009 | |
| WO | 2009152083 A1 | 12/2009 | |
| WO | 2010031816 A1 | 3/2010 | |
| WO | 2010056631 A1 | 5/2010 | |
| WO | 2010077530 A1 | 7/2010 | |
| WO | 2010088414 A2 | 8/2010 | |
| WO | 2010101302 A1 | 9/2010 | |
| WO | 2010111527 A1 | 9/2010 | |
| WO | 2010145998 A1 | 12/2010 | |
| WO | 2011025859 A1 | 3/2011 | |
| WO | 2011043994 A1 | 4/2011 | |
| WO | 2011092120 A1 | 8/2011 | |
| WO | 2011102399 A1 | 8/2011 | |
| WO | 2011117145 A2 | 9/2011 | |
| WO | 2011123419 A1 | 10/2011 | |
| WO | 2012013271 A1 | 2/2012 | |
| WO | 2012041987 A1 | 4/2012 | |
| WO | WO-2012051410 A2 * | 4/2012 | ............. A61P 35/00 |
| WO | 2012101029 A1 | 8/2012 | |
| WO | 2012101032 A1 | 8/2012 | |
| WO | 2012109075 A1 | 8/2012 | |
| WO | 2012113774 A1 | 8/2012 | |
| WO | 2012121992 A1 | 9/2012 | |
| WO | 2012139930 A1 | 10/2012 | |
| WO | 2012143248 A1 | 10/2012 | |
| WO | 2012152763 A1 | 11/2012 | |
| WO | 2012169605 A1 | 12/2012 | |
| WO | 2013000994 A1 | 1/2013 | |
| WO | 2013014039 A1 | 1/2013 | |
| WO | 2013050446 A1 | 4/2013 | |
| WO | 2013050448 A1 | 4/2013 | |
| WO | 2013102059 A1 | 7/2013 | |
| WO | 2013138413 A1 | 9/2013 | |
| WO | 2013152269 A1 | 10/2013 | |
| WO | 2013177241 A1 | 11/2013 | |
| WO | 2014011900 A2 | 1/2014 | |
| WO | 2014019908 A2 | 2/2014 | |
| WO | 2014024750 A1 | 2/2014 | |
| WO | 2014055548 A1 | 4/2014 | |
| WO | 2014071031 A1 | 5/2014 | |
| WO | 2014072220 A1 | 5/2014 | |
| WO | 2014083567 A2 | 6/2014 | |
| WO | 2014092083 A1 | 6/2014 | |
| WO | 2014139324 A1 | 9/2014 | |
| WO | 2014160521 A1 | 10/2014 | |
| WO | 2014184069 A1 | 11/2014 | |
| WO | 2014194127 A1 | 12/2014 | |
| WO | 2014196585 A1 | 12/2014 | |
| WO | 2015017528 A1 | 2/2015 | |
| WO | 2015017533 A1 | 2/2015 | |
| WO | 2015057873 A1 | 4/2015 | |
| WO | 2015058129 A1 | 4/2015 | |
| WO | 2015061572 A1 | 4/2015 | |
| WO | 2015108992 A1 | 7/2015 | |
| WO | 2015112806 A2 | 7/2015 | |
| WO | 2015161274 A1 | 10/2015 | |
| WO | 2015161277 A1 | 10/2015 | |
| WO | 2015191666 A2 | 12/2015 | |
| WO | 2015191667 A1 | 12/2015 | |
| WO | 2016011141 A1 | 1/2016 | |
| WO | 2016011144 A1 | 1/2016 | |
| WO | 2016011147 A1 | 1/2016 | |
| WO | 2016022569 A1 | 2/2016 | |
| WO | 2016057713 A1 | 4/2016 | |
| WO | 2016075224 A1 | 5/2016 | |
| WO | 2016081450 A1 | 5/2016 | |
| WO | 2016113668 A1 | 7/2016 | |
| WO | 2017197240 A1 | 11/2017 | |
| WO | 2018108109 A1 | 6/2018 | |
| WO | 2018129205 A1 | 7/2018 | |
| WO | 2018138039 A1 | 8/2018 | |
| WO | 2018153326 A1 | 8/2018 | |
| WO | 2018161831 A1 | 9/2018 | |
| WO | 2018181054 A1 | 10/2018 | |
| WO | 2018181056 A1 | 10/2018 | |
| WO | 2018197257 A1 | 11/2018 | |
| WO | 2018217439 A1 | 11/2018 | |
| WO | 2019013311 A1 | 1/2019 | |
| WO | 2019052933 A1 | 3/2019 | |
| WO | 2019120085 A1 | 6/2019 | |
| WO | 2019120177 A1 | 6/2019 | |
| WO | 2019161320 A1 | 8/2019 | |
| WO | WO-2019165473 A1 * | 8/2019 | ............. A61P 35/02 |
| WO | 2019195565 A1 | 10/2019 | |
| WO | 2019231226 A1 | 12/2019 | |
| WO | 2020202978 A1 | 10/2020 | |
| WO | 2021113492 A1 | 6/2021 | |
| WO | 2021252661 A1 | 12/2021 | |
| WO | 2022055963 A1 | 3/2022 | |
| WO | 2022195011 A1 | 9/2022 | |
| WO | 2022195462 A1 | 9/2022 | |
| WO | 2022198062 A2 | 9/2022 | |
| WO | 2022214031 A1 | 10/2022 | |
| WO | 2022228547 A1 | 11/2022 | |
| WO | 2022269508 A1 | 12/2022 | |
| WO | 2023011533 A1 | 2/2023 | |
| WO | 2023133284 A2 | 7/2023 | |

OTHER PUBLICATIONS

Kurasawa, Osamu, et al. "2-Aminomethylthieno [3, 2-d] pyrimidin-4 (3H)-ones bearing 3-methylpyrazole hinge binding moiety: Highly potent, selective, and time-dependent inhibitors of Cdc7 kinase." Bioorganic & Medicinal Chemistry 25.14 (2017): 3658-3670.

Kurasawa, Osamu, et al. "Discovery of a novel, highly potent, and selective Thieno [3, 2-d] pyrimidinone-based Cdc7 inhibitor with a quinuclidine moiety (TAK-931) as an orally active investigational

(56) References Cited

OTHER PUBLICATIONS antitumor agent." Journal of Medicinal Chemistry 63.3 (2020): 1084-1104.
Kurasawa, Osamu, et al. "Identification of a new class of potent Cdc7 inhibitors designed by putative pharmacophore model: Synthesis and biological evaluation of 2, 3-dihydrothieno [3, 2-d] pyrimidin-4 (1H)-ones." Bioorganic & Medicinal Chemistry 25.7 (2017): 2133-2147.
Louis, David N., et al. "The 2016 World Health Organization classification of tumors of the central nervous system: a summary." Acta neuropathologica 131 (2016): 803-820.
Montagnoli, Alessia, et al. "Cdc7 inhibition reveals a p53-dependent replication checkpoint that is defective in cancer cells." Cancer research 64.19 (2004): 7110-7116.
Mulligan, Lois M. "RET revisited: expanding the oncogenic portfolio." Nature Reviews Cancer 14.3 (2014): 173-186.
Amit, M., et al. "Upregulation of RET induces perineurial invasion of pancreatic adenocarcinoma." Oncogene 36.23 (2017): 3232-3239.
Andreucci et al., "Targeting the receptor tyrosine kinase RET in combination with aromatase inhibitors in ER positive breast cancer xenografts" Oncotarget, 2017, p. 80543-80553, vol. 7.
Bhinge, Kaustubh, et al. "EGFR mediates activation of RET in lung adenocarcinoma with neuroendocrine differentiation characterized by ASCL1 expression." Oncotarget 8.16 (2017): 27155.
Blom, Karl F., et al. "Preparative LC-MS Purification: Improved Compound-Specific Method Optimization." Journal of Combinatorial Chemistry 6.6 (2004): 874-883.
Chang, Hyun, et al. "EGF induced RET inhibitor resistance in CCDC6-RET lung cancer cells." Yonsei Medical Journal 58.1 (2017): 9-18.
Cheng, An Ning, et al. "Increased Cdc7 expression is a marker of oral squamous cell carcinoma and overexpression of Cdc7 contributes to the resistance to DNA-damaging agents." Cancer letters 337.2 (2013): 218-225.
Cho, Won-Ho, et al. "CDC7 kinase phosphorylates serine residues adjacent to acidic amino acids in the minichromosome maintenance 2 protein." Proceedings of the National Academy of Sciences 103.31 (2006): 11521-11526.
Choschzick, Matthias, et al. "Overexpression of cell division cycle 7 homolog is associated with gene amplification frequency in breast cancer." Human pathology 41.3 (2010): 358-365.
Datta, Arindam, et al. "p53 gain-of-function mutations increase Cdc7-dependent replication initiation." EMBO reports 18.11 (2017): 2030-2050.
Ding K et al., "Artemin, a Member of the Glial Cell Line-derived Neurotrophic Factor Family of Ligands, Is HER2-regulated and Mediates Acquired Trastuzumab Resistance by Promoting Cancer Stem Cell-like Behavior in Mammary Carcinoma Cells" J Biol Chem Jun. 6, 2014, p. 16057-71, vol. 289, No. 23.
Gao L, et al., "Neurotrophic Factor Artemin Promotes Invasiveness and Neurotrophic Function of Pancreatic Adenocarcinoma In Vivo and In Vitro" Pancreas Jan. 2015, p. 134-143, vol. 44.
Hanahan, Douglas, et al. "Hallmarks of cancer: the next generation." cell 144.5 (2011): 646-674.
Hezam K et al., "Artemin promotes oncogenicity, metastasis and drug resistance in cancer cells", Rev Neurosci, Jan. 26, 2018, vol. 29, 93-98.
Hou, Xueqing et al. "Dissecting Trichalcogenasumanenes: π-Bowl to Planar, Invertible Curvature, and Chiral Polycycles." Chemistry—A European Journal (2017), 23(57), 14375-14383.
Hou, Xueqing et al. "Opening two benzene rings on trichalcogenasumanenes toward high performance organic optical-limiting materials." Chemical Communications (2018), 54(78), 10981-10984.
Jiang, Wei, et al. "Mammalian Cdc7-Dbf4 protein kinase complex is essential for initiation of DNA replication." The EMBO journal 18.20 (1999): 5703-5713.
Kato, Shumei, et al. "RET aberrations in diverse cancers: next-generation sequencing of 4,871 patients." Clinical Cancer Research 23.8 (2017): 1988-1997.
Kim, Samuel W., Peter Goedegebuure, and William E. Gillanders. "Mammaglobin-A is a target for breast cancer vaccination." Oncoimmunology 5.2 (2016): e1069940.
Kübler, Hubert, et al. "Self-adjuvanted mRNA vaccination in advanced prostate cancer patients: a first-in-man phase I/IIa study." Journal for immunotherapy of cancer 3.1 (2015): 1-14.
Kulkarni, Anjana A., et al. "Cdc7 kinase is a predictor of survival and a novel therapeutic target in epithelial ovarian carcinoma." Clinical Cancer Research 15.7 (2009): 2417-2425.
Li, Xuexiang et al. "Ring Reconstruction on a Trichalcogenasumanene Buckybowl: A Facile Approach to Donor-Acceptor-Type [5-6-7] Fused Planar Polyheterocycles." Angewandte Chemie, International Edition (2015), 54(1), 267-271.
Lopez-Delisle, Lucille, et al. "Activated ALK signals through the ERK-ETV5-RET pathway to drive neuroblastoma oncogenesis." Oncogene 37.11 (2018): 1417-1429.
Masai, Hisao, et al. "Phosphorylation of MCM4 by Cdc7 Kinase Facilitates Its Interaction with Cdc45 on the Chromatin" Journal of Biological Chemistry 281.51 (2006): 39249-39261.
Mcgranahan, Nicholas, et al., "Clonal heterogeneity and tumor evolution: past, present, and the future." Cell 168.4 (2017): 613-628.
Nelson-Taylor, Sarah K., et al. "Resistance to RET-inhibition in RET-rearranged NSCLC is mediated by reactivation of RAS/MAPK signaling." Molecular cancer therapeutics 16.8 (2017): 1623-1633.
Ott, Patrick A., et al. "An immunogenic personal neoantigen vaccine for patients with melanoma." Nature 547.7662 (2017): 217-221.
Pétursson, Sigthór, "Protecting groups in carbohydrate chemistry." Journal of chemical education 74.11 (1997): 1297.
Rausch et al. "mRNA vaccine CV9103 and CV9104 for the treatment of prostate cancer", Human Vaccin Immunother, 2014 p. 3146-52, vol. 10, No. 11.
Sahin, Ugur, et al. "Personalized RNA mutanome vaccines mobilize poly-specific therapeutic immunity against cancer." Nature 547.7662 (2017): 222-226.
Sun, Yantao et al. "Trichalcogenasumanene ortho-Quinones: Synthesis, Properties, and Transformation into Various Heteropolycycles." Angewandte Chemie, International Edition (2017), 56(43), 13470-13474.
Tang, Zhenya, et al. "Coexistent genetic alterations involving ALK, RET, ROS1 or MET in 15 cases of lung adenocarcinoma." Modern Pathology 31.2 (2018): 307-312.
Yamada, et al., "Regulation and roles of Cdc7 kinase under replication stress", Cell Cycle, 2014 pp. 1859-1866, vol. 13.
Yu, Craig et al., "Air-Stable Benzo[c]thiophene Diimide n-Type π-Electron Core." Organic Letters (2019), 21(12), 4448-4453.
Zeng, Q., et al. "The relationship between over-expression of glial cell-derived neurotrophic factor and its RET receptor with progression and prognosis of human pancreatic cancer." Journal of International Medical Research 36.4 (2008): 656-664.
International Search Report dated 2022-05-23, prepared in International Application No. PCT/US2022/020712.
International Preliminary Report on Patentability dated Sep. 12, 2023, prepared in International Application No. PCT/US2022/020712.
International Search Report dated Mar. 12, 2021, prepared in International Application No. PCT/US2020/063081.
International Preliminary Report on Patentability dated May 17, 2022, prepared in International Application No. PCT/US2020/063081.
International Search Report dated Nov. 15, 2021, prepared in International Application No. PCT/US2021/049415.
International Preliminary Report on Patentability dated Mar. 7, 2023, prepared in International Application No. PCT/US2021/049415.

* cited by examiner

CYCLIC COMPOUNDS AND METHODS OF USING SAME

CROSS-REFERENCE TO RELATED APPLICATIONS

This application is a National Stage application of International Application No. PCT/US2022/020712, filed Mar. 17, 2022, which claims the benefit of U.S. Provisional Application Nos. 63/162,711 and 63/297,058, filed Mar. 18, 2021, and Jan. 6, 2022, respectively.

TECHNICAL FIELD

This present application relates to tricyclic, and other multi-cyclic compounds, that are useful for treating proliferative disorders such as cancer.

BACKGROUND

Cancer is characterized by aberrant cell growth and proliferation. Genomic instability is a hallmark of cancer cells, with high rates of mutation and genomic rearrangements leading to aggressive and therapy-resistant tumors. See Hanahan and Weinberg, Cell, 144, pp. 646-674 (2011) and McGranahan and Swanton, Cell 168, pp. 613-628 (2017). Dysregulation of DNA replication contributes to genomic instability and tumorigenesis. Eukaryotic cells divide by a directed, highly regulated step-wise process known as the cell cycle. DNA replication is an essential part of the highly-regulated, step-wise cell cycle, and this tight regulation ensures that DNA replication occurs only once during S-phase, and occurs with high-fidelity.

During the late G1-to-S phase, CDC7 kinase (also known as DDK) is activated by binding to its regulatory protein, DBF4 (ASK in eukaryotes), which then phosphorylates chromatin loaded minichromosome maintenance (MCM) 2,4 and 6 proteins at multiple phosphorylation sites to initiate DNA synthesis. See Jiang, et al., EMBO J., 18, pp. 5703-5713 (1999), Cho, et al., Proc. Natl. Acad. Sci. U.S.A., 103, pp. 11521-11526 (2006) and Masai, et al., J Biol Chem., 281, pp. 39249-39261 (2006). CDC7 kinase plays important roles in the maintenance of DNA replication forks and DNA damage response pathways. See Yamada, et al., Cell Cycle 13, pp. 1859-1866 (2014).

CDC7 is a highly conserved serine/threonine kinase from yeast to humans. Knockdown of CDC7 was shown to cause cell death in cancer cells, but not in normal cells, in which p53-dependent pathways arrest the cell cycle in G1 phase. The apoptotic response induced in cancer cells by CDC7 depletion is not mediated by p53, but rather by p38 MAPK. See Montagnoli, et al., Cancer Res., 64, pp. 7110-7116 (2004) and Im and Lee, J. Biol. Chem., 283, pp. 25171-25177 (2008). In addition, CDC7 up-regulation has been correlated with poor prognosis in various cancer types. See, e.g., Kulkarni, et al., Clin. Cancer Res., 15, pp. 2417-2425 (2009); Choschzick, et al., Hum. Pathol., 41, pp. 358-365 (2010); Datta, et al., EMBO Rep., 18, pp. 2030-2050 (2017); Cheng, et al., Cancer Lett., 337, 218-225 (2013).

SUMMARY

It has now been found that certain fused compounds are inhibitors of CDC7 kinase, and are useful for treating diseases such as proliferative diseases such as cancers.

Accordingly, provided herein is a compound of the Formula (I):

(I)

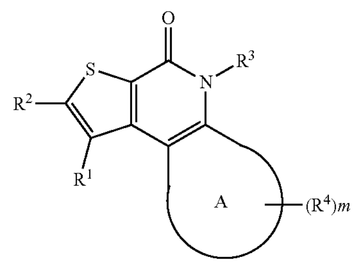

or a pharmaceutically acceptable salt thereof, wherein $R^1$, $R^2$, $R^3$, $R^4$, Ring A and m are as defined herein.

Also provided herein is a pharmaceutical composition comprising a compound of Formula (I), or a pharmaceutically acceptable salt thereof, and at least one pharmaceutically acceptable excipient.

Also provided herein is a method of inhibiting cell proliferation, in vitro or in vivo, comprising contacting a cell with an effective amount of a compound of Formula (I) or a pharmaceutically acceptable salt thereof, or a pharmaceutical composition thereof as defined herein.

Also provided herein is a method of inhibiting CDC7 kinase activity, in vitro or in vivo, comprising contacting a cell with an effective amount of a compound of Formula (I) or a pharmaceutically acceptable salt thereof, or a pharmaceutical composition thereof as defined herein.

Also provided herein is a method of treating cancer in a subject in need of such treatment, comprising administering to the subject an effective amount of a compound of Formula (I), or a pharmaceutically acceptable salt thereof, or a pharmaceutical composition thereof as defined herein.

Also provided herein is a method of treating a CDC7-associated disease or disorder in a subject in need of such treatment, comprising administering to the subject an effective amount of a compound of Formula (I), or a pharmaceutically acceptable salt thereof, or a pharmaceutical composition thereof as defined herein.

Also provided herein is a method of treating a cancer in a subject in need thereof, comprising administering an effective amount of a compound of Formula (I), or a pharmaceutically acceptable salt thereof, or a pharmaceutical composition thereof as defined herein, to a subject identified as having a cancer associated with CDC7.

Also provided herein is a method of treating cancer and/or inhibiting metastasis associated with a particular cancer in a subject in need of such treatment, comprising administering to the subject an effective amount of a compound of Formula (I), or a pharmaceutically acceptable salt thereof or a pharmaceutical composition thereof as defined herein.

Also provided herein is a compound of Formula (I), or a pharmaceutically acceptable salt thereof, or a pharmaceutical composition thereof as defined herein for use in the treatment of cancer.

Also provided herein is a compound of Formula (I), or a pharmaceutically acceptable salt thereof, or a pharmaceutical composition thereof as defined herein for use in the treatment of a CDC7-associated disease or disorder.

Also provided herein is a compound of Formula (I), or a pharmaceutically acceptable salt thereof or a pharmaceutical composition thereof as defined herein for use in the treatment of cancer and/or inhibiting metastasis associated with a particular cancer.

Also provided herein is a compound of Formula (I), or a pharmaceutically acceptable salt thereof for use in the inhibition of CDC7 kinase activity.

Also provided herein is a compound of Formula (I), or a pharmaceutically acceptable salt thereof or a pharmaceutical composition thereof as defined herein, for use in the treatment of a CDC7-associated disease or disorder.

Also provided herein is a compound of Formula (I), or a pharmaceutically acceptable salt thereof, as defined herein in the manufacture of a medicament for the treatment of cancer and/or inhibiting metastasis associated with a particular cancer.

Also provided herein is a compound of Formula (I), or a pharmaceutically acceptable salt thereof, defined herein in the manufacture of a medicament for the inhibition of CDC7 kinase activity.

Also provided herein is a compound of Formula (I), or a pharmaceutically acceptable salt thereof, as defined herein, in the manufacture of a medicament for the treatment of a CDC7-associated disease or disorder.

Also provided are methods of treating an individual with a CDC7-associated cancer that include administering a compound of Formula (I), or a pharmaceutically acceptable salt thereof, before, during, or after administration of other anticancer drug(s) (e.g., a first CDC7 kinase inhibitor or another kinase inhibitor).

Also provided herein is a process for preparing a compound of Formula (I), or a pharmaceutically acceptable salt thereof.

Also provided herein is a compound of Formula (I), or a pharmaceutically acceptable salt thereof obtained by a process of preparing the compound as defined herein.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and from the claims.

DETAILED DESCRIPTION

Definitions

The term "compound," as used herein is meant to include all stereoisomers, geometric isomers, tautomers, and isotopically enriched variants of the structures depicted. Compounds herein identified by name or structure as one particular tautomeric form are intended to include other tautomeric forms unless otherwise specified.

The term "tautomer," as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the disclosure, and the naming of the compounds does not exclude any tautomer. An example of a tautomeric forms includes the following example:

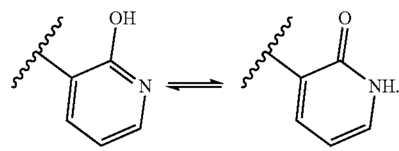 [SMILES: *c1cccnc1O ; *c1ccc[nH]c1=O]

It will be appreciated that certain compounds provided herein may contain one or more centers of asymmetry and may therefore be prepared and isolated in a mixture of isomers such as a racemic mixture, or in an enantiomerically pure form.

The term "halo" refers to one of the halogens, group 17 of the periodic table. In particular the term refers to fluorine, chlorine, bromine and iodine. Preferably, the term refers to fluorine or chlorine.

The term "C1-C6 alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. Alkyl groups may be unsubstituted or substituted by one or more substituents as described herein.

The term "C1-C6 haloalkyl" refers to a hydrocarbon chain substituted with at least one halogen atom independently chosen at each occurrence, for example fluorine, chlorine, bromine and iodine. The halogen atom may be present at any position on the hydrocarbon chain. For example, C1-C6 haloalkyl may refer to chloromethyl, fluoromethyl, difluoromethyl, trifluoromethyl, chloroethyl e.g. 1-chloroethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "C1-C6 alkoxy" refers to a C1-C6 alkyl group which is attached to a molecule via oxygen. This includes moieties where the alkyl part may be linear or branched, such as methoxy, ethoxy, n-propoxy, iso-propoxy, n-butoxy, sec-butoxy, tert-butoxy, n-pentoxy and n-hexoxy.

As used herein, the term "hydroxyl" refers to an —OH radical.

The term "C1-C6 hydroxyalkyl" refers to a hydrocarbon chain substituted with one hydroxyl radical. The hydroxyl radical may be present at any position on the hydrocarbon chain. For example, C1-C6 hydroxyalkyl may refer to hydroxymethyl, hydroxyethyl e.g. 1-hydroxyethyl and 2-hydroxyethyl, and 2-hydroxyisopropyl.

As used herein, the term "aryl" refers to a 6-10 all carbon mono- or bicyclic aromatic ring systems. Non-limiting examples of aryl groups include phenyl and naphthyl.

As used herein, the term "heteroaryl" refers to a 5-10 membered mono- or bicyclic group wherein each ring in the system is aromatic; wherein one or more carbon atoms in at least one ring in the system is/are replaced with an heteroatom independently selected from N, O, and S. Non-limiting examples of heteroaryl groups include pyridine, pyrimidine, pyrrole, imidazole, and indole.

As used herein, the term "cycloalkyl" refers to a saturated or partially unsaturated mono- or bicyclic carbon group having 3 to 10 ring atoms; wherein bicyclic systems include fused, spiro (optionally referred to as "spirocycloalkyl" groups), and bridged ring systems. Fused cycloalkyl groups can include one ring that is aromatic and another ring that is saturated or partially saturated, such as 1,2,3,4-tetrahydronaphthalene and 2,3-dihydro-1H-indene. Non-limiting examples of cycloalkyl groups include cyclopropyl, cyclohexyl, spiro[2.3]hexyl, and bicyclo[1.1.1]pentyl. As a substituent, for example on an alkyl group, a cycloalkyl group can share a carbon atom with the alkyl chain.

The term "heterocyclyl" refers to a saturated or partially unsaturated hydrocarbon monocyclic or bicyclic ring system that is not fully aromatic having at least one heteroatom within the ring selected from N, O and S. Bicyclic heterocyclyl groups include fused, spiro (optionally referred to as "spiroheterocyclyl" groups), and bridged ring systems. Fused heterocyclyl groups can contain one ring that is aromatic, and another ring that is saturated or partially saturated, such as 5,6,7,8-tetrahydroquinoline and indoline. The heterocyclyl group may be denoted as a "3 to 10 membered heterocyclyl group," which is a ring system containing 3, 4, 5, 6, 7, 8, 9 or 10 atoms at least one being a heteroatom. For example there may be 1, 2 or 3 heteroatoms, optionally 1 or 2. The heterocyclyl group may be bonded to the rest of the molecule through any carbon atom or through a heteroatom such as nitrogen. Exemplary heterocyclyl groups include, but are not limited to, piperidinyl, piperazinyl, morpholino, tetrahydropyranyl, azetidinyl, oxetanyl, and 2-azaspiro[3.3]heptanyl. As a substituent, for example on an alkyl group, a heterocyclyl group can share a carbon atom with the alkyl chain.

As used herein, the term "geminal" refers to substituent atoms or groups attached to the same atom in a molecule.

As used herein, the term "oxo" refers to an "=O" group attached to a carbon atom.

As used herein, the symbol 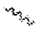 depicts the point of attachment of an atom or moiety to the indicated atom or group in the remainder of the molecule.

It is to be understood that the A ring in compounds of Formula (I) comprising does not contain two adjacent oxygen atoms or two adjacent S atoms.

The compounds of Formula (I) include pharmaceutically acceptable salts thereof. In addition, the compounds of Formula (I) also include other salts of such compounds which are not necessarily pharmaceutically acceptable salts, and which may be useful as intermediates for preparing and/or purifying compounds of Formula (I) and/or for separating enantiomers of compounds of Formula (I). Non-limiting examples of pharmaceutically acceptable salts of compounds of Formula (I) include trifluoroacetic acid and hydrochloride salts.

It will further be appreciated that the compounds of Formula (I) or their salts may be isolated in the form of solvates, and accordingly that any such solvate is included within the scope of the present disclosure. For example, compounds of Formula (I) and salts thereof can exist in unsolvated as well as solvated forms with pharmaceutically acceptable solvents such as water, ethanol, and the like.

In some embodiments, the compounds of Formula (I) include the compounds of Examples 1-96 and pharmaceutically acceptable salts and solvates thereof. In some embodiments, the compounds of Formula (I) are in the free base form. In some embodiments, the compounds of Formula (I) are in the salt form (e.g., a pharmaceutically acceptable salt).

In some embodiments, the compounds of Formula (I) include stereoisomers and pharmaceutically acceptable salts and solvates thereof. In some embodiments, the compounds of Formula (I) are in the free base form. In some embodiments, the compounds of Formula (I) are in the salt form.

The term "pharmaceutically acceptable" indicates that the compound, or salt or composition thereof is compatible chemically and/or toxicologically with the other ingredients comprising a formulation and/or the subject being treated therewith.

Protecting groups can be a temporary substituent which protects a potentially reactive functional group from undesired chemical transformations. The choice of the particular protecting group employed is well within the skill of one of ordinary skill in the art. A number of considerations can determine the choice of protecting group including, but not limited to, the functional group being protected, other functionality present in the molecule, reaction conditions at each step of the synthetic sequence, other protecting groups present in the molecule, functional group tolerance to conditions required to remove the protecting group, and reaction conditions for the thermal decomposition of the compounds provided herein. The field of protecting group chemistry has been reviewed (Greene, T. W.; Wuts, P. G. M. *Protective Groups in Organic Synthesis,* 2.sup.nd ed.; Wiley: New York, 1991).

A nitrogen protecting group can be any temporary substituent which protects an amine moiety from undesired chemical transformations. Examples of moieties formed when such protecting groups are bonded to an amine include, but are not limited to allylamine, benzylamines (e.g., benzylamine, p-methoxybenzylamine, 2,4-dimethoxybenzylamine, and tritylamine), acetylamide, trichloroacetamide, trifluoroacetamide, pent-4-enamide, phthalimides, carbamates (e.g., methyl carbamate, t-butyl carbamate, benzyl carbamate, allyl carbamates, 2,2,2-trichloroethyl carbamate, and 9-fluorenylmethyl carbamate), imines, and sulfonamides (e.g., benzene sulfonamide, p-toluenesulfonamide, and p-nitrobenzenesulfonamide).

An oxygen protecting group can be any temporary substituent which protects a hydroxyl moiety from undesired chemical transformations. Examples of moieties formed when such protecting groups are bonded to a hydroxyl include, but are not limited to esters (e.g., acetyl, t-butyl carbonyl, and benzoyl), benzyl (e.g., benzyl, p-methoxybenzyl, and 2,4-dimethoxybenzyl, and trityl), carbonates (e.g., methyl carbonate, allyl carbonate, 2,2,2-trichloroethyl carbonate and benzyl carbonate) ketals, and acetals, and ethers.

Compounds provided herein may also contain unnatural proportions of atomic isotopes at one or more of the atoms that constitute such compounds. That is, an atom, in particular when mentioned in relation to a compound according to Formula (I), comprises all isotopes and isotopic mixtures of that atom, either naturally occurring or synthetically produced, either with natural abundance or in an isotopically enriched form. For example, when hydrogen is mentioned, it is understood to refer to $^{1}H$, $^{2}H$, $^{3}H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof; unless expressly noted otherwise. For example, in deuteroalkyl and deuteroalkoxy groups, where one or more hydrogen atoms are specifically replaced with deuterium ($^{2}H$). As some of the aforementioned isotopes are radioactive, the compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present disclosure.

For illustrative purposes, general methods for preparing the compounds are provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

The ability of test compounds to act as CDC7 inhibitors may be demonstrated by the biological and computational assays described herein. $IC_{50}$ values are shown in Tables 2 and 3.

Compounds of Formula (I) (e.g., any one of Formulas (I-A) through (I-P)), or a pharmaceutically acceptable salt thereof, are useful for treating diseases and disorders which can be treated with a CDC7 kinase inhibitor, such as CDC7-associated cancers, including hematological cancers and solid tumors.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the term "subject" refers to any animal, including mammals such as mice, rats, other rodents, rabbits, dogs, cats, swine, cattle, sheep, horses, primates, and humans. In some embodiments, the subject is a human. In some embodiments, the subject has experienced and/or exhibited at least one symptom of the disease or disorder to be treated and/or prevented.

In some embodiments, the subject has been identified or diagnosed as having a cancer with a dysregulation of a CDC7 gene, a CDC7 protein, or expression or activity, or level of any of the same (a CDC7-associated cancer) (e.g., as determined using a regulatory agency-approved, e.g., FDA-approved, assay or kit). In some embodiments, the subject has a tumor that is positive for a dysregulation of a CDC7 gene, a CDC7 protein, or expression or activity, or level of any of the same (e.g., as determined using a regulatory agency-approved assay or kit). The subject can be a subject with a tumor(s) that is positive for a dysregulation of a CDC7 gene, a CDC7 protein, or expression or activity, or level of any of the same (e.g., identified as positive using a regulatory agency-approved, e.g., FDA-approved, assay or kit). The subject can be a subject whose tumors have a dysregulation of a CDC7 gene, a CDC7 protein, or expression or activity, or a level of the same (e.g., where the tumor is identified as such using a regulatory agency-approved, e.g., FDA-approved, kit or assay). In some embodiments, the subject is suspected of having a CDC7-associated cancer. In some embodiments, the subject has a clinical record indicating that the subject has a tumor that has a dysregulation of a CDC7 gene, a CDC7 protein, or expression or activity, or level of any of the same (and optionally the clinical record indicates that the subject should be treated with any of the compositions provided herein). In some embodiments, the subject is a pediatric subject. In some embodiments, the subject has been identified or diagnosed as having a cancer that, based on histological examination, is determined to be associated with a dysregulation of a CDC7 gene, a CDC7 protein, or expression or activity, or level of any of the same (a CDC7-associated cancer).

The term "pediatric subject" as used herein refers to a subject under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In some embodiments, compounds of Formula (I), or a pharmaceutically acceptable salt thereof are useful for preventing diseases and disorders as defined herein (for example, autoimmune diseases, inflammatory diseases, and cancer). The term "preventing" as used herein means the prevention of the onset, recurrence or spread, in whole or in part, of the disease or condition as described herein, or a symptom thereof.

The term "CDC7-associated cancer" as used herein refers to cancers associated with or having a dysregulation of a CDC7 gene, a CDC7 kinase (also called herein CDC7 kinase protein), or the expression or activity or level of any (e.g., one or more) of the same (e.g., any of the types of dysregulation of a CDC7 gene, a CDC7 kinase, a CDC7 kinase domain, or the expression or activity or level of any of the same described herein). Non-limiting examples of a CDC7-associated disease or disorder include, for example, cancer and gastrointestinal disorders such as irritable bowel syndrome (IBS).

The term "CDC7-associated cancer" as used herein refers to cancers associated with or having a dysregulation of a CDC7 gene, a CDC7 kinase, or expression or activity, or level of any of the same. Non-limiting examples of a CDC7-associated cancer are described herein.

The phrase "dysregulation of a CDC7 gene, a CDC7 kinase, or the expression or activity or level of any of the same" refers to a genetic mutation (e.g., a chromosomal translocation that results in the expression of a fusion protein including a CDC7 kinase domain and a fusion partner, a mutation in a CDC7 gene that results in the expression of a CDC7 protein that includes a deletion of at least one amino acid as compared to a wild-type CDC7 protein, a mutation in a CDC7 gene that results in the expression of a CDC7 protein with one or more point mutations as compared to a wild-type CDC7 protein, a mutation in a CDC7 gene that results in the expression of a CDC7 protein with at least one inserted amino acid as compared to a wild-type CDC7 protein, a gene duplication that results in an increased level of CDC7 protein in a cell, or a mutation in a regulatory sequence (e.g., a promoter and/or enhancer) that results in an increased level of CDC7 protein in a cell), an alternative spliced version of a CDC7 mRNA that results in a CDC7 protein having a deletion of at least one amino acid in the CDC7 protein as compared to the wild-type CDC7 protein), or increased expression (e.g., increased levels) of a wild-type CDC7 kinase in a mammalian cell due to aberrant cell signaling and/or dysregulated autocrine/paracrine signaling (e.g., as compared to a control non-cancerous cell). As another example, a dysregulation of a CDC7 gene, a CDC7 protein, or expression or activity, or level of any of the same, can be a mutation in a CDC7 gene that encodes a CDC7 protein that is constitutively active or has increased activity as compared to a protein encoded by a CDC7 gene that does not include the mutation. As a further example, an increased copy number of the CDC7 gene can result in overexpression of CDC7 kinase. For example, a dysregulation of a CDC7 gene, a CDC7 protein, or expression or activity, or level of any of the same, can be the result of a gene or chromosome translocation which results in the expression of a fusion protein that contains a first portion of CDC7 that includes a functional kinase domain, and a second portion of a partner protein (i.e., that is not CDC7). In some examples, dysregulation of a CDC7 gene, a CDC7 protein, or expression or activity or level of any of the same can be a result of a gene translocation of one CDC7 gene with another non-CDC7 gene.

The term "wild-type" describes a nucleic acid (e.g., a CDC7 gene or a CDC7 mRNA) or protein (e.g., a CDC7 protein) that is found in a subject that does not have a CDC7-associated disease, e.g., a CDC7-associated cancer (and optionally also does not have an increased risk of developing a CDC7-associated disease and/or is not suspected of having a CDC7-associated disease), or is found in a cell or tissue from a subject that does not have a CDC7-associated disease, e.g., a CDC7-associated cancer (and optionally also does not have an increased risk of developing a CDC7-associated disease and/or is not suspected of having a CDC7-associated disease).

The term "regulatory agency" refers to a country's agency for the approval of the medical use of pharmaceutical agents with the country. For example, a non-limiting example of a regulatory agency is the U.S. Food and Drug Administration (FDA).

Provided herein are compounds of Formula (I):

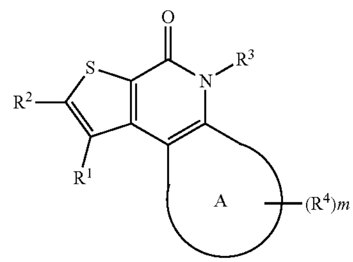

(I)

or a pharmaceutically acceptable salt thereof, wherein:

$R^1$ is hydrogen or halogen;

$R^2$ is a 5-6 membered heteroaryl optionally substituted with 1 or 2 substituents independently selected from the group consisting of halogen and C1-C6 alkyl; or a 5-6 membered heterocyclyl optionally substituted with 1 or 2 substituents independently selected from the group consisting of halogen and C1-C6 alkyl;

$R^3$ is hydrogen or C1-C6 alkyl;

Ring A is a C6-C10 cycloalkyl or a 6-10 membered heterocyclyl;

each $R^4$ is independently selected from the group consisting of halogen, hydroxyl, C1-C6 alkyl, C1-C6 alkoxy, C1-C6 hydroxyalkyl, C1-C6 haloalkyl, C1-C6 alkoxy (C1-C6 alkyl)-, —C(═O)C1-C6 alkyl, C2-C6 alkynyl, C3-C6 cycloalkyl, —$NR^AR^B$, and 4-6 membered heterocyclyl optionally substituted with 1 or 2 independently selected halogen; each $R^A$ and $R^B$ is independently hydrogen or C1-C6 alkyl; and m is 0, 1, 2, 3, or 4.

In some embodiments, m is 1. In some embodiments, m is 2. In some embodiments, m is 3. In some embodiments, m is 4.

In some embodiments, $R^2$ is a 5 membered heteroaryl optionally substituted with 1 or 2 substituents independently selected from the group consisting of halogen and C1-C6 alkyl. In some embodiments, $R^2$ is a 5 membered heteroaryl substituted with 1 or 2 substituents independently selected from the group consisting of halogen and C1-C6 alkyl.

In some embodiments, $R^2$ is a 5 membered heteroaryl group selected from the group consisting of pyrrolyl, pyrazolyl, imidazolyl, triazolyl, tetrazolyl, furanyl, thiophenyl, oxazolyl, isoxazolyl, isothiazolyl, thiazolyl, furazanyl, oxadiazolyl, thiadiazolyl, oxatriazolyl, and thiatriazolyl. In some embodiments, the 5 membered heteroaryl of $R^2$ is pyrazolyl or isothiazolyl. In some embodiments, $R^2$ is 4-pyrazolyl, 5-pyrazolyl, or 5-isothiazolyl.

In some embodiments, $R^2$ is a 6 membered heteroaryl optionally substituted with 1 or 2 substituents independently selected from the group consisting of halogen and C1-C6 alkyl. In some embodiments, $R^2$ is a 6 membered heteroaryl substituted with 1 or 2 substituents independently selected from the group consisting of halogen and C1-C6 alkyl.

In some embodiments, $R^2$ is a 6 membered heteroaryl group selected from the group consisting of pyridyl, pyrimidinyl, pyrazinyl, pyridazinyl, and triazinyl. In some embodiments, the 6 membered heteroaryl of $R^2$ is pyridyl, pyrimidinyl, or pyridazinyl. In some embodiments, the 6 membered heteroaryl of $R^2$ is pyridyl. In some embodiments, $R^2$ is 4-pyridyl. In some embodiments, $R^2$ is 4-pyrimidinyl. In some embodiments, $R^2$ is 4-pyridazinyl.

In some embodiments, the heteroaryl of $R^2$ is substituted with one substituent selected from halogen and C1-C6 alkyl. In some embodiments, the heteroaryl of $R^2$ is substituted with one substituent selected from fluoro, chloro, and methyl. In some embodiments, the heteroaryl of $R^2$ is substituted with two substituents independently selected from halogen and C1-C6 alkyl. In some embodiments, the heteroaryl of $R^2$ is substituted with two substituents independently selected from fluoro and methyl.

In some embodiments, the substituents on $R^2$ are the same. In some embodiments, the substituents on $R^2$ are different.

In some embodiments, $R^2$ is an unsubstituted 5-6 membered heteroaryl, such as an unsubstituted pyrazolyl, isothiazolyl, pyridyl, or pyridazinyl.

In some embodiments, $R^2$ is a 5-6 membered heterocyclyl optionally substituted with 1 or 2 substituents independently selected from the group consisting of halogen and C1-C6 alkyl. In some embodiments, $R^2$ is an unsubstituted 5-6 membered heterocyclyl. In some embodiments, $R^2$ is morpholinyl, piperidinyl, or piperazinyl. In some embodiments, $R^2$ is morpholinyl. In some embodiments, $R^2$ is 4-morpholinyl.

In some embodiments, Ring A is C6-C10 cycloalkyl. In some embodiments, Ring A is cyclohexyl. In some embodiments, Ring A is bicyclo[2.2.2]octanyl.

In some embodiments, Ring A is 6-10 membered heterocyclyl. In some embodiments, Ring A is tetrahydropyranyl. In some embodiments, Ring A is piperidinyl.

In some embodiments, one or two $R^4$ is independently halogen. In some embodiments, one $R^4$ is fluoro or chloro. In some embodiments, one $R^4$ is fluoro. In some embodiments, one $R^4$ is chloro. In some embodiments, two $R^4$ are fluoro.

In some embodiments, one $R^4$ is hydroxyl.

In some embodiments, one $R^4$ is independently C1-C6 alkyl. In some embodiments, one or two $R^4$ is independently selected C1-C6 alkyl. In some embodiments, one $R^4$ is independently selected from the group consisting of $—CH_3$, $—CH_2CH_3$, $—CH(CH_3)_2$, $—CH(CH_3)CH_2CH_3$, $—C(CH_3)_2CH_2CH_3$, and $—C(CH_3)_3$.

In some embodiments, each $R^4$ is independently C1-C6 alkoxy. In some embodiments, one $R^4$ is C1-C6 alkoxy. In some embodiments, each $R^4$ is independently methoxy, ethoxy, or isopropoxy. In some embodiments, one $R^4$ is methoxy, ethoxy, or isopropoxy. In some embodiments, each $R^4$ is methoxy. In some embodiments, one $R^4$ is methoxy.

In some embodiments, one $R^4$ is C1-C6 hydroxyalkyl. In some embodiments, one $R^4$ is C1-C6 hydroxyalkyl. In some embodiments, one $R^4$ is $—CH_2OH$ or $—C(CH_3)_2OH$. In some embodiments, one $R^4$ is $—CH_2OH$ or $—C(CH_3)_2OH$.

In some embodiments, one $R^4$ is C1-C6 haloalkyl. In some embodiments, one or two $R^4$ are independently selected C1-C6 haloalkyl. In some embodiments, one $R^4$ is $—CF_3$. In some embodiments, one $R^4$ is $—CHF_2$. In some embodiments, one $R^4$ is $—CF_3$. In some embodiments, one $R^4$ is $—CHF_2$. In some embodiments, one $R^4$ is $—CF_2CH_3$. In some embodiments, one $R^4$ is $CH_2CF_2CH_3$.

In some embodiments, one $R^4$ is C1-C6 alkoxy(C1-C6 alkyl)-. In some embodiments, one $R^4$ is C1-C3 alkoxy(C1-C3 alkyl)-. In some embodiments, one $R^4$ is independently methoxy(C1-C6 alkyl)-. In some embodiments, one $R^4$ is $—CH_2OCH_3$.

In some embodiments, one $R^4$ is —C(=O)C1-C6 alkyl. In some embodiments, $R^4$ is $C(=O)CH_3$.

In some embodiments, one $R^4$ is C2-C6 alkynyl. In some embodiments, one $R^4$ is 1-propynyl.

In some embodiments, one $R^4$ is C3-C6 cycloalkyl. In some embodiments, $R^4$ is cyclopentyl.

In some embodiments, one $R^4$ is $—NR^AR^B$. In some embodiments, one of R A and R B is hydrogen and the other of $R^A$ and $R^B$ is C1-C6 alkyl. In some embodiments, $R^A$ and $R^B$ are both C1-C6 alkyl. In some embodiments, $R^4$ is $—NH_2$.

In some embodiments, one $R^4$ is a 4-6 membered heterocyclyl optionally substituted with 1 or 2 independently selected halogen. In some embodiments, one $R^4$ is a 4-6 membered heterocyclyl substituted with 1 or 2 independently selected halogen. In some embodiments, one $R^4$ is a 4-6 membered heterocyclyl substituted with 1 or 2 fluoro. In some embodiments, one $R^4$ is a 4-6 membered heterocyclyl substituted with germinal difluoro groups.

In some embodiments, one $R^4$ is azetidinyl, oxetanyl, pyrrolidinyl, tetrahydrofuryl, piperidinyl, piperazinyl, tetrahydrofuryl, morpholinyl, or dioxanyl; each optionally substituted with 1 or 2 independently selected halogen. In some embodiments, one $R^4$ is pyrrolidinyl optionally substituted with 1 or 2 independently selected halogen. In some embodiments, one $R^4$ is pyrrolidinyl substituted with 1 or 2 independently selected halogen. In some embodiments, one $R^4$ is azetidinyl optionally substituted with 1 or 2 independently selected halogen. In some embodiments, one $R^4$ is azetidinyl substituted with 1 or 2 independently selected halogen. In some embodiments, the 1 or 2 independently selected halogen are fluoro. In some embodiments, the 2 independently selected halogen are germinal difluoro groups.

In some embodiments, one $R^4$ is an unsubstituted 4-6 membered heterocyclyl. In some embodiments, the unsubstituted 4-6 membered heterocyclyl of $R^4$ is azetidinyl, oxetanyl, pyrrolidinyl, tetrahydrofuryl, piperidinyl, piperazinyl, tetrahydrofuryl, morpholinyl, or dioxanyl. In some embodiments, one $R^4$ is an unsubstituted pyrrolidinyl or unsubstituted azetidinyl.

In some embodiments, one $R^4$ is selected from the group consisting of

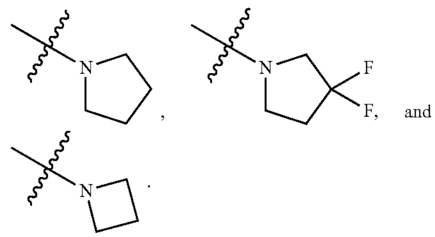

, and .

In some embodiments, m is 2, 3, or 4; and two of the 2, 3, or 4 $R^4$ groups are geminal. In some embodiments, m is 2; and both (i.e., two) $R^4$ groups are geminal. In some embodiments, m is 3; and wherein two of the three $R^4$ groups are geminal. In some embodiments, m is 4; and wherein each pair of $R^4$ groups are geminal.

In some embodiments, $R^1$ is halogen. In some embodiments, $R^1$ is fluoro or chloro. In some embodiments, $R^1$ is fluoro. In some embodiments, $R^1$ is hydrogen.

In some embodiments, $R^3$ is C1-C6 alkyl. In some embodiments, $R^3$ is methyl. In some embodiments, $R^3$ is hydrogen.

In some embodiments, m is 2; one $R^4$ is hydroxyl; and the other $R^4$ is C1-C6 alkyl.

In some embodiments, m is 2 and each $R^4$ is fluoro.

In some embodiments, m is 2; one $R^4$ is hydroxyl; and the other $R^4$ is C1-C6 haloalkyl.

In some embodiments, m is 2; one $R^4$ is hydroxyl; and the other $R^4$ is C2-C6 alkynyl.

In some embodiments, m is 2; one $R^4$ is hydroxyl; and the other $R^4$ is C3-C6 cycloalkyl.

In some embodiments, m is 2; one $R^4$ is hydroxyl; and the other $R^4$ is C1-C6 alkoxy(C1-C6 alkyl)-.

In some embodiments, m is 2; each $R^4$ is independently selected C1-C6 alkyl.

In some embodiments, m is 2; one $R^4$ is C1-C6 alkyl; and the other $R^4$ is C1-C6 hydroxyalkyl.

In some embodiments, m is 2; one $R^4$ is C1-C6 alkyl; and the other $R^4$ is C1-C6 alkoxy.

In some embodiments, m is 2; one $R^4$ is C1-C6 alkyl; and the other $R^4$ is $—NR^AR^B$.

In some embodiments, m is 2; one $R^4$ is C1-C6 alkyl; and the other $R^4$ is 4-6 membered heterocyclyl optionally substituted with 1 or 2 independently selected halogen.

In some embodiments, m is 4; two $R^4$ are fluoro; one $R^4$ is C1-C6 alkoxy; and one $R^4$ is C1-C6 alkyl.

In some embodiments, m is 4; two $R^4$ are fluoro; one $R^4$ is C1-C6 hydroxyalkyl; and one $R^4$ is C1-C6 alkyl.

In some embodiments, m is 4; two $R^4$ are fluoro; one $R^4$ is hydroxyl; and one $R^4$ is C1-C6 alkyl.

In some embodiments, m is 4; two $R^4$ are fluoro; one $R^4$ is hydroxyl; and one $R^4$ is C1-C6 alkoxy(C1-C6 alkyl)-.

In some embodiments, $R^1$ is hydrogen; $R^2$ is an unsubstituted pyrazolyl; m is 2; one $R^4$ is hydroxyl; and the other $R^4$ is C1-C6 alkyl.

In some embodiments, $R^1$ is hydrogen; $R^2$ is an unsubstituted pyrazolyl; m is 2 and each $R^4$ is fluoro.

In some embodiments, $R^1$ is hydrogen; $R^2$ is an unsubstituted pyrazolyl; m is 2; one $R^4$ is hydroxyl; and the other $R^4$ is C1-C6 haloalkyl.

In some embodiments, $R^1$ is hydrogen; $R^2$ is an unsubstituted pyrazolyl; m is 4; two $R^4$ are fluoro; one $R^4$ is C1-C6 alkoxy; and one $R^4$ is C1-C6 alkyl.

In some embodiments, $R^1$ is hydrogen; $R^2$ is an unsubstituted pyrazolyl; m is 4; two $R^4$ are fluoro; one $R^4$ is C1-C6 hydroxyalkyl; and one $R^4$ is C1-C6 alkyl.

In some embodiments, $R^1$ is hydrogen; $R^2$ is an unsubstituted pyridinyl; m is 2; one $R^4$ is hydroxyl; and the other $R^4$ is C1-C6 alkyl.

In some embodiments, $R^1$ is hydrogen; $R^2$ is an unsubstituted pyridinyl; m is 2 and each $R^4$ is fluoro.

In some embodiments, $R^1$ is hydrogen; $R^2$ is an unsubstituted pyridinyl; m is 2; one $R^4$ is hydroxyl; and the other $R^4$ is C1-C6 haloalkyl.

In some embodiments, $R^1$ is hydrogen; $R^2$ is an unsubstituted pyridinyl; m is 4; two $R^4$ are fluoro; one $R^4$ is C1-C6 alkoxy; and one $R^4$ is C1-C6 alkyl.

In some embodiments, $R^1$ is hydrogen; $R^2$ is an unsubstituted pyridinyl; m is 4; two $R^4$ are fluoro; one $R^4$ is C1-C6 hydroxyalkyl; and one $R^4$ is C1-C6 alkyl.

In some embodiments, $R^1$ is hydrogen; $R^2$ is an unsubstituted isothiazolyl; m is 2; one $R^4$ is hydroxyl; and the other $R^4$ is C1-C6 alkyl.

In some embodiments, $R^1$ is hydrogen; $R^2$ is an unsubstituted isothiazolyl; m is 2 and each $R^4$ is fluoro.

In some embodiments, $R^1$ is hydrogen; $R^2$ is an unsubstituted isothiazolyl; m is 2; one $R^4$ is hydroxyl; and the other $R^4$ is C1-C6 haloalkyl.

In some embodiments, $R^1$ is hydrogen; $R^2$ is an unsubstituted isothiazolyl; m is 4; two $R^4$ are fluoro; one $R^4$ is C1-C6 alkoxy; and one $R^4$ is C1-C6 alkyl.

In some embodiments, $R^1$ is hydrogen; $R^2$ is an unsubstituted isothiazolyl; m is 4; two $R^4$ are fluoro; one $R^4$ is C1-C6 hydroxyalkyl; and one $R^4$ is C1-C6 alkyl.

In some embodiments, Ring A is cyclohexyl; m is 2; one $R^4$ is hydroxyl; and the other $R^4$ is C1-C6 alkyl.

In some embodiments, Ring A is cyclohexyl; m is 2 and each $R^4$ is fluoro.

In some embodiments, Ring A is cyclohexyl; m is 2; one $R^4$ is hydroxyl; and the other $R^4$ is C1-C6 haloalkyl.

In some embodiments, Ring A is cyclohexyl; m is 4; two $R^4$ are fluoro; one $R^4$ is C1-C6 alkoxy; and one $R^4$ is C1-C6 alkyl.

In some embodiments, Ring A is cyclohexyl; m is 4; two $R^4$ are fluoro; one $R^4$ is C1-C6 hydroxyalkyl; and one $R^4$ is C1-C6 alkyl.

In some embodiments, Ring A is bicyclo[2.2.2]octanyl; m is 2; one $R^4$ is hydroxyl; and the other $R^4$ is C1-C6 alkyl.

In some embodiments, Ring A is bicyclo[2.2.2]octanyl; m is 2 and each $R^4$ is fluoro.

In some embodiments, Ring A is bicyclo[2.2.2]octanyl; m is 2; one $R^4$ is hydroxyl; and the other $R^4$ is C1-C6 haloalkyl.

In some embodiments, Ring A is bicyclo[2.2.2]octanyl; m is 4; two $R^4$ are fluoro; one $R^4$ is C1-C6 alkoxy; and one $R^4$ is C1-C6 alkyl.

In some embodiments, Ring A is bicyclo[2.2.2]octanyl; m is 4; two $R^4$ are fluoro; one $R^4$ is C1-C6 hydroxyalkyl; and one $R^4$ is C1-C6 alkyl.

In some embodiments, Ring A is tetrahydropyranyl; m is 2; one $R^4$ is hydroxyl; and the other $R^4$ is C1-C6 alkyl.

In some embodiments, Ring A is tetrahydropyranyl; m is 2 and each $R^4$ is fluoro.

In some embodiments, Ring A is tetrahydropyranyl; m is 2; one $R^4$ is hydroxyl; and the other $R^4$ is C1-C6 haloalkyl.

In some embodiments, Ring A is piperidinyl; m is 3; one $R^4$ is hydroxyl; one $R^4$ is C1-C6 alkyl; and one $R^4$ is —C(═O)C1-C6 alkyl. In some embodiments when Ring A is piperidinyl, one $R^4$ is attached to the piperidinyl nitrogen atom.

In some embodiments, Ring A is tetrahydropyranyl; m is 4; two $R^4$ are fluoro; one $R^4$ is C1-C6 alkoxy; and one $R^4$ is C1-C6 alkyl.

In some embodiments, Ring A is tetrahydropyranyl; m is 4; two $R^4$ are fluoro; one $R^4$ is C1-C6 hydroxyalkyl; and one $R^4$ is C1-C6 alkyl.

In some embodiments, the compounds of Formula (I-A), (I-B), (I-C), (I-D), (I-E), (I-F), (I-G), (I-H), (I-I), (I-J), (I-K), (I-L), (I-M), (I-N), (I-O), and (I-P), and pharmaceutically acceptable salts thereof, as described herein, $R^1$, $R^2$, $R^4$, and m are as described with respect to Formula (I), or a pharmaceutically acceptable salt thereof.

In some embodiments, the compound of Formula (I) is a compound of Formula (I-A):

Formula (I-A)

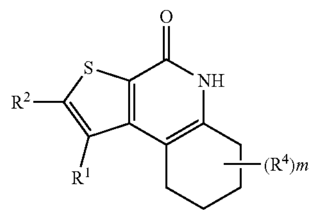

or a pharmaceutically acceptable salt thereof.

In some embodiments, the compound of Formula (I) is a compound of Formula (I-B):

Formula (I-B)

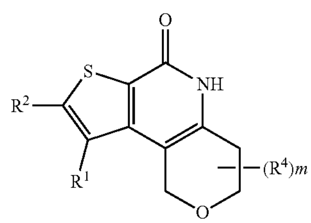

or a pharmaceutically acceptable salt thereof.

In some embodiments, the compound of Formula (I) is a compound of Formula (I-C):

Formula (I-C)

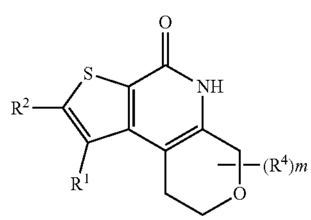

or a pharmaceutically acceptable salt thereof.

In some embodiments, the compound of Formula (I) is a compound of Formula (I-D):

Formula (I-D)

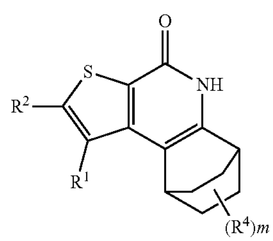

or a pharmaceutically acceptable salt thereof.

In some embodiments, the compound of Formula (I) is a compound of Formula (I-E):

Formula (I-E)

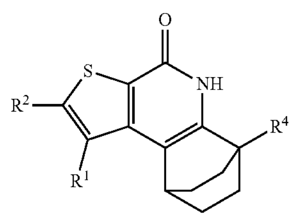

or a pharmaceutically acceptable salt thereof.

In some embodiments, the compound of Formula (I) is a compound of Formula I-F):

Formula (I-F)

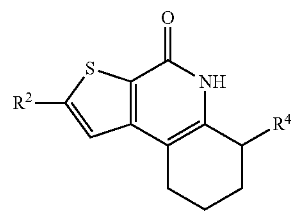

or a pharmaceutically acceptable salt thereof.

In some embodiments, the compound of Formula (I) is a compound of Formula I-G):

Formula (I-G)

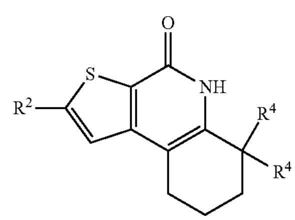

or a pharmaceutically acceptable salt thereof.

In some embodiments, the compound of Formula (I) is a compound of Formula I-H):

Formula (I-H)

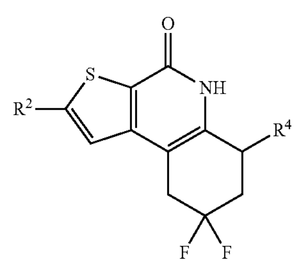

or a pharmaceutically acceptable salt thereof.

In some embodiments, the compound of Formula (I) is a compound of Formula I-I):

Formula (I-I)

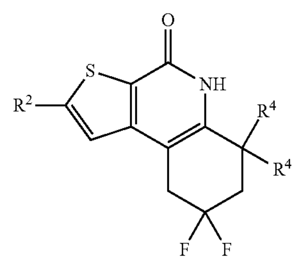

or a pharmaceutically acceptable salt thereof.

In some embodiments, the compound of Formula (I) is a compound of Formula I-J):

Formula (I-J)

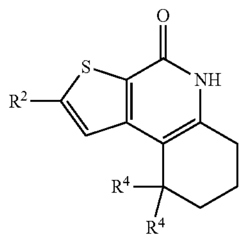

or a pharmaceutically acceptable salt thereof.

In some embodiments, the compound of Formula (I) is a compound of Formula I-K):

Formula (I-K)

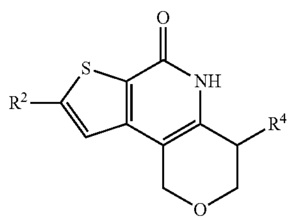

or a pharmaceutically acceptable salt thereof.

In some embodiments, the compound of Formula (I) is a compound of Formula I-L):

Formula (I-L)

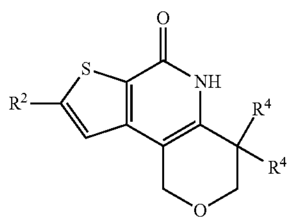

or a pharmaceutically acceptable salt thereof.

In some embodiments, the compound of Formula (I) is a compound of Formula I-M):

Formula (I-M)

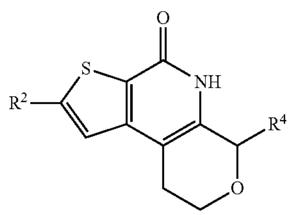

or a pharmaceutically acceptable salt thereof.

In some embodiments, the compound of Formula (I) is a compound of Formula I-N):

Formula (I-N)

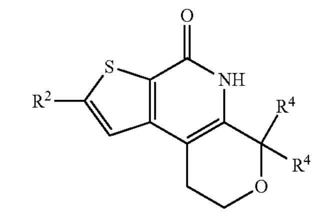

or a pharmaceutically acceptable salt thereof.

In some embodiments, the compound of Formula (I) is a compound of Formula I-O):

Formula (I-O)

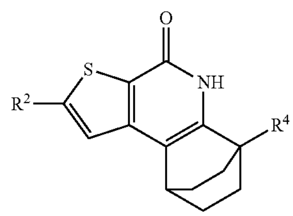

or a pharmaceutically acceptable salt thereof.

In some embodiments, the compound of Formula (I) is a compound of Formula I-P):

Formula (I-P)

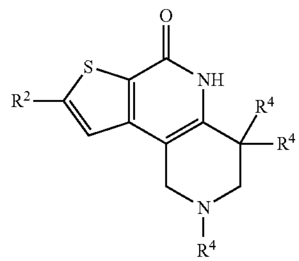

or a pharmaceutically acceptable salt thereof.

Table 1 depicts compounds of Formula (I). Unless otherwise specified, all stereochemistry in Table 1 is understood to be arbitrarily assigned.

In some embodiments, the compound of Formula (I), or a pharmaceutically acceptable salt thereof, is a compound selected from Table 1, or a pharmaceutically acceptable salt thereof.

TABLE 1

| Example compounds | |
|---|---|
| Compound No. | Structure |
| 1 | 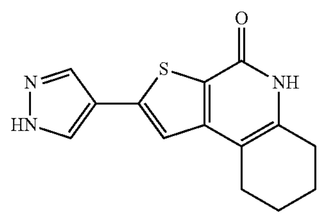 [SMILES: O=c1[nH]c2c(c3cc(-c4cn[nH]c4)sc13)CCCC2] |

TABLE 1-continued
| Example compounds | |
|---|---|
| Compound No. | Structure |
| 2 | 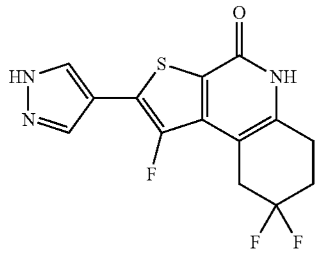 [SMILES: O=c1[nH]c2c(c3c(F)c(-c4cn[nH]c4)sc13)CC(F)(F)CC2] |
| 3 | 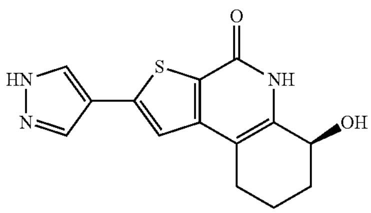 [SMILES: O=c1[nH]c2c(c3cc(-c4cn[nH]c4)sc13)CCC[C@@H]2O] |
| 4 | 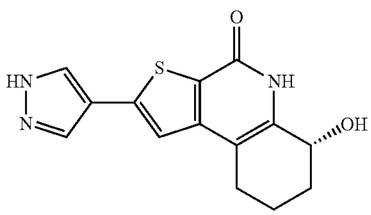 [SMILES: O=c1[nH]c2c(c3cc(-c4cn[nH]c4)sc13)CCC[C@H]2O] |
| 5 | 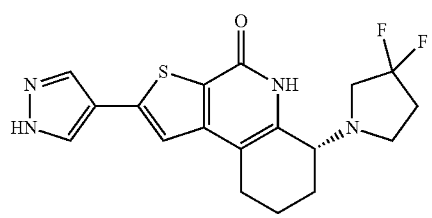 [SMILES: O=c1[nH]c2c(c3cc(-c4cn[nH]c4)sc13)CCC[C@H]2N1CCC(F)(F)C1] |
| 6 | 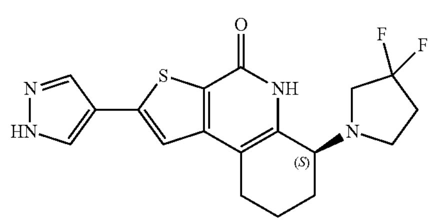 |
| 7 | 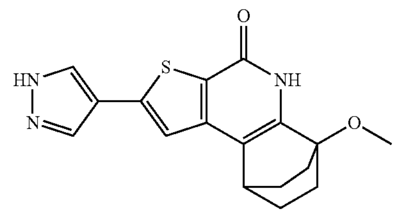 [SMILES: COC12CCC(CC1)c1c2[nH]c(=O)c2sc(-c3cn[nH]c3)cc12] |
TABLE 1-continued
| Example compounds | |
|---|---|
| Compound No. | Structure |
| 8 | 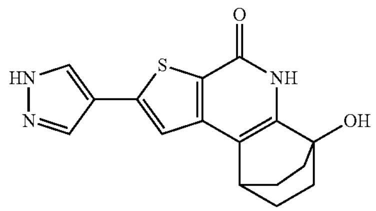 [SMILES: O=c1[nH]c2c(c3cc(-c4cn[nH]c4)sc13)C1CCC2(O)CC1] |
| 9 | 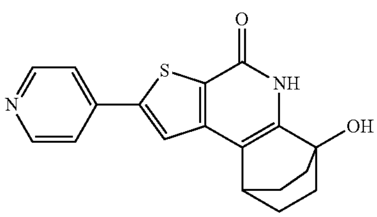 [SMILES: O=c1[nH]c2c(c3cc(-c4ccncc4)sc13)C1CCC2(O)CC1] |
| 10 | 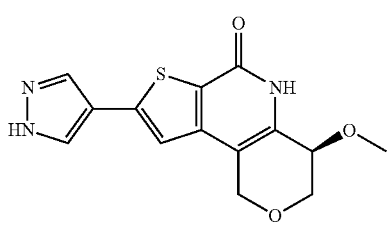 [SMILES: CO[C@H]1COCc2c1[nH]c(=O)c1sc(-c3cn[nH]c3)cc21] |
| 11 | 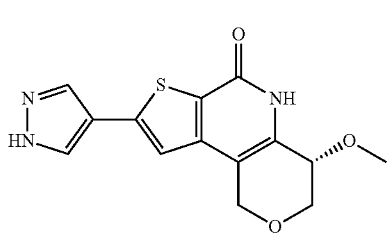 [SMILES: CO[C@@H]1COCc2c1[nH]c(=O)c1sc(-c3cn[nH]c3)cc21] |
| 12 | 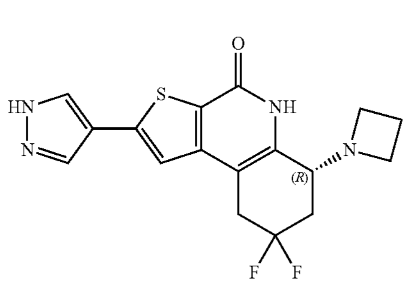 |
| 13 | 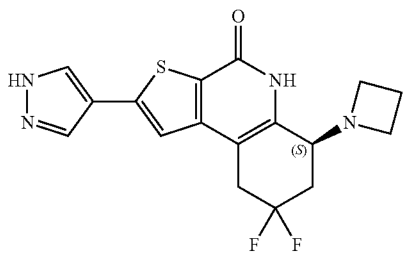 |

TABLE 1-continued
| Example compounds | |
|---|---|
| Compound No. | Structure |
| 14 | 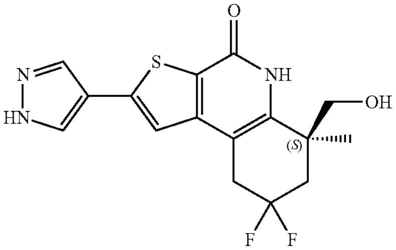 |
| 15 | 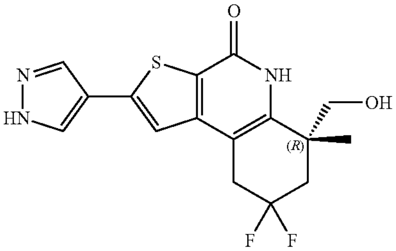 |
| 16 | 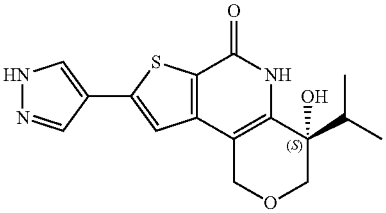 |
| 17 | 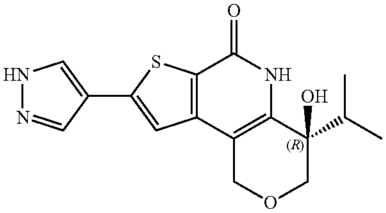 |
| 18 | 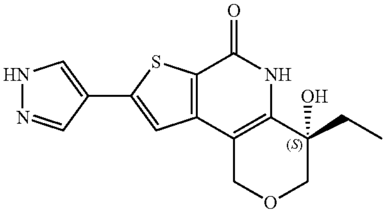 |
| 19 | 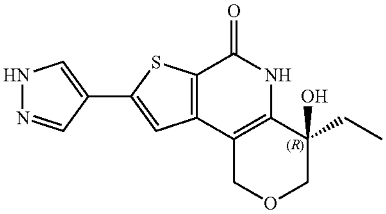 |
| 20 | 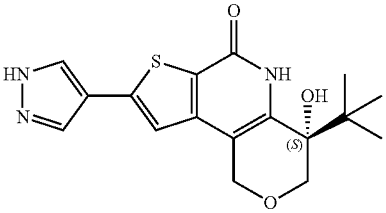 |
| 21 | 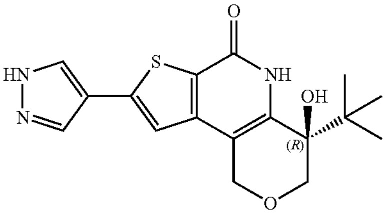 |
| 22 | 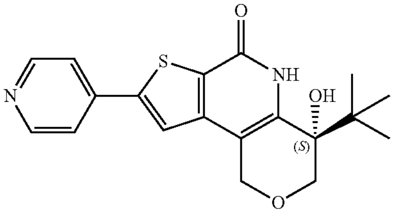 |
| 23 | 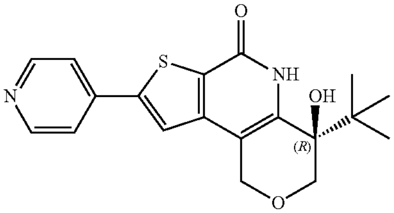 |
| 24 | 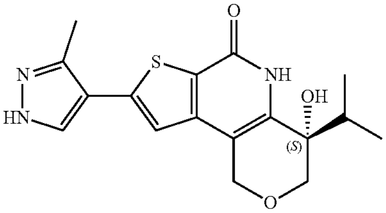 |
| 25 | 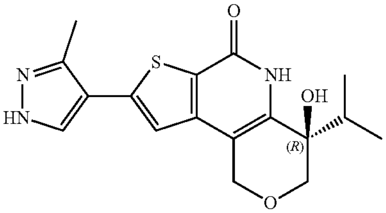 |
| 26 | 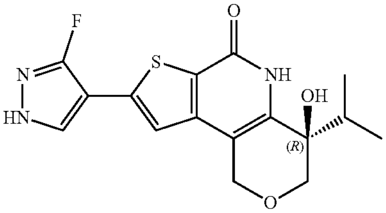 |

TABLE 1-continued
| Example compounds | |
|---|---|
| Compound No. | Structure |
| 27 | 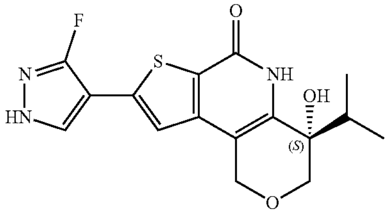 |
| 28 | 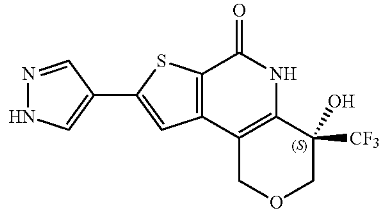 |
| 29 | 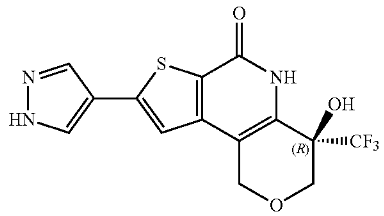 |
| 30 | 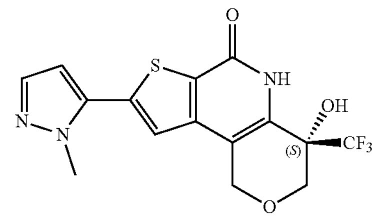 |
| 31 | 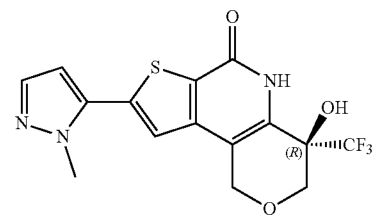 |
| 32 | 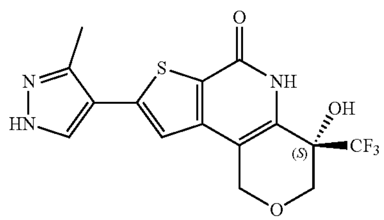 |
TABLE 1-continued
| Example compounds | |
|---|---|
| Compound No. | Structure |
| 33 | 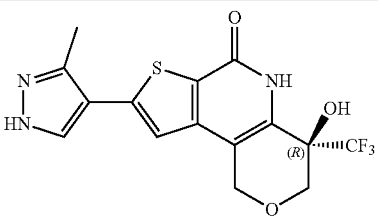 |
| 34 | 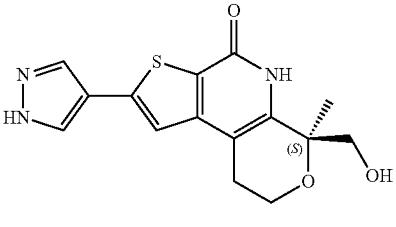 |
| 35 | 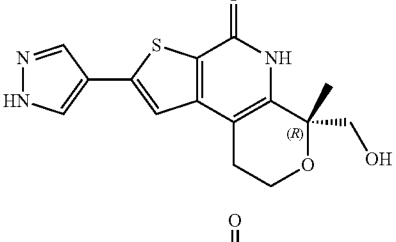 |
| 36 | 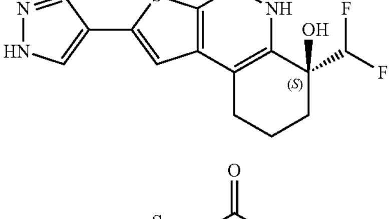 |
| 37 | 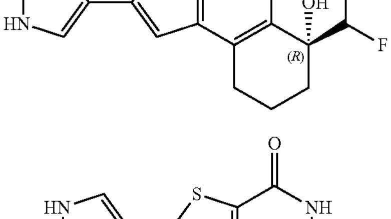 |
| 38 | 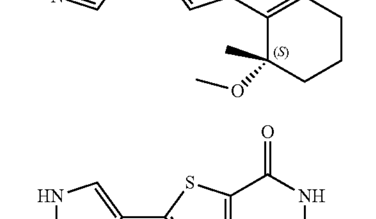 |
| 39 | 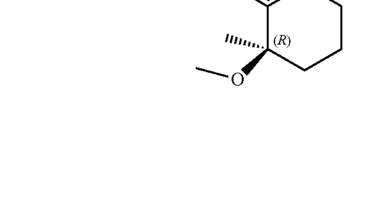 |

TABLE 1-continued
| Example compounds | |
|---|---|
| Compound No. | Structure |
| 40 | 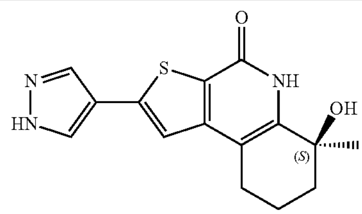 |
| 41 | 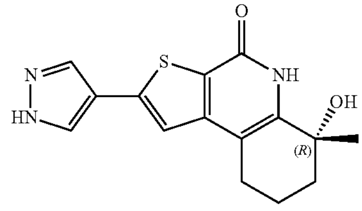 |
| 42 | 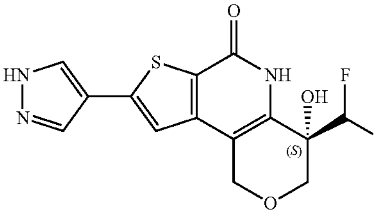 |
| 43 | 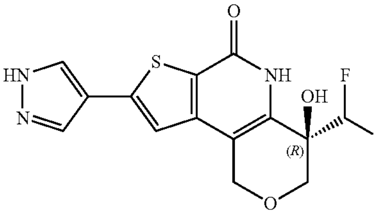 |
| 44 | 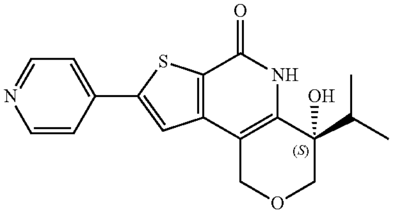 |
| 45 | 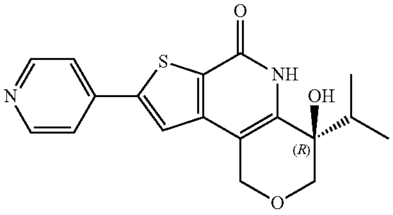 |
| 46 | 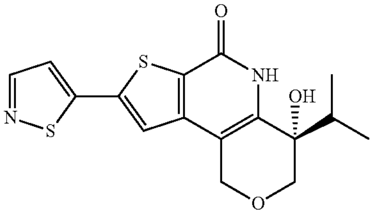 [SMILES: CC(C)[C@@]1(O)COCc2c1[nH]c(=O)c1sc(-c3ccns3)cc21] |
TABLE 1-continued
| Example compounds | |
|---|---|
| Compound No. | Structure |
| 47 | 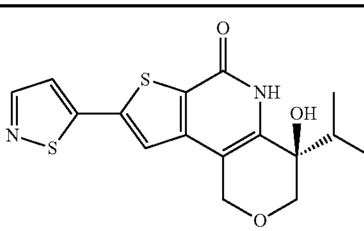 |
| 48 | 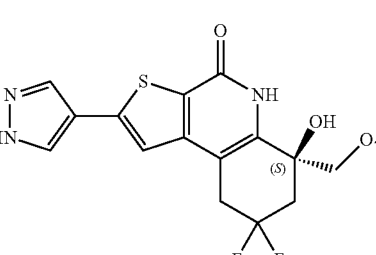 |
| 49 | 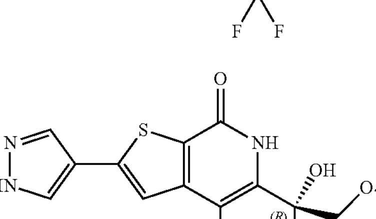 |
| 50 | 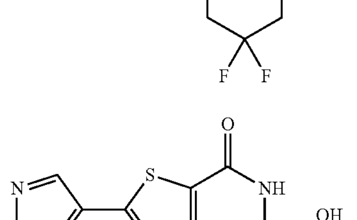 |
| 51 | 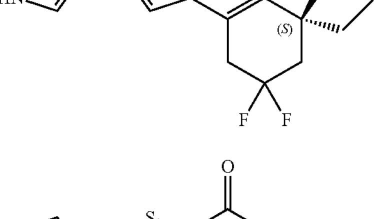 |
| 52 | 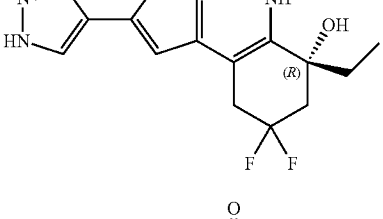 |

TABLE 1-continued
| Example compounds | |
|---|---|
| Compound No. | Structure |
| 53 | 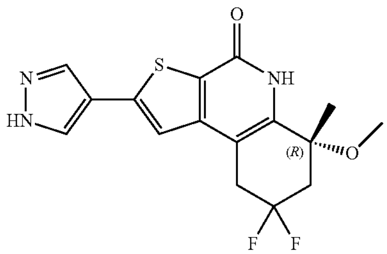 |
| 54 | 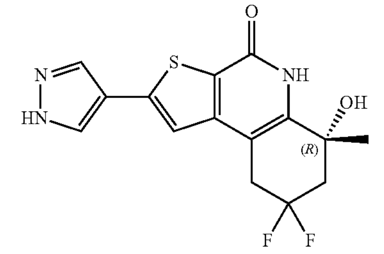 |
| 55 | 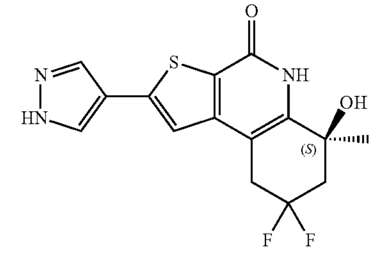 |
| 56 | 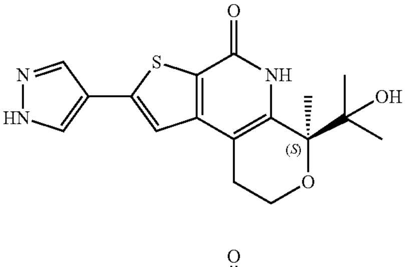 |
| 57 | 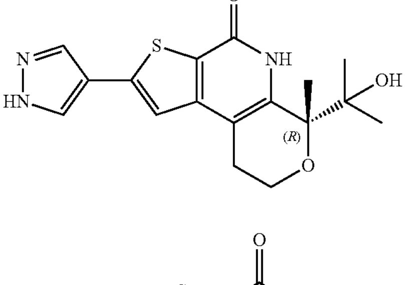 |
| 58 | 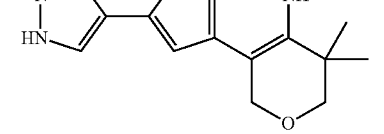 |
TABLE 1-continued
| Example compounds | |
|---|---|
| Compound No. | Structure |
| 59 | 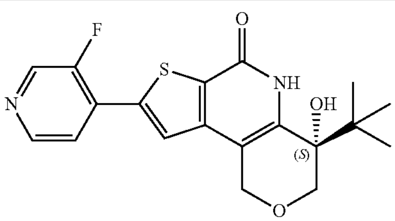 |
| 60 | 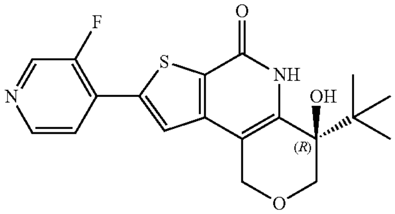 |
| 61 | 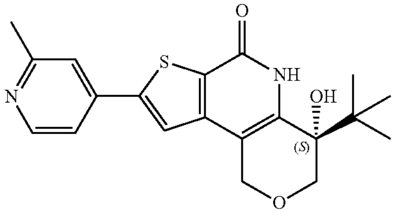 |
| 62 | 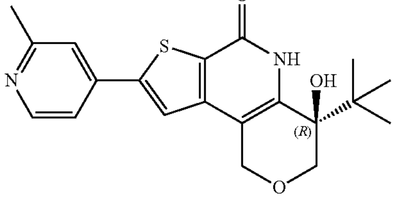 |
| 63 | 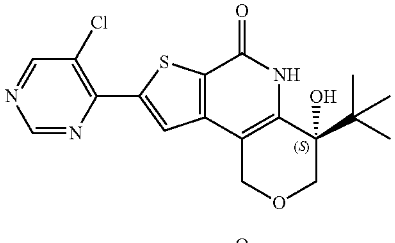 |
| 64 | 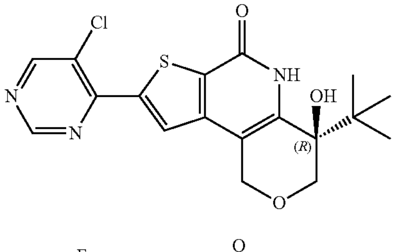 |
| 65 | 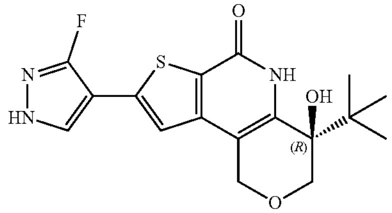 |

TABLE 1-continued
| Example compounds | |
|---|---|
| Compound No. | Structure |
| 66 | 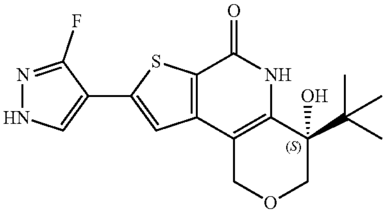 |
| 67 | 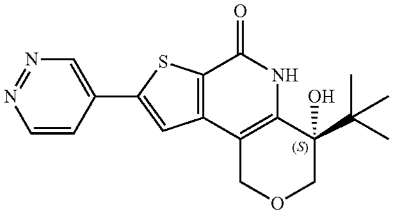 |
| 68 | 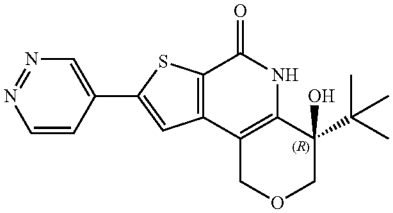 |
| 69 | 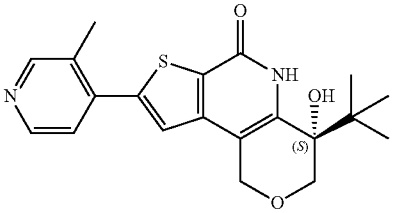 |
| 70 | 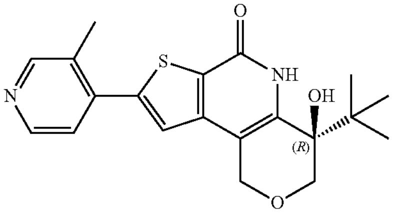 |
| 71 | 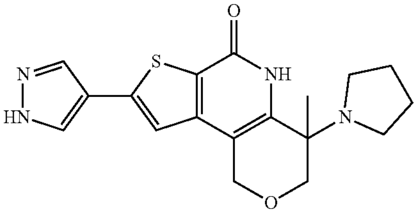 [SMILES: CC1(N2CCCC2)COCc2c1[nH]c(=O)c1sc(-c3cn[nH]c3)cc21] |
TABLE 1-continued
| Example compounds | |
|---|---|
| Compound No. | Structure |
| 72 | 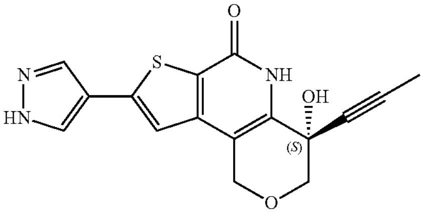 |
| 73 | 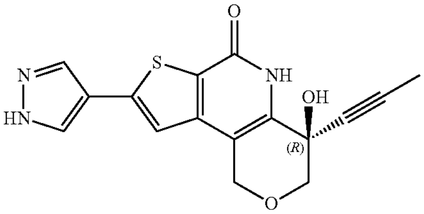 |
| 74 | 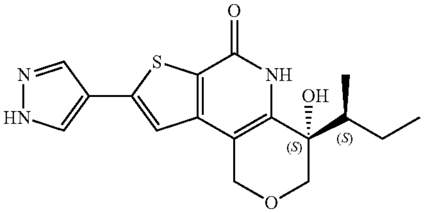 |
| 75 | 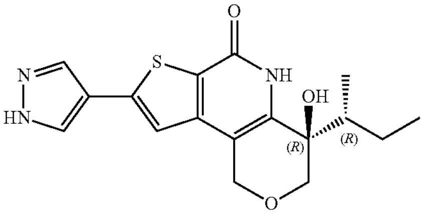 |
| 76 | 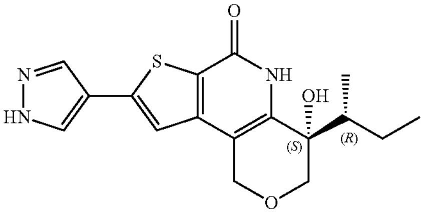 |
| 77 | 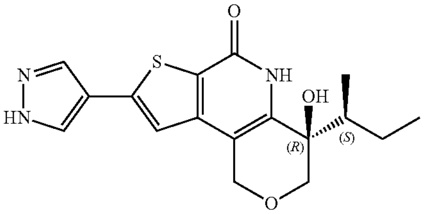 |
| 78 | 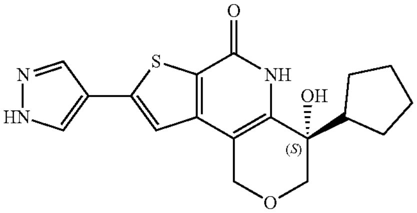 |

TABLE 1-continued
| Example compounds | |
|---|---|
| Compound No. | Structure |
| 79 | 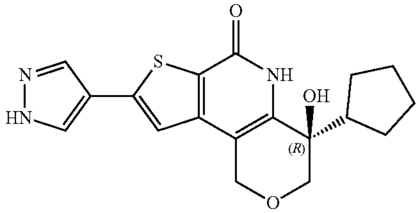 |
| 80 | 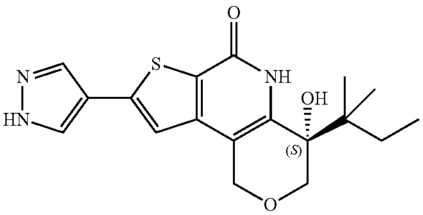 |
| 81 | 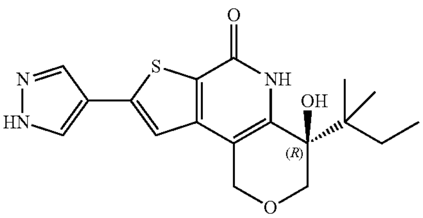 |
| 82 | 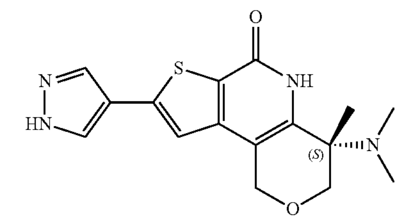 |
| 83 | 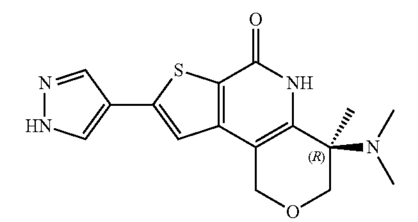 |
| 84 | 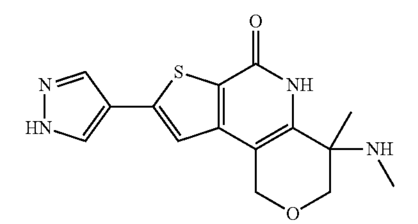 [SMILES: CNC1(C)COCc2c1[nH]c(=O)c1sc(-c3cn[nH]c3)cc21] |
TABLE 1-continued
| Example compounds | |
|---|---|
| Compound No. | Structure |
| 85 | 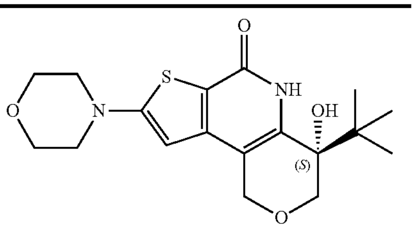 |
| 86 | 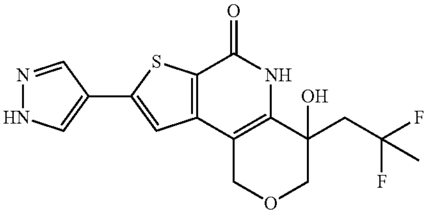 [SMILES: CC(F)(F)CC1(O)COCc2c1[nH]c(=O)c1sc(-c3cn[nH]c3)cc21] |
| 87 | 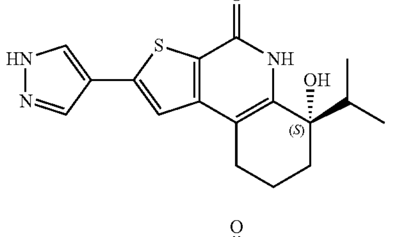 |
| 88 | 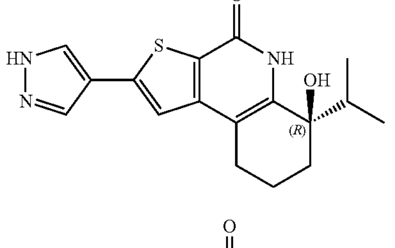 |
| 89 | 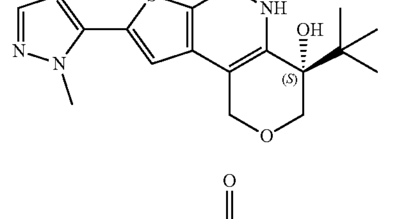 |
| 90 | 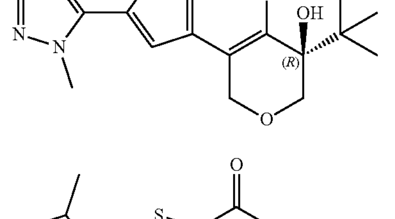 |
| 91 | 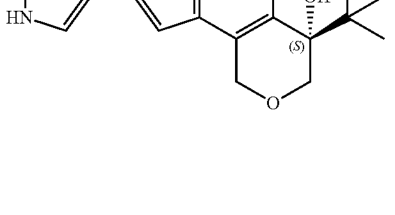 |

TABLE 1-continued

| Example compounds | |
|---|---|
| Compound No. | Structure |
| 92 | 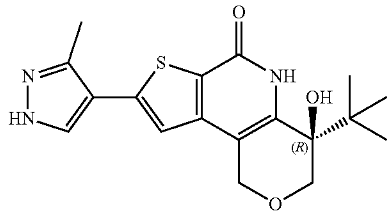 |
| 93 | 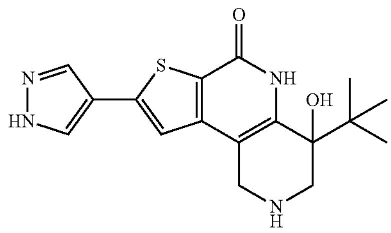 [SMILES: CC(C)(C)C1(O)CNCc2c1[nH]c(=O)c1sc(-c3cn[nH]c3)cc21] |
| 94 | 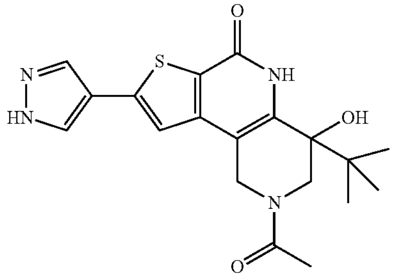 [SMILES: CC(=O)N1Cc2c([nH]c(=O)c3sc(-c4cn[nH]c4)cc23)C(O)(C(C)(C)C)C1] |
| 95 | 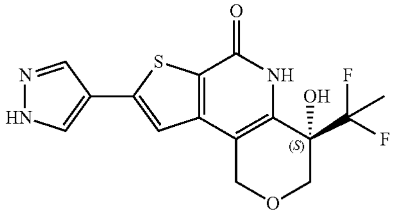 |
| 96 | 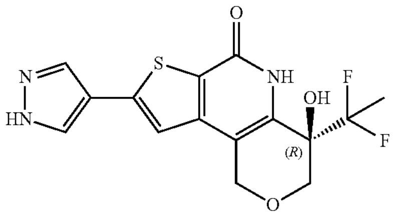 |

Methods of Treatment

Provided herein is a method of treating cancer (e.g., a CDC7-associated cancer) in a subject in need of such treatment, the method comprising administering to the subject a therapeutically effective amount of a compound of Formula (I), or a pharmaceutically acceptable salt thereof or a pharmaceutical composition thereof. For example, provided herein are methods for treating a CDC7-associated cancer in a subject in need of such treatment, the method comprising a) detecting a dysregulation of a CDC7 gene, a CDC7 kinase, or the expression or activity or level of any of the same in a sample from the subject; and b) administering a therapeutically effective amount of a compound of Formula (I), or a pharmaceutically acceptable salt thereof. In some embodiments, the dysregulation of a CDC7 gene, a CDC7 kinase, or the expression or activity or level of any of the same includes one or more fusion proteins.

In some embodiments of any of the methods or uses described herein, the cancer (e.g., CDC7-associated cancer) is a hematological cancer. In some embodiments of any of the methods or uses described herein, the cancer (e.g., CDC7-associated cancer) is a solid tumor. In some embodiments of any of the methods or uses described herein, the cancer (e.g., CDC7-associated cancer) is a lung cancer (e.g., small cell lung carcinoma or non-small cell lung carcinoma), thyroid cancer (e.g., papillary thyroid cancer, medullary thyroid cancer (e.g., sporadic medullary thyroid cancer or hereditary medullary thyroid cancer), differentiated thyroid cancer, recurrent thyroid cancer, or refractory differentiated thyroid cancer), thyroid adenoma, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, or cervical cancer. In some embodiments of any of the methods or uses described herein, the cancer (e.g., CDC7-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, cutaneous angiosarcoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy-associated breast cancer, primary central nervous system lymphoma, primary peritoneal cancer, prostate cancer, rectal cancer, colon cancer, colonic neoplasms, renal cell cancer, CDC7 inoblastoma, rhabdomyosarcoma, salivary gland cancer, sarcoma, Sezary syndrome, skin cancer, Spitz tumors, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and uCDC7er, unknown primary carcinoma, uCDC7hral cancer, uterine cancer, uterine sarcoma, vaginal cancer, vulvar cancer, and Wilms' tumor.

In some embodiments, a hematological cancer (e.g., hematological cancers that are CDC7-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In some embodiments, the hematological cancer (e.g., the hematological cancer that is a CDC7-associated cancer) is AML or CMML.

In some embodiments, the cancer (e.g., the CDC7-associated cancer) is a solid tumor. Examples of solid tumors (e.g., solid tumors that are CDC7-associated cancers) include, for example, thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma. See, for example, Nature Reviews Cancer, 2014, 14, 173-186.

In some embodiments, the cancer is selected from the group consisting of lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

In some embodiments, the subject is a human.

Compounds of Formula (I) and pharmaceutically acceptable salts and solvates thereof are also useful for treating a CDC7-associated cancer.

Accordingly, also provided herein is a method for treating a subject diagnosed with or identified as having a CDC7-associated cancer, e.g., any of the exemplary CDC7-associated cancers disclosed herein, comprising administering to the subject a therapeutically effective amount of a compound of Formula (I), or a pharmaceutically acceptable salt thereof, or a pharmaceutical composition thereof as defined herein. In some embodiments, a compound of Formula (I), or a pharmaceutically acceptable salt thereof, is selected from Examples 1-96, or a pharmaceutically acceptable salt thereof. In some embodiments, the compound of Formula (I), or a pharmaceutically acceptable salt thereof, administered to the subject is a compound of Formula (I-A), (I-B), (I-C), (I-D), (I-E), (I-F), (I-G), (I-H), (I-I), (I-J), (I-K), (I-L), (I-M), (I-N), (I-O), or (I-P), or a pharmaceutically acceptable salt of any of the foregoing.

Dysregulation of a CDC7 kinase, a CDC7 gene, or the expression or activity or level of any (e.g., one or more) of the same can contribute to tumorigenesis. For example, a fusion protein can have increased kinase activity as compared to a wild-type CDC7 protein, increased expression (e.g., increased levels) of a wild-type CDC7 kinase in a mammalian cell can occur due to aberrant cell signaling and/or dysregulated autocrine/paracrine signaling (e.g., as compared to a control non-cancerous cell), CDC7 mRNA splice variants may also result in dysregulation of CDC7.

In some embodiments, the compounds provided herein exhibit brain and/or central nervous system (CNS) penetrance. Such compounds are capable of crossing the blood brain barrier and inhibiting a CDC7 kinase in the brain and/or other CNS structures. In some embodiments, the compounds provided herein are capable of crossing the blood brain barrier in an effective amount. For example, treatment of a subject with cancer (e.g., a CDC7-associated cancer such as a CDC7-associated brain or CNS cancer) can include administration (e.g., oral administration) of the compound to the subject. In some such embodiments, the compounds provided herein are useful for treating a primary brain tumor or metastatic brain tumor. For example, the compounds can be used in the treatment of one or more of gliomas such as glioblastoma (also known as glioblastoma multiforme), astrocytomas, oligodendrogliomas, ependymomas, and mixed gliomas, meningiomas, medulloblastomas, gangliogliomas, schwannomas (neurilemmomas), and carniopharyngiomas (see, for example, the tumors listed in Louis, D. N. et al. *Acta Neuropathol* 131(6), 803-820 (June 2016)). In some embodiments, the brain tumor is a primary brain tumor. In some embodiments, the subject has previously been treated with another anticancer agent, e.g., another CDC7 inhibitor (e.g., a compound that is not a compound of General Formula (I)) or a multi-kinase inhibitor. In some embodiments, the brain tumor is a metastatic brain tumor. In some embodiments, the subject has previously been treated with another anticancer agent, e.g., another CDC7 inhibitor (e.g., a compound that is not a compound of Formula (I)) or a multi-kinase inhibitor.

In some embodiments of any of the methods or uses described herein, an assay used to determine whether the subject has a dysregulation of a CDC7 gene, or a CDC7 kinase, or expression or activity or level of any of the same, using a sample from a subject can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a CDC7 gene, a CDC7 kinase, or expression or activity or levels of any of the same. In some embodiments, the sample is a biological sample or a biopsy sample (e.g., a paraffin-embedded biopsy sample) from the subject. In some embodiments, the subject is a subject suspected of having a CDC7-associated cancer, a subject having one or more symptoms of a CDC7-associated cancer, and/or a subject that has an increased risk of developing a CDC7-associated cancer).

In some embodiments, dysregulation of a CDC7 gene, a CDC7 kinase, or the expression or activity or level of any of the same can be identified using a liquid biopsy (variously referred to as a fluid biopsy or fluid phase biopsy). Liquid biopsy methods can be used to detect total tumor burden and/or the dysregulation of a CDC7 gene, a CDC7 kinase, or the expression or activity or level of any of the same. Liquid biopsies can be performed on biological samples obtained relatively easily from a subject (e.g., via a simple blood draw) and are generally less invasive than traditional methods used to detect tumor burden and/or dysregulation of a CDC7 gene, a CDC7 kinase, or the expression or activity or level of any of the same. In some embodiments, liquid biopsies can be used to detect the presence of dysregulation of a CDC7 gene, a CDC7 kinase, or the expression or activity or level of any of the same at an earlier stage than traditional methods. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a CDC7 gene, a CDC7 kinase, or the expression or activity or level of any of the same.

In some embodiments, ctDNA derived from a single gene can be detected using a liquid biopsy. In some embodiments, ctDNA derived from a plurality of genes (e.g., 2, 3, 4, 5, 6, 7, 8, 9, 10, 15, 20, 25, 30, 35, 40, 45, 50, 55, 60, 65, 70, 75, 80, 85, 90, 95, 100 or more, or any number of genes in between these numbers) can be detected using a liquid biopsy. In some embodiments, ctDNA derived from a plurality of genes can be detected using any of a variety of commercially-available testing panels (e.g., commercially-available testing panels designed to detect dysregulation of a CDC7 gene, a CDC7 kinase, or the expression or activity or level of any of the same). Liquid biopsies can be used to detect dysregulation of a CDC7 gene, a CDC7 kinase, or the expression or activity or level of any of the same including, without limitation, point mutations or single nucleotide variants (SNVs), copy number variants (CNVs), genetic fusions (e.g., translocations or rearrangements), insertions, deletions, or any combination thereof. In some embodiments, a liquid biopsy can be used to detect a germline mutation. In some embodiments, a liquid biopsy can be used to detect a somatic mutation. In some embodiments, a liquid biopsy can be used to detect a primary genetic mutation (e.g., a primary mutation or a primary fusion that is associated with initial development of a disease, e.g., cancer). In some embodiments, a dysregulation of a CDC7 gene, a CDC7 kinase, or the expression or activity or level of any of the same identified using a liquid biopsy is also present in a cancer cell that is present in the subject (e.g., in a tumor). In some embodiments, any of the types of dysregulation of a CDC7 gene, a CDC7 kinase, or the expression or activity or level of any of the same described herein can be detected using a liquid biopsy. In some embodiments, a genetic mutation identified via a liquid biopsy can be used to identify the subject as a candidate for a particular treatment. For example, detection of dysregulation of a CDC7 gene, a CDC7 kinase, or the expression or activity or level of any of the same in the subject can indicate that the subject will be responsive to a treatment that includes administration of a compound of Formula (I), or a pharmaceutically acceptable salt thereof.

Liquid biopsies can be performed at multiple times during a course of diagnosis, a course of monitoring, and/or a course of treatment to determine one or more clinically relevant parameters including, without limitation, progression of the disease and/or efficacy of a treatment. For example, a first liquid biopsy can be performed at a first time point and a second liquid biopsy can be performed at a second time point during a course of diagnosis, a course of monitoring, and/or a course of treatment. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable). In some embodiments, a treatment to be administered to a subject can include a compound of Formula (I), or a pharmaceutically acceptable salt thereof.

In some embodiments, the efficacy of a compound of Formula (I), or a pharmaceutically acceptable salt thereof, can be determined by assessing the allele frequency of a dysregulation of a CDC7 gene in cfDNA obtained from a subject at different time points, e.g., cfDNA obtained from the subject at a first time point and cfDNA obtained from the subject at a second time point, where at least one dose of a compound of Formula (I), or a pharmaceutically acceptable salt thereof, is administered to the subject between the first and second time points. Some embodiments of these methods can further include administering to the subject at least one dose of the compound of Formula (I), or a pharmaceutically acceptable salt thereof, between the first and second time points. For example, a reduction (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction) in the allele frequency (AF) of the dysregulation of a CDC7 gene in the cfDNA obtained from the subject at the second time point as compared to the allele frequency (AF) of the dysregulation of a CDC7 gene in the cfDNA obtained from the subject at the first time point indicates that the compound of Formula (I), or a pharmaceutically acceptable salt thereof, was effective in the subject. In some embodiments, the AF is reduced such that the level is below the detection limit of the instrument. Alternatively, an increase in the allele frequency (AF) of the dysregulation of a CDC7 gene in the cfDNA obtained from the subject at the second time point as compared to the allele frequency (AF) of the dysregulation of a CDC7 gene in the cfDNA obtained from the subject at the first time point indicates that the compound of Formula (I), or a pharmaceutically acceptable salt thereof, was not effective in the subject. Some embodiments of these methods can further include, administering additional doses of a compound of Formula (I), or a pharmaceutically acceptable salt thereof, to a subject in which a compound of Formula (I), or a pharmaceutically acceptable salt thereof, was determined to be effective. Some embodiments of these methods can further include, administering a different treatment (e.g., a treatment that does not include the administration of a compound of Formula (I), or a pharmaceutically acceptable salt thereof, as a monotherapy) to a subject in which a compound of Formula (I), or a pharmaceutically acceptable salt thereof, was determined not to be effective.

In some embodiments, the CDC7-associated cancer is a high microsatellite instability (MSI-H) cancer. In other embodiments, the CDC7-associated cancer is not a high microsatellite instability (MSI-H) cancer. In some embodiments, the MSI-H status is determined by detection of repetitive DNA sequences selected from the group consisting of: mononucleotide repeat markers, dinucleotide repeat markers, quasimonomorphic markers, or a combination of any of the foregoing.

In some embodiments, a tumor associated with the cancer comprises a phenotype selected from the group consisting of: chromosome instability (CIN), a spindle checkpoint assembly defect, a mitosis defect, a Gl/S checkpoint defect, and combinations thereof. In some embodiments, a tumor associated with the cancer comprises a Wnt signaling pathway mutation. In some embodiments, the Wnt signaling pathway mutation is selected from the group consisting of: an Adenomatous polyposis *coli* (APC) gene mutation, a FAT1 mutation, a FAT4 mutation, or a combination of any of the foregoing.

In some examples of these methods, the time difference between the first and second time points can be about 1 day to about 1 year, about 1 day to about 11 months, about 1 day to about 10 months, about 1 day to about 9 months, about 1 day to about 8 months, about 1 day to about 7 months, about 1 day to about 6 months, about 1 day to about 5 months, about 1 day to about 4 months, about 1 day to about 3 months, about 1 day to about 10 weeks, about 1 day to about 2 months, about 1 day to about 6 weeks, about 1 day to about 1 month, about 1 day to about 25 days, about 1 day to about 20 days, about 1 day to about 15 days, about 1 day to about 10 days, about 1 day to about 5 days, about 2 days to about 1 year, about 5 days to about 1 year, about 10 days to about 1 year, about 15 days to about 1 year, about 20 days to about 1 year, about 25 days to about 1 year, about 1 month to about 1 year, about 6 weeks to about 1 year, about 2 months to about 1 year, about 3 months to about 1 year, about 4 months to about 1 year, about 5 months to about 1 year, about 6 months to about 1 year, about 7 months to about 1 year, about 8 months to about 1 year, about 9 months to about 1 year, about 10 months to about 1 year, about 11 months to about 1 year, about 1 day to about 7 days, about 1 day to about 14 days, about 5 days to about 10 days, about 5 day to about 20 days, about 10 days to about 20 days, about 15 days to about 1 month, about 15 days to about 2 months, about 1 week to about 1 month, about 2 weeks to about 1 month, about 1 month to about 3 months, about 3 months to about 6 months, about 4 months to about 6 months, about 5 months to about 8 months, or about 7 months to about 9 months. In some embodiments of these methods, the subject can be previously identified as having a cancer having a dysregulated CDC7 gene (e.g., any of the examples of a dysregulated CDC7 gene described herein). In some embodiments of these methods, a subject can have been previously diagnosed as having any of the types of cancer described herein. In some embodiments of these methods, the subject can have one or more metastases (e.g., one or more brain metastases).

In some of the above embodiments, the cfDNA comprises ctDNA such as CDC7-associated ctDNA. For example, the cfDNA is ctDNA such as CDC7-associated ctDNA. In some embodiments, at least some portion of cfDNA is determined to be CDC7-associated ctDNA, for example, a sequenced and/or quantified amount of the total cfDNA is determined to have a CDC7 fusion and/or overexpression of CDC7.

In the field of medical oncology it is normal practice to use a combination of different forms of treatment to treat each subject with cancer. In medical oncology the other component(s) of such conjoint treatment or therapy in addition to compositions provided herein may be, for example, surgery, radiotherapy, and chemotherapeutic agents, such as other kinase inhibitors, signal transduction inhibitors and/or monoclonal antibodies. For example, a surgery may be open surgery or minimally invasive surgery. Compounds of Formula (I), or a pharmaceutically acceptable salt thereof therefore may also be useful as adjuvants to cancer treatment, that is, they can be used in combination with one or more additional therapies or therapeutic agents, for example, a chemotherapeutic agent that works by the same or by a different mechanism of action. In some embodiments, a compound of Formula (I), or a pharmaceutically acceptable salt thereof, can be used prior to administration of an additional therapeutic agent or additional therapy. For example, a subject in need thereof can be administered one or more doses of a compound of Formula (I), or a pharmaceutically acceptable salt thereof for a period of time and then undergo at least partial resection of the tumor. In some embodiments, the treatment with one or more doses of a compound of Formula (I), or a pharmaceutically acceptable salt thereof reduces the size of the tumor (e.g., the tumor burden) prior to the at least partial resection of the tumor. In some embodiments, a subject in need thereof can be administered one or more doses of a compound of Formula (I), or a pharmaceutically acceptable salt thereof for a period of time and under one or more rounds of radiation therapy. In some embodiments, the treatment with one or more doses of a compound of Formula (I), or a pharmaceutically acceptable salt thereof reduces the size of the tumor (e.g., the tumor burden) prior to the one or more rounds of radiation therapy.

In some embodiments, a subject has a cancer (e.g., a locally advanced or metastatic tumor) that is refractory or intolerant to standard therapy (e.g., administration of a chemotherapeutic agent, such as a first CDC7 inhibitor or a multikinase inhibitor, immunotherapy, or radiation (e.g., radioactive iodine)). In some embodiments, a subject has a cancer (e.g., a locally advanced or metastatic tumor) that is refractory or intolerant to prior therapy (e.g., administration of a chemotherapeutic agent, such as a first CDC7 inhibitor or a multikinase inhibitor, immunotherapy, or radiation (e.g., radioactive iodine)). In some embodiments, a subject has a cancer (e.g., a locally advanced or metastatic tumor) that has no standard therapy. In some embodiments, a subject is CDC7-kinase inhibitor naïve. For example, the subject is naïve to treatment with a selective CDC7-kinase inhibitor. In some embodiments, a subject is not CDC7-kinase inhibitor naïve.

In some embodiments, a subject has undergone prior therapy. In some embodiments, a subject having NSCLC (e.g., a CDC7-associated NSCLS) has received treatment with a platinum-based chemotherapy, PD-1/PDL1 immunotherapy, or both prior to treatment with a compound of Formula (I), or a pharmaceutically acceptable salt thereof. In some embodiments, a subject having a thyroid cancer (e.g., a CDC7-associated thyroid cancer) has received treatment with one or more of sorafenib, lenvatinib, and radioactive iodine prior to treatment with a compound of Formula (I), or a pharmaceutically acceptable salt thereof. In some embodiments, a subject having a colorectal cancer (e.g., a CDC7-associated colorectal cancer) has received treatment with a fluoropyrimidine-based chemotherapy, with or without ant-VEGF-directed therapy or anti-EGFR-directed therapy, prior to treatment with a compound of Formula (I), or a pharmaceutically acceptable salt thereof. In some embodiments, a subject having a pancreatic cancer (e.g., a CDC7-associated pancreatic cancer) has received treatment with one or more of a fluoropyrimidine-based chemotherapy, a gemcitabine-based chemotherapy, and a S-1 chemotherapy prior to treatment with a compound of Formula (I), or a pharmaceutically acceptable salt thereof. In some embodiments, a subject having a breast cancer (e.g., a CDC7-associated breast cancer) has received treatment with one or more of anthracycline, taxane, HER2-directed therapy, and hormonal therapy prior to treatment with a compound of Formula (I), or a pharmaceutically acceptable salt thereof. In some embodiments, a subject having a MTC (e.g., a CDC7-associated MTC cancer) has received treatment with one or more of cabozantinib and vandetanib prior to treatment with a compound of Formula (I), or a pharmaceutically acceptable salt thereof.

In some embodiments of any of the methods described herein, the compound of Formula (I), or a pharmaceutically acceptable salt thereof, is administered in combination with an effective amount of at least one additional therapeutic agent selected from one or more additional therapies or therapeutic (e.g., chemotherapeutic) agents.

Non-limiting examples of additional therapeutic agents include: other CDC7-targeted therapeutic agents (i.e. a first or second CDC7 kinase inhibitor), other kinase inhibitors (e.g., receptor tyrosine kinase-targeted therapeutic agents (e.g., Trk inhibitors or EGFR inhibitors)), signal transduction pathway inhibitors, checkpoint inhibitors, modulators of the apoptosis pathway (e.g., obatoclax); cytotoxic chemotherapeutics, angiogenesis-targeted therapies, immune-targeted agents, including immunotherapy, and radiotherapy.

In some embodiments, the other CDC7-targeted therapeutic is a multikinase inhibitor exhibiting CDC7 inhibition activity. In some embodiments, the other CDC7-targeted therapeutic inhibitor is selective for a CDC7 kinase. Exemplary CDC7 kinase inhibitors can exhibit inhibition activity ($IC_{50}$) against a CDC7 kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a CDC7 kinase inhibitors can exhibit inhibition activity ($IC_{50}$) against a CDC7 kinase of less than about 25 nM, less than about 10 nM, less than about 5 nM, or less than about 1 nM as measured in an assay as provided herein.

Non-limiting examples of kinase-targeted therapeutic agents (e.g., a first CDC7 inhibitor or a second CDC7 inhibitor) include TAK931, SRA141, and PHA-767491.

Non-limiting examples of multi-kinase inhibitors include alectinib (9-Ethyl-6,6-dimethyl-8-[4-(morpholin-4-yl)piperidin-1-yl]-11-oxo-6,11-dihydro-5H-benzo[b]carbazole-3-carbonitrile); amuvatinib (MP470, HPK56) (N-(1,3-benzodioxol-5-ylmethyl)-4-([1]benzofuro[3,2-d]pyrimidin-4-yl)piperazine-1-carbothioamide); apatinib (YN968D1) (N-[4-(1-cyanocyclopentyl) phenyl-2-(4-picolyl)amino-3-Nicotinamide methanesulphonate); cabozantinib (Cometriq XL-184) (N-(4-((6,7-Dimethoxyquinolin-4-yl)oxy)phenyl)-N'-(4-fluorophenyl)cyclopropane-1,1-dicarboxamide); dovitinib (TKI258; GFKI-258; CHIR-258) ((3Z)-4-amino-5-fluoro-3-[5-(4-methylpiperazin-1-yl)-1,3-dihydrobenzimidazol-2-ylidene]quinolin-2-one); famitinib (5-[2-(diethylamino)ethyl]-2-[(Z)-(5-fluoro-2-oxo-1H-indol-3-ylidene)methyl]-3-methyl-6,7-dihydro-1H-pyrrolo[3,2-c]pyridin-4-one); fedratinib (SAR302503, TG101348) (N-(2-Methyl-2-propanyl)-3-{[5-methyl-2-({4-[2-(1-pyrrolidinyl)ethoxy]phenyl}amino)-4-pyrimidinyl]amino}benzenesulfonamide); foCDC7inib (XL880, EXEL-2880, GSK1363089, GSK089) (N1'-[3-fluoro-4-[[6-methoxy-7-(3-morpholinopropoxy)-4-quinolyl]oxy]phenyl]-N1-(4-fluorophenyl)cyclopropane-1,1-dicarboxamide); fostamantinib (R788) (2H-Pyrido[3,2-b]-1,4-oxazin-3(4H)-one, 6-[[5-fluoro-2-[(3,4,5-trimethoxyphenyl)amino]-4-pyrimidinyl]amino]-2,2-dimethyl-4-[(phosphonooxy)methyl]-, sodium salt (1:2)); ilorasertib (ABT-348) (1-(4-(4-amino-7-(1-(2-hydroxyethyl)-1H-pyrazol-4-yl)thieno[3,2-c]pyridin-3-yl)phenyl)-3-(3-fluorophenyl)urea); lenvatinib (E7080, Lenvima) (4-[3-chloro-4-(cyclopropylaminocarbonyl)aminophenoxy]-7-methoxy-6-quinolinecarboxamide); motesanib (AMG 706) (N-(3,3-Dimethyl-2,3-dihydro-1H-indol-6-yl)-2-[(pyridin-4-ylmethyl)amino]pyridine-3-carboxamide); nintedanib (3-Z-[1-(4-(N-((4-methyl-piperazin-1-yl)-methylcarbonyl)-N-methyl-amino)-anilino)-1-phenyl-methylene]-6-methyloxycarbonyl-2-indolinone); ponatinib (AP24534) (3-(2-Imidazo[1,2-b]pyridazin-3-ylethynyl)-4-methyl-N-[4-[(4-methylpiperazin-1-yl)methyl]-3-(trifluoromethyl)phenyl]benzamide); PP242 (torkinib) (2-[4-Amino-1-(1-methylethyl)-1H-pyrazolo[3,4-d]pyrimidin-3-yl]-1H-indol-5-ol); quizartinib (1-(5-(tert-Butyl)isoxazol-3-yl)-3-(4-(7-(2-morpholinoethoxy)benzo[d]imidazo[2,1-b]thiazol-2-yl)phenyl)urea); regorafenib (BAY 73-4506, stivarga) (4-[4-({[4-Chloro-3-(trifluoromethyl)phenyl]carbamoyl}amino)-3-fluorophenoxy]-N-methylpyridine-2-carboxamide hydrate); RXDX-105 (CEP-32496, agerafenib) (1-(3-((6,7-dimethoxyquinazolin-4-yl)oxy)phenyl)-3-(5-(1,1,1-trifluoro-2-methylpropan-2-yl)isoxazol-3-yl)urea); semaxanib (SU5416) ((3Z)-3-[(3,5-dimethyl-1H-pyrrol-2-yl)methylidene]-1,3-dihydro-2H-indol-2-one); sitravatinib (MGCD516, MG516) (N-(3-Fluoro-4-{[2-(5-{[(2-methoxyethyl)amino]methyl}-2-pyridinyl)thieno[3,2-b]pyridin-7-yl]oxy}phenyl)-N'-(4-fluorophenyl)-1,1-cyclopropanedicarboxamide); sorafenib (BAY 43-9006) (4-[4-[[[[4-chloro-3-(trifluoromethyl)phenyl]amino]carbonyl]amino]phenoxy]-N-methyl-2-pyridinecarboxamide); vandetanib (N-(4-bromo-2-fluorophenyl)-6-methoxy-7-[(1-methylpiperidin-4-yl)methoxy]quinazolin-4-amine); vatalanib (PTK787, PTK/ZK, ZK222584) (N-(4-chlorophenyl)-4-(pyridin-4-ylmethyl)phthalazin-1-amine); AD-57 (N-[4-[4-amino-1-(1-methylethyl)-1H-pyrazolo[3,4-d]pyrimidin-3-yl]phenyl]-N'-[3-(trifluoromethyl)phenyl]-urea); AD-80 (1-[4-(4-amino-1-propan-2-ylpyrazolo[3,4-d]pyrimidin-3-yl)phenyl]-3-[2-fluoro-5-(trifluoromethyl)phenyl]urea); AD-81 (1-(4-(4-amino-1-isopropyl-1H-pyrazolo[3,4-d]pyrimidin-3-yl)phenyl)-3-(4-chloro-3-(trifluoromethyl)phenyl)urea); ALW-II-41-27 (N-(5-((4-((4-ethylpiperazin-1-yl)methyl)-3-(trifluoromethyl)phenyl)carbamoyl)-2-methylphenyl)-5-(thiophen-2-yl)nicotinamide); BPR1K871 (1-(3-chlorophenyl)-3-(5-(2-((7-(3-(dimethylamino)propoxy)quinazolin-4-yl)amino)ethyl)thiazol-2-yl)urea); CLM3 (1-phenethyl-N-(1-phenylethyl)-1H-pyrazolo[3,4-d]pyrimidin-4-amine); EBI-907 (N-(2-chloro-3-(1-cyclopropyl-8-methoxy-3H-pyrazolo[3,4-c]isoquinolin-7-yl)-4-fluorophenyl)-3-fluoropropane-1-sulfonamide); NVP-AST-487 (N-[4-[(4-ethyl-1-piperazinyl)methyl]-3-(trifluoromethyl)phenyl]-N'-[4-[[6-(methylamino)-4-pyrimidinyl]oxy]phenyl]-urea); NVP-BBT594 (BBT594) (5-((6-acetamidopyrimidin-4-yl)oxy)-N-(4-((4-methylpiperazin-1-yl)methyl)-3-(trifluoromethyl)phenyl)indoline-1-carboxamide); PD173955 (6-(2,6-dichlorophenyl)-8-methyl-2-(3-methylsulfanylanilino)pyrido[2,3-d]pyrimidin-7-one); PP2 (4-amino-5-(4-chlorophenyl)-7-(dimethylethyl)pyrazolo[3,4-d]pyrimidine); PZ-1 (N-(5-(tert-butyl)isoxazol-3-yl)-2-(4-(5-(1-methyl-1H-pyrazol-4-yl)-1Hbenzo[d]imidazol-1-yl)phenyl)acetamide); RPI-1 (1,3-dihydro-5,6-dimethoxy-3-[(4-hydroxyphenyl)methylene]-H-indol-2-one; (3E)-3-[(4-hydroxyphenyl)methylidene]-5,6-dimethoxy-1H-indol-2-one); SGI-7079 (3-[2-[[3-fluoro-4-(4-methyl-1-piperazinyl)phenyl]amino]-5-methyl-7H-pyrrolo[2,3-d]pyrimidin-4-yl]-benzeneacetonitrile); SPP86 (1-Isopropyl-3-(phenylethynyl)-1H-pyrazolo[3,4-d]pyrimidin-4-amine); SU4984 (4-[4-[(E)-(2-oxo-1H-indol-3-ylidene)methyl]phenyl]piperazine-1-carbaldehyde); sunitinb (SU11248) (N-(2-Diethylaminoethyl)-5-[(Z)-(5-fluoro-2-oxo-1H-indol-3-ylidene)methyl]-2,4-dimethyl-1H-pyrrole-3-carboxamide); TG101209 (N-tert-butyl-3-(5-methyl-2-(4-(4-methylpiperazin-1-yl)phenylamino)pyrimidin-4-ylamino)benzenesulfonamide); Withaferin A ((4β,5β,6β,22R)-4,27-Dihydroxy-5,6:22,26-diepoxyergosta-2,24-diene-1,26-dione); XL-999 ((Z)-5-((l-ethylpiperidin-4-yl)amino)-3-((3-fluorophenyl)(5-methyl-1H-imidazol-2-yl)methylene)indolin-2-one); BPR1J373 (a 5-phenylthiazol-2-ylamine-pyrimidine derivative); CG-806 (CG'806); DCC-2157; GTX-186; HG-6-63-01 ((E)-3-(2-(4-chloro-1H-pyrrolo[2,3-b]pyridin-5-yl)vinyl)-N-(4-((4-ethylpiperazin-1-yl)methyl)-3-(trifluoromethyl)phenyl)-4-methylbenzamide); SW-01 (Cyclobenzaprine hydrochloride); XMD15-44 (N-(4-((4-ethylpiperazin-1-yl)methyl)-3-(trifluoromethyl)phenyl)-4-methyl-3-(pyridin-3-ylethynyl)benzamide (generated from structure)); Y078-DM1 (an antibody drug conjugate composed of a CDC7 antibody (Y078) linked to a derivative of the cytotoxic agent maytansine); Y078-DM4 (an antibody drug conjugate composed of a CDC7 antibody (Y078) linked to a derivative of the cytotoxic agent maytansine); ITRI-305 (D0N5TB, DIB003599); BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide); BLU6864; DS-5010; GSK3179106; GSK3352589; NMS-E668; TAS0286/HM05; TPX0046; and N-(3-(2-(dimethylamino)ethoxy)-5-(trifluoromethyl)phenyl)-2-(4-(4-ethoxy-6-oxo-1,6-dihydropyridin-3-yl)-2-fluorophenyl)acetamide.

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Gö 6976, GNF-5837, GTx-186, GW 441756, LOX0-101, MGCD516, PLX7486, RXDX101, VM-902A, TPX-0005, TSR-011, GNF-4256, N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea, AZ623, AZ64, (S)-5-Chloro-N2-(1-(5-fluoropyridin-2-yl)ethyl)-N4-(5-isopropoxy-1H-pyrazol-3-yl)pyrimidine-2,4-diamine, AZD7451, CEP-751, CT327, sunitinib, GNF-8625, and (R)-1-(6-(6-(2-(3-fluorophenyl)pyrrolidin-1-yl)imidazo[1,2-b]pyridazin-3-yl)-[2,4'-bipyridin]-2'-yl)piperidin-4-ol.

Non-limiting examples of a BRAF inhibitor include dabrafenib, vemurafenib (also called RG7204 or PLX4032), sorafenib tosylate, PLX-4720, GDC-0879, BMS-908662 (Bristol-Meyers Squibb), LGX818 (Novartis), PLX3603 (Hofmann-LaRoche), RAF265 (Novartis), R05185426 (Hofmann-LaRoche), and GSK2118436 (GlaxoSmithKline). Additional examples of a BRAF inhibitor are known in the art.

In some embodiments, the receptor tyrosine kinase inhibitor is an epidermal growth factor receptor typrosine kinase inhibitor (EGFR). For example, EGFR inhibitors can include osimertinib (merelectinib, Tagrisso), erlotinib (Tarceva), gefitinib (Iressa), cetuximab (Erbitux), necitumumab (Portrazza), neratinib (Nerlynx), lapatinib (Tykerb), panitumumab (Vectibix), and vandetanib (Caprelsa).

In some embodiments, signal transduction pathway inhibitors include Ras-Raf-MEK-ERK pathway inhibitors (e.g., binimetinib, selumetinib, encorafenib, sorafenib, trametinib, and vemurafenib), PI3K-Akt-mTOR-S6K pathway inhibitors (e.g., everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3]benzodiazepin-8-yl]-cyclohexaneacetamide), PLX3397, PLX7486, PLX8394, PLX9486, PRN1008, PRN1371, RXDX103, RXDX106, RXDX108, and T G101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

In some embodiments, an additional therapy or therapeutic agent can include a histidyl-tRNA synthetase (HRS) polypeptide or an expressible nucleotide that encodes the HRS polypeptide.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab or amatuximab.

In some embodiments, the immunotherapy is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine In some embodiments, the immunotherapy includes blinatumomab (AMG103; Blincyto®) or midostaurin (Rydapt).

In some embodiments, the immunotherapy includes a toxin. In some embodiments, the immunotherapy is denileukin diftitox (Ontak®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is *bacillus* Calmette-Guerin (BCG) therapy.

In some embodiments, the immunotherapy is an oncolytic virus therapy. In some embodiments, the oncolytic virus therapy is talimogene alherparepvec (T-VEC; Imlygic®).

In some embodiments, the immunotherapy is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy is a peptide vaccine. In some embodiments, the peptide vaccine is nelipepimut-S (E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; WO 2016/075224; WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis. For example, overexpression of glial cell-derived neurotrophic factor (GDNF) and its CDC7 receptor tyrosine kinase have been correlated with cancer proliferation and metastasis. See, e.g., Zeng, et al. *J. Int. Med. Res.* (2008) 36(4): 656-64.

Accordingly, also provided herein are methods for inhibiting, preventing, aiding in the prevention, or decreasing the symptoms of metastasis of a cancer in a subject in need thereof, the method comprising administering to the subject an effective amount of a compound of Formula (I), or a pharmaceutically acceptable salt thereof or a pharmaceutical composition thereof. Such methods can be used in the treatment of one or more of the cancers described herein. See, e.g., US Publication No. 2013/0029925; International Publication No. WO 2014/083567; and U.S. Pat. No. 8,568,998. See also, e.g., Hezam K et al., *Rev Neurosci* 2018 Jan. 26; 29:93-98; Gao L, et al., Pancreas 2015 January; 44:134-143; Ding K et al., *J Biol Chem* 2014 Jun. 6; 289:16057-71; and Amit M et al., *Oncogene* 2017 Jun. 8; 36:3232-3239. In some embodiments, the cancer is a CDC7-associated cancer. In some embodiments, the compound of Formula (I), or a pharmaceutically acceptable salt thereof is used in combination with an additional therapy or another therapeutic agent, including a chemotherapeutic agent, such as a kinase inhibitor. For example, a first or second CDC7 kinase inhibitor. In some embodiments, the additional therapeutic agent is crizotinib. In some embodiments, the additional therapeutic agent is osimertinib. In some embodiments, the subject has been administered one or more doses of a compound of Formula (I), or a pharmaceutically acceptable salt thereof, prior to administration of the pharmaceutical composition. In some embodiments, the cancer is a lung cancer (e.g., a CDC7-associated lung cancer). In some embodiments, the additional therapeutic agent is a PARP inhibitor (e.g., olaparib). In some embodiments, the additional therapeutic agent is an ATR inhibitor (e.g., ceralasertib). In some embodiments, the additional therapeutic agent is a Wee 1 inhibitor (e.g., AZD-1775). In some embodiments, the additional therapeutic agent is an EGFR inhibitor (e.g., lapatinib).

The term "metastasis" is an art known term and means the formation of an additional tumor (e.g., a solid tumor) at a site distant from a primary tumor in a subject, where the additional tumor includes the same or similar cancer cells as the primary tumor.

Also provided are methods of decreasing the risk of developing a metastasis or an additional metastasis in a subject having a CDC7-associated cancer that include: selecting, identifying, or diagnosing a subject as having a CDC7-associated cancer, and administering an effective amount of a compound of Formula (I), or a pharmaceutically acceptable salt thereof to the subject selected, identified, or diagnosed as having a CDC7-associated cancer. Also provided are methods of decreasing the risk of developing a metastasis or an additional metastasis in a subject having a CDC7-associated cancer that includes administering an effective amount of a compound of Formula (I), or a pharmaceutically acceptable salt thereof to a subject having a CDC7-associated cancer. The decrease in the risk of developing a metastasis or an additional metastasis in a subject having a CDC7-associated cancer can be compared to the risk of developing a metastasis or an additional metastasis in the subject prior to treatment, or as compared to a subject or a population of subjects having a similar or the same CDC7-associated cancer that has received no treatment or a different treatment. In some embodiments, the additional therapeutic agent is crizotinib. In some embodiments, the additional therapeutic agent is osimertinib. In some embodiments, the subject has been administered one or more doses of a compound of Formula (I), or a pharmaceutically acceptable salt thereof, prior to administration of the pharmaceutical composition. In some embodiments, the cancer is a lung cancer (e.g., a CDC7-associated lung cancer).

The phrase "risk of developing a metastasis" means the risk that a subject having a primary tumor will develop an additional tumor (e.g., a solid tumor) at a site distant from a primary tumor in a subject over a set period of time, where the additional tumor includes the same or similar cancer cells as the primary tumor. Methods for reducing the risk of developing a metastasis in a subject having a cancer are described herein.

The phrase "risk of developing additional metastases" means the risk that a subject having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

Treatment of a subject having a cancer with a multi-kinase inhibitor (MKI) or target-specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) can result in dysregulation of a CDC7 gene, a CDC7 kinase, or the expression or activity or level of the same in the cancer, and/or resistance to a CDC7 inhibitor. See, e.g., Bhinge et al., *Oncotarget* 8:27155-27165, 2017; Chang et al., *Yonsei Med. J.* 58:9-18, 2017; and Lopez-Delisle et al., doi: 10.1038/s41388-017-0039-5, *Oncogene* 2018.

Treatment of a subject having a cancer with a CDC7 inhibitor in combination with a multi-kinase inhibitor or a target-specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) can have increased therapeutic efficacy as compared to treatment of the same subject or a similar subject with the CDC7 inhibitor as a monotherapy, or the multi-kinase inhibitor or the target-specific kinase inhibitor as a monotherapy. See, e.g., Tang et al., doi: 10.1038/modpathol.2017.109, *Mod. Pathol.* 2017; Andreucci et al., *Oncotarget* 7:80543-80553, 2017; Nelson-Taylor et al., *Mol. Cancer Ther.* 16:1623-1633, 2017; and Kato et al., *Clin. Cancer Res.* 23:1988-1997, 2017.

Provided herein are methods of treating a subject having a cancer (e.g., any of the cancers described herein) and previously administered a multi-kinase inhibitor (MKI) or a target-specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) (e.g., as a monotherapy) that include: administering to the subject (i) an effective dose of a compound of Formula (I), or a pharmaceutically acceptable salt thereof as a monotherapy, or (ii) an effective dose of a compound of Formula (I), or a pharmaceutically acceptable salt thereof, and an effective dose of the previously administered MKI or the previously administered target-specific kinase inhibitor.

Provided herein are methods of treating a subject having a cancer (e.g., any of the cancers described herein) previously administered a MKI or a target specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) (e.g., as a monotherapy) that include: identifying a subject having a cancer cell that has a dysregulation of a CDC7 gene, a CDC7 kinase, or the expression or activity or level of the same; and administering to the identified subject (i) an effective dose of a compound of Formula (I), or a pharmaceutically acceptable salt thereof as a monotherapy, or (ii) an effective dose of a compound of Formula (I), or a pharmaceutically acceptable salt thereof, and an effective dose of the previously administered MKI or the previously administered target-specific kinase inhibitor.

Provided herein are methods of treating a subject having a cancer (e.g., any of the cancers described herein) that include: administering to a subject an effective amount of a MKI or a target-specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) (e.g., as a monotherapy) for a first period of time; after the period of time, identifying a subject having a cancer cell that has a dysregulation of a CDC7 gene, a CDC7 kinase, or the expression or activity or level of the same; and administering to the identified subject (i) an effective dose of a compound of Formula (I), or a pharmaceutically acceptable salt thereof as a monotherapy, or (ii) an effective dose of a compound of Formula (I), or a pharmaceutically acceptable salt thereof, and an effective dose of the previously administered MKI or the previously administered target-specific kinase inhibitor.

Also provided is a method for inhibiting CDC7 kinase activity in a mammalian cell, comprising contacting the mammalian cell with a compound of Formula (I). In some embodiments, the contacting is in vitro. In some embodiments, the contacting is in vivo. In some embodiments, the contacting is in vivo, wherein the method comprises administering an effective amount of a compound of Formula (I), or a pharmaceutically acceptable salt thereof to a subject having a mammalian cell having CDC7 kinase activity. In some embodiments, the mammalian cell is a mammalian cancer cell. In some embodiments, the mammalian cancer cell is any cancer as described herein. In some embodiments, the mammalian cancer cell is a CDC7-associated mammalian cancer cell.

Also provided is a method for inhibiting CDC7 kinase activity in a mammalian cell, comprising contacting the mammalian cell with a compound of Formula (I). In some embodiments, the contacting is in vitro. In some embodiments, the contacting is in vivo. In some embodiments, the contacting is in vivo, wherein the method comprises administering an effective amount of a compound of Formula (I), or a pharmaceutically acceptable salt thereof to a mammal having a mammalian cell having CDC7 kinase activity. In some embodiments, the mammalian cell is a mammalian cancer cell. In some embodiments, the mammalian cancer cell is any cancer as described herein. In some embodiments, the mammalian cancer cell is a CDC7-associated mammalian cancer cell. In some embodiments, the mammalian cell is a gastrointestinal mammalian cell.

As used herein, the term "contacting" refers to the bringing together of indicated moieties in an in vitro system or an in vivo system. For example, "contacting" a CDC7 kinase with a compound provided herein includes the administration of a compound provided herein to a subject, such as a human, having a CDC7 kinase, as well as, for example, introducing a compound provided herein into a sample containing a mammalian cellular or purified preparation containing the CDC7 kinase.

Also provided herein is a method of inhibiting mammalian cell proliferation, in vitro or in vivo, the method comprising contacting a mammalian cell with an effective amount of a compound of Formula (I), or a pharmaceutically acceptable salt thereof, or a pharmaceutical composition thereof as defined herein.

A "CDC7 kinase inhibitor" as defined herein includes any compound exhibiting CDC7 inhibition activity. In some embodiments, a CDC7 kinase inhibitor is selective for a CDC7 kinase. Exemplary CDC7 kinase inhibitors can exhibit inhibition activity ($IC_{50}$) against a CDC7 kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a CDC7 kinase inhibitor can exhibit inhibition activity ($IC_{50}$) against a CDC7 kinase of less than about 25 nM, less than about 10 nM, less than about 5 nM, or less than about 1 nM as measured in an assay as provided herein.

As used herein, a "first CDC7 kinase inhibitor" or "first CDC7 inhibitor" is a CDC7 kinase inhibitor as defined herein, but which does not include a compound of Formula (I), or a pharmaceutically acceptable salt thereof as defined herein. As used herein, a "second CDC7 kinase inhibitor" or a "second CDC7 inhibitor" is a CDC7 kinase inhibitor as defined herein, but which does not include a compound of Formula (I), or a pharmaceutically acceptable salt thereof as defined herein. When both a first and a second CDC7 inhibitor are present in a method provided herein, the first and second CDC7 kinase inhibitor are different.

Exemplary first and second CDC7 kinase inhibitors are described herein. In some embodiments, a first or second CDC7 kinase inhibitor can be selected from the group consisting of TAK931, SRA141, and PHA-767491.

The phrase "effective amount" means an amount of compound that, when administered to a subject in need of such treatment, is sufficient to (i) treat a CDC7-associated disease or disorder (such as a CDC7-associated cancer), (ii) attenuate, ameliorate, or eliminate one or more symptoms of the particular disease, condition, or disorder, or (iii) delay the onset of one or more symptoms of the particular disease, condition, or disorder described herein. The amount of a compound of Formula (I), or a pharmaceutically acceptable salt thereof that will correspond to such an amount will vary depending upon factors such as the particular compound, disease condition and its severity, the identity (e.g., weight) of the subject in need of treatment, but can nevertheless be routinely determined by one skilled in the art.

When employed as pharmaceuticals, compounds of Formula (I), including pharmaceutically acceptable salts thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula (I) or pharmaceutically acceptable salt thereof, in combination with one or more pharmaceutically acceptable excipients. In some embodiments, the compound of Formula (I), or a pharmaceutically acceptable salt thereof, present in the composition is a compound of Formula (I-A), (I-B), (I-C), (I-D), (I-E), (I-F), (I-G), (I-H), (I-I), (I-J), (I-K), (I-L), (I-M), (I-N), (I-O), or (I-P), or a pharmaceutically acceptable salt of any of the foregoing.

For example, a pharmaceutical composition prepared using a compound of Formula (I) or a pharmaceutically acceptable salt thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula (I) or a pharmaceutically acceptable salt thereof with a pharmaceutically acceptable carrier. Pharmaceutical compositions containing a compound of Formula (I) or a pharmaceutically acceptable salt thereof as the active ingredient can be prepared by intimately mixing the compound of Formula (I), or a pharmaceutically acceptable salt thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In preparing the compositions in oral dosage form, any of the usual pharmaceutical media can be employed. Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Solid oral preparations can also be coated with substances such as sugars or be enteric-coated so as to modulate major site of absorption. For parenteral administration, the carrier will usually consist of sterile water and other ingredients can be added to increase solubility or preservation. Injectable suspensions or solutions can also be prepared utilizing aqueous carriers along with appropriate additives. The pharmaceutical compositions herein will contain, per dosage unit, e.g., tablet, capsule, powder, injection, teaspoonful and the like, an amount of the active ingredient necessary to deliver an effective dose as described herein.

The compositions comprising a compound of Formula (I) or a pharmaceutically acceptable salt thereof can be formulated in a unit dosage form, each dosage containing from about 1 to about 1,000 mg (1 g) of the active ingredient. The term "unit dosage form" refers to physically discrete units suitable as unitary dosages for human subjects and other subjects, each unit containing a predetermined quantity of active material (i.e., a compound of Formula (I) or a pharmaceutically acceptable salt thereof) calculated to produce the desired therapeutic effect, in association with a suitable pharmaceutical excipient.

The active compound may be effective over a wide dosage range and is generally administered in a pharmaceutically effective amount. Optimal dosages to be administered can be readily determined by those skilled in the art. It will be understood, therefore, that the amount of the compound actually administered will usually be determined by a physician, and will vary according to the relevant circumstances, including the mode of administration, the actual compound administered, the strength of the preparation, the condition to be treated, and the advancement of the disease condition. In addition, factors associated with the particular subject being treated, including subject response, age, weight, diet, time of administration and severity of the subject's symptoms, will result in the need to adjust dosages.

One skilled in the art will recognize that both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy subjects and/or those suffering from a given disorder, can be completed according to methods well known in the clinical and medical arts.

Provided herein are pharmaceutical kits useful, for example, in the treatment of CDC7-associated diseases or disorders, such as cancer, which include one or more containers containing a pharmaceutical composition comprising an effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

Materials and Methods

The compounds provided herein, including salts thereof, can be prepared using known organic synthesis techniques and can be synthesized according to any of numerous possible synthetic routes.

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, $1^{st}$ Ed., Oxford University Press, 2000; *March's Advanced Organic Chemistry: Reactions, Mechanisms, and Structure*, $5^{th}$ Ed., Wiley-Interscience Publication, 2001; and Peturssion, S. et al., "*Protecting Groups in Carbohydrate Chemistry*," *J. Chem. Educ.*, 74(11), 1297 (1997).

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004), normal phase silica chromatography, and supercritical fluid chromatography (SFC).

Unless otherwise specified, the stereochemistry of Compounds 1-58 in the Examples below are understood to be arbitrarily assigned.

All solvents and reagents were obtained from commercial sources and used without further purification unless indicated otherwise. Anhydrous solvents were purchased and used as supplied. Reactions were monitored by thin-layer chromatography (TLC), visualizing with a UV lamp (254 nm) and $KMnO_4$ stain. NMR spectra were obtained on a Bruker Neo 400M spectrometer operating at 400 MHz. Chemical shifts are reported in parts per million (δ) from the tetramethylsilane resonance in the indicated solvent. LC-Mass spectra were taken with Agilent 1260-6125B single quadrupole mass spectrometer using a Welch Biomate column (C18, 2.7 μm, 4.6*50 mm) or waters H-Class SQD2 system. The detection was by DAD (254 nm and 210 nm and 280 nm). Chiral HPLC was performed on the Waters acquity UPC2 system under base-containing on Daicel chiralpak AD-H (5 μm, 4.6*250 mm), Daicel chiralpak OD-H (5 μm, 4.6*250 mm), Daicel chiralpak IG-3 (3 μm, 4.6*150 mm), Chiral Technologies Europe AD-3 (3 μm, 3.0*150 mm) and Trefoil™ Technology Trefoil™ AMY1 (2.5 μm, 3.0*150 mm). The detection was by DAD (254 nm). Preparative HPLC was performed on GILSON Trilution LC system using a Welch XB-C18 column (Sum, 21.2*150 mm). Flash chromatography was carried out on Biotage Isolera Prime system using Welch WelFlash flash columns (40-63 μm). The compounds synthesized are all with purity ≥95% unless otherwise specified.

Abbreviations

*=an indication that the amount of the solvent or reagent preceding the "*" is used in the technique for a number of times equal to the number following the "*".
° C.=degrees Celsius
$^1$H NMR=proton nuclear magnetic resonance spectrum
AcOH=acetic acid
$Boc_2O$=tert-butoxycarbonyl anhydride
con.=concentrated
d=doublet
DCM=dichloromethane
DIAD=diisopropylazodicarboxylate
DIPEA=N,N-diisopropylethylamine
DMF=N,N-dimethylformamide
EA=ethyl acetate
ESI=electrospray ionization
g=gram(s)
h=hour(s)
HATU=(1-[Bis(dimethylamino)methylene]-1H-1,2,3-triazolo[4,5-b]pyridinium 3-oxide hexafluorophosphate, Hexafluorophosphate Azabenzotriazole Tetramethyl Uronium
HPLC=high-performance liquid chromatography
LCMS=liquid chromatograph-mass spectrum
M=mass
m/z=mass-to-charge ratio
MeCN=acetonitrile
MeOH=methanol
MeONa=sodium methoxide
mg=milligram(s)
mL=milliliter
mmol=millimole(s)
mol=mole(s)
MS=mass spectrum
NBS=N-bromosuccinimide
obsd.=observed
$PCy_3$=tricyclohexylphosphine
$Pd(AcO)_2$=palladium (II) acetate
$Pd(dppf)Cl_2$=(1,1'-Bis(diphenylphosphino)ferrocene)palladium(II) dichloride
PE=petroleum ether
ppm=parts per million
PTSA=para-toluenesulfonic acid
rt=room temperature
SFC=supercritical fluid chromatography
s=singlet
t=triplet
TBAF=tetrabutylammonium fluoride
TFA=trifluoroacetic acid
THF=tetrahydrofuran
TLC=thin-layer chromatography
Trixiephos=rac-2-(Di-tert-butylphosphino)-1,1'-binaphthyl Example 1—Compound 1: 2-(1H-pyrazol-4-yl)-6,7,8,9-tetrahydrothieno[2,3-c]quinolin-4(5H)-one Compound 1

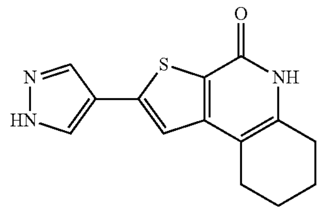

Step A: 6,7,8,9-tetrahydro-4H-thieno[2,3-c]chromen-4-one

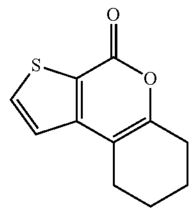 [SMILES: O=c1oc2c(c3ccsc13)CCCC2]

To a solution of methyl 3-bromothiophene-2-carboxylate (1.00 g, 4.52 mmol, 1.0 eq.), (5-diphenylphosphanyl-9,9-dimethyl-xanthen-4-yl)-diphenyl-phosphane (787 mg, 1.36 mmol, 0.3 eq.), cesium carbonate (3.68 g, 11.30 mmol, 2.5 eq.), sodium metabisulfite (172 mg, 0.90 mmol, 0.2 eq.) and tris(dibenzylideneacetone)dipalladium (824 mg, 0.90 mmol, 0.20 eq.) in toluene (40.0 mL) was added cyclohexanone (888 mg, 9.04 mmol, 2.0 eq.) at rt. The reaction mixture was stirred at 105° C. for 16 h under $N_2$. The solvent was concentrated to dryness and the residue was purified by flash chromatography ($SiO_2$, 0-10% EtOAc in PE) to afford 6,7,8,9-tetrahydro-4H-thieno[2,3-c]chromen-4-one (600 mg, 64%). MS obsd. ($ESI^+$): 207.0 [$(M+H)^+$].

Step B: 2-iodo-6,7,8,9-tetrahydro-4H-thieno[2,3-c]chromen-4-one

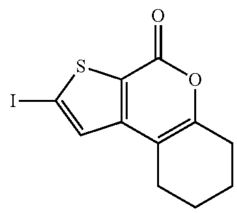 [SMILES: O=c1oc2c(c3cc(I)sc13)CCCC2]

To a solution of 6,7,8,9-tetrahydro-4H-thieno[2,3-c]chromen-4-one (400 mg, 1.94 mmol, 1.0 eq.) in THF (15.0 mL) was added (diisopropylamino)lithium (2 M in THF, 1.1 mL, 2.2 mmol, 1.1 eq.) at −78° C. The mixture was stirred for 30 min at −78° C., then 12 (492 mg, 1.94 mmol, 1.0 eq.)

was added. The mixture was stirred for 1 h at −78° C., then quenched with aqueous $Na_2SO_3$ (10 mL) at 0° C. The mixture was extracted with DCM (10 mL×3), and the combined organic phases were washed with water (20 mL), dried over anhydrous $Na_2SO_4$, filtered and concentrated. The residue was purified by flash column chromatography ($SiO_2$, 0-10% EtOAc in PE) to afford 2-iodo-6,7,8,9-tetrahydro-4H-thieno[2,3-c]chromen-4-one (300 mg, 46%). MS obsd. (ESI+): 333.1 [(M+H)+].

Step C: 2-(1H-pyrazol-4-yl)-6,7,8,9-tetrahydro-4H-thieno[2,3-c]chromen-4-one

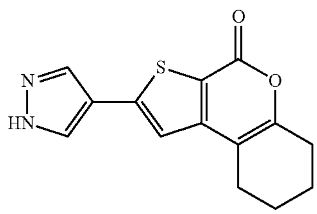 [SMILES: O=c1oc2c(c3cc(-c4cn[nH]c4)sc13)CCCC2]

To a solution of 2-iodo-6,7,8,9-tetrahydro-4H-thieno[2,3-c]chromen-4-one (300 mg, 903 μmol, 1.0 eq.), 4-(4,4,5,5-tetramethyl-1,3,2-dioxaborolan-2-yl)-1H-pyrazole (175 mg, 900 μmol, 1.0 eq.), sodium carbonate (287.18 mg, 2.71 mmol, 3.0 eq.) and dicyclohexyl-[2-(2,4,6-triisopropylphenyl)phenyl]phosphane (129 mg, 270.96 μmol, 0.3 eq.) in water (2.0 mL) and 1,4-dioxane (10.0 mL) was added [1,1'-Bis(diphenylphosphino) ferrocene]dichloropalladium (II) (132 mg, 181 μmol, 0.20 eq.) at rt. The mixture was stirred for 2 h at 110° C. in a microwave reactor, then concentrated, and the residue was purified by flash column chromatography ($SiO_2$, 0-50% EtOAc in PE) to afford 2-(1H-pyrazol-4-yl)-6,7,8,9-tetrahydro-4H-thieno[2,3-c]chromen-4-one (230 mg, 93%). MS obsd. (ESI+): 273.2 [(M+H)+].

Step D: 2-(1H-pyrazol-4-yl)-6,7,8,9-tetrahydrothieno[2,3-c]quinolin-4(5H)-one (Compound 1)

Compound 1

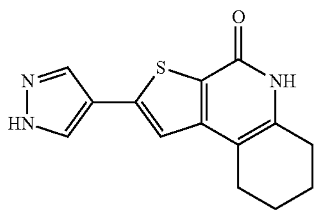

To a solution of 2-(1H-pyrazol-4-yl)-6,7,8,9-tetrahydro-4H-thieno[2,3-c]chromen-4-one (230 mg, 844.59 μmol, 1.0 eq.) in methanol (2.0 mL) was added aqueous ammonia (6.0 mL, 28% w/w). The mixture was stirred for 16 h at 120° C. in a sealed tube. After cooling to room temperature, the mixture was concentrated to dryness. The residue was dissolved in DMF and purified by preparative HPLC to afford 2-(1H-pyrazol-4-yl)-6,7,8,9-tetrahydrothieno[2,3-c]quinolin-4(5H)-one (14 mg, 6.0%). MS obsd. (ESI+): 272.1 [(M+H)+]; $^1$H NMR (400 MHz, DMSO-d6) δ ppm: 13.19 (s, 1H), 11.15 (s, 1H), 8.28 (brs, 1H), 7.96 (brs, 1H), 7.42 (s, 1H), 2.67-2.62 (m, 2H), 2.53-2.50 (m, 2H), 1.75 (s, 4H).

Example 2—Compound 2: 1,8,8-trifluoro-2-(1H-pyrazol-4-yl)-5,6,7,9-tetrahydrothieno[2,3-c]quinolin-4-one Compound 2

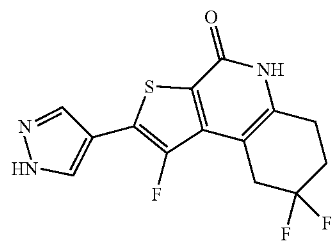

Step A: Methyl 3,5-dibromo-4-fluoro-thiophene-2-carboxylate

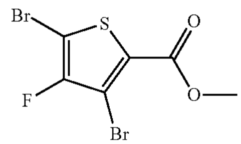

To a solution of methyl 4-fluorothiophene-2-carboxylate (1.00 g, 6.24 mmol, 1.0 eq.) in carbon tetrachloride (5.0 mL) was added $FeBr_3$ (1.29 g, 4.37 mmol, 1.0 eq.) and bromine (39.9 g, 250 mmol, 20.0 mL, 40.0 eq.) at 25° C. and the mixture was stirred for 16 h at 25° C. The mixture was concentrated and purified by flash column chromatography ($SiO_2$, 0-15% EtOAc in PE) to afford methyl 3,5-dibromo-4-fluoro-thiophene-2-carboxylate (480 mg, 24.0%). $^1$H NMR (400 MHz, $CDCl_3$) δ ppm: 3.91 (s, 3H).

Step B: Methyl 3-bromo-4-fluoro-5-[1-(2-trimethylsilylethoxymethyl)pyrazol-4-yl]thiophene-2-carboxylate

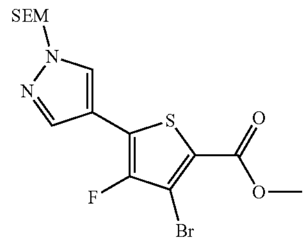 [SMILES: COC(=O)c1sc(-c2cnn(COCC[Si](C)(C)C)c2)c(F)c1Br]

A solution of palladium(II) acetate (8 mg, 0.04 mmol, 0.05 eq.) and (5-diphenylphosphanyl-9,9-dimethyl-xanthen-4-yl)-diphenyl-phosphane (22 mg, 0.04 mmol, 0.05 eq.) in THF (10.0 mL) was stirred at 25° C. for 5 min under $N_2$. To the mixture was added methyl 3,5-dibromo-4-fluoro-thiophene-2-carboxylate (240 mg, 0.75 mmol, 1.0 eq.), trimethyl-[2-[[4-(4,4,5,5-tetramethyl-1,3,2-dioxaborolan-2-yl)pyrazol-1-yl]methoxy]ethyl]silane (367 mg, 1.13 mmol, 1.5 eq.) and tripotassium orthophosphate (481 mg, 2.26 mmol, 3.0 eq.) and the mixture was stirred for 16 h at 60° C. under $N_2$. The mixture was then concentrated in vacuo and purified by flash column chromatography ($SiO_2$, 0-30% EtOAc in PE) to afford the methyl 3-bromo-4-fluoro-5-[1-(2-trimethylsilylethoxymethyl)pyrazol-4-yl]thiophene-2-carboxylate (168 mg, 51%). MS obsd. (ESI+): $^{79}Br/^{81}Br$ 435.3/437.3 $[(M+H)^+]$.

Step C: 1,8,8-trifluoro-2-[1-(2-trimethylsilylethoxymethyl)pyrazol-4-yl]-7,9-dihydro-6H-thieno[2,3-c]chromen-4-one

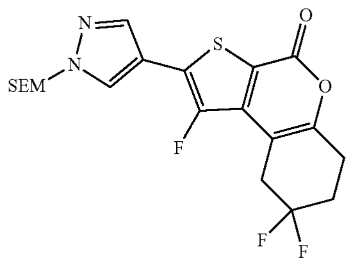 [SMILES: C[Si](C)(C)CCOCn1cc(-c2sc3c(=O)oc4c(c3c2F)CC(F)(F)CC4)cn1]

To a solution of methyl 3-bromo-4-fluoro-5-[1-(2-trimethylsilylethoxymethyl)pyrazol-4-yl]thiophene-2-carboxylate (464 mg, 1.07 mmol, 1.0 eq.) in toluene (100.0 mL) was added tris(dibenzylideneacetone)dipalladium (98 mg, 0.11 mmol, 0.10 eq.), 4,5-Bis(diphenylphosphino)-9,9-dimethylxanthene (93 mg, 0.16 mmol, 0.15 eq.), cesium carbonate (1.0 g, 3.20 mmol, 3.0 eq.), sodium metabisulfite (20 mg, 0.11 mmol, 0.1 eq.) and 4,4-difluorocyclohexanone (429 mg, 3.20 mmol, 3.0 eq.). The mixture was purged with $N_2$, then heated to 105° C. and stirred for 16 h. The mixture was concentrated to dryness, and the residue was purified by flash chromatography ($SiO_2$, 0-30% EtOAc in PE) to afford the product 1,8,8-trifluoro-2-[1-(2-trimethylsilylethoxymethyl)pyrazol-4-yl]-7,9-dihydro-6H-thieno[2,3-c]chromen-4-one (217 mg, 44%). MS obsd. (ESI+): 457.3 $[(M+H)^+]$.

Step D: 1,8,8-trifluoro-2-[1-(2-trimethylsilylethoxymethyl)pyrazol-4-yl]-5,6,7,9-tetrahydrothieno[2,3-c]quinolin-4-one

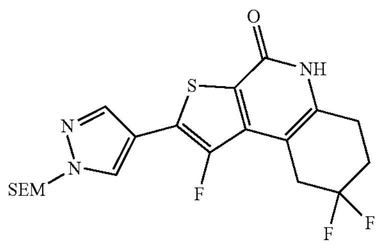 [SMILES: C[Si](C)(C)CCOCn1cc(-c2sc3c(=O)[nH]c4c(c3c2F)CC(F)(F)CC4)cn1]

To a solution of 1,8,8-trifluoro-2-[1-(2-trimethylsilylethoxymethyl)pyrazol-4-yl]-7,9-dihydro-6H-thieno[2,3-c]chromen-4-one (110 mg, 0.24 mmol, 1.0 eq.) in MeOH (5.0 mL) was added ammonium hydroxide (4.5 g, 128 mmol, 5.0 mL, 320 eq.) at 25° C., and the mixture was stirred for 8 h at 95° C. under microwave irradiation. The solution was cooled and concentrated to afford 1,8,8-trifluoro-2-[1-(2-trimethylsilylethoxymethyl)pyrazol-4-yl]-5,6,7,9-tetrahydrothieno[2,3-c]quinolin-4-one (109 mg, crude), which was used for the next step without further purification. MS obsd. $(ESI^+)$: 456.3 $[(M+H)^+]$.

Step E: 1,8,8-trifluoro-2-(1H-pyrazol-4-yl)-5,6,7,9-tetrahydrothieno[2,3-c]quinolin-4-one (Compound 2)

Compound 2

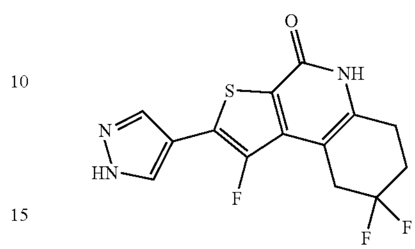

To a solution of 1,8,8-trifluoro-2-[1-(2-trimethylsilylethoxymethyl)pyrazol-4-yl]-5,6,7,9-tetrahydrothieno[2,3-c]quinolin-4-one (109 mg, 0.24 mmol, 1.0 eq.) in DCM (1.0 mL) was added 2,2,2-trifluoroacetic acid (5.9 g, 52 mmol, 4.0 mL, 220 eq.), and the mixture was stirred for 1 h at 25° C. The mixture was concentrated to dryness, and the residue was purified by flash column chromatography ($SiO_2$, 0-8% MeOH in DCM) to afford an impure product. The residue was further purified by reverse phase column chromatography (C18 $SiO_2$, 0-40% MeCN, 0.1% FA in water) to afford 1,8,8-trifluoro-2-(1H-pyrazol-4-yl)-5,6,7,9-tetrahydrothieno[2,3-c]quinolin-4-one (22 mg, 28%). MS obsd. $(ESI^+)$: 326.2 $[(M+H)^+]$.

Examples 3 and 4—Compounds 3 and 4: (S)-6-hydroxy-2-(1H-pyrazol-4-yl)-6,7,8,9-tetrahydrothieno[2,3-c]quinolin-4(5H)-one (Compound 3) & (R)-6-hydroxy-2-(1H-pyrazol-4-yl)-6,7,8,9-tetrahydrothieno[2,3-c]quinolin-4(5H)-one (Compound 4) (Stereochemistry of Compounds 3 and 4 is Arbitrarily Assigned)

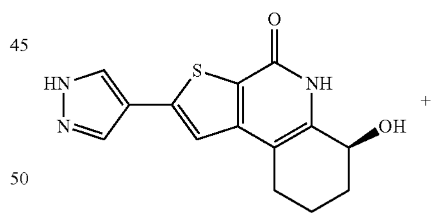

+

Compound 3

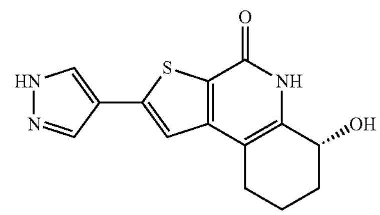

Compound 4

Step A: 2-benzyloxycyclohexanol

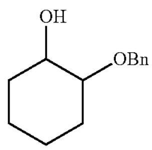 [SMILES: OC1CCCCC1OCc1ccccc1]

BnOH (910 mg, 20 mmol, 2.0 eq.) was added dropwise to a stirred suspension of NaH (820 mg, 21.4 mmol, 60% in mineral oil, 2.0 eq.) in anhydrous DMF (25 mL) at 0° C. The mixture was stirred at 0° C. for 1 hour before addition of 7-oxabicyclo[4.1.0]heptane (1.0 g, 10 mmol, 1.0 eq.). The mixture was heated to 60° C. for 2 h, then cooled. Water was added, and the mixture was extracted with EtOAc. The combined organic layers were washed with brine, dried over anhydrous $Na_2SO_4$, filtered, and concentrated under vacuum. The residue was purified by flash column chromatography ($SiO_2$, 0-50% EtOAc in PE) to give 2-benzyloxycyclohexanol (1.0 g, 48%). MS obsd. ($ESI^+$): 207.3 [$(M+H)^+$].

Step B: 2-benzyloxycyclohexanone

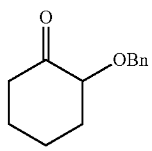 [SMILES: O=C1CCCCC1OCc1ccccc1]

Oxalyl chloride (738 mg, 5.82 mmol, 1.2 eq.) was dissolved in anhydrous DCM (5.0 mL) under a nitrogen atmosphere and cooled to −78° C. A solution of DMSO (909 mg, 11.6 mmol, 2.0 eq.) in anhydrous DCM (5.0 mL) was added dropwise, and the resulting mixture was stirred for 20 min. 2-Benzyloxycyclohexanol (1.0 g, 4.85 mmol, 1.0 eq.) in anhydrous DCM (5.0 mL) was added dropwise to form a white precipitate. The mixture was stirred for 30 min, warmed to −60° C., and anhydrous triethylamine (2.5 g, 24 mmol, 3.4 mL, 1.0 eq.) was added dropwise. The mixture was held at −60° C. for 5 min then warmed to room temperature for 2 h. The reaction was quenched with $H_2O$ and extracted with EtOAc. The organic layers were combined, washed with brine, dried over anhydrous sodium sulfate, filtered, and concentrated under vacuum. The residue was purified by flash column chromatography ($SiO_2$, 0-50% EtOAc in PE) to afford 2-benzyloxycyclohexanone (770 mg, 78%). MS obsd. ($ESI^+$): 205.2 [$(M+H)^+$].

Step C: 6-(benzyloxy)-6,7,8,9-tetrahydrothieno[2,3-c]chromen-4-one

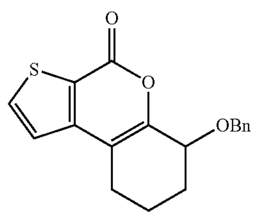 [SMILES: O=c1oc2c(c3ccsc13)CCCC2OCc1ccccc1]

To a solution of methyl 3-bromothiophene-2-carboxylate (1.0 g, 4.5 mmol, 1.0 eq.) in toluene (15 mL) was added 2-benzyloxycyclohexanone (1.4 g, 6.8 mmol, 1.5 eq.), tris(dibenzylideneacetone)dipalladium (414 mg, 0.45 mmol, 0.1 eq.), 4,5-bis(diphenylphosphino)-9,9-dimethylxanthene (785 mg, 1.36 mmol, 0.30 eq.), cesium carbonate (3.0 g, 9.1 mmol, 2.0 eq.) and sodium metabisulfite (170 mg, 0.90 mmol, 0.20 eq.). The reaction was purged with nitrogen and stirred for 3 h at 105° C. The mixture was concentrated in vacuo, and the residue was purified by flash column chromatography ($SiO_2$, 0-50% EtOAc in PE) to afford 6-(benzyloxy)-6,7,8,9-tetrahydrothieno[2,3-c]chromen-4-one (450 mg, 32%). MS obsd. ($ESI^+$): 313.3 [$(M+H)^+$].

Step D: 6-(benzyloxy)-2-iodo-6,7,8,9-tetrahydrothieno[2,3-c]chromen-4-one

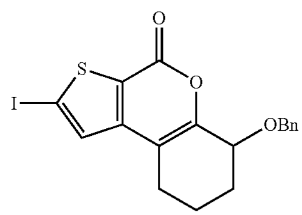 [SMILES: O=c1oc2c(c3cc(I)sc13)CCCC2OCc1ccccc1]

To a solution of 6-benzyloxy-6,7,8,9-tetrahydrothieno[2,3-c]chromen-4-one (350 mg, 1.12 mmol, 1.0 eq.) and 12 (569 mg, 2.24 mmol, 2.0 eq.) in THF (5.0 mL) was added LDA (2 M in THF, 2.2 mL, 4.0 eq.) at −65° C. The mixture was stirred at −65° C. for 1 h, then quenched with $H_2O$ and extracted with EtOAc. The combined organic layers were washed with brine, dried over anhydrous sodium sulfate, filtered, and concentrated in vacuo, and the residue was purified by flash column chromatography ($SiO_2$, 0-50% EtOAc in PE) to afford 6-(benzyloxy)-2-iodo-6,7,8,9-tetrahydrothieno[2,3-c]chromen-4-one (300 mg, 61%). MS obsd. ($ESI^+$): 439.3 [$(M+H)^+$].

Step E: 6-(benzyloxy)-2-(1-((2-(trimethylsilyl)ethoxy)methyl)-1H-pyrazol-4-yl)-6,7,8,9-tetrahydro-4H-thieno[2,3-c]chromen-4-one

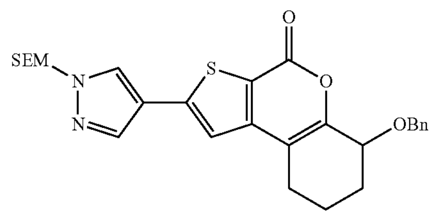 [SMILES: C[Si](C)(C)CCOCn1cc(-c2cc3c4c(oc(=O)c3s2)C(OCc2ccccc2)CCC4)cn1]

A suspension of trimethyl-[2-[[4-(4,4,5,5-tetramethyl-1,3,2-dioxaborolan-2-yl)pyrazol-1-yl]methoxy]ethyl]silane (444 mg, 1.37 mmol, 1.2 eq.), 6-(benzyloxy)-2-iodo-6,7,8,9-tetrahydrothieno[2,3-c]chromen-4-one (500 mg, 1.10 mmol, 1.0 eq.), Pd(dppf)$Cl_2$ (80 mg, 0.11 mmol, 0.1 eq.), X-Phos (104 mg, 0.22 mmol, 0.2 eq.), and $Cs_2CO_3$ (1.08 g, 3.30 mmol, 3.0 eq.) in a mixture of 1,4-dioxane (15.0 mL) and $H_2O$ (5.0 mL) was irradiated in a microwave reactor at 110° C. for 2 h. The mixture was cooled and extracted with EtOAc. The organic layer was concentrated to dryness, and the residue was purified by flash column chromatography (SiO$_2$, 0-70% EtOAc in PE) to afford 6-(benzyloxy)-2-(1-((2-(trimethylsilyl)ethoxy)methyl)-1H-pyrazol-4-yl)-6,7,8,9-tetrahydro-4H-thieno[2,3-c]chromen-4-one (450 mg, 80%). MS obsd. (ESI$^+$): 509.7 [(M+H)$^+$].

Step F: 6-(benzyloxy)-2-(1-((2-(trimethylsilyl)ethoxy)methyl)-1H-pyrazol-4-yl)-6,7,8,9-tetrahydrothieno[2,3-c]quinolin-4(5H)-one

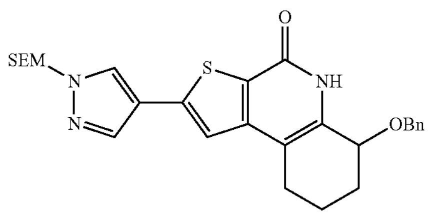 [SMILES: C[Si](C)(C)CCOCn1cc(-c2cc3c4c([nH]c(=O)c3s2)C(OCc2ccccc2)CCC4)cn1]

A suspension of 6-(benzyloxy)-2-(1-((2-(trimethylsilyl)ethoxy)methyl)-1H-pyrazol-4-yl)-6,7,8,9-tetrahydro-4H-thieno[2,3-c]chromen-4-one (500 mg, 1.32 mmol, 1.0 eq.) in a mixture of MeOH (7.0 mL) and 25% aqueous ammonia (7.0 mL) was irradiated in a microwave reactor at 100° C. for 3 h. The resulting solid was filtered, washed with MeOH and dried to afford 6-(benzyloxy)-2-(1-((2-(trimethylsilyl)ethoxy)methyl)-1H-pyrazol-4-yl)-6,7,8,9-tetrahydrothieno[2,3-c]quinolin-4(5H)-one (250 mg, 50%). MS obsd. (ESI$^+$): 508.7 [(M+H)$^+$]

Step G: (S)-6-hydroxy-2-(1H-pyrazol-4-yl)-6,7,8,9-tetrahydrothieno[2,3-c]quinolin-4(5H)-one (Compound 3) & (R)-6-hydroxy-2-(1H-pyrazol-4-yl)-6,7,8,9-tetrahydrothieno[2,3-c]quinolin-4(5H)-one (Compound 4)

Compound 3

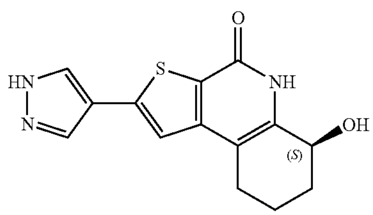

Compound 4

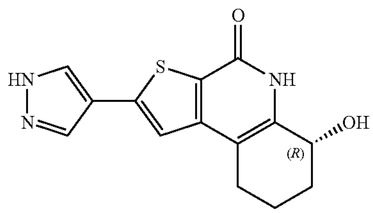

A solution of 6-benzyloxy-2-[1-(2-trimethylsilylethoxymethyl)pyrazol-4-yl]-6,7,8,9-tetrahydro-5H-thieno[2,3-c]quinolin-4-one (250 mg, 0.49 mmol, 1.0 eq.) in trifluoroacetic acid (10.0 mL) was heated at 70° C. for 1 h. The solvent was removed, and to the residue was added $NH_3$ (7 M in MeOH, 5.0 mL). The mixture was stirred at rt for 5 min, concentrated, and the residue was purified via preparative HPLC to afford 6-hydroxy-2-(1H-pyrazol-4-yl)-6,7,8,9-tetrahydrothieno[2,3-c]quinolin-4(5H)-one (60 mg, 40%). MS obsd. (ESI$^+$): 288.4 [(M+H)$^+$].

The racemic product was separated by chiral SFC to afford each enantiomer. (S)-6-hydroxy-2-(1H-pyrazol-4-yl)-6,7,8,9-tetrahydrothieno[2,3-c]quinolin-4(5H)-one (Compound 3): MS obsd. (ESI$^+$): 288.2 [(M+H)$^+$]. (R)-6-hydroxy-2-(1H-pyrazol-4-yl)-6,7,8,9-tetrahydrothieno[2,3-c]quinolin-4(5H)-one (Compound 4): MS obsd. (ESI$^+$): 288.2 [(M+H)$^+$]; $^1$H NMR (400 MHz, DMSO-d6) δ ppm: 13.20 (s, 1H), 10.82 (s, 1H), 8.30 (s, 1H), 7.96 (s, 1H), 7.47 (s, 1H), 5.22 (d, J=5.6 Hz, 1H), 4.49-4.46 (m, 1H), 2.70-2.65 (m, 1H), 2.51-2.49 (m, 1H), 1.89-1.82 (m, 2H), 1.78-1.69 (m, 2H).

Examples 5 and 6—Compounds 5 and 6: (R)-6-(3,3-difluoropyrrolidin-1-yl)-2-(1H-pyrazol-4-yl)-6,7,8,9-tetrahydrothieno[2,3-c]quinolin-4(5H)-one (Compound 5) & (S)-6-(3,3-difluoropyrrolidin-1-yl)-2-(1H-pyrazol-4-yl)-6,7,8,9-tetrahydrothieno[2,3-c]quinolin-4(5H)-one (Compound 6). (Stereochemistry of Compounds 5 and 6 is Arbitrarily Assigned)

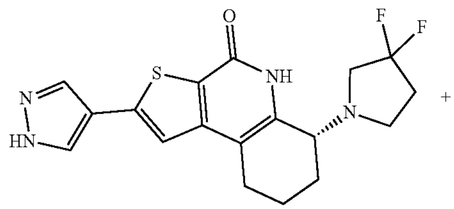

+

Compound 5

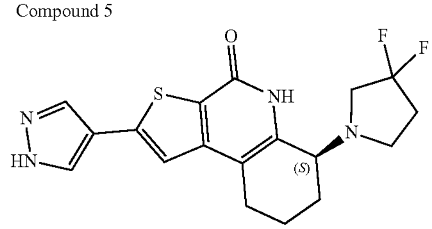

Compound 6

Step A: 6-bromo-2-(1H-pyrazol-4-yl)-6,7,8,9-tetrahydrothieno[2,3-c]quinolin-4(5H)-one

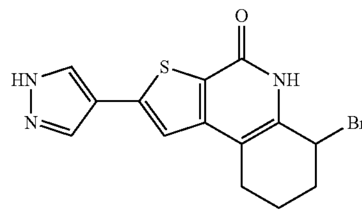 [SMILES: O=c1[nH]c2c(c3cc(-c4cn[nH]c4)sc13)CCCC2Br]

A suspension of 6-hydroxy-2-(1H-pyrazol-4-yl)-6,7,8,9-tetrahydro-5H-thieno[2,3-c]quinolin-4-one (120 mg, 0.41 mmol, 1.0 eq.) in TMSBr (8.0 mL) was stirred in a sealed tube at 80° C. for 6 h. The solvent was removed in vacuo, and the residue was used directly in the next step without further purification. MS obsd. (ESI$^+$): 302.4 [(M−Br+$OCH_3$)+H)$^+$].

Step B: (R)-6-(3,3-difluoropyrrolidin-1-yl)-2-(1H-pyrazol-4-yl)-6,7,8,9-tetrahydrothieno[2,3-c]quinolin-4(5H)-one (Compound 5) and (S)-6-(3,3-difluoropyrrolidin-1-yl)-2-(1H-pyrazol-4-yl)-6,7,8,9-tetrahydrothieno[2,3-c]quinolin-4(5H)-one (Compound 6)

Compound 5

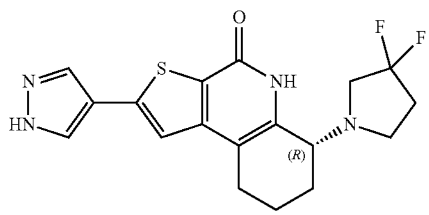

Compound 6

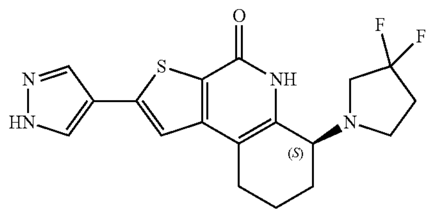

A suspension of 3,3-Difluoropyrrolidine hydrochloride (1.9 g, 14 mmol, 20 eq.) and N,N-diisopropylethylamine (1.8 g, 13.88 mmol, 20.0 eq.) in MeCN (10.0 mL) was stirred at rt for 2 h. The solid was filtered off, and the filtrate was added to a sealed vial which contained 6-bromo-2-(1H-pyrazol-4-yl)-6,7,8,9-tetrahydro-5H-thieno[2,3-c]quinolin-4-one (200 mg, 0.69 mmol, 1.0 eq.). To the vial was added NaI (103 mg, 0.69 mmol, 1.0 eq.). The mixture was stirred at rt for 16 h, then concentrated in vacuo, and the residue was purified via flash column chromatography ($SiO_2$, 0-100% EtOAc in PE) to afford racemic 6-(3,3-difluoropyrrolidin-1-yl)-2-(1H-pyrazol-4-yl)-6,7,8,9-tetrahydrothieno[2,3-c]quinolin-4(5H)-one (60 mg, 19%). MS obsd. ($ESI^+$): 377.5 $[(M+H)^+]$.

The individual enantiomers were separated via chiral SFC. (R)-6-(3,3-difluoropyrrolidin-1-yl)-2-(1H-pyrazol-4-yl)-6,7,8,9-tetrahydrothieno[2,3-c]quinolin-4(5H)-one (Compound 5): MS obsd. ($ESI^+$): 377.3 $[(M+H)^+]$; $^1H$ NMR (400 MHz, DMSO-d6) δ ppm: 13.20 (s, 1H), 10.53 (s, 1H), 8.30 (s, 1H), 7.96 (s, 1H), 7.47 (s, 1H), 3.73 (t, J=5.6 Hz, 1H), 3.06-2.93 (m, 2H), 2.87-2.78 (m, 2H), 2.68-2.62 (m, 2H), 2.30-2.22 (m, 2H), 1.98-1.95 (m, 1H), 1.84-1.77 (m, 2H), 1.74-1.71 (m, 1H). (S)-6-(3,3-difluoropyrrolidin-1-yl)-2-(1H-pyrazol-4-yl)-6,7,8,9-tetrahydrothieno[2,3-c]quinolin-4(5H)-one (Compound 6): MS obsd. ($ESI^+$): 377.3 $[(M+H)^+]$.

Examples 7 and 8—Compounds 7 and 8: 6-methoxy-2-(1H-pyrazol-4-yl)-6,7,8,9-tetrahydro-, 9-ethanothieno[2,3-c]quinolin-4(5H)-one (Compound 7) & 6-hydroxy-2-(1H-pyrazol-4-yl)-6,7,8,9-tetrahydro-6,9-ethanothieno[2,3-c]quinolin-4(5H)-one (Compound 8)

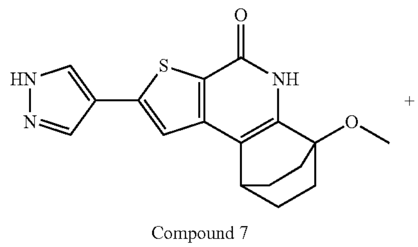

+

Compound 7

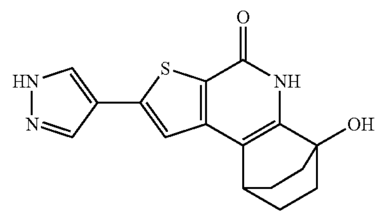

Compound 8

Step A: 6-methoxy-2-(1-((2-(trimethylsilyl)ethoxy)methyl)-1H-pyrazol-4-yl)-6,7,8,9-tetrahydro-4H-6,9-ethanothieno[2,3-c]chromen-4-one

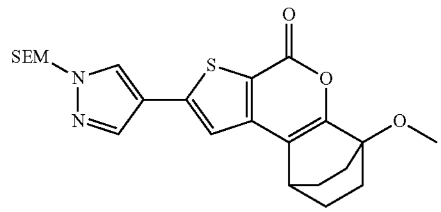 [SMILES: COC12CCC(CC1)c1c2oc(=O)c2sc(-c3cnn(COCC[Si](C)(C)C)c3)cc12]

Cesium carbonate (230 mg, 720 μmol, 3.0 eq.) and Sphos-Pd-$G_3$ (37 mg, 48 μmol, 0.2 eq.) was added to a solution of methyl 3-bromo-5-(1-((2-(trimethylsilyl)ethoxy)methyl)-1H-pyrazol-4-yl)thiophene-2-carboxylate (100 mg, 240 μmol, 1.0 eq.) and 1-methoxybicyclo[2.2.2]octan-2-one (74 mg, 480 μmol, 2.0 eq., synthesized according to the procedure described in WO2007070201) in toluene (6.0 mL). The mixture was heated at 105° C. under nitrogen for 8 h before being concentrated in vacuo. The resulting residue was purified by flash column chromatography ($SiO_2$, 0-25% EtOAc in PE) to give 6-methoxy-2-(1-((2-(trimethylsilyl)ethoxy)methyl)-1H-pyrazol-4-yl)-6,7,8,9-tetrahydro-4H-6,9-ethanothieno[2,3-c]chromen-4-one (32 mg, 24%, 82% purity). MS obsd. ($ESI^+$): 459.4 $[(M+H)^+]$.

Step B: 6-methoxy-2-(1-((2-(trimethylsilyl)ethoxy)methyl)-1H-pyrazol-4-yl)-6,7,8,9-tetrahydro-6,9-ethanothieno[2,3-c]quinolin-4(5H)-one

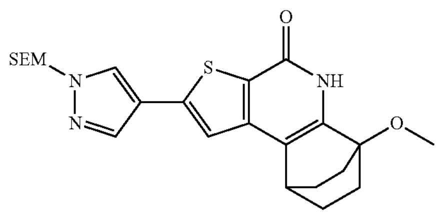 [SMILES: COC12CCC(CC1)c1c2[nH]c(=O)c2sc(-c3cnn(COCC[Si](C)(C)C)c3)cc12]

To a solution of 6-methoxy-2-(1-((2-(trimethylsilyl)ethoxy)methyl)-1H-pyrazol-4-yl)-6,7,8,9-tetrahydro-4H-6,9-ethanothieno[2,3-c]chromen-4-one (20 mg, 44 μmol, 1.0 eq.) in isopropanol (3.0 mL) was added aqueous ammonia (17% w/w, 12.0 mL). The mixture was stirred at 60° C. for 16 h, then concentrated in vacuo and purified by flash column chromatography ($SiO_2$ 0-5% MeOH in DCM) to afford 6-methoxy-2-(1-((2-(trimethylsilyl)ethoxy)methyl)-1H-pyrazol-4-yl)-6,7,8,9-tetrahydro-6,9-ethanothieno[2,3-c]quinolin-4(5H)-one (10 mg, 24%, 48% purity). MS obsd. ($ESI^+$): 458.4 $[(M+H)^+]$.

Step C: 6-methoxy-2-(1H-pyrazol-4-yl)-6,7,8,9-tetrahydro-6,9-ethanothieno[2,3-c]quinolin-4(5H)-one (Compound 7)

Compound 7

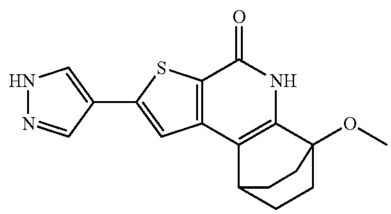

A solution of 6-methoxy-2-(1-((2-(trimethylsilyl)ethoxy)methyl)-1H-pyrazol-4-yl)-6,7,8,9-tetrahydro-6,9-ethanothieno[2,3-c]quinolin-4(5H)-one (28 mg, ~50% purity, 29 μmol, 1.0 eq.) in DCM (4.0 mL) was cooled to 0° C. before trifluoroacetic acid (1.0 mL) was added. The mixture was stirred at room temperature for 2 h, then concentrated in vacuo and purified by preparative HPLC to afford 6-methoxy-2-(1H-pyrazol-4-yl)-6,7,8,9-tetrahydro-6,9-ethanothieno[2,3-c]quinolin-4(5H)-one (Compound 7, 5 mg, 51%). MS obsd. ($ESI^+$): 328.1 $[(M+H)^+]$; $^1H$ NMR (400 MHz, DMSO-d6) δ ppm: 13.16 (s, 1H), 10.52 (s, 1H), 8.10 (s, 2H), 7.59 (s, 1H), 3.39 (s, 3H), 3.40-3.92 (m, 1H), 2.12 (t, J=10.4 Hz, 2H), 1.88 (t, J=10.4 Hz, 2H), 1.49-1.44 (m, 2H), 1.36-1.31 (m, 2H).

Step D: 6-hydroxy-2-(1H-pyrazol-4-yl)-6,7,8,9-tetrahydro-6,9-ethanothieno[2,3-c]quinolin-4(5H)-one (Compound 8)

Compound 8

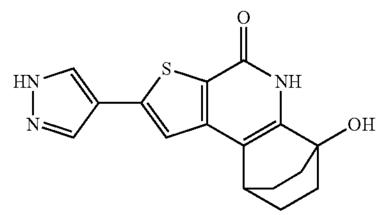

A solution of 6-methoxy-2-(1H-pyrazol-4-yl)-6,7,8,9-tetrahydro-6,9-ethanothieno[2,3-c]quinolin-4(5H)-one (55 mg, 120 μmol, 1.0 eq) in HBr (40% aq., 5.0 mL) was heated to 100° C. for 8 h. The mixture was concentrated in vacuo and purified by reverse phase column chromatography (C18 $SiO_2$, 0-40% MeCN in Water, 0.1% $NH_4HCO_3$ in water) to give the 6-hydroxy-2-(1H-pyrazol-4-yl)-6,7,8,9-tetrahydro-6,9-ethanothieno[2,3-c]quinolin-4(5H)-one (Example 8, 16.2 mg, 31%). MS obsd. ($ESI^+$): 314.2 $[(M+H)^+]$; $^1H$ NMR (400 MHz, DMSO-d6) δ ppm: 13.17 (s, 1H), 10.22 (s, 1H), 8.14 (brs, 2H), 7.58 (s, 1H), 5.72 (s, 1H), 3.30 (s, 1H), 1.84-1.80 (m, 4H), 1.43 (d, J=6.4 Hz, 4H).

Example 9—Compound 9: 6-hydroxy-2-(pyridin-4-yl)-6,7,8,9-tetrahydro-6,9-ethanothieno[2,3-c]quinolin-4(5H)-one Compound 9

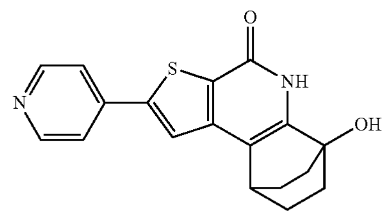

Step A: methyl 3-bromo-5-(pyridin-4-yl)thiophene-2-carboxylate

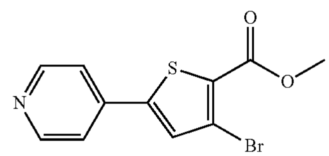 [SMILES: COC(=O)c1sc(-c2ccncc2)cc1Br]

Cesium carbonate (210 mg, 680 μmol, 2.0 eq.), Pd(dppf)$Cl_2$ (240 mg, 330 μmol, 1.0 eq.) and dicyclohexyl-[2-(2,4,6-triisopropylphenyl)phenyl]phosphane (160 mg, 330 μmol, 1.0 eq.) was added to a solution of methyl 3,5-dibromothiophene-2-carboxylate (100 mg, 330 μmol, 1.0 eq.) and 4-pyridylboronic acid (45 mg, 370 μmol, 1.1 eq.) in 1,4-dioxane (10.0 mL). The mixture was degassed with $N_2$ twice before being heated to 80° C. for 1 h. The mixture was concentrated in vacuo, then purified by column chromatography ($SiO_2$, 0-25% EtOAc in PE) afforded methyl 3-bromo-5-(pyridin-4-yl)thiophene-2-carboxylate (65 mg, 56%). MS obsd. ($ESI^+$): 298.0 [$(M+H)^+$].

Step B: 6-methoxy-2-(pyridin-4-yl)-6,7,8,9-tetrahydro-4H-6,9-ethanothieno[2,3-c]chromen-4-one

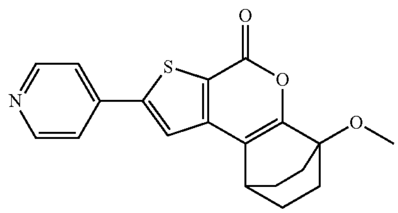 [SMILES: COC12CCC(CC1)c1c2oc(=O)c2sc(-c3ccncc3)cc12]

Cesium carbonate (330 mg, 1.0 mmol, 3.0 eq.) and Sphos-Pd-G3 (52 mg, 67 μmol, 0.2 eq.) were added to a solution of methyl 3-bromo-5-(4-pyridyl)thiophene-2-carboxylate (100 mg, 340 μmol, 1.0 eq.) and 1-methoxybicyclo [2.2.2]octan-2-one (100 mg, 670 μmol, 2.0 eq.) in toluene (4.0 mL). The mixture was stirred at 100° C. for 16 h under nitrogen, concentrated in vacuo and purified by flash column chromatography ($SiO_2$, 0-10% MeOH in DCM) to give 6-methoxy-2-(pyridin-4-yl)-6,7,8,9-tetrahydro-4H-6,9-ethanothieno[2,3-c]chromen-4-one (21 mg, 16%, 82% purity). MS obsd. ($ESI^+$): 340.4 [$(M+H)^+$].

Step C: 6-methoxy-2-(pyridin-4-yl)-6,7,8,9-tetrahydro-4H-6,9-ethanothieno[2,3-c]chromen-4-one

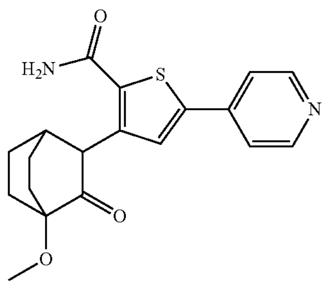 [SMILES: COC12CCC(CC1)C(c1cc(-c3ccncc3)sc1C(N)=O)C2=O]

To a solution of 6-methoxy-2-(pyridin-4-yl)-6,7,8,9-tetrahydro-4H-6,9-ethanothieno[2,3-c]chromen-4-one (15 mg, 44.19 μmol, 1.0 eq.) in isopropanol (4.0 mL) was added a solution of aqueous ammonia (25% w/w, 16.0 mL). The mixture was stirred at 60° C. for 16 h then concentrated in vacuo to give 6-methoxy-2-(pyridin-4-yl)-6,7,8,9-tetrahydro-4H-6,9-ethanothieno[2,3-c]chromen-4-one (15 mg, crude), which was used without further purification. MS obsd. ($ESI^+$): 357.3 [$(M+H)^+$].

Step D: 6-methoxy-2-(pyridin-4-yl)-6,7,8,9-tetrahydro-6,9-ethanothieno[2,3-c]quinolin-4(5H)-one

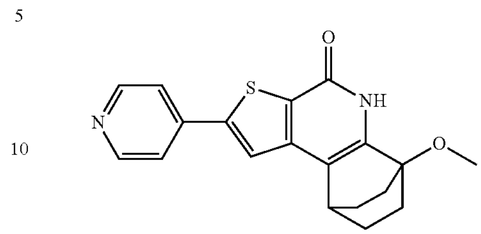

Crude 3-(4-methoxy-3-oxobicyclo[2.2.2]octan-2-yl)-5-(pyridin-4-yl)thiophene-2-carboxamide (30 mg) was dissolved in toluene (4.0 mL) and p-toluenesulfonic acid (3 mg, 17 μmol, 0.20 eq). The mixture was stirred at 100° C. for 1 h before $NaHCO_3$ (sat. aq. 10 mL) was added. The mixture was extracted with EtOAc (3×15 mL), and the combined organic layers were dried over $Na_2SO_4$ and filtered. Concentration in vacuo afforded 6-methoxy-2-(pyridin-4-yl)-6,7,8,9-tetrahydro-6,9-ethanothieno[2,3-c]quinolin-4(5H)-one (28 mg, crude) which was used without further purification. MS obsd. ($ESI^+$): 339.2 [$(M+H)^+$].

Step E: 6-hydroxy-2-(pyridin-4-yl)-6,7,8,9-tetrahydro-6,9-ethanothieno[2,3-c]quinolin-4(5H)-one (Compound 9)

Compound 9

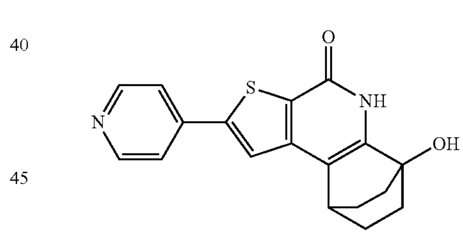

A solution of 6-methoxy-2-(pyridin-4-yl)-6,7,8,9-tetrahydro-6,9-ethanothieno[2,3-c]quinolin-4(5H)-one (30 mg, 89 μmol) in HBr (48% aq, 4.0 mL) was heated to 100° C. for 16 h, concentrated in vacuo, and purified by preparative HPLC to afford 6-hydroxy-2-(pyridin-4-yl)-6,7,8,9-tetrahydro-6,9-ethanothieno[2,3-c]quinolin-4(5H)-one (Compound 9, 11 mg, 38%). MS obsd. ($ESI^+$): 325.1 [$(M+H)^+$]; $^1H$ NMR (400 MHz, DMSO-d6) δ ppm: 10.59 (s, 1H), 8.68-8.67 (m, 2H), 8.23 (s, 1H), 7.82-7.81 (m, 2H), 5.76 (s, 1H), 3.43-3.41 (m, 1H), 1.85-1.78 (m, 4H), 1.46-1.43 (m, 4H).

Examples 10 and 11—Compounds 10 and 11: (R)-4-methoxy-8-(1H-pyrazol-4-yl)-1,3,4,5-tetrahydro-6H-pyrano[4,3-b]thieno[3,2-d]pyridin-6-one (Compound 10) & (S)-4-methoxy-8-(1H-pyrazol-4-yl)-1,3,4,5-tetrahydro-6H-pyrano[4,3-b]thieno[3,2-d]pyridin-6-one (Compound 11) (Stereochemistry is Arbitrarily Assigned)

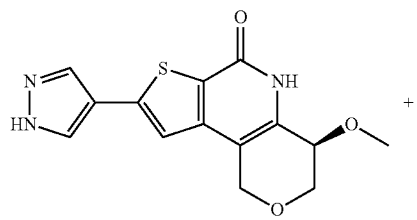

+

Compound 10

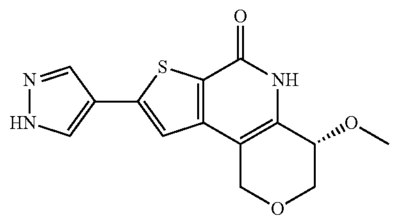

Compound 11

Step A: 4-methoxy-8-(1-((2-(trimethylsilyl)ethoxy)methyl)-1H-pyrazol-4-yl)-3,4-dihydro-1H,6H-pyrano[4,3-b]thieno[3,2-d]pyran-6-one

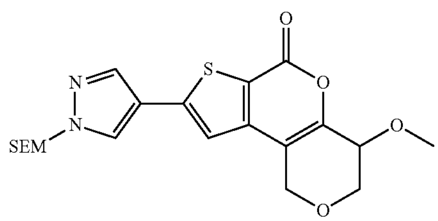 [SMILES: COC1COCc2c1oc(=O)c1sc(-c3cnn(COCC[Si](C)(C)C)c3)cc21]

To a solution of methyl 3-bromo-5-(1-((2-(trimethylsilyl)ethoxy)methyl)-1H-pyrazol-4-yl)thiophene-2-carboxylate (300 mg, 0.72 mmol, 1.0 eq., prepared in an analogous fashion to Compound 9 step A) and 3-methoxytetrahydropyran-4-one (190 mg, 1.4 mmol, 2.0 eq., synthesis described in WO2005014537) in toluene (7.0 mL) was added sodium metabisulfite (14 mg, 72 μmol, 0.1 eq.), $Cs_2CO_3$ (700 mg, 2.2 mmol, 3.0 eq.), $Pd_2(dba)_3$ (130 mg, 0.14 mmol, 0.2 eq.) and Xantphos (170 mg, 0.29 mmol, 0.4 eq.). The mixture was stirred at 100° C. for 16 h, concentrated, and purified by column chromatography ($SiO_2$, 0-25% EtOAc in PE) to afford 4-methoxy-8-(1-((2-(trimethylsilyl)ethoxy)methyl)-1H-pyrazol-4-yl)-3,4-dihydro-1H,6H-pyrano[4,3-b]thieno[3,2-d]pyran-6-one (160 mg, 51%). MS obsd. ($ESI^+$): 435.4 $[(M+H)^+]$.

Step B: 4-methoxy-8-(1-((2-(trimethylsilyl)ethoxy)methyl)-1H-pyrazol-4-yl)-3,4-dihydro-1H,6H-pyrano[4,3-b]thieno[3,2-d]pyran-6-one

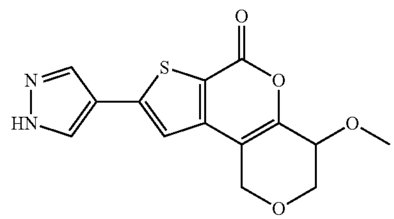 [SMILES: COC1COCc2c1oc(=O)c1sc(-c3cn[nH]c3)cc21]

A solution of 4-methoxy-8-(1-((2-(trimethylsilyl)ethoxy)methyl)-1H-pyrazol-4-yl)-3,4-dihydro-1H,6H-pyrano[4,3-b]thieno[3,2-d]pyran-6-one (160 mg, 0.37 mmol, 1.0 eq.) in 1:4 trifluoroacetic acid/DCM (10 mL) was stirred for 2 h at rt. The mixture was concentrated to give 4-methoxy-8-(1-((2-(trimethylsilyl)ethoxy)methyl)-1H-pyrazol-4-yl)-3,4-dihydro-1H,6H-pyrano[4,3-b]thieno[3,2-d]pyran-6-one (112 mg, crude) which was used without further purification. MS obsd. ($ESI^+$): 305.2 $[(M+H)^+]$.

Step C: (R)-4-methoxy-8-(1H-pyrazol-4-yl)-1,3,4,5-tetrahydro-6H-pyrano[4,3-b]thieno[3,2-d]pyridin-6-one (Compound 10) and (S)-4-methoxy-8-(1H-pyrazol-4-yl)-1,3,4,5-tetrahydro-6H-pyrano[4,3-b]thieno[3,2-d]pyridin-6-one (Compound 11)

Compound 10

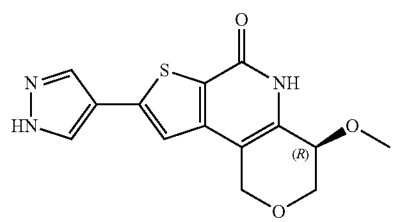

Compound 11

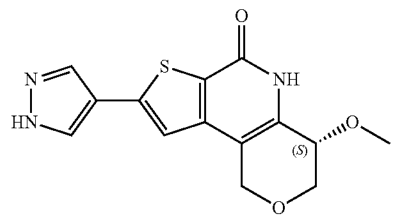

A solution of 4-methoxy-8-(1-((2-(trimethylsilyl)ethoxy)methyl)-1H-pyrazol-4-yl)-3,4-dihydro-1H,6H-pyrano[4,3-b]thieno[3,2-d]pyran-6-one (110 mg, 1.0 eq) in $NH_4OH$/MeOH=1/1 (10 mL) was stirred 6 h at 100° C. in a microwave reactor. The mixture was concentrated in vacuo and purified by preparative HPLC to afford racemic 4-methoxy-8-(1H-pyrazol-4-yl)-1,3,4,5-tetrahydro-6H-pyrano[4,3-b]thieno[3,2-d]pyridin-6-one (75 mg, 77%). MS obsd. ($ESI^+$): 304.2 $[(M+H)^+]$.

Individual enantiomers were separated by chiral SFC. (R)-4-methoxy-8-(1H-pyrazol-4-yl)-1,3,4,5-tetrahydro-6H-pyrano[4,3-b]thieno[3,2-d]pyridin-6-one (Compound 10): MS obsd. ($ESI^+$): 304.2 $[(M+H)^+]$; $^1H$ NMR (400 MHz, DMSO-d6) δ ppm: 13.23 (s, 1H), 11.53 (s, 1H), 8.30 (brs, 2H), 7.44 (s, 1H), 4.88-4.69 (m, 1H), 4.64-4.46 (m, 1H), 4.18 (d, J=12.0 Hz, 1H), 4.01 (s, 1H), 3.70 (d, J=12.0 Hz, 1H), 3.39 (s, 3H). (S)-4-methoxy-8-(1H-pyrazol-4-yl)-1,3,4,5-tetrahydro-6H-pyrano[4,3-b]thieno[3,2-d]pyridin-6-one (Compound 11): MS obsd. ($ESI^+$): 304.2 [$(M+H)^+$].

Examples 12 and 13—Compounds 12 and 13: (S)-6-(azetidin-1-yl)-8,8-difluoro-2-(1H-pyrazol-4-yl)-6,7,8,9-tetrahydrothieno[2,3-c]quinolin-4(5H)-one (Compound 12) & (R)-6-(azetidin-1-yl)-8,8-difluoro-2-(1H-pyrazol-4-yl)-6,7,8,9-tetrahydrothieno[2,3-c]quinolin-4(5H)-one (Compound 13) (Stereochemistry is Arbitrarily Assigned)

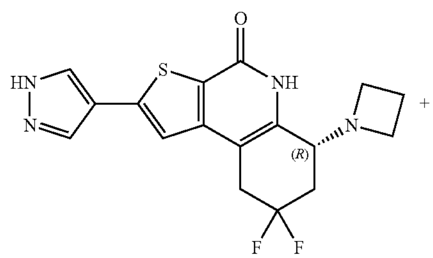

+

Compound 12

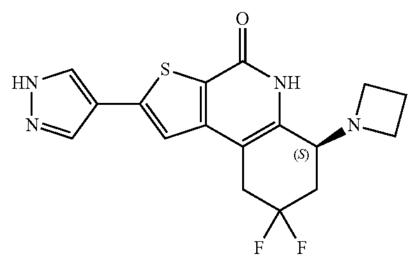

Compound 13

Step A: 5,5-difluoro-2,2-dimethoxy-cyclohexanol

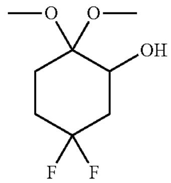

4,4-Difluorocyclohexanone (4.0 g, 30 mmol, 1.0 eq.) and KOH (4.0 g, 72 mmol, 3.0 eq.) were dissolved in MeOH (80.0 mL). The mixture was cooled to 0° C., and a solution of 12 (8.3 g, 33 mmol, 1.1 eq. in 100.0 mL MeOH) was added dropwise over 1 h. The reaction was stirred at room temperature for 18 h, concentrated in vacuo, and the oil was suspended in 80 mL of DCM. The precipitate was filtered off and the solution was concentrated to afford crude 5,5-difluoro-2,2-dimethoxy-cyclohexanol (4.2 g, crude).

Step B: (((5,5-difluoro-2,2-dimethoxycyclohexyl)oxy)methyl)benzene

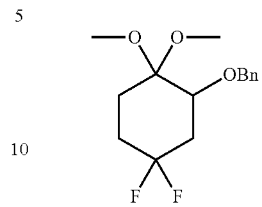

Sodium hydride (610 mg, 15 mmol, 60% in mineral oil, 1.2 eq.) was added to a solution of BnBr (2.8 g, 17 mmol, 1.3 eq.) in DMF (30.0 mL) at 0° C. After 30 min, 5,5-difluoro-2,2-dimethoxy-cyclohexanol (2.5 g crude, 13 mmol, 1.0 eq.) was added, and the mixture was stirred for 16 h at rt. The mixture was poured into water and extracted by EtOAc (15 mL×2). The organic layer was dried, filtered, concentrated and purified by column chromatography ($Si_2O$, 0-12% EtOAc in PE) to afford (((5,5-difluoro-2,2-dimethoxycyclohexyl)oxy)methyl)benzene (3.2 g, 64%). $^1H$ NMR (400 MHz, $CDCl_3$) δ ppm: 7.37-7.25 (m, 5H), 4.72 (d, J=12.0 Hz, 1H), 4.56 (d, J=12.0 Hz, 1H), 3.70 (t, J=8.0 Hz, 1H), 3.24 (s, 3H), 3.22 (s, 3H), 2.38-2.35 (m, 1H), 2.11-1.74 (m, 5H).

Step C: 2-(benzyloxy)-4,4-difluorocyclohexan-1-one

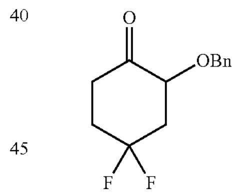

To a solution of (((5,5-difluoro-2,2-dimethoxycyclohexyl)oxy)methyl)benzene (2.2 g, 7.7 mmol, 1.0 eq.) in acetone (60.0 mL) was added 12 (195 mg, 768 μmol, 0.1 eq.). After 30 min, $Na_2S_2O_3$ (sat. aq.) was added, and the aqueous phase was extracted with DCM (15 mL×3). The combined organic phases were washed with $Na_2S_2O_3$ (sat. aq.), filtered and concentrated. Purification by column chromatography ($SiO_2$, 0-8% EtOAc in PE) afforded 2-(benzyloxy)-4,4-difluorocyclohexan-1-one (1.3 g, 70%). $^1H$ NMR (400 MHz, $CDCl_3$): δ ppm: 7.36-7.25 (m, 5H), 4.85 (d, J=11.2 Hz, 1H), 4.51 (d, J=11.2 Hz, 1H), 4.15-4.11 (m, 1H), 2.75-2.14 (m, 6H).

Step D: 6-(benzyloxy)-8,8-difluoro-2-(1-((2-(trimethylsilyl)ethoxy)methyl)-1H-pyrazol-4-yl)-6,7,8,9-tetrahydro-4H-thieno[2,3-c]chromen-4-one

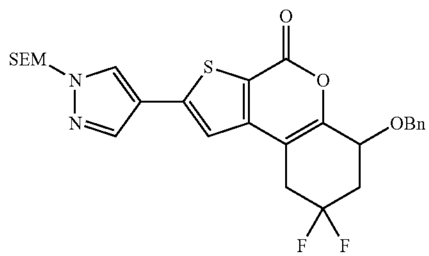 [SMILES: C[Si](C)(C)CCOCn1cc(-c2cc3c4c(oc(=O)c3s2)C(OCc2ccccc2)CC(F)(F)C4)cn1]

To a solution of methyl 3-bromo-5-[1-(2-trimethylsilylethoxymethyl)pyrazol-4-yl]thiophene-2-carboxylate (400 mg, 960 μmol, 1.0 eq.) and 2-(benzyloxy)-4,4-difluorocyclohexan-1-one (460 mg, 1.9 mmol, 2.0 eq.) in toluene (80.0 mL) was added $Cs_2CO_3$ (940 mg, 2.9 mmol, 3.0 eq.), $Pd_2(dba)_3$ (180 mg, 190 μmol, 0.2 eq.), Xantphos (170 mg, 270 μmol, 0.3 eq.) and $Na_2S_2O_5$ (54 mg, 290 μmol, 0.3 eq.). The mixture was stirred and heated at 105° C. for 16 h. The mixture was cooled, filtered and concentrated, and the residue purified by silica gel chromatography ($SiO_2$, 0-28% EtOAc in PE) afforded 6-(benzyloxy)-8,8-difluoro-2-(1-((2-(trimethylsilyl)ethoxy)methyl)-1H-pyrazol-4-yl)-6,7,8,9-tetrahydro-4H-thieno[2,3-c]chromen-4-one (360 mg, 55%). MS obsd. ($ESI^+$): 545.3 [$(M+H)^+$].

Step E: 6-(benzyloxy)-8,8-difluoro-2-(1-((2-(trimethylsilyl)ethoxy)methyl)-1H-pyrazol-4-yl)-6,7,8,9-tetrahydrothieno[2,3-c]quinolin-4(5H)-one

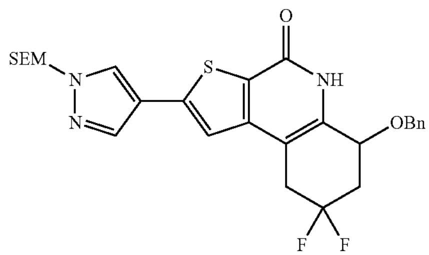 [SMILES: C[Si](C)(C)CCOCn1cc(-c2cc3c4c([nH]c(=O)c3s2)C(OCc2ccccc2)CC(F)(F)C4)cn1]

To a solution of 6-(benzyloxy)-8,8-difluoro-2-(1-((2-(trimethylsilyl)ethoxy)methyl)-1H-pyrazol-4-yl)-6,7,8,9-tetrahydro-4H-thieno[2,3-c]chromen-4-one (150 mg, 200 μmol, 1.0 eq.) in MeOH (8.0 mL) was added aqueous ammonia (30% w/w, 8.0 mL). The mixture was heated in a microwave reactor at 95° C. for 8 h then cooled. The mixture was extracted with DCM (10 mL×3) and the combined organic phases were dried over sodium sulfate, filtered, and concentrated. Purification by column chromatography ($SiO_2$, 0-4% MeOH in DCM) gave 6-(benzyloxy)-8,8-difluoro-2-(1-((2-(trimethylsilyl)ethoxy)methyl)-1H-pyrazol-4-yl)-6,7,8,9-tetrahydrothieno[2,3-c]quinolin-4(5H)-one (90 mg, 69%). MS obsd. ($ESI^+$): 544.4 [$(M+H)^+$].

Step F: 8,8-difluoro-6-hydroxy-2-(1H-pyrazol-4-yl)-6,7,8,9-tetrahydrothieno[2,3-c]quinolin-4(5H)-one

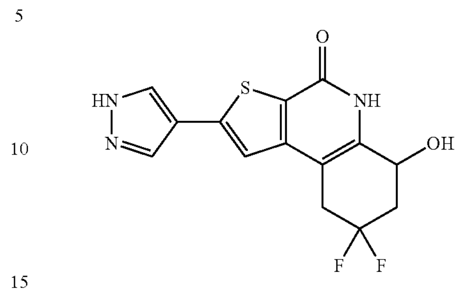

A solution of 6-(benzyloxy)-8,8-difluoro-2-(1-((2-(trimethylsilyl)ethoxy)methyl)-1H-pyrazol-4-yl)-6,7,8,9-tetrahydrothieno[2,3-c]quinolin-4(5H)-one (200 mg, 367 μmol, 1.0 eq.) in DCM (12.0 mL) was cooled to 0° C. and $BCl_3$ (1 M in n-hexane, 3.68 mL, 3.68 mmol, 10 eq.) was added. After 1 h at 0° C., MeOH (3.0 mL) was added, and the solution was concentrated to afford a solid. Trituration (1:1 n-hexane/MeOH) afforded 8,8-difluoro-6-hydroxy-2-(1H-pyrazol-4-yl)-6,7,8,9-tetrahydrothieno[2,3-c]quinolin-4(5H)-one (110 mg, 92% yield) of sufficient purity for the following step. MS obsd. ($ESI^+$): 324.1 [$(M+H)^+$].

Step G: (R)-6-(azetidin-1-yl)-8,8-difluoro-2-(1H-pyrazol-4-yl)-6,7,8,9-tetrahydrothieno[2,3-c]quinolin-4(5H)-one (Compound 12) and (S)-6-(azetidin-1-yl)-8,8-difluoro-2-(1H-pyrazol-4-yl)-6,7,8,9-tetrahydrothieno[2,3-c]quinolin-4(5H)-one (Compound 13)

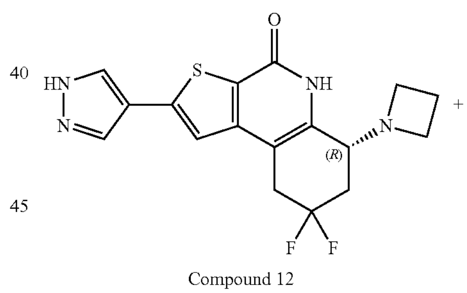

+

Compound 12

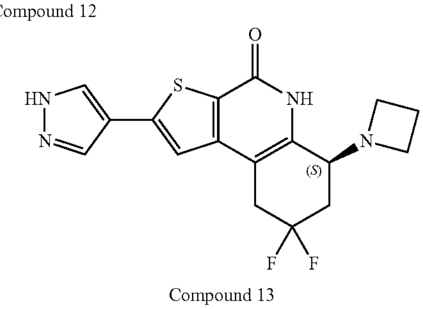

Compound 13

To 8,8-difluoro-6-hydroxy-2-(1H-pyrazol-4-yl)-6,7,8,9-tetrahydrothieno[2,3-c]quinolin-4(5H)-one (70 mg, 190 μmol, 1.0 eq.) was slowly added $SOCl_2$ (2.5 g, 21 mmol, 1.5 mL, 11 eq.) at rt. After 4 h, the mixture was concentrated. The concentrate, which contained 6-chloro-8,8-difluoro-2-(1H-pyrazol-4-yl)-5,6,7,9-tetrahydrothieno[2,3-c]quinolin-4-one was dissolved in MeCN (3.0 mL), and KI (241 mg, 1.45 mmol, 10.0 eq.) and azetidine (170 mg, 2.9 mmol, 20. eq.) were added. The mixture was stirred for 12 h at rt before being concentrated and purified via reverse-phase chromatography to afford 6-(azetidin-1-yl)-8,8-difluoro-2-(1H-pyrazol-4-yl)-6,7,8,9-tetrahydrothieno[2,3-c]quinolin-4(5H)-one (34 mg, 55%, 85% purity). MS obsd. ($ESI^+$): 363.3 $[(M+H)^+]$.

The individual enantiomers were separated via chiral SFC. (R)-6-(azetidin-1-yl)-8,8-difluoro-2-(1H-pyrazol-4-yl)-6,7,8,9-tetrahydrothieno[2,3-c]quinolin-4(5H)-one (Compound 12): MS obsd. ($ESI^+$): 363.4 $[(M+H)^+]$. (S)-6-(azetidin-1-yl)-8,8-difluoro-2-(1H-pyrazol-4-yl)-6,7,8,9-tetrahydrothieno[2,3-c]quinolin-4(5H)-one (Compound 13): MS obsd. ($ESI^+$): 363.3 $[(M+H)^+]$.

Examples 14 and 15—Compounds 14 and 15: (S)-8,8-difluoro-6-(hydroxymethyl)-6-methyl-2-(1H-pyrazol-4-yl)-6,7,8,9-tetrahydrothieno[2,3-c]quinolin-4(5H)-one (Compound 14) & (R)-8,8-difluoro-6-(hydroxymethyl)-6-methyl-2-(1H-pyrazol-4-yl)-6,7,8,9-tetrahydrothieno[2,3-c]quinolin-4(5H)-one (Compound 15) (Stereochemistry is Arbitrarily Assigned)

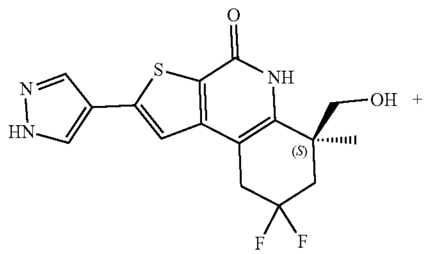

+

Compound 14

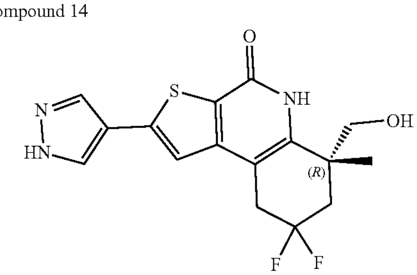

Compound 15

Step A: methyl 5,5-difluoro-2-hydroxycyclohex-1-ene-1-carboxylate

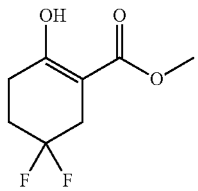

A solution of 4,4-difluorocyclohexanone (2.0 g, 15 mmol, 1.0 eq.) in DMF (4.0 mL) was added to a 0° C. suspension of NaH (430 mg, 18 mmol, 60% in mineral oil, 1.2 eq.) in DMF (13.0 mL). After 30 min at 0° C., a solution of dimethyl carbonate (1.6 g, 18 mmol, 1.5 mL, 1.2 eq.) in DMF (3.0 mL) was added and the mixture was stirred at rt for 16 h before addition of $NH_4Cl$ (sat. aq.). The mixture was diluted with water (10 mL) and extracted with DCM (20 mL×3). The combined organic layers were dried ($Na_2SO_4$), concentrated in vacuo, and purified by column chromatography ($SiO_2$, 0-8% EtOAc in PE) to afford methyl 5,5-difluoro-2-hydroxycyclohex-1-ene-1-carboxylate (2.0 g, 70%). $^1H$ NMR (400 MHz, $CDCl_3$) δ ppm: 12.17 (s, 1H), 3.78 (s, 3H), 2.74 (t, J=14.4 Hz, 2H), 2.55 (t, J=6.8 Hz, 2H), 2.17-2.07 (m, 2H).

Step B: methyl 5,5-difluoro-1-methyl-2-oxocyclohexane-1-carboxylate

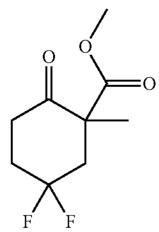

To a flask containing of methyl 5,5-difluoro-2-hydroxycyclohex-1-ene-1-carboxylate (1.0 g, 6.4 mmol, 1.0 eq.) in acetone (12.0 mL) was added $K_2CO_3$ (2.7 g, 19 mmol, 3.0 eq.) and iodomethane (2.7 g, 19 mmol, 3.0 eq.) at room temperature. The mixture was heated to 50° C. and stirred for 3 h before water was added. The mixture was extracted with t-butyl methyl ether (30 mL×3), and the combined organic layers were washed with water, brine, and dried ($Na_2SO_4$). Filtration, concentration in vacuo, and purification by column chromatography ($SiO_2$, 0-15% EtOAc in PE) afforded methyl 5,5-difluoro-1-methyl-2-oxocyclohexane-1-carboxylate (800 mg, 66%). $^1H$ NMR (400 MHz, $CDCl_3$) δ ppm: 3.76 (s, 3H), 3.09-2.88 (m, 2H), 2.61-2.54 (m, 1H), 2.46-2.35 (m, 1H), 2.26-1.98 (m, 2H), 1.37 (d, J=0.8 Hz, 3H).

Step C: methyl 8,8-difluoro-6-methyl-4-oxo-2-(1-((2-(trimethylsilyl)ethoxy)methyl)-1H-pyrazol-4-yl)-6,7,8,9-tetrahydro-4H-thieno[2,3-c]chromene-6-carboxylate

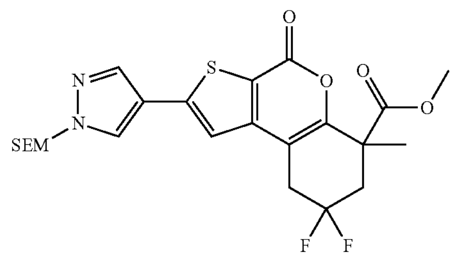 [SMILES: COC(=O)C1(C)CC(F)(F)Cc2c1oc(=O)c1sc(-c3cnn(COCC[Si](C)(C)C)c3)cc21]

To a solution of methyl 3-iodo-5-(1-((2-(trimethylsilyl)ethoxy)methyl)-1H-pyrazol-4-yl)thiophene-2-carboxylate (200 mg, 430 μmol, 1.0 eq.) and methyl 5,5-difluoro-1-methyl-2-oxocyclohexane-1-carboxylate (180 mg, 860 μmol, 2.0 eq.) in toluene (12.0 mL) was added $Cs_2CO_3$ (420 mg, 1.3 mmol, 3.0 eq.), $Pd_2(dba)_3$ (79 mg, 86 μmol, 0.2 eq.), Xantphos (74 mg, 130 μmol, 0.30 eq.) and $Na_2S_2O_5$ (16 mg, 86 μmol, 0.2 eq.). The mixture was heated in a microwave reactor to 105° C. for 2 h before being cooled, concentrated, and purified ($SiO_2$, 0-32% EtOAc in PE). The material was further purified via reverse-phase chromatography to give methyl 8,8-difluoro-6-methyl-4-oxo-2-(1-((2-(trimethylsilyl)ethoxy)methyl)-1H-pyrazol-4-yl)-6,7,8,9-tetrahydro-4H-thieno[2,3-c]chromene-6-carboxylate (100 mg, 46%). MS obsd. ($ESI^+$): 511.4 [$(M+H)^+$].

Step D: 8,8-difluoro-6-(hydroxymethyl)-6-methyl-2-(1-((2-(trimethylsilyl)ethoxy)methyl)-1H-pyrazol-4-yl)-6,7,8,9-tetrahydro-4H-thieno[2,3-c]chromen-4-one

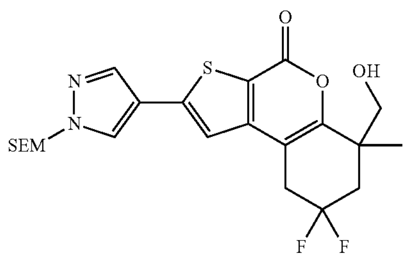 [SMILES: CC1(CO)CC(F)(F)Cc2c1oc(=O)c1sc(-c3cnn(COCC[Si](C)(C)C)c3)cc21]

eq.) To a cooled (0° C.) solution of methyl 8,8-difluoro-6-methyl-4-oxo-2-(1-((2-(trimethylsilyl)ethoxy)methyl)-1H-pyrazol-4-yl)-6,7,8,9-tetrahydro-4H-thieno[2,3-c]chromene-6-carboxylate (100 mg, 200 μmol, 1.0 eq.) in EtOH (12.0 mL) was added $CaCl_2$ (45 mg, 410 μmol, 2.0 eq.). After 10 min, $NaBH_4$ (116 mg, 3.08 mmol, 15.0 eq.) was added, and the ice bath was removed. The mixture was stirred for 20 min at rt before being cooled to 0° C. and $NH_4Cl$ (sat. aq.) was added. The mixture was extracted with DCM (10 mL×3) and the combined organic phases were dried ($Na_2SO_4$), filtered, and concentrated. Purification by column chromatography ($SiO_2$ 0-70% EtOAc in PE) afforded 8,8-difluoro-6-(hydroxymethyl)-6-methyl-2-(1-((2-(trimethylsilyl)ethoxy)methyl)-1H-pyrazol-4-yl)-6,7,8,9-tetrahydro-4H-thieno[2,3-c]chromen-4-one (55 mg, 48%). MS obsd. ($ESI^+$): 483.4 [$(M+H)^+$].

Step E: 8,8-difluoro-6-(hydroxymethyl)-6-methyl-2-(1-((2-(trimethylsilyl)ethoxy)methyl)-1H-pyrazol-4-yl)-6,7,8,9-tetrahydrothieno[2,3-c]quinolin-4(5H)-one

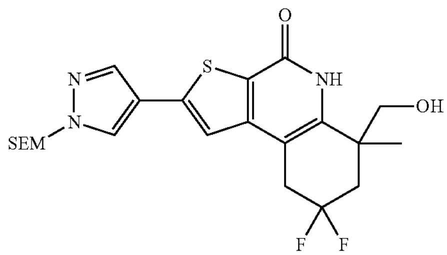 [SMILES: CC1(CO)CC(F)(F)Cc2c1[nH]c(=O)c1sc(-c3cnn(COCC[Si](C)(C)C)c3)cc21]

To a solution of 8,8-difluoro-6-(hydroxymethyl)-6-methyl-2-(1-((2-(trimethylsilyl)ethoxy)methyl)-1H-pyrazol-4-yl)-6,7,8,9-tetrahydro-4H-thieno[2,3-c]chromen-4-one (98 mg, 200 μmol, 1.0 eq.) in MeOH (5.0 mL) was added aqueous ammonia (5.0 mL, 30% w/w). The mixture was heated in a microwave reactor to 95° C. for 8 h. The mixture was concentrated and purified by column chromatography ($SiO_2$ 0-7% MeOH in DCM) to give 8,8-difluoro-6-(hydroxymethyl)-6-methyl-2-(1-((2-(trimethylsilyl)ethoxy)methyl)-1H-pyrazol-4-yl)-6,7,8,9-tetrahydrothieno[2,3-c]quinolin-4(5H)-one (68 mg, 56%). MS obsd. ($ESI^+$): 482.4 [$(M+H)^+$].

Step F: (S)-8,8-difluoro-6-(hydroxymethyl)-6-methyl-2-(1H-pyrazol-4-yl)-6,7,8,9-tetrahydrothieno[2,3-c]quinolin-4(5H)-one (Compound 14) and (R)-8,8-difluoro-6-(hydroxymethyl)-6-methyl-2-(1H-pyrazol-4-yl)-6,7,8,9-tetrahydrothieno[2,3-c]quinolin-4(5H)-one (Compound 15)

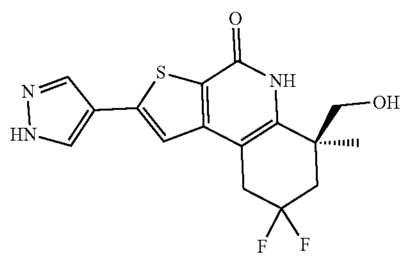

+

Compound 14

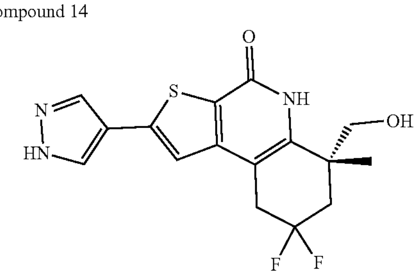

Compound 15

To a cooled (0° C.) solution of 8,8-difluoro-6-(hydroxymethyl)-6-methyl-2-(1-((2-(trimethylsilyl)ethoxy)methyl)-1H-pyrazol-4-yl)-6,7,8,9-tetrahydrothieno[2,3-c]quinolin-4(5H)-one (43 mg, 89 μmol) in DCM (4.0 mL) was added Trifluoroacetic acid (2.0 mL). The mixture was warmed to rt and stirred for 2 h before being concentrated in vacuo and purified by reverse phase chromatography to afford 8,8-difluoro-6-(hydroxymethyl)-6-methyl-2-(1H-pyrazol-4-yl)-6,7,8,9-tetrahydrothieno[2,3-c]quinolin-4(5H)-one (22 mg, 69%). MS obsd. ($ESI^+$): 352.0 [$(M+H)^+$]; $^1H$ NMR (400 MHz, DMSO-d6): δ ppm 13.22 (s, 1H), 10.86 (s, 1H), 8.28 (s, 1H), 7.98 (s, 1H), 7.53 (s, 1H), 5.23 (s, 1H), 3.84 (d, J=10.8 Hz, 1H), 3.41 (d, J=10.4 Hz, 1H), 3.29-3.13 (m, 2H), 2.58-2.46 (m, 1H), 2.03-1.94 (m, 1H), 1.30 (s, 3H).

The individual enantiomers were separated via chiral SFC to afford each enantiomer. (S)-8,8-difluoro-6-(hydroxymethyl)-6-methyl-2-(1H-pyrazol-4-yl)-6,7,8,9-tetrahydrothieno[2,3-c]quinolin-4(5H)-one (Compound 14): MS obsd. ($ESI^+$): 352.1 [$(M+H)^+$]. (R)-8,8-difluoro-6-(hydroxymethyl)-6-methyl-2-(1H-pyrazol-4-yl)-6,7,8,9-tetrahydrothieno[2,3-c]quinolin-4(5H)-one (Compound 15): MS obsd. ($ESI^+$): 352.1 [$(M+H)^+$].

Examples 16 and 17—Compounds 16 and 17: (S)-4-hydroxy-4-isopropyl-8-(1H-pyrazol-4-yl)-1,3,4,5-tetrahydro-6H-pyrano[4,3-b]thieno[3,2-d]pyridin-6-one (Compound 16) and (R)-4-hydroxy-4-isopropyl-8-(1H-pyrazol-4-yl)-1,3,4,5-tetrahydro-6H-pyrano[4,3-b]thieno[3,2-d]pyridin-6-one (Compound 17)

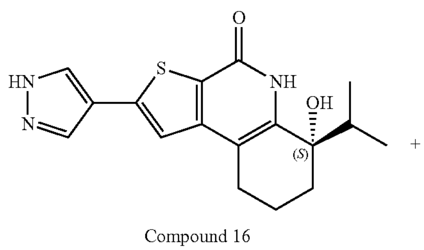

+

Compound 16

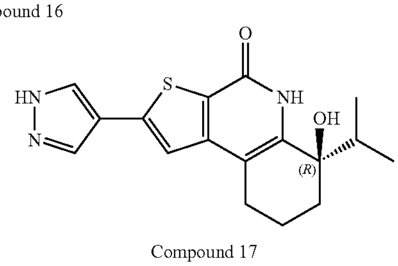

Compound 17

Step A: 4-(benzyloxy)-8-(1-((2-(trimethylsilyl)ethoxy)methyl)-1H-pyrazol-4-yl)-3,4-dihydro-1H,6H-pyrano[4,3-b]thieno[3,2-d]pyran-6-one

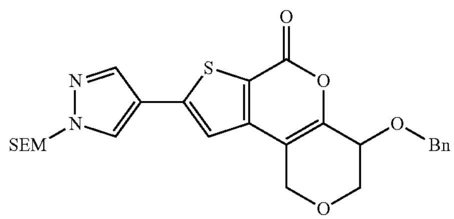 [SMILES: C[Si](C)(C)CCOCn1cc(-c2cc3c4c(oc(=O)c3s2)C(OCc2ccccc2)COC4)cn1]

To a solution of methyl 3-bromo-5-(1-((2-(trimethylsilyl)ethoxy)methyl)-1H-pyrazol-4-yl)thiophene-2-carboxylate (5.0 g, 12 mmol, 1.0 eq.) and 3-(benzyloxy)tetrahydro-4H-pyran-4-one (4.9 g, 24 mmol, 2.0 eq.) in 1,4-dioxane (600 mL) was added $Na_2S_2O_5$ (228 mg, 1.20 mmol, 0.1 eq.), $Cs_2CO_3$ (12 g, 36 mmol, 3.0 eq.), $Pd_2(dba)_3$ (2.19 g, 2.40 mmol, 0.20 eq.) and Xantphos (2.8 g, 4.8 mmol, 0.40 eq.). The mixture was degassed with $N_2$ twice then stirred and heated at 100° C. for 16 h. The mixture was filtered and concentrated in vacuo, and purified by flash column chromatography ($SiO_2$, 0-60% EtOAc in PE) to give 4-(benzyloxy)-8-(1-((2-(trimethylsilyl)ethoxy)methyl)-1H-pyrazol-4-yl)-3,4-dihydro-1H,6H-pyrano[4,3-b]thieno[3,2-d]pyran-6-one (3.5 g, 38% yield, 81% purity). MS obsd. ($ESI^+$): 511.5 [$(M+H)^+$].

Step B: 4-(benzyloxy)-8-(1-((2-(trimethylsilyl)ethoxy)methyl)-1H-pyrazol-4-yl)-1,3,4,5-tetrahydro-6H-pyrano[4,3-b]thieno[3,2-d]pyridin-6-one

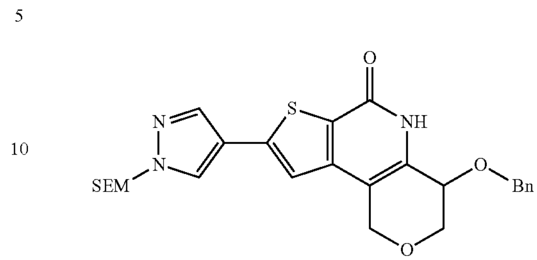

A solution of 4-(benzyloxy)-8-(1-((2-(trimethylsilyl)ethoxy)methyl)-1H-pyrazol-4-yl)-3,4-dihydro-1H,6H-pyrano[4,3-b]thieno[3,2-d]pyran-6-one (1.00 g, 1.6 mmol, 81% purity, 1.0 eq.) and $NH_4OH$ (6 mL) in MeOH (6.0 mL) was stirred at 100° C. for 6 h with microwave heating. The mixture was concentrated in vacuo to give the residue, which was purified by flash column chromatography ($SiO_2$, 0-10% MeOH in DCM) to give 4-(benzyloxy)-8-(1-((2-(trimethylsilyl)ethoxy)methyl)-1H-pyrazol-4-yl)-1,3,4,5-tetrahydro-6H-pyrano[4,3-b]thieno[3,2-d]pyridin-6-one (560 mg, 68%). MS obsd. ($ESI^+$): 510.2 [$(M+H)^+$].

Step C: 4-hydroxy-8-(1H-pyrazol-4-yl)-1,3,4,5-tetrahydro-6H-pyrano[4,3-b]thieno[3,2-d]pyridin-6-one

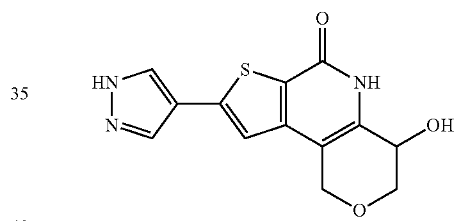

To a solution of 4-(benzyloxy)-8-(1-((2-(trimethylsilyl)ethoxy)methyl)-1H-pyrazol-4-yl)-1,3,4,5-tetrahydro-6H-pyrano[4,3-b]thieno[3,2-d]pyridin-6-one (300 mg, 590 μmol, 1.0 eq.) in DCM (2.0 mL) was added and $BCl_3$ (1 M in hexane, 5.9 mL, 10 eq.). The mixture was stirred at 0° C. for 15 min then concentrated in vacuo to afford 4-hydroxy-8-(1H-pyrazol-4-yl)-1,3,4,5-tetrahydro-6H-pyrano[4,3-b]thieno[3,2-d]pyridin-6-one (170 mg, crude) which was used in the next reaction without further purification. MS obsd. ($ESI^+$): 290.0 [$(M+H)^+$].

Step D: Tert-butyl 4-(4-hydroxy-6-oxo-3,4,5,6-tetrahydro-1H-pyrano[4,3-b]thieno[3,2-d]pyridin-8-yl)-1H-pyrazole-1-carboxylate

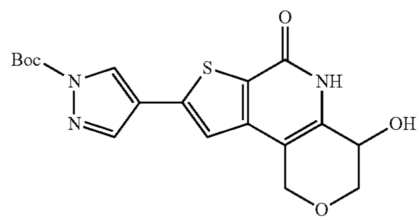 [SMILES: CC(C)(C)OC(=O)n1cc(-c2cc3c4c([nH]c(=O)c3s2)C(O)COC4)cn1]

To a suspension of 4-hydroxy-8-(1H-pyrazol-4-yl)-1,3,4,5-tetrahydro-6H-pyrano[4,3-b]thieno[3,2-d]pyridin-6-one (170 mg, crude) in DMF (2.0 mL) was added trimethylamine (119 mg, 1.18 mmol, 2.0 eq.), DMAP (36 mg, 290 μmol, 0.5 eq.) and $(Boc)_2O$ (130 mg, 590 μmol, 1.0 eq.). The mixture was stirred at room temperature for 10 min then poured into water and extracted by EtOAc/THF (10:1, 15 mL×2). The combined organic layers were dried, filtered, concentrated and purified by flash column chromatography ($SiO_2$, 0-10% MeOH in DCM) to afford tert-butyl 4-(4-hydroxy-6-oxo-3,4,5,6-tetrahydro-1H-pyrano[4,3-b]thieno[3,2-d]pyridin-8-yl)-1H-pyrazole-1-carboxylate (130 mg, 56% over 2 steps). MS obsd. ($ESI^+$): 390.0 [$(M+H)^+$].

Step E: Tert-butyl 4-(4,6-dioxo-3,4,5,6-tetrahydro-1H-pyrano[4,3-b]thieno[3,2-d]pyridin-8-yl)-1H-pyrazole-1-carboxylate

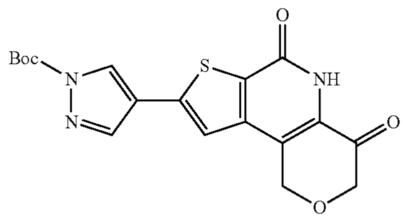 [SMILES: CC(C)(C)OC(=O)n1cc(-c2cc3c4c([nH]c(=O)c3s2)C(=O)COC4)cn1]

Dess-Martin Periodinane (425 mg, 1.00 mmol, 3.0 eq.) was added to a solution of tert-butyl 4-(4-hydroxy-6-oxo-3,4,5,6-tetrahydro-1H-pyrano[4,3-b]thieno[3,2-d]pyridin-8-yl)-1H-pyrazole-1-carboxylate (130 mg, 334 μmol, 1.0 eq.) in DCM (3.0 mL) and DMF (3.0 mL) at 0° C. The mixture was stirred at room temperature for 2 h, then saturated $Na_2S_2O_3$ (aq) and $NaHCO_3$ (aq) was added along with water (10 mL). The mixture was extracted with DCM/MeOH (10:1, 20 mL×3), and the combined organic layers were dried, filtered, concentrated and purified by flash column chromatography ($SiO_2$, 0-10% MeOH in DCM) to give tert-butyl 4-(4,6-dioxo-3,4,5,6-tetrahydro-1H-pyrano[4,3-b]thieno[3,2-d]pyridin-8-yl)-1H-pyrazole-1-carboxylate (70 mg, 54%). MS obsd. ($ESI^+$): 388.0 [$(M+H)^+$].

Step F: (S)-4-hydroxy-4-isopropyl-8-(1H-pyrazol-4-yl)-1,3,4,5-tetrahydro-6H-pyrano[4,3-b]thieno[3,2-d]pyridin-6-one (Compound 16) and (R)-4-hydroxy-4-isopropyl-8-(1H-pyrazol-4-yl)-1,3,4,5-tetrahydro-6H-pyrano[4,3-b]thieno[3,2-d]pyridin-6-one (Compound 17)

Compound 16

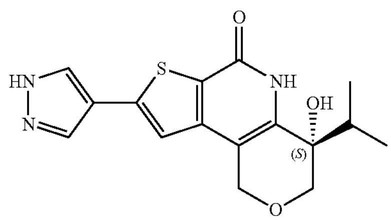

-continued

Compound 17

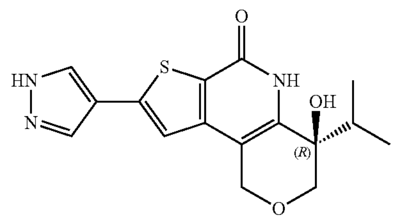

To a solution of tert-butyl 4-(4,6-dioxo-3,4,5,6-tetrahydro-1H-pyrano[4,3-b]thieno[3,2-d]pyridin-8-yl)-1H-pyrazole-1-carboxylate (1.96 g, 5.06 mmol, 1.0 eq.) in anhydrous THF (6.0 mL) was added i-PrMgCl—LiCl (1.3 M in THF, 80 mL, 20 eq.). The mixture was stirred at 0° C. for 30 min, then quenched by saturated aqueous $NH_4Cl$ and extracted by EtOAc/THF (10:1, 30 mL×2). The combined organic layers were dried, filtered, concentrated and purified by flash column chromatography ($SiO_2$, 0-10% MeOH in DCM) to afford racemic 4-hydroxy-4-isopropyl-8-(1H-pyrazol-4-yl)-1,3,4,5-tetrahydro-6H-pyrano[4,3-b]thieno[3,2-d]pyridin-6-one (680 mg, 41%). MS obsd. ($ESI^+$): 332.0 [$(M+H)^+$].

The individual enantiomers were separated via chiral SFC. (S)-4-hydroxy-4-isopropyl-8-(1H-pyrazol-4-yl)-1,3,4,5-tetrahydro-6H-pyrano[4,3-b]thieno[3,2-d]pyridin-6-one (Compound 16): MS obsd. ($ESI^+$): 332.0 [$(M+H)^+$]; $^1H$ NMR (400 MHz, DMSO-d6): δ ppm: 13.22 (s, 1H), 10.81 (s, 1H), 8.29 (s, 1H), 7.96 (s, 1H), 7.41 (s, 1H), 5.25 (s, 1H), 4.67 (s, 2H), 3.96 (d, J=11.6 Hz, 1H), 3.53 (d, J=11.6 Hz, 1H), 2.41-2.34 (m, 1H), 1.00 (d, J=6.8 Hz, 3H), 0.76 (d, J=6.8 Hz, 3H). (R)-4-hydroxy-4-isopropyl-8-(1H-pyrazol-4-yl)-1,3,4,5-tetrahydro-6H-pyrano[4,3-b]thieno[3,2-d]pyridin-6-one (Compound 17): MS obsd. ($ESI^+$): 332.0 [$(M+H)^+$].

Examples 18 and 19—Compounds 18 and 19: (S)-4-ethyl-4-hydroxy-8-(1H-pyrazol-4-yl)-1,3,4,5-tetrahydro-6H-pyrano[4,3-b]thieno[3,2-d]pyridin-6-one (Compound 18) & (R)-4-ethyl-4-hydroxy-8-(1H-pyrazol-4-yl)-1,3,4,5-tetrahydro-6H-pyrano[4,3-b]thieno[3,2-d]pyridin-6-one (Compound 19)

Compound 18

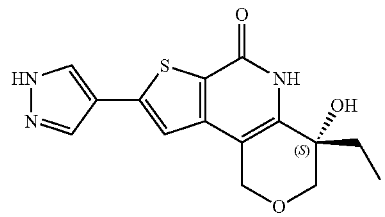

Compound 19

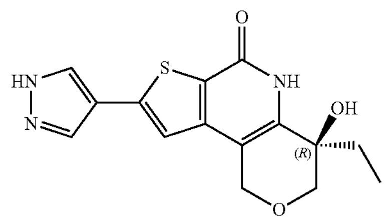

To a solution of tert-butyl 4-(4,6-dioxo-3,4,5,6-tetrahydro-1H-pyrano[4,3-b]thieno[3,2-d]pyridin-8-yl)-1H-pyrazole-1-carboxylate (180 mg, 460 μmol) in anhydrous THF (2.0 mL) was added EtMgCl (2 M in THF, 12.0 mL, 52 eq.), and the mixture was stirred at 0° C. for 1 h. The mixture was quenched by saturated $NH_4Cl$ (aq) and extracted with EtOAc:THF (10:1, 30 mL×2). The combined organic layers were dried, filtered, concentrated and purified by flash column chromatography ($SiO_2$, 0-10% MeOH in DCM) to afford racemic 4-ethyl-4-hydroxy-8-(1H-pyrazol-4-yl)-1,3,4,5-tetrahydro-6H-pyrano[4,3-b]thieno[3,2-d]pyridin-6-one (60 mg, 41%). MS obsd. ($ESI^+$): 318.1 [$(M+H)^+$].

The individual enantiomers were separated via chiral SFC. (S)-4-ethyl-4-hydroxy-8-(1H-pyrazol-4-yl)-1,3,4,5-tetrahydro-6H-pyrano[4,3-b]thieno[3,2-d]pyridin-6-one (Compound 18): MS obsd. ($ESI^+$): 318.0 [$(M+H)^+$]; $^1H$ NMR (400 MHz, DMSO-d6) δ ppm: 13.22 (s, 1H), 10.88 (s, 1H), 8.29 (s, 1H), 7.95 (s, 1H), 7.40 (s, 1H), 5.28 (s, 1H), 4.86-4.49 (m, 2H), 3.85 (d, J=11.2 Hz, 1H), 3.54 (d, J=11.2 Hz, 1H), 2.00-1.79 (m, 2H), 0.85 (t, J=7.6 Hz, 3H). (R)-4-ethyl-4-hydroxy-8-(1H-pyrazol-4-yl)-1,3,4,5-tetrahydro-6H-pyrano[4,3-b]thieno[3,2-d]pyridin-6-one (Compound 19): MS obsd. ($ESI^+$): 318.0 [$(M+H)^+$].

Examples 20 and 21—Compounds 20 and 21: (S)-4-(tert-butyl)-4-hydroxy-8-(1H-pyrazol-4-yl)-3,4-dihydro-1H-pyrano[4,3-b]thieno[3,2-d]pyridin-6(5H)-one (Compound 20) & (R)-4-(tert-butyl)-4-hydroxy-8-(1H-pyrazol-4-yl)-3,4-dihydro-1H-pyrano[4,3-b]thieno[3,2-d]pyridin-6(5H)-one (Compound 21). (Stereochemistry for Compounds 20 and 21 is Arbitrarily Assigned)

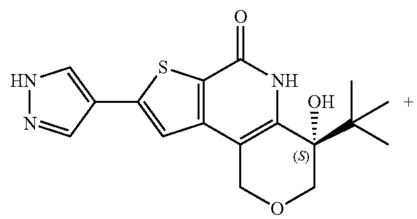

+

Compound 20

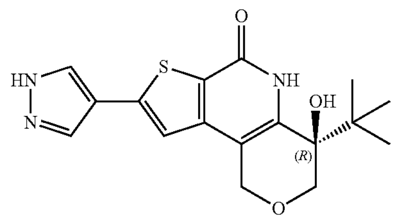

Compound 21

To a solution of tert-butyl 4-(4,6-dioxo-3,4,5,6-tetrahydro-1H-pyrano[4,3-b]thieno[3,2-d]pyridin-8-yl)-1H-pyrazole-1-carboxylate (50 mg, 0.13 mmol, 1.0 eq.) in anhydrous THF (4.0 mL) was added t-BuMgCl (1 M in THF, 3.9 mL, 30 eq.) at 0° C. The mixture was stirred at 0° C. for 0.5 h. The mixture was quenched with saturated aqueous $NH_4Cl$ solution (10 mL) and extracted with EtOAc (20 mL×3). The combined organic layers were washed with brine, dried over anhydrous sodium sulfate, filtered and concentrated under vacuum. The residue was purified by flash column chromatography ($SiO_2$, 0-10% MeOH in DCM) to afford racemic 4-(tert-butyl)-4-hydroxy-8-(1H-pyrazol-4-yl)-3,4-dihydro-1H-pyrano[4,3-b]thieno[3,2-d]pyridin-6(5H)-one (10 mg, 23%). MS obsd. ($ESI^+$): 346.5 [$(M+H)^+$].

The individual enantiomers were separated via chiral SFC. (S)-4-(tert-butyl)-4-hydroxy-8-(1H-pyrazol-4-yl)-3,4-dihydro-1H-pyrano[4,3-b]thieno[3,2-d]pyridin-6(5H)-one (Compound 20): MS obsd. ($ESI^+$): 346.1 [$(M+H)^+$]; $^1H$ NMR (400 MHz, DMSO-$d_6$) δ ppm: 13.23 (s, 1H), 10.02 (s, 1H), 8.29 (s, 1H), 7.97 (s, 1H), 7.40 (s, 1H), 5.32 (s, 1H), 4.80 (m, 2H), 4.14 (d, J=11.6 Hz, 1H), 3.46 (d, J=11.6 Hz, 1H), 1.03 (s, 9H). (R)-4-(tert-butyl)-4-hydroxy-8-(1H-pyrazol-4-yl)-3,4-dihydro-1H-pyrano[4,3-b]thieno[3,2-d]pyridin-6(5H)-one (Compound 21): MS obsd. ($ESI^+$): 346.1 [$(M+H)^+$].

Examples 22 and 23—Compounds 22 and 23: (S)-4-(tert-butyl)-4-hydroxy-8-(pyridin-4-yl)-1,3,4,5-tetrahydro-6H-pyrano[4,3-b]thieno[3,2-d]pyridin-6-one (Compound 22) & (R)-4-(tert-butyl)-4-hydroxy-8-(pyridin-4-yl)-1,3,4,5-tetrahydro-6H-pyrano[4,3-b]thieno[3,2-d]pyridin-6-one (Compound 23) (Stereochemistry for Compounds 22 and 23 is Arbitrarily Assigned)

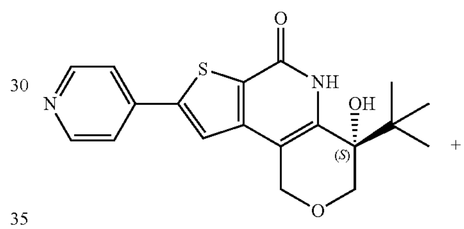

+

Compound 22

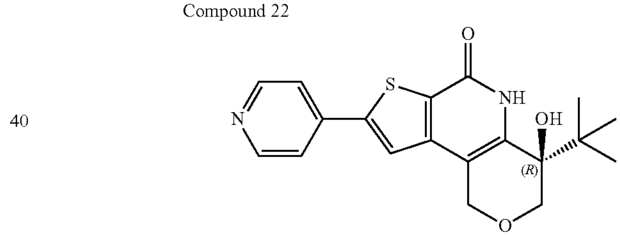

Compound 23

Step A: 4-(benzyloxy)-8-(pyridin-4-yl)-3,4-dihydro-1H,6H-pyrano[4,3-b]thieno[3,2-d]pyran-6-one

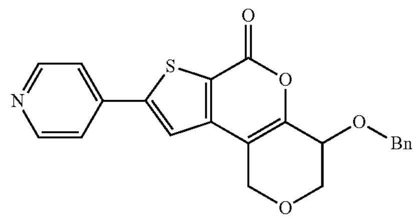 [SMILES: O=c1oc2c(c3cc(-c4ccncc4)sc13)COCC2OCc1ccccc1]

To a solution of methyl 3-bromo-5-(4-pyridyl)thiophene-2-carboxylate (1.0 g, 3.4 mmol, 1.0 eq.) and 3-benzyloxytetrahydropyran-4-one (1.4 g, 6.7 mmol, 2.0 eq.) in toluene (50.0 mL) was added $Cs_2CO_3$ (2.2 g, 6.71 mmol, 2.0 eq.), $Pd_2(dba)_3$ (614 mg, 0.67 mmol, 0.2 eq.), Xantphos (582 mg, 1.01 mmol, 0.3 eq.) and $Na_2S_2O_5$ (64 mg, 0.34 mmol, 0.1 eq.) at room temperature under $N_2$ atmosphere. The mixture was stirred at 105° C. for 16 h, cooled, filtered, and concentrated in vacuo. The residue was purified by flash chromatography ($SiO_2$, 0-10% MeOH in DCM) to afford 4-(benzyloxy)-8-(pyridin-4-yl)-3,4-dihydro-1H,6H-pyrano[4,3-b]thieno[3,2-d]pyran-6-one (457 mg, 32%). MS obsd. ($ESI^+$): 392.1 [$(M+H)^+$].

Step B: 4-(benzyloxy)-8-(pyridin-4-yl)-1,3,4,5-tetrahydro-6H-pyrano[4,3-b]thieno[3,2-d]pyridin-6-one

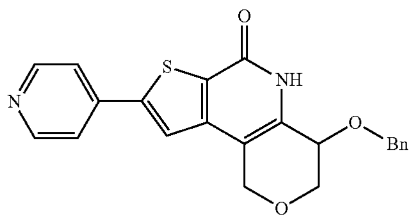 [SMILES: O=c1[nH]c2c(c3cc(-c4ccncc4)sc13)COCC2OCc1ccccc1]

To a solution of 4-(benzyloxy)-8-(pyridin-4-yl)-3,4-dihydro-1H,6H-pyrano[4,3-b]thieno[3,2-d]pyran-6-one (1.0 g, 2.55 mmol, 1.0 eq.) in MeOH (9.0 mL) was added $NH_4OH$ (9.0 mL). The mixture was heated in a microwave reactor at 100° C. for 3 h and monitored by LCMS to completion. The mixture was filtered, and the filter cake was washed with MeOH (50.0 mL) and dried under vacuum to afford 4-(benzyloxy)-8-(pyridin-4-yl)-1,3,4,5-tetrahydro-6H-pyrano[4,3-b]thieno[3,2-d]pyridin-6-one (512 mg, 50%). MS obsd. ($ESI^+$): 391.2 [$(M+H)^+$].

Step C: 4-hydroxy-8-(pyridin-4-yl)-1,3,4,5-tetrahydro-6H-pyrano[4,3-b]thieno[3,2-d]pyridin-6-one

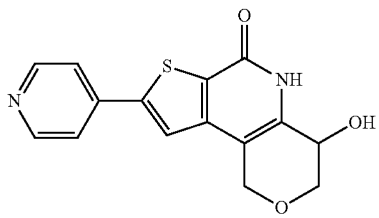 [SMILES: O=c1[nH]c2c(c3cc(-c4ccncc4)sc13)COCC2O]

To a solution of 4-(benzyloxy)-8-(pyridin-4-yl)-1,3,4,5-tetrahydro-6H-pyrano[4,3-b]thieno[3,2-d]pyridin-6-one (475 mg, 1.22 mmol, 1.0 eq.) in DCM (12.0 mL) was added $BCl_3$ (1 M in DCM, 12.2 mL, 10.0 eq.). The mixture was stirred at room temperature for 1 h, then quenched with aq. $NaHCO_3$ (24.0 mL) and diluted with EtOAc (25.0 mL). The mixture was filtered and the filter cake was washed with EtOAc (25.0 mL) and dried under vacuum to afford 4-hydroxy-8-(pyridin-4-yl)-1,3,4,5-tetrahydro-6H-pyrano[4,3-b]thieno[3,2-d]pyridin-6-one (360 mg, 92%). MS obsd. ($ESI^+$): 301.0 [$(M+H)^+$].

Step D: 8-(pyridin-4-yl)-1,5-dihydro-6H-pyrano[4,3-b]thieno[3,2-d]pyridine-4,6(3H)-dione

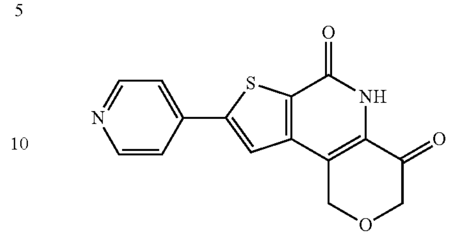

To a solution of 4-hydroxy-8-(pyridin-4-yl)-1,3,4,5-tetrahydro-6H-pyrano[4,3-b]thieno[3,2-d]pyridin-6-one (10 mg, 0.033 mmol, 1.0 eq.) in DCM (1.0 mL) and DMF (1.0 mL) was added Dess-Martin periodinane (140 mg, 0.333 mmol, 10 eq.). The mixture was stirred at room temperature for 2 h then quenched with saturated aqueous $NaHCO_3$ solution (2.0 mL) and extracted with EtOAc (10 mL×2). The combined organic phases were dried over sodium sulfate, filtered and concentrated. The residue was purified by silica gel chromatography ($SiO_2$, 1-30% MeOH in DCM) to afford 8-(pyridin-4-yl)-1,5-dihydro-6H-pyrano[4,3-b]thieno[3,2-d]pyridine-4,6(3H)-dione (6 mg, 60%). MS obsd. ($ESI^+$): 299.3 [$(M+H)^+$].

Step E: (S)-4-(tert-butyl)-4-hydroxy-8-(pyridin-4-yl)-1,3,4,5-tetrahydro-6H-pyrano[4,3-b]thieno[3,2-d]pyridin-6-one (Compound 22) & (R)-4-(tert-butyl)-4-hydroxy-8-(pyridin-4-yl)-1,3,4,5-tetrahydro-6H-pyrano[4,3-b]thieno[3,2-d]pyridin-6-one (Compound 23)

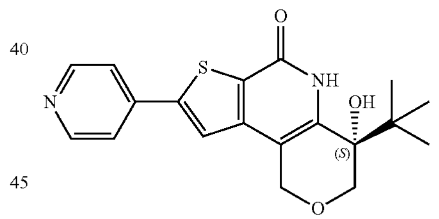

+

Compound 22

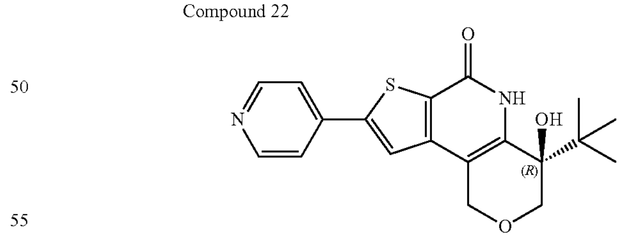

Compound 23

To a solution of 8-(pyridin-4-yl)-1,5-dihydro-6H-pyrano[4,3-b]thieno[3,2-d]pyridine-4,6(3H)-dione (25 mg, 0.08 mmol, 1.0 eq.) in anhydrous THF (1.5 mL) was added t-BuMgBr (1 M in THF, 1.7 mL, 20.0 eq.) at 0° C. The mixture was stirred at 0° C. for 2 h. The mixture was quenched with saturated aqueous $NH_4Cl$ solution (2.0 mL), extracted with EtOAc (20.0 mL×3). The combined organic layers were washed with brine, dried over anhydrous sodium sulfate, filtered and concentrated in vacuo. The residue was purified by flash column chromatography ($SiO_2$, 0-10% MeOH in DCM) to afford racemic 4-(tert-butyl)-4-hydroxy-8-(pyridin-4-yl)-1,3,4,5-tetrahydro-6H-pyrano[4,3-b]thieno[3,2-d]pyridin-6-one (5 mg, 17%). MS obsd. ($ESI^+$): 357.1 $[(M+H)^+]$.

The individual enantiomers were separated via chiral SFC. (S)-4-(tert-butyl)-4-hydroxy-8-(pyridin-4-yl)-1,3,4,5-tetrahydro-6H-pyrano[4,3-b]thieno[3,2-d]pyridin-6-one (Compound 22): MS obsd. ($ESI^+$): 357.2 $[(M+H)^+]$; $^1H$ NMR (400 MHz, DMSO-d6) δ ppm: 10.35 (s, 1H), 8.70 (d, J=6.0 Hz, 2H), 8.03 (s, 1H), 7.82 (d, J=6.0 Hz, 2H), 5.35 (s, 1H), 4.87 (m, 2H), 4.15 (d, J=11.2 Hz, 1H), 3.47 (d, J=11.2 Hz, 1H), 1.03 (s, 9H). (R)-4-(tert-butyl)-4-hydroxy-8-(pyridin-4-yl)-1,3,4,5-tetrahydro-6H-pyrano[4,3-b]thieno[3,2-d]pyridin-6-one (Compound 23): MS obsd. ($ESI^+$): 357.2 $[(M+H)^+]$.

Examples 24 and 25—Compounds 24 and 25: (S)-4-hydroxy-4-isopropyl-8-(3-methyl-1H-pyrazol-4-yl)-1,3,4,5-tetrahydro-6H-pyrano[4,3-b]thieno[3,2-d]pyridin-6-one (Compound 24) & (R)-4-hydroxy-4-isopropyl-8-(3-methyl-1H-pyrazol-4-yl)-1,3,4,5-tetrahydro-6H-pyrano[4,3-b]thieno[3,2-d]pyridin-6-one (Compound 25) (Stereochemistry for Compounds 24 and 25 is Arbitrarily Assigned)

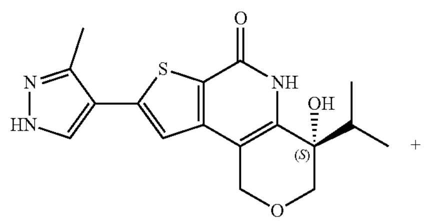

+

Compound 24

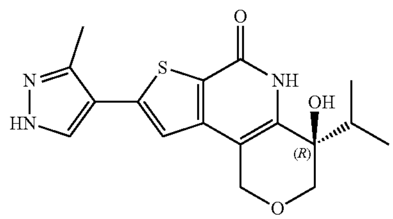

Compound 25

Synthesized via analogous route to Compounds 16 and 17. (S)-4-hydroxy-4-isopropyl-8-(3-methyl-1-pyrazol-4-yl)-1,3,4,5-tetrahydro-6H-pyrano[4,3-b]thieno[3,2-d]pyridin-6-one (Compound 24). MS obsd. ($ESI^+$): 346.2 $[(M+H)^+]$; $^1H$ NMR (400 MHz, DMSO-d6) δ ppm: 12.94 (brs, 1H), 10.81 (brs, 1H), 7.96 (brs, 1H), 7.29 (s, 1H), 5.27 (s, 1H), 4.69 (s, 2H), 3.96 (d, J=11.8 Hz, 1H), 3.53 (d, J=11.6 Hz, 1H), 2.48 (s, 3H), 2.40-2.34 (m, 1H), 1.00 (d, J=6.8 Hz, 3H), 0.76 (d, J=6.8 Hz, 3H). (R)-4-hydroxy-4-isopropyl-8-(3-methyl-1H-pyrazol-4-yl)-1,3,4,5-tetrahydro-6H-pyrano[4,3-b]thieno[3,2-d]pyridin-6-one (Compound 25). MS obsd. ($ESI^+$): 346.2 $[(M+H)^+]$.

Examples 26 and 27—Compounds 26 and 27: (R)-8-(3-fluoro-1H-pyrazol-4-yl)-4-hydroxy-4-isopropyl-1,3,4,5-tetrahydro-6H-pyrano[4,3-b]thieno[3,2-d]pyridin-6-one (Compound 26) & (S)-8-(3-fluoro-1H-pyrazol-4-yl)-4-hydroxy-4-isopropyl-1,3,4,5-tetrahydro-6H-pyrano[4,3-b]thieno[3,2-d]pyridin-6-one (Compound 27) (Stereochemistry for Compounds 26 and 27 is Arbitrarily Assigned)

Compound 26

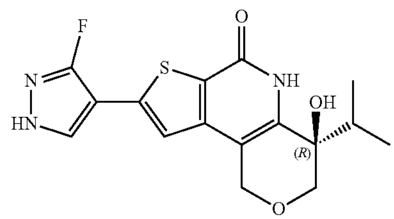

Compound 27

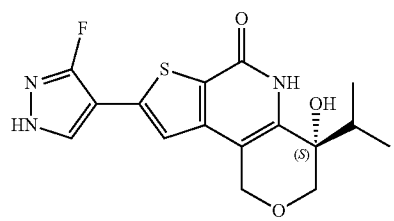

Step A: 4-bromo-3-fluoro-1-((2-(trimethylsilyl)ethoxy)methyl)-1H-pyrazole

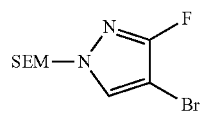 [SMILES: C[Si](C)(C)CCOCn1cc(Br)c(F)n1]

To a solution of 4-bromo-3-fluoro-1H-pyrazole (1.5 g, 9.1 mmol, 1.0 eq.) in DMF (15 mL) was added sodium hydride (60% in mineral oil, 700 mg, 18 mmol, 2.0 eq.) at 0° C. The mixture was stirred at 0° C. for 10 min., then 2-(chloromethoxy)ethyl-trimethyl-silane (2.27 g, 13.6 mmol, 2.41 mL, 1.5 eq.) was added. The mixture was stirred at room temperature for 2 h then quenched by addition of saturated $NH_4Cl$ (aq) followed by water (200 mL). The mixture was extracted with EtOAc (50 mL×3) and the combined organic phases were washed with brine, dried over anhydrous sodium sulfate, filtered and concentrated in vacuo to give the residue, which was purified by flash column chromatography ($SiO_2$, 0-4% EtOAc in PE) to afford 4-bromo-3-fluoro-1-((2-(trimethylsilyl)ethoxy)methyl)-1H-pyrazole (2.6 g, 96%); $^1H$ NMR (400 MHz, $CDCl_3$) δ ppm: 7.45 (d, J=2.0 Hz, 1H), 5.24 (d, J=0.8 Hz, 2H), 3.58 (m, 2H), 0.92 (m, 2H), 0.00 (s, 9H).

Step B: 3-fluoro-4-(4,4,5,5-tetramethyl-1,3,2-dioxaborolan-2-yl)-1-((2-(trimethylsilyl)ethoxy)methyl)-1H-pyrazole

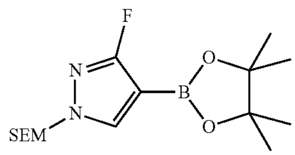 [SMILES: CC1(C)OB(c2cn(COCC[Si](C)(C)C)nc2F)OC1(C)C]

A mixture of 4-bromo-3-fluoro-1-((2-(trimethylsilyl)ethoxy)methyl)-1H-pyrazole (850 mg, 2.88 mmol, 1.0 eq.), 4,4,5,5-tetramethyl-2-(4,4,5,5-tetramethyl-1,3,2-dioxaborolan-2-yl)-1,3,2-dioxaborolane (804 mg, 3.17 mmol, 1.1 eq.), Pd(dppf)$Cl_2$ (421 mg, 576 μmol, 0.2 eq.), and potassium acetate (848 mg, 8.64 mmol, 3.0 eq.) in 1,4-dioxane (17.0 mL) was heated at 100° C. under nitrogen for 16 h. The mixture was cooled and concentrated in vacuo, then water (50 mL) was added and the mixture was extracted with EtOAc (40 mL×3). The combined organic phases were washed with brine, dried over anhydrous sodium sulfate, filtered and concentrated under vacuum to afford a residue, which was purified by flash column chromatography ($SiO_2$, 0-8% EtOAc in PE) to afford 3-fluoro-4-(4,4,5,5-tetramethyl-1,3,2-dioxaborolan-2-yl)-1-((2-(trimethylsilyl)ethoxy)methyl)-1H-pyrazole (650 mg, 66%). $^1$H NMR (400 MHz, $CDCl_3$) δ ppm: 7.66 (d, J=2.4 Hz, 1H), 5.26 (s, 2H), 3.59 (m, 2H), 1.34 (s, 12H), 0.92 (m, 2H), 0.00 (s, 9H).

Step C: methyl 3-bromo-5-(3-fluoro-1-((2-(trimethylsilyl)ethoxy)methyl)-1H-pyrazol-4-yl)thiophene-2-carboxylate

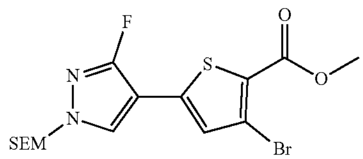 [SMILES: COC(=O)c1sc(-c2cn(COCC[Si](C)(C)C)nc2F)cc1Br]

A solution of methyl 3,5-dibromothiophene-2-carboxylate (1.37 g, 4.56 mmol, 1.2 eq.), 3-fluoro-4-(4,4,5,5-tetramethyl-1,3,2-dioxaborolan-2-yl)-1-((2-(trimethylsilyl)ethoxy)methyl)-1H-pyrazole (1.3 g, 3.80 mmol, 1.0 eq.), Xantphos (440 mg, 760 μmol, 0.20 eq.), $K_3PO_4$ (2.4 g, 11 mmol, 3.0 eq.) and Pd$(OAc)_2$ (85 mg, 380 μmol, 0.10 eq.) in THF (60.0 mL) was degassed with $N_2$, and the mixture was stirred at 60° C. for 16 h. The mixture was filtered and concentrated in vacuo, and the residue was purified by flash column chromatography ($SiO_2$, 0-7% EtOAc in PE) to afford 3-bromo-5-(3-fluoro-1-((2-(trimethylsilyl)ethoxy)methyl)-1H-pyrazol-4-yl)thiophene-2-carboxylate (810 mg, 49%). MS obsd. ($ESI^+$): $^{79}$Br/$^{81}$Br 435.2, 437.2 [$(M+H)^+$].

Step D: 4-(benzyloxy)-8-(3-fluoro-1-((2-(trimethylsilyl)ethoxy)methyl)-1H-pyrazol-4-yl)-4-isopropyl-3,4-dihydro-1H,6H-pyrano[4,3-b]thieno[3,2-d]pyran-6-one

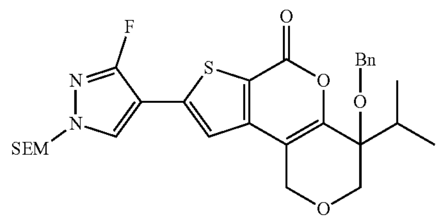 [SMILES: CC(C)C1(OCc2ccccc2)COCc2c1oc(=O)c1sc(-c3cn(COCC[Si](C)(C)C)nc3F)cc21]

To a solution of 3-bromo-5-(3-fluoro-1-((2-(trimethylsilyl)ethoxy)methyl)-1H-pyrazol-4-yl)thiophene-2-carboxylate (400 mg, 918.73 μmol, 1.0 eq.), 3-(benzyloxy)-3-isopropyltetrahydro-4H-pyran-4-one (462 mg, 1.86 mmol, 2.0 eq., prepared in an analogous fashion to Compound 28 steps B-C) and cesium carbonate (909 mg, 2.79 mmol, 3.0 eq.) in toluene (20.0 mL) was added $Pd_2(dba)_3$ (170 mg, 186 μmol, 0.20 eq.) and Xantphos (215 mg, 372 μmol, 0.40 eq.). The mixture was degassed with $N_2$ twice and stirred at 105° C. for 16 h. The mixture was filtered and concentrated under vacuum to afford a residue, which was purified by flash column chromatography ($SiO_2$, 0-16% EtOAc in PE) to afford 4-(benzyloxy)-8-(3-fluoro-1-((2-(trimethylsilyl)ethoxy)methyl)-1H-pyrazol-4-yl)-4-isopropyl-3,4-dihydro-1H,6H-pyrano[4,3-b]thieno[3,2-d]pyran-6-one (275 mg, 51%). MS obsd. ($ESI^+$): 571.3 [$(M+H)^+$].

Step E: 8-(3-fluoro-1H-pyrazol-4-yl)-4-hydroxy-4-isopropyl-3,4-dihydro-1H,6H-pyrano[4,3-b]thieno[3,2-d]pyran-6-one

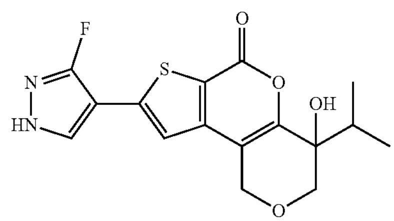 [SMILES: CC(C)C1(O)COCc2c1oc(=O)c1sc(-c3c[nH]nc3F)cc21]

To a solution of 4-(benzyloxy)-8-(3-fluoro-1-((2-(trimethylsilyl)ethoxy)methyl)-1H-pyrazol-4-yl)-4-isopropyl-3,4-dihydro-1H,6H-pyrano[4,3-b]thieno[3,2-d]pyran-6-one (275 mg, 482 μmol, 1.0 eq.) in DCM (12.0 mL) was added $BCl_3$ (1 M, 1.93 mL, 4.0 eq.) at 0° C., and the mixture was stirred at 0° C. for 40 min. The mixture was concentrated via a stream of nitrogen, and the pH was adjusted to around 9 by progressively adding $NH_4OH$ (aq.) at 0° C. The mixture was concentrated in vacuo to afford 8-(3-fluoro-1H-pyrazol-4-yl)-4-hydroxy-4-isopropyl-3,4-dihydro-1H,6H-pyrano[4,3-b]thieno[3,2-d]pyran-6-one (400 mg, crude), which was used without further purification. MS obsd. ($ESI^+$): 351.1 [$(M+H)^+$].

Step F: (R)-8-(3-fluoro-1H-pyrazol-4-yl)-4-hydroxy-4-isopropyl-1,3,4,5-tetrahydro-6H-pyrano[4,3-b]thieno[3,2-d]pyridin-6-one Compound 26) & (S)-8-(3-fluoro-1H-pyrazol-4-yl)-4-hydroxy-4-isopropyl-1,3,4,5-tetrahydro-6H-pyrano[4,3-b]thieno[3,2-d]pyridin-6-one (Compound 27)

Compound 26

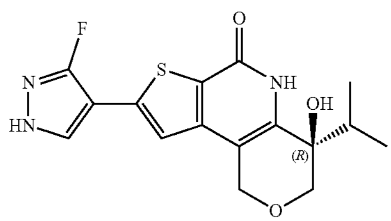

Compound 27

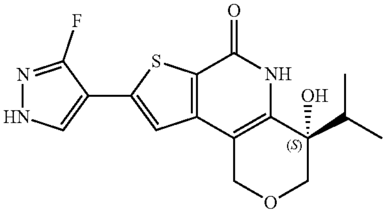

To a solution of 8-(3-fluoro-1H-pyrazol-4-yl)-4-hydroxy-4-isopropyl-3,4-dihydro-1H,6H-pyrano[4,3-b]thieno[3,2-d]pyran-6-one (400 mg, crude) in isopropanol (6.5 mL) was added aqueous $NH_4OH$ solution (6.5 mL). The mixture was stirred at 95° C. for 4 h under microwave heating then concentrated and purified by flash column chromatography ($SiO_2$, 0-6% MeOH in DCM) to afford 8-(3-fluoro-1H-pyrazol-4-yl)-4-hydroxy-4-isopropyl-1,3,4,5-tetrahydro-6H-pyrano[4,3-b]thieno[3,2-d]pyridin-6-one (75 mg, 31% over 2 steps). MS obsd. ($ESI^+$): 350.1 [$(M+H)^+$].

The racemic mixture was separated via chiral SFC to afford each enantiomer. (R)-8-(3-fluoro-1H-pyrazol-4-yl)-4-hydroxy-4-isopropyl-1,3,4,5-tetrahydro-6H-pyrano[4,3-b]thieno[3,2-d]pyridin-6-one (Compound 26): MS obsd. ($ESI^+$): 350.0 [$(M+H)^+$]; $^1H$ NMR (400 MHz, DMSO-d6) δ ppm: 12.89 (brs, 1H), 10.90 (brs, 1H), 8.32 (d, J=1.2 Hz, 1H), 7.35 (s, 1H), 5.27 (s, 1H), 4.68 (s, 2H), 3.96 (d, J=12.0 Hz, 1H), 3.53 (d, J=12.0 Hz, 1H), 2.41-2.34 (m, 1H), 1.00 (d, J=6.8 Hz, 3H), 0.76 (d, J=6.8 Hz, 3H). (S)-8-(3-fluoro-1H-pyrazol-4-yl)-4-hydroxy-4-isopropyl-1,3,4,5-tetrahydro-6H-pyrano[4,3-b]thieno[3,2-d]pyridin-6-one (Compound 27): MS obsd. ($ESI^+$): 350.0 [$(M+H)^+$].

Examples 28 and 29—Compounds 28 and 29: (S)-4-hydroxy-8-(1H-pyrazol-4-yl)-4-(trifluoromethyl)-1,3,4,5-tetrahydro-6H-pyrano[4,3-b]thieno[3,2-d]pyridin-6-one (Compound 28) & (R)-4-hydroxy-8-(1H-pyrazol-4-yl)-4-(trifluoromethyl)-1,3,4,5-tetrahydro-6H-pyrano[4,3-b]thieno[3,2-d]pyridin-6-one (Compound 29) (Stereochemistry for Compounds 28 and 29 is Arbitrarily Assigned)

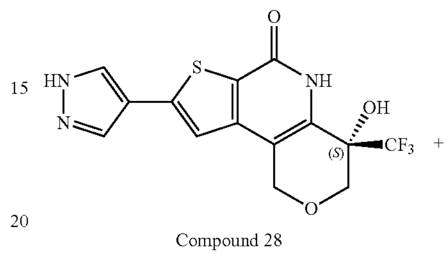

Compound 28

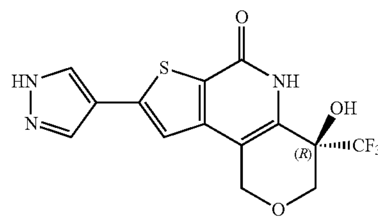

Compound 29

Step A: 4,4-dimethoxy-3-(trifluoromethyl)tetrahydro-2H-pyran-3-ol

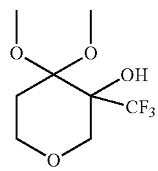

To a solution of 4,4-dimethoxydihydro-2H-pyran-3(4H)-one (500 mg, 3.12 mmol, 1.0 eq., synthesized according to the procedure described in WO2013152269) in THF (5.0 mL) was added TBAF (81.6 mg, 312 μmol, 90.4 μL, 0.10 eq.) at 0° C. The mixture was stirred at 0° C. for 10 min. before trimethyl(trifluoromethyl)silane (666 mg, 4.68 mmol, 744 230 L, 1.5 eq.) was added dropwise. The mixture was allowed to warm to room temperature where it was stirred for 16 h. The mixture was concentrated and purified by flash column chromatography ($SiO_2$, 12-25% EtOAc in PE) to afford 4,4-dimethoxy-3-(trifluoromethyl)tetrahydro-2H-pyran-3-ol (480 mg, 66%). $^1H$ NMR (400 MHz, $CDCl_3$) δ ppm: 4.02-3.99 (m, 2H), 3.85-3.82 (m, 2H), 3.37 (s, 6H), 2.03-2.02 (m, 2H).

Step B: 3-(benzyloxy)-4,4-dimethoxy-3-(trifluoromethyl)tetrahydro-2H-pyran

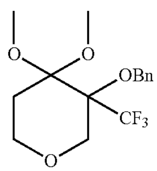 [SMILES: COC1(OC)CCOCC1(OCc1ccccc1)C(F)(F)F]

To a solution of 4,4-dimethoxy-3-(trifluoromethyl)tetrahydropyran-3-ol (1 g, 4.34 mmol, 1.0 eq.) in DMF (8.0 mL) was added NaH (333 mg, 8.69 mmol, 60% in mineral oil, 2.0 eq.) at 0° C. The mixture was stirred at 0° C. for 10 min. then bromoethylbenzene (1.49 g, 8.69 mmol, 1.03 mL, 2.0 eq.) was added dropwise. The mixture was stirred at room temperature for 3 h then quenched with saturated $NH_4Cl$ (aq.), diluted with water (120 mL), and extracted with EtOAc (50 mL×3). The combined organic layers were dried over anhydrous sodium sulfate, filtered and concentrated to give the residue, which was purified by flash column chromatography ($SiO_2$, 0-7% EtOAc in PE) to give the 3-(benzyloxy)-4,4-dimethoxy-3-(trifluoromethyl)tetrahydro-2H-pyran (690 mg, 49%). $^1$H NMR (400 MHz, $CDCl_3$) δ ppm: 7.38-7.20 (m, 5H), 4.87 (d, J=10.5 Hz, 1H), 4.75 (d, J=10.5 Hz, 1H), 4.13-4.06 (m, 2H), 3.77-3.70 (m, 2H), 3.39 (s, 3H), 3.37 (s, 3H), 2.22-2.16 (m, 1H), 1.99-1.93 (m, 1H).

Step C: 3-(benzyloxy)-3-(trifluoromethyl)tetrahydro-4H-pyran-4-one

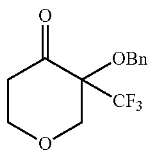 [SMILES: O=C1CCOCC1(OCc1ccccc1)C(F)(F)F]

To a solution of 3-(benzyloxy)-4,4-dimethoxy-3-(trifluoromethyl)tetrahydro-2H-pyran (690 mg, 2.15 mmol, 1.0 eq.) in acetone (15.0 mL) was added iodine (54.68 mg, 215.42 μmol. 0.1 eq.). The reaction mixture stirred at room temperature for 1 h then quenched with saturated $Na_2SO_3$ (aq) (25 mL) and extracted into DCM (35 mL×3). The combined organic layers were dried over anhydrous sodium sulfate, filtered and concentrated. The residue was purified by flash column chromatography ($SiO_2$, 0-8% EtOAc in PE) to afford 3-(benzyloxy)-3-(trifluoromethyl)tetrahydro-4H-pyran-4-one (550 mg, 93%). $^1$H NMR (400 MHz, $CDCl_3$) δ ppm: 7.39-7.20 (m, 5H), 4.90 (d, J=11.0 Hz, 1H), 4.62 (d, J=11.0 Hz, 1H), 4.33 (d, J=12.8 Hz, 1H), 4.23-4.17 (m, 1H), 3.90 (d, J=12.8 Hz, 1H), 3.88-3.81 (m, 1H), 3.02-2.94 (m, 1H), 2.54-2.48 (m, 1H).

Step D: 4-(benzyloxy)-4-(trifluoromethyl)-8-(1-((2-(trimethylsilyl)ethoxy)methyl)-1H-pyrazol-4-yl)-3,4-dihydro-1H,6H-pyrano[4,3-b]thieno[3,2-d]pyran-6-one

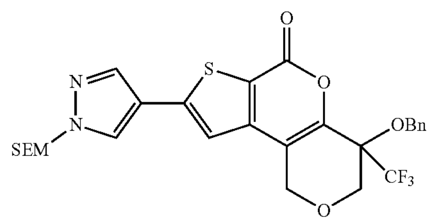 [SMILES: C[Si](C)(C)CCOCn1cc(-c2cc3c4c(oc(=O)c3s2)C(OCc2ccccc2)(C(F)(F)F)COC4)cn1]

To a solution of methyl 3-bromo-5-(1-((2-(trimethylsilyl)ethoxy)methyl)-1H-pyrazol-4-yl)thiophene-2-carboxylate (200 mg, 480 μmol, 1.0 eq.), 3-benzyloxy-3-(trifluoromethyl)tetrahydropyran-4-one (263 mg, 958 μmol, 2.0 eq.) and cesium carbonate (468 mg, 1.44 mmol, 3.0 eq.) in toluene (12.0 mL) was added $Pd_2(dba)_3$ (87.8 mg, 95.8 μmol, 0.2 eq.) and Xantphos (111 mg, 192 μmol, 0.4 eq.). The mixture was degassed with $N_2$ and stirred at 105° C. for 16 h. The mixture was filtered and concentrated in vacuo then purified by flash column chromatography ($SiO_2$, 0-20% EtOAc in PE) to afford 4-(benzyloxy)-4-(trifluoromethyl)-8-(1-((2-(trimethylsilyl)ethoxy)methyl)-1H-pyrazol-4-yl)-3,4-dihydro-1H,6H-pyrano[4,3-b]thieno[3,2-d]pyran-6-one (185 mg, 66%). MS obsd. (ESI$^+$): 579.5 [(M+H)$^+$].

Step E: 4-(benzyloxy)-4-(trifluoromethyl)-8-(1-((2-(trimethylsilyl)ethoxy)methyl)-1H-pyrazol-4-yl)-1,3,4,5-tetrahydro-6H-pyrano[4,3-b]thieno[3,2-d]pyridin-6-one

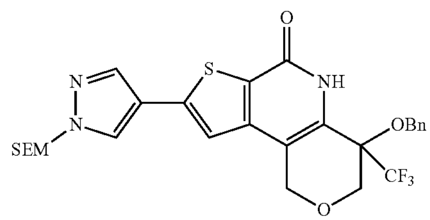 [SMILES: C[Si](C)(C)CCOCn1cc(-c2cc3c4c([nH]c(=O)c3s2)C(OCc2ccccc2)(C(F)(F)F)COC4)cn1]

To a solution of 4-(benzyloxy)-4-(trifluoromethyl)-8-(1-((2-(trimethylsilyl)ethoxy)methyl)-1H-pyrazol-4-yl)-3,4-dihydro-1H,6H-pyrano[4,3-b]thieno[3,2-d]pyran-6-one (185 mg, 320 μmol) in MeOH (5.0 mL) was added ammonium hydroxide (5.0 mL). The mixture was stirred at 100° C. for 6 h in a microwave reactor then concentrated under vacuum to afford a residue, which was purified by flash column chromatography ($SiO_2$, 0-4% MeOH in DCM) to give 4-(benzyloxy)-4-(trifluoromethyl)-8-(1-((2-(trimethylsilyl)ethoxy)methyl)-1H-pyrazol-4-yl)-1,3,4,5-tetrahydro-6H-pyrano[4,3-b]thieno[3,2-d]pyridin-6-one (105 mg, 57%). MS obsd. (ESI$^+$): 578.3 [(M+H)$^+$].

Step F: (S)-4-hydroxy-8-(1H-pyrazol-4-yl)-4-(trifluoromethyl)-1,3,4,5-tetrahydro-6H-pyrano[4,3-b]thieno[3,2-d]pyridin-6-one (Compound 28) & (R)-4-hydroxy-8-(1H-pyrazol-4-yl)-4-(trifluoromethyl)-1,3,4,5-tetrahydro-6H-pyrano[4,3-b]thieno[3,2-d]pyridin-6-one (Compound 29)

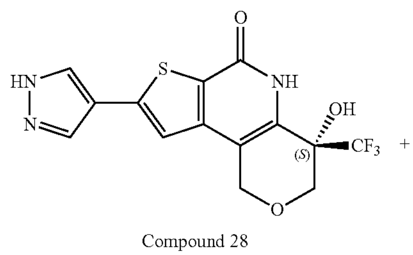

Compound 28

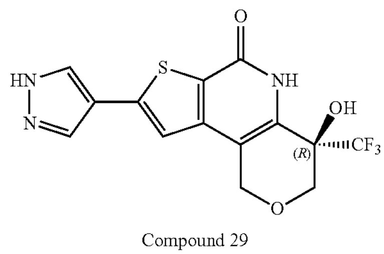

Compound 29

4-(Benzyloxy)-4-(trifluoromethyl)-8-(1-((2-(trimethylsilyl)ethoxy)methyl)-1H-pyrazol-4-yl)-1,3,4,5-tetrahydro-6H-pyrano[4,3-b]thieno[3,2-d]pyridin-6-one (105 mg, 181.76 μmol, 1.0 eq.) was dissolved in trifluoroacetic acid (2.6 mL) at 0° C. The mixture was stirred for 2 h at 60° C. under microwave irradiation then concentrated, and the pH was adjusted to around 9 by progressively adding $NH_3$/MeOH (7 M). The mixture was concentrated in vacuo and purified by flash column chromatography ($SiO_2$, 0-6% MeOH in DCM) to give racemic 4-hydroxy-8-(1H-pyrazol-4-yl)-4-(trifluoromethyl)-1,3,4,5-tetrahydro-6H-pyrano[4,3-b]thieno[3,2-d]pyridin-6-one (54 mg, 83%). MS obsd. ($ESI^+$): 358.0 [$(M+H)^+$].

The individual enantiomers were separated via chiral SFC. (S)-4-hydroxy-8-(1H-pyrazol-4-yl)-4-(trifluoromethyl)-1,3,4,5-tetrahydro-6H-pyrano[4,3-b]thieno[3,2-d]pyridin-6-one (Compound 28): MS obsd. ($ESI^+$): 358.0 [$(M+H)^+$]; $^1H$ NMR (400 MHz, DMSO-d6) δ ppm: 13.25 (s, 1H), 10.94 (s, 1H), 8.27 (brs, 2H), 7.48 (s, 1H), 7.13 (s, 1H), 4.89-4.77 (m, 2H), 4.23 (d, J=12.4 Hz, 1H), 3.71 (m, 1H). (R)-4-hydroxy-8-(1H-pyrazol-4-yl)-4-(trifluoromethyl)-1,3,4,5-tetrahydro-6H-pyrano[4,3-b]thieno[3,2-d]pyridin-6-one (Compound 29): MS obsd. ($ESI^+$): 358.0 [$(M+H)^+$].

Examples 30 and 31—Compounds 30 and 31: (S)-4-hydroxy-8-(1-methyl-1H-pyrazol-5-yl)-4-(trifluoromethyl)-1,3,4,5-tetrahydro-6H-pyrano[4,3-b]thieno[3,2-d]pyridin-6-one (Compound 30) and (R)-4-hydroxy-8-(1-methyl-1H-pyrazol-5-yl)-4-(trifluoromethyl)-1,3,4,5-tetrahydro-6H-pyrano[4,3-b]thieno[3,2-d]pyridin-6-one (Compound 31) (Stereochemistry for Compounds 30 and 31 is Arbitrarily Assigned)

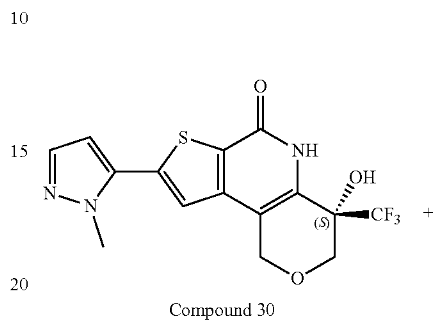

Compound 30

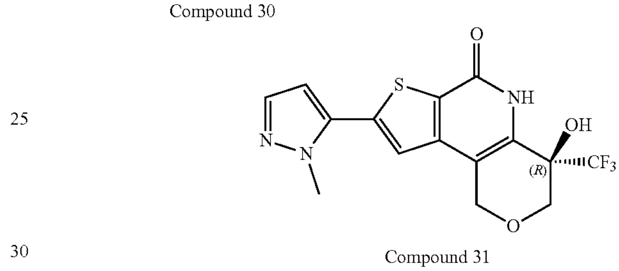

Compound 31

Synthesized by analogous route to Compounds 28 and 29. (S)-4-hydroxy-8-(1-methyl-1H-pyrazol-5-yl)-4-(trifluoromethyl)-1,3,4,5-tetrahydro-6H-pyrano[4,3-b]thieno[3,2-d]pyridin-6-one (Compound 30). MS obsd. ($ESI^+$): 372.1 [$(M+H)^+$]; $^1H$ NMR (400 MHz, DMSO-d6) δ ppm: 11.21 (brs, 1H), 7.65 (s, 1H), 7.54 (d, J=2.0 Hz, 1H), 7.19 (brs, 1H), 6.72 (d, J=2.0 Hz, 1H), 4.96 (d, J=15.2 Hz, 1H), 4.81 (d, J=15.2 Hz, 1H), 4.25 (d, J=12.0 Hz, 1H), 4.05 (s, 3H), 3.71 (d, J=12.0 Hz, 1H). (R)-4-hydroxy-8-(1-methyl-1H-pyrazol-5-yl)-4-(trifluoromethyl)-1,3,4,5-tetrahydro-6H-pyrano[4,3-b]thieno[3,2-d]pyridin-6-one (Compound 31). MS obsd. ($ESI^+$): 372.1 [$(M+H)^+$].

Examples 32 and 33—Compounds 32 and 33: (S)-4-hydroxy-8-(5-methyl-1H-pyrazol-4-yl)-4-(trifluoromethyl)-1,3,4,5-tetrahydro-6H-pyrano[4,3-b]thieno[3,2-d]pyridin-6-one (Compound 32) & (R)-4-hydroxy-8-(5-methyl-1H-pyrazol-4-yl)-4-(trifluoromethyl)-1,3,4,5-tetrahydro-6H-pyrano[4,3-b]thieno[3,2-d]pyridin-6-one (Compound 33) (Stereochemistry for Compounds 32 and 33 is Arbitrarily Assigned)

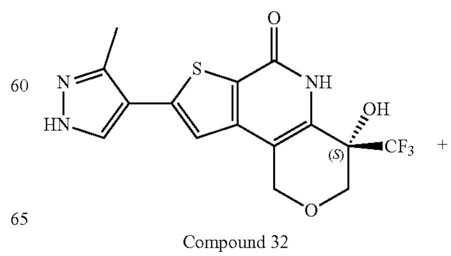

Compound 32

-continued

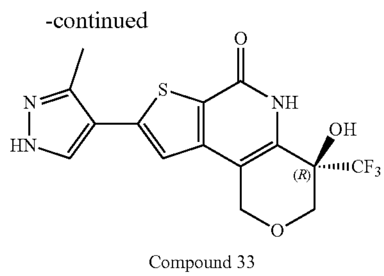

Compound 33

Synthesized by analogous route to Compounds 28 and 29. (S)-4-hydroxy-8-(5-methyl-1H-pyrazol-4-yl)-4-(trifluoromethyl)-1,3,4,5-tetrahydro-6H-pyrano[4,3-b]thieno[3,2-d] pyridin-6-one. MS obsd. ($ESI^+$): 372.0 [$(M+H)^+$]; $^1H$ NMR (400 MHz, DMSO-d6) δ ppm: 12.98 (brs, 1H), 10.90 (brs, 1H), 8.23-7.86 (m, 1H), 7.35 (s, 1H), 7.14 (s, 1H), 4.92 (d, 15.02 Hz, 1H), 4.78 (d, 15.02 Hz, 1H), 4.24 (d, J=12.0 Hz, 1H), 3.70 (d, J=12.0 Hz, 1H), 2.43 (s, 3H). (R)-4-hydroxy-8-(5-methyl-1H-pyrazol-4-yl)-4-(trifluoromethyl)-1,3,4,5-tetrahydro-6H-pyrano[4,3-b]thieno[3,2-d]pyridin-6-one. MS obsd. ($ESI^+$): 372.0 [$(M+H)^+$].

Examples 34 and 35—Compounds 34 and 35: (S)-4-(hydroxymethyl)-4-methyl-8-(1H-pyrazol-4-yl)-1,5-dihydro-2H-pyrano[3,4-b]thieno[3,2-d]pyridin-6(4H)-one (Compound 34) & (R)-4-(hydroxymethyl)-4-methyl-8-(1H-pyrazol-4-yl)-1,5-dihydro-2H-pyrano[3,4-b]thieno[3,2-d]pyridin-6(4H)-one (Compound 35) (Stereochemistry for Compounds 34 and 35 is Arbitrarily Assigned)

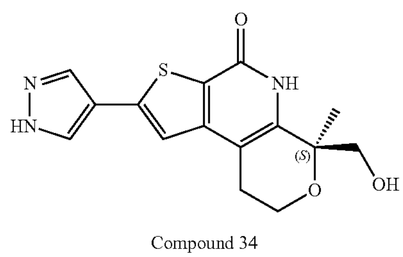

+

Compound 34

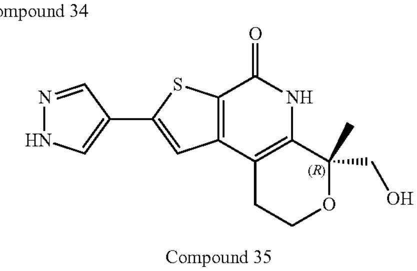

Compound 35

Step A: Benzyl 2-(2-hydroxytetrahydrofuran-2-yl)acetate

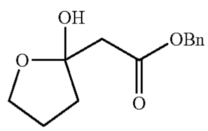 [SMILES: O=C(CC1(O)CCCO1)OCc1ccccc1]

A mixture of benzyl 2-bromoacetate (19.2 g, 83.6 mmol, 1.2 eq.), indium (9.60 g, 83.6 mmol, 1.2 eq.), tetrahydrofuran-2-one (6.0 g, 69.7 mmol, 1.0 eq.) and THF (21.0 mL) was stirred at 70° C. for 16 h. The reaction was quenched with saturated aqueous $NaHCO_3$ solution (20 ml) and extracted with EtOAc (60 mL×2). The combined organic layers were washed with brine, dried over anhydrous sodium sulfate, filtered and concentrated. Purification by flash column chromatography ($SiO_2$, 10-20% EtOAc in DCM) afforded benzyl 2-(2-hydroxytetrahydrofuran-2-yl)acetate (4.0 g, 24%). MS obsd. ($ESI^+$): 219.2 [$(M+H-H_2O)^+$].

Step B: Benzyl 2-diazo-6-hydroxy-3-oxohexanoate

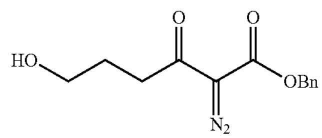

To a solution of benzyl 2-(2-hydroxytetrahydrofuran-2-yl)acetate (700 mg, 2.96 mmol, 1.0 eq.) and N-diazo-2,4,6-triisopropyl-benzenesulfonamide (1.01 g, 3.26 mmol, 1.1 eq) in THF (10.0 mL) was added N,N-diethylethanamine (900 mg, 8.9 mmol, 3.0 eq.) at 0° C. The mixture was stirred at room temperature for 16 h, then concentrated. The residue was purified by flash column chromatography ($SiO_2$, 15-30% EtOAc in PE) to give benzyl 2-diazo-6-hydroxy-3-oxo-hexanoate (1.18 g, 81%). MS obsd. ($ESI^+$): 263.2 [$(M+H)^+$].

Step C: Benzyl 3-oxotetrahydro-2H-pyran-2-carboxylate

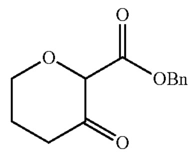 [SMILES: O=C1CCCOC1C(=O)OCc1ccccc1]

A solution of benzyl 2-diazo-6-hydroxy-3-oxo-hexanoate (1.0 g, 3.81 mmol, 1.0 eq.) in benzene (50.0 mL) was added to a solution of $Rh_2(OAc)_4$ (50.0 mg, 113 μmol, 0.030 eq.) in benzene (50.0 mL) dropwise over 35 min at 100° C. The mixture was stirred at 100° C. for 1 h, then filtered and concentrated to give benzyl 3-oxotetrahydro-2H-pyran-2-carboxylate (180 mg, crude), which was used in the next step without purification. MS obsd. ($ESI^+$): 235.2 [$(M+H)^+$].

Step D: benzyl 2-methyl-3-oxotetrahydro-2H-pyran-2-carboxylate

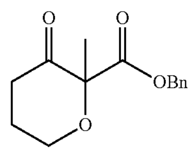 [SMILES: CC1(C(=O)OCc2ccccc2)OCCCC1=O]

To a solution of benzyl 3-oxotetrahydro-2H-pyran-2-carboxylate (890 mg, 3.80 mmol, 1.0 eq.) in DMF (15 mL) was added sodium hydride (247 mg, 5.70 mmol, 60% in mineral oil, 1.5 eq.) at −20° C. The mixture was stirred for 10 min., then iodomethane (1.62 g, 11.40 mmol, 3.0 eq.) was added, and the mixture was stirred at room temperature for 16 h. The mixture was poured into water and extracted with ethyl acetate (30 mL×2). The combined organic layers were washed with brine, dried over anhydrous sodium sulfate, filtered and concentrated in vacuo, and the residue was purified by flash column chromatography ($SiO_2$, 0-10% EtOAc in PE) to give benzyl 2-methyl-3-oxotetrahydro-2H-pyran-2-carboxylate (474 mg, 50%). MS obsd. ($ESI^+$): 271.0 $[(M+Na)^+]$.

Step E: Benzyl 4-methyl-6-oxo-8-(1-((2-(trimethylsilyl)ethoxy)methyl)-1H-pyrazol-4-yl)-1,2,4,6-tetrahydropyrano[3,4-b]thieno[3,2-d]pyran-4-carboxylate

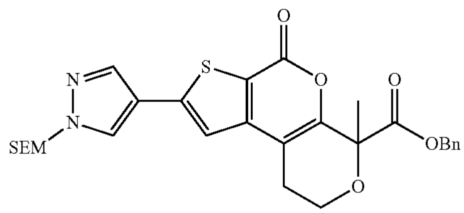 [SMILES: CC1(C(=O)OCc2ccccc2)OCCc2c1oc(=O)c1sc(-c3cnn(COCC[Si](C)(C)C)c3)cc21]

A mixture of methyl 3-bromo-5-[1-(2-trimethylsilylethoxymethyl)pyrazol-4-yl]thiophene-2-carboxylate (84.1 mg, 201 μmol, 1.0 eq.), benzyl 2-methyl-3-oxotetrahydro-2H-pyran-2-carboxylate (100 mg, 403 μmol, 2.0 eq.), sodium metabisulfite (11.5 mg, 60.4 μmol, 0.3 eq.), $Cs_2CO_3$ (197 mg, 604 μmol, 3.0 eq.), Sphos-Pd-G3 (31.4 mg, 40.3 μmol, 0.2 eq.) and toluene (15.0 mL) was stirred for 16 h at 105° C. The mixture was poured into water and extracted with EtOAc (70 mL×2). The combined organic layers were washed with brine, dried over anhydrous sodium sulfate, filtered, and concentrated. The residue was purified by flash column chromatography ($SiO_2$, 0-25% EtOAc in PE) to give benzyl 4-methyl-6-oxo-8-(1-((2-(trimethylsilyl)ethoxy) methyl)-1H-pyrazol-4-yl)-1,2,4,6-tetrahydropyrano[3,4-b] thieno[3,2-d]pyran-4-carboxylate (78 mg, 70%). MS obsd. ($ESI^+$): 553.5 $[(M+H)^+]$.

Step F: 4-(hydroxymethyl)-4-methyl-8-(1-((2-(trimethylsilyl)ethoxy)methyl)-1H-pyrazol-4-yl)-1,4-dihydropyrano[3,4-b]thieno[3,2-d]pyran-6(2H)-one

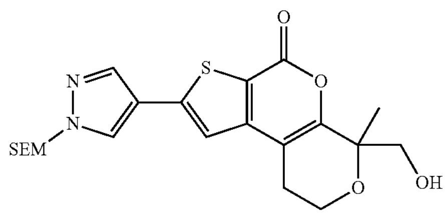 [SMILES: CC1(CO)OCCc2c1oc(=O)c1sc(-c3cnn(COCC[Si](C)(C)C)c3)cc21]

A mixture of benzyl 4-methyl-6-oxo-8-(1-((2-(trimethylsilyl)ethoxy)methyl)-1H-pyrazol-4-yl)-1,2,4,6-tetrahydropyrano[3,4-b]thieno[3,2-d]pyran-4-carboxylate (50 mg, 90.5 μmol, 1.0 eq.), dichlorocalcium (50.2 mg, 452 μmol, 5 eq.) and EtOH (5.0 mL) was stirred for 20 min at rt., then sodium borohydride (51.3 mg, 1.36 mmol, 15.0 eq.) was added in portions to the mixture at 0° C. followed by stirring for 20 min at room temperature. The mixture was poured into water and extracted with EtOAc (30 mL×2). The combined organic layers were washed with brine, dried over anhydrous sodium sulfate, filtered, and concentrated. The residue was purified by flash column chromatography ($SiO_2$, 50% EtOAc in PE) to give 4-(hydroxymethyl)-4-methyl-8-(1-((2-(trimethylsilyl)ethoxy)methyl)-1H-pyrazol-4-yl)-1,4-dihydropyrano[3,4-b]thieno[3,2-d]pyran-6(2H)-one (20 mg, 49%). MS obsd. ($ESI^+$): 449.2 $[(M+H)^+]$.

Step G: 4-(hydroxymethyl)-4-methyl-8-(1-((2-(trimethylsilyl)ethoxy)methyl)-1H-pyrazol-4-yl)-1,5-dihydro-2H-pyrano[3,4-b]thieno[3,2-d]pyridin-6(4H)-one

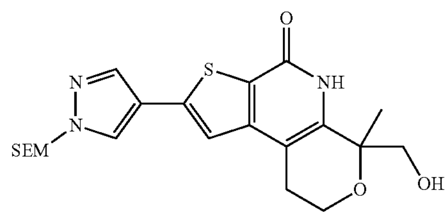 [SMILES: CC1(CO)OCCc2c1[nH]c(=O)c1sc(-c3cnn(COCC[Si](C)(C)C)c3)cc21]

A mixture of 4-(hydroxymethyl)-4-methyl-8-(1-((2-(trimethylsilyl)ethoxy)methyl)-1H-pyrazol-4-yl)-1,4-dihydropyrano[3,4-b]thieno[3,2-d]pyran-6(2H)-one (60 mg, 134 μmol), ammonium hydroxide (3.5 mL) and MeOH (3.5 mL) was stirred for 3 h at 100° C. in a microwave reactor. The mixture was concentrated under vacuum, and the residue was purified by flash column chromatography ($SiO_2$, 15-35% EtOAc in PE) to give 4-(hydroxymethyl)-4-methyl-8-(1-((2-(trimethylsilyl)ethoxy)methyl)-1H-pyrazol-4-yl)-1,5-dihydro-2H-pyrano[3,4-b]thieno[3,2-d]pyridin-6(4H)-one (20 mg, 33%). MS obsd. ($ESI^+$): 448.5 $[(M+H)^+]$.

Step H: (S)-4-(hydroxymethyl)-4-methyl-8-(1H-pyrazol-4-yl)-1,5-dihydro-2H-pyrano[3,4-b]thieno[3,2-cl]pyridin-6(4H)-one (Compound 34) & (R)-4-(hydroxymethyl)-4-methyl-8-(1H-pyrazol-4-yl)-1,5-dihydro-2H-pyrano[3,4-b]thieno[3,2-d]pyridin-6(4H)-one (Compound 35)

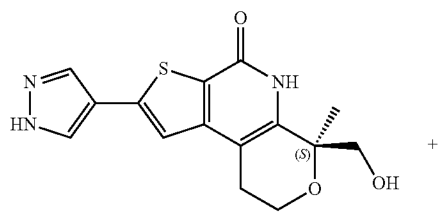

Compound 34

+

-continued

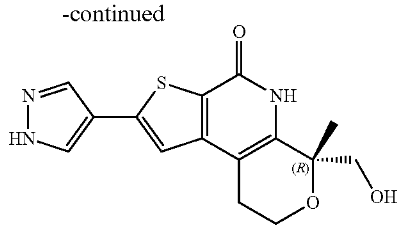

Compound 35

Trichloroborane (1 M, 890 μL, 5.0 eq.) was added to a solution of 4-(hydroxymethyl)-4-methyl-8-(1-((2-(trimethyl silyl)ethoxy)methyl)-1H-pyrazol-4-yl)-1,5-dihydro-2H-pyrano[3,4-b]thieno[3,2-d]pyridin-6(4H)-one (80 mg, 180 μmol) in DCM (50.0 mL) at 0° C. The mixture was stirred for 2 h at room temperature, then quenched with MeOH and concentrated in vacuo. The residue was basified with $NaHCO_3$ and purified by column chromatography ($SiO_2$, 0-6% MeOH in DCM) to give racemic 4-(hydroxymethyl)-4-methyl-8-(1H-pyrazol-4-yl)-1,5-dihydro-2H-pyrano[3,4-b]thieno[3,2-d]pyridin-6(4H)-one (32 mg, 56%). MS obsd. ($ESI^+$): 318.5 [$(M+H)^+$].

The individual enantiomers were separated via chiral SFC. (S)-4-(hydroxymethyl)-4-methyl-8-(1H-pyrazol-4-yl)-1,5-dihydro-2H-pyrano[3,4-b]thieno[3,2-d]pyridin-6(4H)-one (Compound 34): MS obsd. ($ESI^+$): 318.0 [$(M+H)^+$]; $^1H$ NMR (400 MHz, DMSO-d6) δ ppm: 13.22 (brs, 1H), 10.90 (brs, 1H), 8.31 (s, 1H), 7.97 (s, 1H), 7.48 (s, 1H), 4.87 (s, 1H), 4.09-3.96 (m, 1H), 3.93-3.72 (m, 2H), 3.51 (d, J=11.6 Hz, 1H), 2.86-2.58 (m, 2H), 1.39 (s, 3H). (R)-4-(hydroxymethyl)-4-methyl-8-(1H-pyrazol-4-yl)-1,5-dihydro-2H-pyrano[3,4-b]thieno[3,2-d]pyridin-6(4H)-one (Compound 35): MS obsd. ($ESI^+$): 318.0 [$(M+H)^+$].

Examples 36 and 37—Compounds 36 and 37: (S)-6-(difluoromethyl)-6-hydroxy-2-(1H-pyrazol-4-yl)-6,7,8,9-tetrahydrothieno[2,3-c]quinolin-4(5H)-one (Compound 36) & (R)-6-(difluoromethyl)-6-hydroxy-2-(1H-pyrazol-4-yl)-6,7,8,9-tetrahydrothieno[2,3-c]quinolin-4(5H)-one (Compound 37) (Stereochemistry for Compounds 36 and 37 is Arbitrarily Assigned)

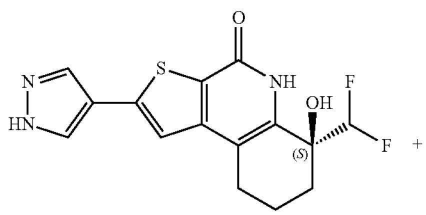

+

Compound 36

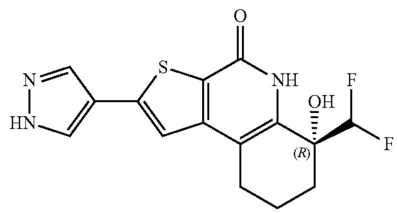

Compound 37

Step A: 2-(1-((2-(trimethylsilyl)ethoxy)methyl)-1H-pyrazol-4-yl)-8,9-dihydro-4H-thieno[2,3-c]chromene-4,6(7H)-dione

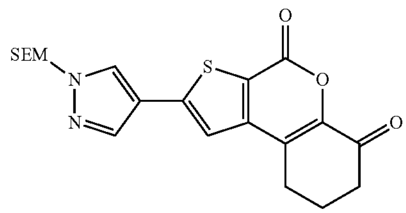 [SMILES: C[Si](C)(C)CCOCn1cc(-c2cc3c4c(oc(=O)c3s2)C(=O)CCC4)cn1]

Methyl 3-bromo-5-(1-((2-(trimethylsilyl)ethoxy)methyl)-1H-pyrazol-4-yl)thiophene-2-carboxylate (200 mg, 480 μmol, 1.0 eq) and cyclohexane-1,2-dione (1.1 g, 9.6 mmol, 20 eq) were dissolved in anhydrous toluene (40.0 mL) before Sphos-Pd-G3 (56 mg, 96 mol, 0.20 eq), $Cs_2CO_3$ (470 mg, 1.40 mmol, 3.0 eq), and $Na_2S_2O_5$ (18 mg, 0.096 mmol, 0.20 eq) were added. The mixture was degassed with $N_2$ and heated to 105° C. for 16 h. The mixture was cooled, concentrated in vacuo, and purified by flash column chromatography ($SiO_2$, 0-45% EtOAc in PE). Further purification ($SiO_2$, 0-8% MeOH in DCM) afforded 2-(1-((2-(trimethylsilyl)ethoxy)methyl)-1H-pyrazol-4-yl)-8,9-dihydro-4H-thieno[2,3-c]chromene-4,6(7H)-dione (20 mg, 10%). MS obsd. ($ESI^+$): 417.5 [$(M+H)^+$].

Step B: 6-(difluoromethyl)-6-hydroxy-2-(1-((2-(trimethylsilyl)ethoxy)methyl)-1H-pyrazol-4-yl)-6,7,8,9-tetrahydro-4H-thieno[2,3-c]chromen-4-one

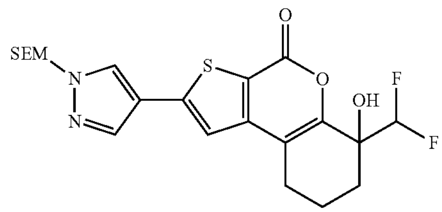 [SMILES: C[Si](C)(C)CCOCn1cc(-c2cc3c4c(oc(=O)c3s2)C(O)(C(F)F)CCC4)cn1]

Cesium fluoride (55 mg, 0.36 mmol, 2.5 eq) was added to a solution of 2-(1-((2-(trimethylsilyl)ethoxy)methyl)-1H-pyrazol-4-yl)-8,9-dihydro-4H-thieno[2,3-c]chromene-4,6(7H)-dione (60 mg, 0.144 mmol, 1.0 eq) in anhydrous DMF (4.0 mL) under an $N_2$ atmosphere followed by difluoromethyl (trimethyl)silane (90 mg, 0.72 mmol, 100 μL, 5.0 eq). The mixture was stirred for 24 h at rt, then diluted with water (50 mL), and extracted with EtOAc (40 mL×4). The combined organic phases were dried ($Na_2SO_4$), filtered and concentrated. Purification ($SiO_2$, 0-39% EtOAc in PE) afforded 6-(difluoromethyl)-6-hydroxy-2-(1-((2-(trimethylsilyl)ethoxy)methyl)-1H-pyrazol-4-yl)-6,7,8,9-tetrahydro-4H-thieno[2,3-c]chromen-4-one (23 mg, 34%). MS obsd. (ESI+): 469.4 [$(M+H)^+$].

Step C: 6-(difluoromethyl)-6-hydroxy-2-(1-((2-(trimethylsilyl)ethoxy)methyl)-1H-pyrazol-4-yl)-6,7,8,9-tetrahydro-4H-thieno[2,3-c]chromen-4-one

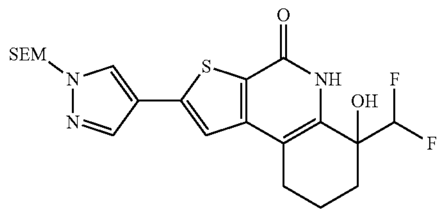 [SMILES: C[Si](C)(C)CCOCn1cc(-c2cc3c4c([nH]c(=O)c3s2)C(O)(C(F)F)CCC4)cn1]

6-(Difluoromethyl)-6-hydroxy-2-(1-((2-(trimethylsilyl)ethoxy)methyl)-1H-pyrazol-4-yl)-6,7,8,9-tetrahydro-4H-thieno[2,3-c]chromen-4-one (65 mg, 0.14 mmol) was added to $NH_4OH$ (5.0 mL, sat. aq.) followed by MeOH (5.0 mL). The mixture was heated to 95° C. in a microwave reactor for 10 h. then concentrated to afford 6-(difluoromethyl)-6-hydroxy-2-(1-((2-(trimethylsilyl)ethoxy)methyl)-1H-pyrazol-4-yl)-6,7,8,9-tetrahydro-4H-thieno[2,3-c]chromen-4-one (65 mg, crude). This material was used in the next step without further purification. MS obsd. (ESI+): 468.5 [(M+H)$^+$].

Step D: (S)-6-(difluoromethyl)-6-hydroxy-2-(1H-pyrazol-4-yl)-6,7,8,9-tetrahydrothieno[2,3-c]quinolin-4(5H)-one (Compound 36) and (R)-6-(difluoromethyl)-6-hydroxy-2-(1H-pyrazol-4-yl)-6,7,8,9-tetrahydrothieno[2,3-c]quinolin-4(5H)-one (Compound 37)

Compound 36

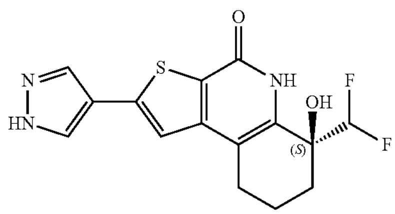

Compound 37

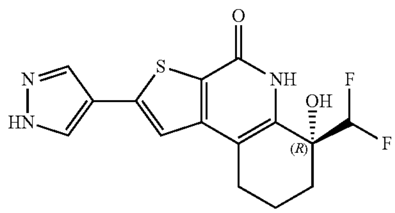

6-(difluoromethyl)-6-hydroxy-2-(1-((2-(trimethylsilyl)ethoxy)methyl)-1H-pyrazol-4-yl)-6,7,8,9-tetrahydro-4H-thieno[2,3-c]chromen-4-one (180 mg, 370 μmol) was dissolved in DCM (15.0 mL) and cooled to 0° C. before trifluoroacetic acid (3.0 mL) was added. The reaction mixture was allowed to warm to rt, and after 4 h the mixture was concentrated in vacuo. The residue was purified (C18 $SiO_2$ 0-25% MeCN in water (0.1% $NH_4OH$)) to afford racemic 6-(difluoromethyl)-6-hydroxy-2-(1H-pyrazol-4-yl)-6,7,8,9-tetrahydrothieno[2,3-c]quinolin-4(5H)-one (40 mg, 26%). MS obsd. (ESI$^+$): 388.4 [(M+H)$^+$].

The individual enantiomers were separated via chiral SFC. (S)-6-(difluoromethyl)-6-hydroxy-2-(1H-pyrazol-4-yl)-6,7,8,9-tetrahydrothieno[2,3-c]quinolin-4(5H)-one (Compound 36): MS obsd. (ESI$^+$): 388.1 [(M+H)$^+$]. (R)-6-(difluoromethyl)-6-hydroxy-2-(1H-pyrazol-4-yl)-6,7,8,9-tetrahydrothieno[2,3-c]quinolin-4(5H)-one (Compound 37): MS obsd. (ESI+): 388.1 [(M+H)$^+$]; $^1$H NMR (400 MHz, DMSO-d6) δ ppm: 13.22 (s, 1H), 10.68 (s, 1H), 8.32 (s, 1H), 7.98 (s, 1H), 7.54 (s, 1H), 6.52 (t, J=55.6 Hz, 1H), 6.26 (s, 1H), 2.77-2.73 (m, 1H), 2.68-2.61 (m, 1H), 2.10-2.04 (m, 1H), 1.87-1.85 (m, 3H).

Examples 38 and 39—Compounds 38 and 39: (S)-9-methoxy-9-methyl-2-(1H-pyrazol-4-yl)-6,7,8,9-tetrahydrothieno[2,3-c]quinolin-4(5H)-one (Compound 38) & (R)-9-methoxy-9-methyl-2-(1H-pyrazol-4-yl)-6,7,8,9-tetrahydrothieno[2,3-c]quinolin-4(5H)-one (Compound 39) (Stereochemistry for Compounds 38 and 39 is Arbitrarily Assigned)

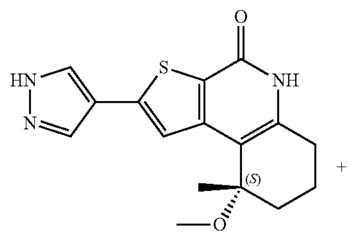

+

Compound 38

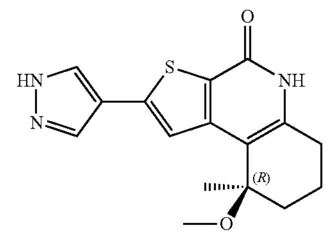

Compound 39

Step A: 7,8-dihydro-4H-thieno[2,3-c]chromene-4,9(6H)-dione

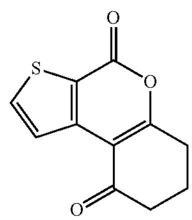 [SMILES: O=C1CCCc2oc(=O)c3sccc3c21]

Methyl 3-bromothiophene-2-carboxylate (0.50 g, 2.3 mmol, 1.0 eq.) and cyclohexane-1,3-dione (1.5 g, 14 mmol, 6.0 eq.) was dissolved in toluene (80.0 mL) before $Cs_2CO_3$ (2.2 g, 6.8 mmol, 3.0 eq.) and SPhos-Pd-G3 (180 mg, 230 μmol, 0.10 eq.) were added. The mixture was heated to 105° C. for 16 h, cooled, and diluted with $H_2O$ (50 mL). The mixture was extracted with EtOAc (50 mL×3), and the combined organic phases were washed with brine (50 mL), dried ($Na_2SO_4$), filtered, and concentrated. Purification by column chromatography ($SiO_2$, 0-20% EtOAc in PE to afforded 7,8-dihydro-4H-thieno[2,3-c]chromene-4,9(6H)-dione (82 mg, 14%). MS obsd. ($ESI^+$): 221.2 [$(M+H)^+$].

Step B: 7,8-dihydrothieno[2,3-c]quinoline-4,9(5H, 6H)-dione

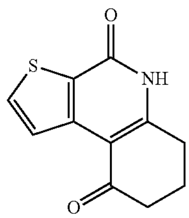 [SMILES: O=C1CCCc2[nH]c(=O)c3sccc3c21]

7,8-Dihydro-4H-thieno[2,3-c]chromene-4,9(6H)-dione (550 mg, 2.50 mmol, 1.0 eq.) was dissolved in MeOH (8.0 mL) before $NH_4OH$ (8 mL, sat. aq.) was added. The reaction mixture was heated to 90° C. for 4 h in a microwave reactor, cooled, concentrated in vacuo. Purification by column chromatography ($SiO_2$, 0-25% MeOH in DCM) afforded 7,8-dihydrothieno[2,3-c]quinoline-4,9(5H,6H)-dione (420 mg, 77%). MS obsd. ($ESI^+$): 220.2 [$(M+H)^+$].

Step C: 5-((2-(trimethylsilyl)ethoxy)methyl)-7,8-dihydrothieno[2,3-c]quinoline-4,9(5H,6H)-dione

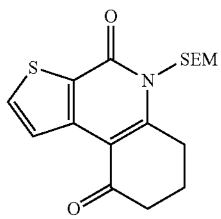 [SMILES: C[Si](C)(C)CCOCn1c2c(c3ccsc3c1=O)C(=O)CCC2]

A solution of 7,8-dihydrothieno[2,3-c]quinoline-4,9(5H, 6H)-dione (1.3 g, 5.9 mol, 1.0 eq.) in anhydrous DMF (60.0 mL) was cooled to 0° C. before NaH (360 mg, 8.9 mmol, 60% in mineral oil, 1.5 eq.) was added. After 30 min, 2-(chloromethoxy)ethyl-trimethyl-silane (2.0 g, 12 mmol, 2.1 mL, 2.0 eq.) was added, and the mixture was warmed to rt where it was stirred for 2 h. Water (150 mL) was added, and the mixture was extracted with EtOAc (100 mL×3). The combined organic phases were washed (brine, 100 mL), dried ($Na_2SO_4$), filtered and concentrated in vacuo. Purification by column chromatography ($SiO_2$, 0-30% EtOAc in PE) afforded 5-((2-(trimethylsilyl)ethoxy)methyl)-7,8-dihydrothieno[2,3-c]quinoline-4,9(5H,6H)-dione (1.0 g, 48%). MS obsd. ($ESI^+$): 350.5 [$(M+H)^+$].

Step D: 9-hydroxy-9-methyl-54(2-(trimethylsilyl) ethoxy)methyl)-6,7,8,9-tetrahydrothieno[2,3-c]quinolin-4(5H)-one

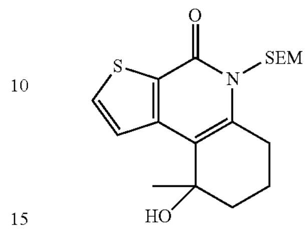

5-((2-(Trimethylsilyl)ethoxy)methyl)-7,8-dihydrothieno [2,3-c]quinoline-4,9(5H,6H)-dione (1.0 g, 2.9 mmol, 1.0 eq.) was dissolved in THF (30.0 mL) and the solution was cooled to 0° C. before methylmagnesium bromide (1 M, 57.0 mL, 57 mmol, 20 eq.) was added. The reaction mixture was warmed to rt and stirred for 2 h before water (100 mL) was added. The mixture was extracted with EtOAc (100 mL×3), and the combined organic phases were washed with brine (100 mL), dried ($Na_2SO_4$), filtered, and concentrated in vacuo. Purification by column chromatography ($SiO_2$ 0-30% EtOAc in PE) afforded 9-hydroxy-9-methyl-5-((2-(trimethylsilyl)ethoxy)methyl)-6,7,8,9-tetrahydrothieno[2,3-c]quinolin-4(5H)-one (320 mg, 27%). MS obsd. ($ESI^+$): 366.5 [$(M+H)^+$].

Step E: 9-methoxy-9-methyl-5-((2-(trimethylsilyl) ethoxy)methyl)-6,7,8,9-tetrahydrothieno[2,3-c]quinolin-4(5H)-one

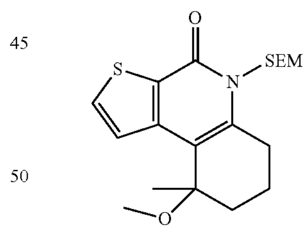

Sodium hydride (145 mg, 3.61 mmol, 60% in mineral oil, 4.0 eq.) and iodomethane (1.3 g, 9.0 mmol, 0.6 mL, 10.0 eq.) were added to a solution of 9-hydroxy-9-methyl-5-((2-(trimethylsilyl)ethoxy)methyl)-6,7,8,9-tetrahydrothieno[2,3-c] quinolin-4(5H)-one (330 mg, 0.90 mmol, 1.0 eq.) in anhydrous THF (15.0 mL). After 2 h, water (50 mL) was added, and the mixture was extracted with EtOAc (30 mL×3). The combined organic phases were washed with brine (30 mL), dried ($Na_2SO_4$), filtered and concentrated in vacuo. Purification by column chromatography ($SiO_2$, 0-15% EtOAc in PE) afforded 9-methoxy-9-methyl-54(2-(trimethylsilyl) ethoxy)methyl)-6,7,8,9-tetrahydrothieno[2,3-c]quinolin-4 (5H)-one (190 mg, 55%). MS obsd. ($ESI^+$): 380.6 [$(M+H)^+$].

Step F: 2-iodo-9-methoxy-9-methyl-5-((2-(trimethylsilyl)ethoxy)methyl)-6,7,8,9-tetrahydrothieno[2,3-c]quinolin-4(5H)-one

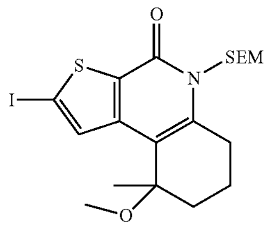 [SMILES: COC1(C)CCCc2c1c1cc(I)sc1c(=O)n2COCC[Si](C)(C)C]

9-Methoxy-9-methyl-5-((2-(trimethylsilyl)ethoxy)methyl)-6,7,8,9-tetrahydrothieno[2,3-c]quinolin-4(5H)-one (140 mg, 0.37 mmol, 1.0 eq.) was dissolved in THF (8.0 mL) and cooled to −65° C. Lithium diisopropylamine (2 M, 0.7 mL, 1.5 mmol, 4.0 eq.) was added followed by iodine (190 mg, 0.74 mmol, 2.0 eq.), and the mixture was stirred at −65° C. for 2 h. Water (10 mL) was added, and the mixture was extracted with EtOAc (10 mL×3). The combined organic phases were washed with brine (10 mL), dried ($Na_2SO_4$), filtered, and concentrated in vacuo. Purification by column chromatography ($SiO_2$, 0-15% EtOAc in PE) afforded 2-iodo-9-methoxy-9-methyl-5-((2-(trimethylsilyl)ethoxy)methyl)-6,7,8,9-tetrahydrothieno[2,3-c]quinolin-4(5H)-one (120 mg, 62%). MS obsd. ($ESI^+$): 506.6 [$(M+H)^+$].

Step G: 9-methoxy-9-methyl-5-((2-(trimethylsilyl)ethoxy)methyl)-2-(1-((2-(trimethylsilyl) ethoxy)methyl)-1H-pyrazol-4-yl)-6,7,8,9-tetrahydrothieno[2,3-c]quinolin-4(5H)-one

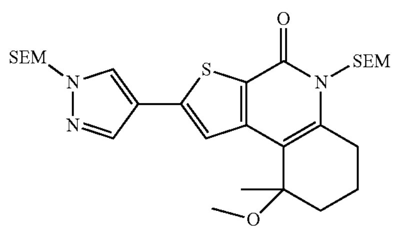 [SMILES: COC1(C)CCCc2c1c1cc(-c3cnn(COCC[Si](C)(C)C)c3)sc1c(=O)n2COCC[Si](C)(C)C]

Pd(dppf)$Cl_2$ (32 mg, 40 μmol, 0.20 eq.), XPhos (42 mg, 90 μmol, 0.40 eq.), and $Na_2CO_3$ (70 mg, 0.65 mmol, 3.0 eq.) were added to a solution of 2-iodo-9-methoxy-9-methyl-5-((2-(trimethylsilyl)ethoxy)methyl)-6,7,8,9-tetrahydrothieno[2,3-c]quinolin-4(5H)-one (110 mg, 0.22 mmol, 1.0 eq.) and trimethyl-[2-[[4-(4,4,5,5-tetramethyl-1,3,2-dioxaborolan-2-yl)pyrazol-1-yl]methoxy]ethyl]silane (110 mg, 0.35 mmol, 1.6 eq.) in $H_2O$/1,4-dioxane (8.0 mL, 1:3 mixture). The mixture was heated to 110° C. for 2 h then concentrated in vacuo. Purification by column chromatography (0-30% EtOAc in PE) afforded 9-methoxy-9-methyl-5-((2-(trimethylsilyl)ethoxy)methyl)-2-(1-((2-(trimethylsilyl)ethoxy)methyl)-1H-pyrazol-4-yl)-6,7,8,9-tetrahydrothieno[2,3-c]quinolin-4(5H)-one (110 mg, 88%). MS obsd. ($ESI^+$): 576.9 [$(M+H)^+$].

Step H: (9S)-9-methoxy-9-methyl-2-(1H-pyrazol-4-yl)-5,6,7,8-tetrahydrothieno[2,3-c]quinolin-4-one (Compound 38) and (9R)-9-methoxy-9-methyl-2-(1H-pyrazol-4-yl)-5,6,7,8-tetrahydrothieno[2,3-c]quinolin-4-one (Compound 39)

Compound 38

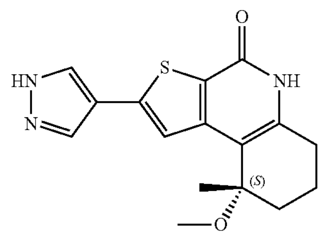

Compound 39

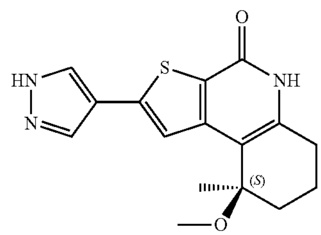

$BCl_3$ (1.0 M, 1.1 mL, 1.1 mmol, 5.0 eq.) was added to a solution of 9-methoxy-9-methyl-5-((2-(trimethylsilyl)ethoxy)methyl)-2-(1-((2-(trimethylsilyl)ethoxy)methyl)-1H-pyrazol-4-yl)-6,7,8,9-tetrahydrothieno[2,3-c]quinolin-4(5H)-one (130 mg, 0.22 mmol, 1.0 eq.) in DCM (13.0 mL) at 0° C. After 10 min, $NH_3$/MeOH was added (to pH 9), and the mixture was concentrated in vacuo. Purification by column chromatography (C18 $SiO_2$, 0-20% MeCN in water (0.1% $NH_4OH$)) afforded racemic 9-methoxy-9-methyl-2-(1H-pyrazol-4-yl)-6,7,8,9-tetrahydrothieno[2,3-c]quinolin-4(5H)-one (24 mg, 34%). MS obsd. ($ESI^+$): 316.2 [$(M+H)^+$].

The individual enantiomers were separated via chiral SFC. (9S)-9-methoxy-9-methyl-2-(1H-pyrazol-4-yl)-5,6,7,8-tetrahydrothieno[2,3-c]quinolin-4-one (Compound 38): MS obsd. ($ESI^+$): 316.2 [$(M+H)^+$]. (9R)-9-methoxy-9-methyl-2-(1H-pyrazol-4-yl)-5,6,7,8-tetrahydrothieno[2,3-c]quinolin-4-one (Compound 39): MS obsd. ($ESI^+$): 316.2 [$(M+H)^+$]; $^1H$ NMR (400 MHz, DMSO-d6) δ ppm: 13.21 (s, 1H), 11.29 (s, 1H), 8.32 (s, 1H), 7.91 (s, 1H), 7.64 (s, 1H), 2.94 (s, 3H), 2.70-2.52 (m, 2H), 2.15-2.01 (m, 1H), 1.95-1.87 (m, 1H), 1.83-1.67 (m, 1H), 1.55-1.65 (m, 1H), 1.50 (m, 3H).

Examples 40 and 41—Compounds 40 and 41: (S)-6-hydroxy-6-methyl-2-(1H-pyrazol-4-yl)-6,7,8,9-tetrahydrothieno[2,3-c]quinolin-4(5H)-one (Compound 40) & (R)-6-hydroxy-6-methyl-2-(1H-pyrazol-4-yl)-6,7,8,9-tetrahydrothieno[2,3-c]quinolin-4(5H)-one (Compound 41) (Stereochemistry for Compounds 40 and 41 is Arbitrarily Assigned)

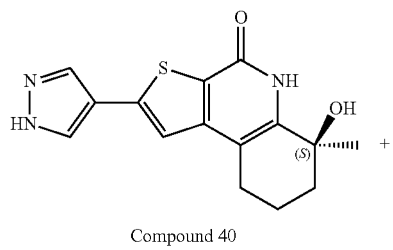

+

Compound 40

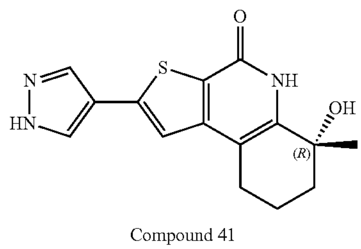

Compound 41

Step A: tert-butyl 4-(6-hydroxy-4-oxo-4,5,6,7,8,9-hexahydrothieno[2,3-c]quinolin-2-yl)-1H-pyrazole-1-carboxylate

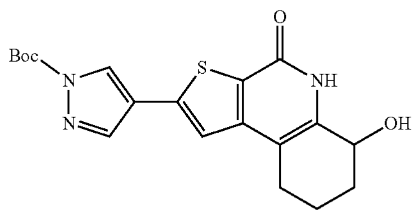 [SMILES: CC(C)(C)OC(=O)n1cc(-c2cc3c4c([nH]c(=O)c3s2)C(O)CCC4)cn1]

Triethylamine (280 mg, 2.8 mmol, 2.0 eq), DMAP (85 mg, 70 μmol, 0.50 eq.) and $(Boc)_2O$ (300 mg, 1.40 mmol, 1.0 eq.) was added to a suspension of 6-hydroxy-2-(1H-pyrazol-4-yl)-6,7,8,9-tetrahydro-5H-thieno[2,3-c]quinolin-4-one (400 mg, 1.40 mmol, 1.0 eq.) in DMF (20.0 mL). The mixture was stirred at rt for 16 h then extracted with EtOAc (50 mL×3). The combined organic phases were washed with brine, dried ($Na_2SO_4$), filtered, and concentrated. Purification by column chromatography ($SiO_2$, 0-100% EtOAc in PE) afforded tert-butyl 4-(6-hydroxy-4-oxo-4,5,6,7,8,9-hexahydrothieno[2,3-c]quinolin-2-yl)-1H-pyrazole-1-carboxylate (400 mg, 74%). MS obsd. ($ESI^+$): 388.5 [$(M+H)^+$].

Step B: tert-butyl 4-(4,6-dioxo-5,7,8,9-tetrahydrothieno[2,3-c]quinolin-2-yl)pyrazole-1-carboxylate

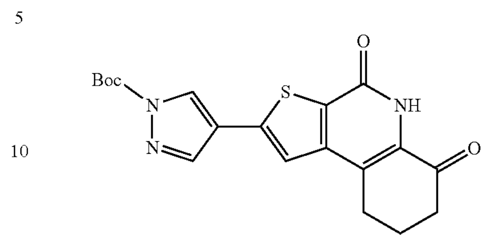

A suspension of tert-butyl 4-(6-hydroxy-4-oxo-4,5,6,7,8,9-hexahydrothieno[2,3-c]quinolin-2-yl)-1H-pyrazole-1-carboxylate (140 mg, 0.36 mmol, 1.0 eq.) and (1,1-diacetoxy-3-oxo-1,2-benziodoxol-1-yl) acetate (110 mg, 3.6 mmol, 10 eq.) in DCM (14.0 mL) was stirred at rt for 1 h. The mixture was concentrated and the residue was purified by column chromatography ($SiO_2$, 0-10% MeOH in DCM) to afford tert-butyl 4-(4,6-dioxo-5,7,8,9-tetrahydrothieno[2,3-c]quinolin-2-yl)pyrazole-1-carboxylate (120 mg, 87%). MS obsd. ($ESI^+$): 386.5 [$(M+H)^+$].

Step C: (S)-6-hydroxy-6-methyl-2-(1H-pyrazol-4-yl)-6,7,8,9-tetrahydrothieno[2,3-c]quinolin-4(5H)-one (Compound 40) and (R)-6-hydroxy-6-methyl-2-(1H-pyrazol-4-yl)-6,7,8,9-tetrahydrothieno[2,3-c]quinolin-4(5H)-one (Compound 41)

Compound 40

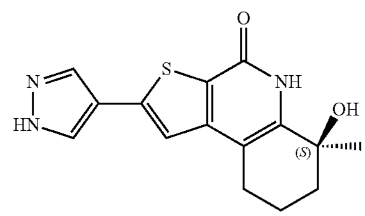

Compound 41

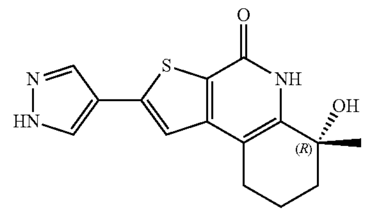

Methylmagnesium bromide (1.0 M, 4.8 mL, 4.8 mmol, 3.0 eq.) was added to a solution of tert-butyl 4-(6-hydroxy-4-oxo-4,5,6,7,8,9-hexahydrothieno[2,3-c]quinolin-2-yl)-1H-pyrazole-1-carboxylate (60 mg, 0.16 mmol, 1.0 eq.) in THF (24.0 mL). The mixture was stirred at rt for 2 h, then MeOH was added, and the resulting mixture was concentrated in vacuo and purified by column chromatography ($SiO_2$, 0-10% MeOH in DCM) to afford racemic 6-hydroxy-6-methyl-2-(1H-pyrazol-4-yl)-6,7,8,9-tetrahydrothieno[2,3-c]quinolin-4(5H)-one (39 mg, 62%).

The individual enantiomers were separated via chiral SFC. (S)-6-hydroxy-6-methyl-2-(1H-pyrazol-4-yl)-6,7,8,9-tetrahydrothieno[2,3-c]quinolin-4(5H)-one (Compound 40): MS obsd. ($ESI^+$): 302.1 [$(M+H)^+$]; $^1H$ NMR (400 MHz, DMSO-d6) δ ppm: 13.10 (s, 1H), 10.51 (s, 1H), 8.12 (s, 2H), 7.46 (s, 1H), 5.12 (s, 1H), 2.32-2.51 (m, 2H), 1.88-1.82 (m, 3H), 1.78-1.67 (m, 1H), 1.46 (s, 3H). (R)-6-hydroxy-6-methyl-2-(1H-pyrazol-4-yl)-6,7,8,9-tetrahydrothieno[2,3-c]quinolin-4(5H)-one (Compound 41): MS obsd. ($ESI^+$): 302.1 [$(M+H)^+$].

Examples 42 and 43—Compounds 42 and 43: (S)-4-(difluoromethyl)-4-hydroxy-8-(1H-pyrazol-4-yl)-1,3,4,5-tetrahydro-6H-pyrano[4,3-b]thieno[3,2-d]pyridin-6-one (Compound 42) & (R)-4-(difluoromethyl)-4-hydroxy-8-(1H-pyrazol-4-yl)-1,3,4,5-tetrahydro-6H-pyrano[4,3-b]thieno[3,2-d]pyridin-6-one (Compound 43) (Stereochemistry for Compounds 42 and 43 is Arbitrarily Assigned)

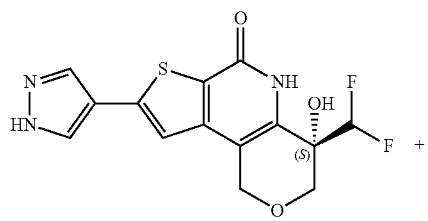

+

Compound 42

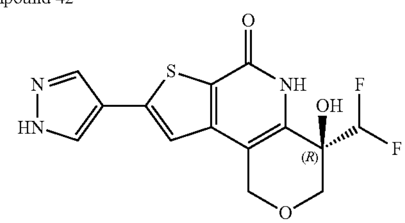

Compound 43

Step A: 4-hydroxy-8-(1-((2-(trimethylsilyl)ethoxy)methyl)-1H-pyrazol-4-yl)-3,4-dihydro-1H,6H-pyrano[4,3-b]thieno[3,2-d]pyran-6-one

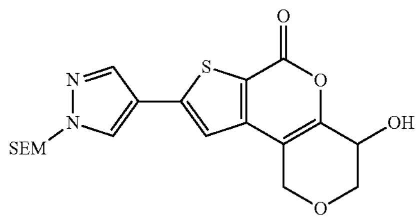 [SMILES: C[Si](C)(C)CCOCn1cc(-c2cc3c4c(oc(=O)c3s2)C(O)COC4)cn1]

Sodium hydride (140 mg, 3.4 mmol, 60% in mineral oil, 2.0 eq.) was added to a cooled (0° C.) solution of 4-hydroxy-8-(1H-pyrazol-4-yl)-3,4-dihydro-1H,6H-pyrano[4,3-b]thieno[3,2-d]pyran-6-one (500 mg, 1.7 mmol, 1.0 eq.) in DMF (20.0 mL). After 10 min at 0° C., SEMCl (370 μL, 350 mg, 2.0 mmol, 1.2 eq.) was slowly added to the mixture. The mixture was stirred for 2 h at rt, then quenched with ammonium chloride (sat. aq.) then extracted with EtOAc (25 mL×3). The combined organic phases were treated with brine, dried ($Na_2SO_4$), filtered, and concentrated. Purification by column chromatography ($SiO_2$, 0-40% EtOAc in DCM) afforded 4-hydroxy-8-(1-((2-(trimethylsilyl)ethoxy)methyl)-1H-pyrazol-4-yl)-3,4-dihydro-1H,6H-pyrano[4,3-b]thieno[3,2-d]pyran-6-one (400 mg, 52%). MS obsd. ($ESI^+$): 421.2 [$(M+H)^+$].

Step B: 8-(1-((2-(trimethylsilyl)ethoxy)methyl)-1H-pyrazol-4-yl)-1H,3H-pyrano[4,3-b]thieno[3,2-d]pyran-4,6-dione

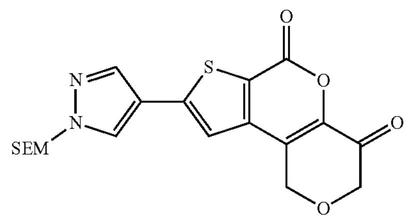 [SMILES: C[Si](C)(C)CCOCn1cc(-c2cc3c4c(oc(=O)c3s2)C(=O)COC4)cn1]

4-Hydroxy-8-(1-((2-(trimethylsilyl)ethoxy)methyl)-1H-pyrazol-4-yl)-3,4-dihydro-1H,6H-pyrano[4,3-b]thieno[3,2-d]pyran-6-one (400 mg, 950 μmol, 1.0 eq.) was dissolved in DCM (20.0 mL) and DMF (20.0 mL), and (1,1-diacetoxy-3-oxo-1,2-benziodoxol-1-yl) acetate (1.2 g, 2.9 mmol, 3.0 eq.) was added. The mixture was stirred at rt for 16 h, then quenched with $Na_2S_2O_3$ (sat. aq.) and $NaHCO_3$ (sat. aq.). The mixture was extracted with EtOAc (30 mL×3), and the combined organic phases were dried ($Na_2SO_4$), filtered, and concentrated. Purification by column chromatography ($SiO_2$, 0-30% EtOAc in DCM) afforded 8-(1-((2-(trimethylsilyl)ethoxy)methyl)-1H-pyrazol-4-yl)-1H,3H-pyrano[4,3-b]thieno[3,2-d]pyran-4,6-dione (270 mg, 63%). MS obsd. ($ESI^+$): 419.2 [$(M+H)^+$], 436.2 [$(M+NH_4)\pm$].

Step C: 4-(difluoromethyl)-4-hydroxy-8-(1-((2-(trimethylsilyl)ethoxy)methyl)-1H-pyrazol-4-yl)-3,4-dihydro-1H,6H-pyrano[4,3-b]thieno[3,2-d]pyran-6-one

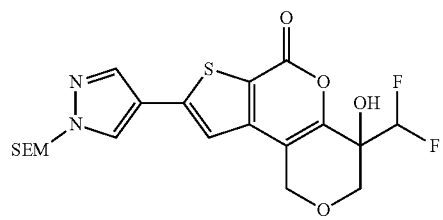 [SMILES: C[Si](C)(C)CCOCn1cc(-c2cc3c4c(oc(=O)c3s2)C(O)(C(F)F)COC4)cn1]

Cesium fluoride (210 mg, 1.4 mmol, 2.5 eq.) was added to a solution of 8-(1-((2-(trimethylsilyl)ethoxy)methyl)-1H-pyrazol-4-yl)-1H,3H-pyrano[4,3-b]thieno[3,2-d]pyran-4,6-dione (270 mg, 560 μmol, 1.0 eq.) in DMF (24.0 mL) followed by $TMSCF_2H$ (350 mg, 2.8 mmol, 400 μL, 5.0 eq.). The mixture was stirred for 16 h. Water was added, and the mixture was extracted with EtOAc (25 mL×5). The combined organic phases were washed with brine, dried ($Na_2SO_4$), filtered, and concentrated. Purification by column chromatography ($SiO_2$, 0-40% EtOAc in PE) afforded 4-(difluoromethyl)-4-hydroxy-8-(1-((2-(trimethylsilyl)ethoxy)methyl)-1H-pyrazol-4-yl)-3,4-dihydro-1H,6H-pyrano[4,3-b]thieno[3,2-d]pyran-6-one (48 mg, 16%). MS obsd. ($ESI^+$): 471.4 [$(M+H)^+$].

Step D: 4-(difluoromethyl)-4-hydroxy-8-(1-((2-(trimethylsilyl)ethoxy)methyl)-1H-pyrazol-4-yl)-1,3,4,5-tetrahydro-6H-pyrano[4,3-b]thieno[3,2-d]pyridin-6-one

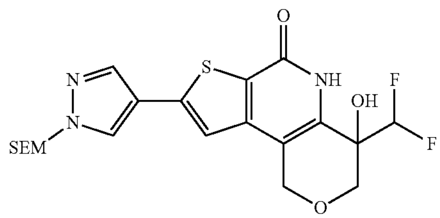 [SMILES: C[Si](C)(C)CCOCn1cc(-c2cc3c4c([nH]c(=O)c3s2)C(O)(C(F)F)COC4)cn1]

Aqueous ammonia (8.0 mL, 25% w/w) was added to a solution of 4-(difluoromethyl)-4-hydroxy-8-(1-((2-(trimethylsilyl)ethoxy)methyl)-1H-pyrazol-4-yl)-3,4-dihydro-1H, 6H-pyrano[4,3-b]thieno[3,2-d]pyran-6-one (140 mg, 260 μmol, 1.0 eq.) in i-PrOH (8.0 mL). The mixture was heated to 100° C. in a microwave reactor for 6 h then cooled and concentrated. Purification by column chromatography ($SiO_2$, 0-8% MeOH in DCM) afforded 4-(difluoromethyl)-4-hydroxy-8-(1-((2-(trimethylsilyl)ethoxy)methyl)-1H-pyrazol-4-yl)-1,3,4,5-tetrahydro-6H-pyrano[4,3-b]thieno[3,2-d]pyridin-6-one (55 mg, 41%). MS obsd. ($ESI^+$): 470.2 $[(M+H)^+]$.

Step E: (S)-4-(difluoromethyl)-4-hydroxy-8-(1H-pyrazol-4-yl)-1,3,4,5-tetrahydro-6H-pyrano[4,3-b]thieno[3,2-d]pyridin-6-one (Compound 42) and (R)-4-(difluoromethyl)-4-hydroxy-8-(1H-pyrazol-4-yl)-1,3,4,5-tetrahydro-6H-pyrano[4,3-b]thieno[3,2-d]pyridin-6-one (Compound 43)

Compound 42

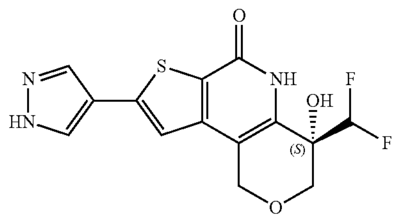

Compound 43

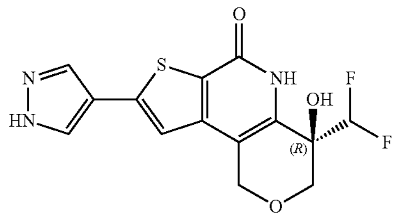

4-(Difluoromethyl)-4-hydroxy-8-(1-((2-(trimethylsilyl)ethoxy)methyl)-1H-pyrazol-4-yl)-1,3,4,5-tetrahydro-6H-pyrano[4,3-b]thieno[3,2-d]pyridin-6-one (10 mg, 21 μmol) was dissolved in DCM: trifluoroacetic acid (4.0 mL, 3:1). The mixture was stirred at rt for 1 h then concentrated and purified by reverse phase HPLC (C18 $SiO_2$, 0-15% MeCN in water (0.1% $NH_4OH$)). Further purification by column chromatography ($SiO_2$, 0-8% MeOH in DCM) afforded racemic 4-(difluoromethyl)-4-hydroxy-8-(1H-pyrazol-4-yl)-1,3,4,5-tetrahydro-6H-pyrano[4,3-b]thieno[3,2-d]pyridin-6-one (1.3 mg, 17%). MS obsd. ($ESI^+$): 340.0 $[(M+H)^+]$.

The individual enantiomers were separated via chiral SFC. (S)-4-(difluoromethyl)-4-hydroxy-8-(1H-pyrazol-4-yl)-1,3,4,5-tetrahydro-6H-pyrano[4,3-b]thieno[3,2-d]pyridin-6-one (Compound 42): MS obsd. ($ESI^+$): 340.2 $[(M+H)^+]$; $^1$H NMR (400 MHz, DMSO-d6) δ ppm: 13.24 (s, 1H), 11.04 (s, 1H), 8.29 (s, 1H), 7.99 (s, 1H), 7.47 (s, 1H), 6.57 (s, 1H), 6.44 (t, J=55.0 Hz, 1H), 4.76 (s, 2H), 4.11 (d, J=12.0 Hz, 1H), 3.72 (d, J=12.0 Hz, 1H). (R)-4-(difluoromethyl)-4-hydroxy-8-(1H-pyrazol-4-yl)-1,3,4,5-tetrahydro-6H-pyrano[4,3-b]thieno[3,2-d]pyridin-6-one (Compound 43): MS obsd. ($ESI^+$): 340.2 $[(M+H)^+]$.

Examples 44 and 45—Compounds 44 and 45: (S)-4-hydroxy-4-isopropyl-8-(pyridin-4-yl)-1,3,4,5-tetrahydro-6H-pyrano[4,3-b]thieno[3,2-d]pyridin-6-one (Compound 44) & (R)-4-hydroxy-4-isopropyl-8-(pyridin-4-yl)-1,3,4,5-tetrahydro-6H-pyrano[4,3-b]thieno[3,2-d]pyridin-6-one (Compound 45) (Stereochemistry for Compounds 44 and 45 are Assigned Arbitrarily)

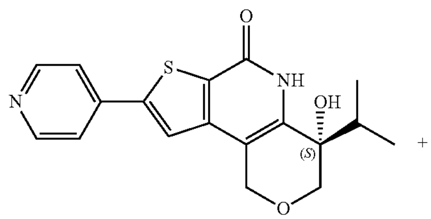

\+

Compound 44

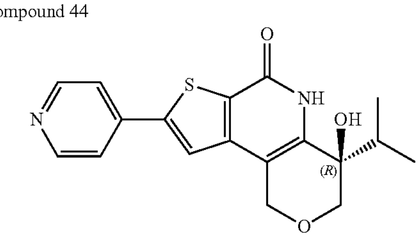

Compound 45

Step A: 4,4-dimethoxy-3-(prop-1-en-2-yl)tetrahydro-2H-pyran-3-ol

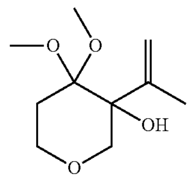

To a solution of 4,4-dimethoxydihydro-2H-pyran-3(4H)-one (5.0 g, 31 mmol, 1.0 eq. synthesized according to the procedure described in WO2013152269) in anhydrous THF (100 mL) under $N_2$ atmosphere was added bromo(isopropenyl)magnesium (1 M, 125.0 mL, 125 mmol, 4.0 eq.) at 0° C. After addition, the mixture was stirred at 0° C. for 30 min. then warmed to 25° C. and stirred at under $N_2$ another 2 h. The mixture was cooled to 0° C. then quenched with saturated $NH_4Cl$ (aq.) (120 mL), diluted with water (100 mL) and extracted with EtOAc (100 mL×3). The combined organic layers were washed with brine (100 mL), dried over anhydrous sodium sulfate, filtered and evaporated in vacuo. Purification by column chromatography ($SiO_2$, 0-25% EtOAc in PE) afforded 4,4-dimethoxy-3-(prop-1-en-2-yl) tetrahydro-2H-pyran-3-ol (3.5 g, 55%). $^1$H NMR (400 MHz, $CDCl_3$) δ ppm: 5.37 (m, 1H), 5.08-5.03 (m, 1H), 3.76 (d, J=11.4 Hz, 1H), 3.72-3.60 (m, 2H), 3.36 (d, J=11.4 Hz, 1H), 3.32 (d, J=2.8 Hz, 6H), 2.08-1.99 (m, 1H), 1.98-1.95 (m, 3H), 1.94-1.87 (m, 1H).

Step B: 3-hydroxy-3-isopropyltetrahydro-4H-pyran-4-one

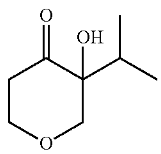

To a 1 L pressure vessel was added 4,4-dimethoxy-3-(prop-1-en-2-yl)tetrahydro-2H-pyran-3-ol (17.5 g, 82.20 mmol) to methanol (500.0 mL), 4 N HCl aq. (20.0 mL), and Pd/C (998.34 mg, 8.22 mmol) under a nitrogen atmosphere. The vessel was sealed and shaken at room temperature under 20 atm of hydrogen pressure for 8 h. Upon purging with nitrogen, the vessel was unsealed, and the mixture was filtered through a Celite pad. The filtrate was concentrated in vacuo to afford 3-hydroxy-3-isopropyltetrahydro-4H-pyran-4-one (10.9 g, 65.46 mmol, 79.63% yield, 95% purity) as a yellow liquid. MS obsd. (ESI$^+$): 159.2 [(M+H)$^+$].

Step C: 4-hydroxy-4-isopropyl-8-(pyridin-4-yl)-3,4-dihydro-1H,6H-pyrano[4,3-b]thieno[3,2-d]pyran-6-one

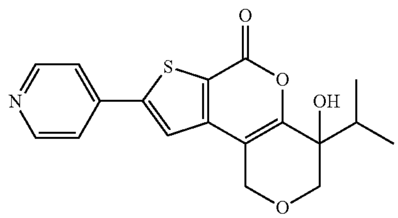 [SMILES: CC(C)C1(O)COCc2c1oc(=O)c1sc(-c3ccncc3)cc21]

To a solution of 3-hydroxy-3-isopropyltetrahydro-4H-pyran-4-one (106 mg, 0.67 mmol, 2.0 eq.) in toluene (10.0 mL) was added methyl 3-bromo-5-(pyridin-4-yl)thiophene-2-carboxylate (100 mg, 0.34 mmol, 1.0 eq.), tris(dibenzylideneacetone)dipalladium (61 mg, 0.67 mmol, 0.20 eq.), 4,5-Bis(diphenylphosphino)-9,9-dimethylxanthene (116 mg, 0.20 mmol, 0.60 eq.), cesium carbonate (219 mg, 0.67 mmol, 2.0 eq.) and sodium metabisulfite (13 mg, 0.070 mmol, 0.20 eq.). The mixture was stirred at 105° C. for 16 h then concentrated. The residue was diluted with water (20 mL), extracted with EtOAc (20 mL×3). The combined organic layers were washed with brine, dried over anhydrous sodium sulfate, filtered and concentrated. The residue was purified by column chromatography ($SiO_2$, 1-50% EtOAc in PE) to afford racemic 4-hydroxy-4-isopropyl-8-(pyridin-4-yl)-3,4-dihydro-1H,6H-pyrano[4,3-b]thieno[3,2-d]pyran-6-one. MS obsd. (ESI$^+$): 344.4 [(M+H)$^+$].

Step D: (S)-4-hydroxy-4-isopropyl-8-(pyridin-4-yl)-1,3,4,5-tetrahydro-6H-pyrano[4,3-b]thieno[3,2-d]pyridin-6-one (Compound 44) & (R)-4-hydroxy-4-isopropyl-8-(pyridin-4-yl)-1,3,4,5-tetrahydro-6H-pyrano[4,3-b]thieno[3,2-d]pyridin-6-one (Compound 45)

Compound 44

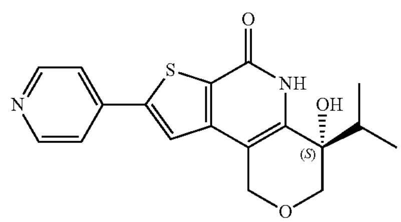

Compound 45

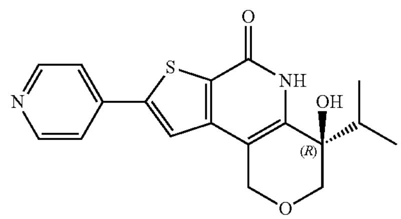

A solution of 4-hydroxy-4-isopropyl-8-(pyridin-4-yl)-3,4-dihydro-1H,6H-pyrano[4,3-b]thieno[3,2-d]pyran-6-one (62 mg, 0.18 mmol, 1.0 eq.) in a mixture of $NH_4OH$ (3.0 mL) and MeOH (3.0 mL) was heated in a microwave reactor at 100° C. for 3 h. The mixture was concentrated and the residue purified by column chromatography ($SiO_2$, 1-5% EtOAc in PE) to afford racemic 4-hydroxy-4-isopropyl-8-(pyridin-4-yl)-1,3,4,5-tetrahydro-6H-pyrano[4,3-b]thieno[3,2-d]pyridin-6-one (17 mg, 28%). MS obsd. (ESI$^+$): 343.5 [(M+H)$^+$].

The individual enantiomers were separated via chiral SFC. (S)-4-hydroxy-4-isopropyl-8-(pyridin-4-yl)-1,3,4,5-tetrahydro-6H-pyrano[4,3-b]thieno[3,2-d]pyridin-6-one (Compound 44): MS obsd. (ESI$^+$): 343.2 [(M+H)$^+$]; $^1$H NMR (400 MHz, DMSO-d6) δ ppm: 11.07 (s, 1H), 8.69 (d, J=6.0 Hz, 2H), 8.04 (s, 1H), 7.81 (d, J=6.0 Hz, 2H), 5.31 (s, 1H), 4.73 (s, 2H), 3.98 (d, J=12.0 Hz, 1H), 3.55 (d, J=11.6 Hz, 1H), 2.39-2.25 (m, 1H), 1.00 (d, J=6.8 Hz, 3H), 0.77 (d, J=7.2 Hz, 3H). (R)-4-hydroxy-4-isopropyl-8-(pyridin-4-yl)-1,3,4,5-tetrahydro-6H-pyrano[4,3-b]thieno[3,2-d]pyridin-6-one (Compound 45): MS obsd. (ESI$^+$): 343.2 [(M+H)$^+$].

Examples 46 and 47—Compounds 46 and 47: (S)-4-hydroxy-4-isopropyl-8-(isothiazol-5-yl)-1,3,4,5-tetrahydro-6H-pyrano[4,3-b]thieno[3,2-d]pyridin-6-one (Compound 46) & (R)-4-hydroxy-4-isopropyl-8-(isothiazol-5-yl)-1,3,4,5-tetrahydro-6H-pyrano[4,3-b]thieno[3,2-d]pyridin-6-one (Compound 47)

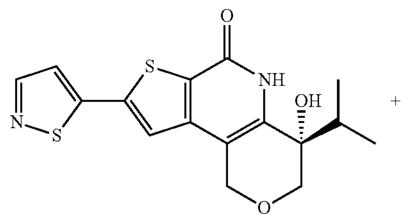

+

Compound 46

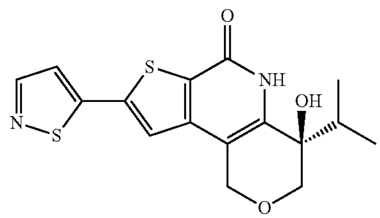

Compound 47

Racemic 4-hydroxy-4-isopropyl-8-(isothiazol-5-yl)-3,4-dihydro-1H-pyrano[4,3-b]thieno[3,2-d]pyridin-6(5H)-one was synthesized via an analogous route to Compounds 43 and 44). Separation via chiral SFC afforded each enantiomer. (S)-4-hydroxy-4-isopropyl-8-(isothiazol-5-yl)-1,3,4,5-tetrahydro-6H-pyrano[4,3-b]thieno[3,2-d]pyridin-6-one (Compound 46): MS obsd. ($ESI^+$): 349.0 [$(M+H)^+$]. (R)-4-hydroxy-4-isopropyl-8-(isothiazol-5-yl)-1,3,4,5-tetrahydro-6H-pyrano[4,3-b]thieno[3,2-d]pyridin-6-one (Compound 47): MS obsd. ($ESI^+$): 349.0 [$(M+H)^+$]; $^1$H NMR (400 MHz, DMSO-$d_6$) δ ppm: 11.10 (s, 1H), 8.64 (d, J=2.0 Hz, 1H), 7.84 (d, J=2.0 Hz, 1H), 7.81 (s, 1H), 5.31 (s, 1H), 4.71 (s, 2H), 3.97 (d, J=11.6 Hz, 1H), 3.54 (d, J=11.6 Hz, 1H), 2.40-2.37 (m, 1H), 1.01-0.99 (d, J=6.8 Hz, 3H), 0.77-0.75 (d, J=6.8 Hz, 3H).

Examples 48 and 49—Compounds 48 and 49: (S)-8,8-difluoro-6-hydroxy-6-(methoxymethyl)-2-(1H-pyrazol-4-yl)-6,7,8,9-tetrahydrothieno[2,3-c]quinolin-4(5H)-one (Compound 48) & (R)-8,8-difluoro-6-hydroxy-6-(methoxymethyl)-2-(1H-pyrazol-4-yl)-6,7,8,9-tetrahydrothieno[2,3-c]quinolin-4(5H)-one (Compound 49)

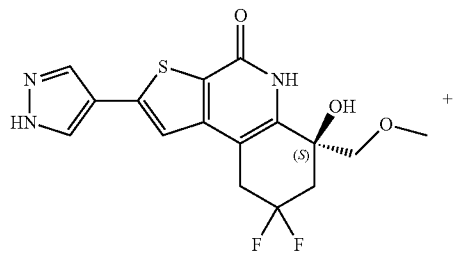

+

Compound 48

-continued

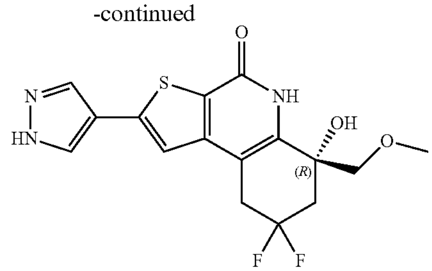

Compound 49

Step A: 5,5-difluoro-2,2-dimethoxycyclohexan-1-one

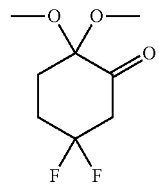

To a solution of 5,5-difluoro-2,2-dimethoxy-cyclohexanol (29.4 g, 150 mmol, synthesized according to the procedure for Compound 12 step A) in DCM (800.0 mL) was added Dess-Martin Periodinane (95.4 g, 225 mmol) portionwise over 20 min. The mixture was stirred for 2 hr. then concentrated. The residue was diluted with water, washed with petroleum ether:ethyl acetate (10:1, 500 mL), and the organic layers were dried over sodium sulfate, filtered and concentrated. The residue was purified by column chromatography ($SiO_2$, 12% EtOAc in PE) to give 5,5-difluoro-2,2-dimethoxycyclohexan-1-one (16.2 g, 55%). $^1$H NMR (400 MHz, $CDCl_3$): δ ppm: 3.27 (s, 6H), 3.04 (t, J=14.4 Hz, 2H), 2.28 ppm (m, 2H), 2.02 (m, 2H).

Step B: 5,5-difluoro-2,2-dimethoxy-1-vinylcyclohexan-1-ol

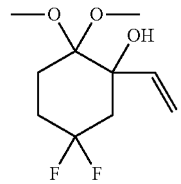

To a solution of 5,5-difluoro-2,2-dimethoxycyclohexan-1-one (1.2 g, 6.2 mmol, 1.0 eq.) in anhydrous THF (30.0 mL) was added bromo(vinyl)magnesium (1 M, 18.5 mL, 3.0 eq.) dropwise at 0° C. The mixture was stirred at room temperature for 1 h. then poured into saturated $NH_4Cl$ (aq.) (10 mL) and extracted with ethyl acetate (40 mL×2). The combined organic layers were washed with brine, dried over anhydrous sodium sulfate, filtered and concentrated in vacuo. The residue was purified by column chromatography ($SiO_2$, 0-10% EtOAc in PE) to give 5,5-difluoro-2,2-dimethoxy-1-vinylcyclohexan-1-ol (630 mg, 45%). $^1$H NMR (400 MHz, $CDCl_3$): δ ppm: 6.19 (dd, J=17.2, 10.8 Hz, 1H), 5.47 (dd, J=17.2, 1.6 Hz, 1H), 5.13 (dd, J=10.8, 1.6 Hz, 1H), 3.24 (s, 3H), 3.23 (s, 3H), 2.54 (s, 1H), 2.16-1.74 (m, 6H).

Step C: (((5,5-difluoro-2,2-dimethoxy-1-vinylcyclohexyl)oxy)methyl)benzene

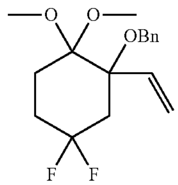 [SMILES: C=CC1(OCc2ccccc2)CC(F)(F)CCC1(OC)OC]

Sodium hydride (305 mg, 7.63 mmol, 60% in mineral oil, 1.5 eq.) was added to a solution of 5,5-difluoro-2,2-dimethoxy-1-vinylcyclohexan-1-ol (1.13 g, 5.08 mmol, 1.0 eq.) in anhydrous DMF (30.0 mL) portionwise at 0° C. The mixture was stirred at 0° C. for 1 h. then benzyl bromide (2.61 g, 15.2 mmol, 3.0 eq.) was added, and the mixture was stirred at room temperature for another 1 h. The mixture was poured into ice water and extracted with DCM (30 mL×2). The combined organic layers were dried over anhydrous sodium sulfate, filtered and concentrated. The residue was purified by column chromatography ($SiO_2$, 0-10% EtOAc in PE) to afford (((5,5-difluoro-2,2-dimethoxy-1-vinylcyclohexyl)oxy)methyl)benzene (1.3 g, 81%). $^1H$ NMR (400 MHz, $CDCl_3$): δ ppm: 7.38-7.28 (m, 5H), 6.13-6.04 (m, 1H), 5.44 (dd, J=11.2, 0.8 Hz, 1H), 5.29 (d, J=18.0 Hz, 1H), 4.44 (dd, J=34.8, 11.2 Hz, 2H), 3.42 (s, 3H), 3.28 (s, 3H), 2.50-1.80 (m, 6H).

Step D: (1-(benzyloxy)-5,5-difluoro-2,2-dimethoxycyclohexyl)methanol

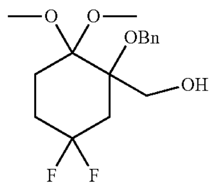 [SMILES: COC1(OC)CCC(F)(F)CC1(CO)OCc1ccccc1]

Ozone was bubbled through a solution of (((5,5-difluoro-2,2-dimethoxy-1-vinylcyclohexyl)oxy)methyl)benzene (650 mg, 2.08 mmol, 1.0 eq.) in DCM (20.0 mL) at −78° C. The mixture was stirred for 30 min at −78° C. then allowed to warm to rt. MeOH (5.0 ml) and $NaBH_4$ (236 mg, 6.24 mmol, 3.0 eq.) were added, and the mixture was stirred for 5 min. The mixture was poured into water and extracted with ethyl acetate (70 mL×2). The combined organic layers were washed with brine, dried over anhydrous sodium sulfate, filtered and concentrated. The residue was purified by column chromatography ($SiO_2$ 15-30% EtOAc in PE) to afford (1-(benzyloxy)-5,5-difluoro-2,2-dimethoxycyclohexyl) methanol (1.1 g, 83%). $^1H$ NMR (400 MHz, $CDCl_3$): δ ppm: 7.36-7.19 (m, 5H), 4.53 (d, J=1.6 Hz, 2H), 3.92 (d, J=12.2 Hz, 1H), 3.69-3.57 (m, 1H), 3.38 (s, 3H), 3.25 (s, 3H), 2.35 (m, 2H), 2.08-1.85 (m, 4H).

Step E: (((5,5-difluoro-2,2-dimethoxy-1-(methoxymethyl)cyclohexyl)oxy)methyl)benzene

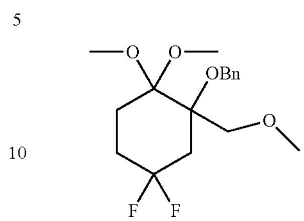

Sodium hydride (265 mg, 6.64 mmol, 60% in mineral oil, 1.4 eq.) was added portionwise to a solution of (1-(benzyloxy)-5,5-difluoro-2,2-dimethoxycyclohexyl)methanol (1.5 g, 4.74 mmol, 1.0 eq.) in anhydrous DMF (30.0 mL) at 0° C. The mixture was stirred for 1 h at room temperature then iodomethane (6.73 g, 47.4 mmol, 10 eq.) was added. The mixture was stirred for 2 h then poured into ice water and extracted with DCM (60 mL×2). The combined organic layers were dried over anhydrous sodium sulfate, filtered and concentrated. The residue was purified by column chromatography ($SiO_2$, 0-10% EtOAc in PE) to afford (((5,5-difluoro-2,2-dimethoxy-1-(methoxymethyl)cyclohexyl)oxy)methyl)benzene (1.2 g, 76%). $^1H$ NMR (400 MHz, $CDCl_3$): δ ppm: 7.38-7.17 (m, 5H), 4.72 (s, 2H), 3.74 (s, 2H), 3.39 (s, 3H), 3.34 (s, 3H), 3.30 (s, 3H), 2.64-2.25 (m, 3H), 2.22-1.75 (m, 3H).

Step F: 2-(benzyloxy)-4,4-difluoro-2-(methoxymethyl)cyclohexan-1-one

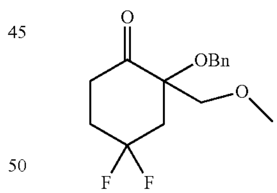

A mixture of (((5,5-difluoro-2,2-dimethoxy-1-(methoxymethyl)cyclohexyl)oxy)methyl)benzene (1.33 g, 4.03 mmol, 1.0 eq.), 12 (102 mg, 402 μmol, 0.1 eq.) and acetone (30.0 mL) was stirred for 2 h at room temperature. The mixture was poured into water, quenched with saturated $Na_2S_2O_3$ (aq), and extracted with DCM (60 mL×3). The combined organic layers were dried over anhydrous sodium sulfate, filtered and concentrated. The residue was purified by flash column chromatography ($SiO_2$, 0-5% EtOAc in PE) to afford 2-(benzyloxy)-4,4-difluoro-2-(methoxymethyl)cyclohexan-1-one (1.05 g, 91%). $^1H$ NMR (400 MHz, $CDCl_3$): δ ppm: 7.42-7.26 (m, 5H), 4.60 (dd, J=11.4 Hz, 1H), 4.40 (dd, J=11.4 Hz, 1H), 3.68 (m, 2H), 3.37 (s, 3H), 2.92-2.62 (m, 2H), 2.52-2.23 (m, 4H).

Step G: 6-(benzyloxy)-8,8-difluoro-6-(methoxymethyl)-2-(1-((2-(trimethylsilyl)ethoxy)methyl)-1H-pyrazol-4-yl)-6,7,8,9-tetrahydro-4H-thieno[2,3-c]chromen-4-one

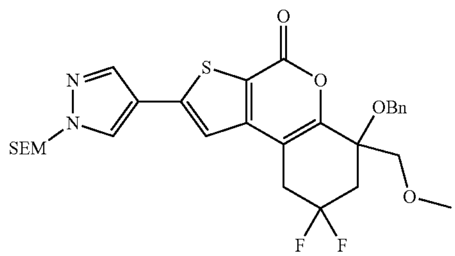 [SMILES: COCC1(OCc2ccccc2)CC(F)(F)Cc2c1oc(=O)c1sc(-c3cnn(COCC[Si](C)(C)C)c3)cc21]

A mixture of methyl 3-bromo-5-[1-(2-trimethylsilylethoxymethyl)pyrazol-4-yl]thiophene-2-carboxylate (660 mg, 1.6 mmol, 1.8 eq.), 2-(benzyloxy)-4,4-difluoro-2-(methoxymethyl)cyclohexan-1-one (250 mg, 880 μmol, 1.0 eq.), sodium metabisulfite (50 mg, 263 μmol, 0.3 eq.), cesium carbonate (859 mg, 2.64 mmol, 3.0 eq.), Sphos-Pd-G3 (137 mg, 175 μmol, 0.20 eq.) and toluene (50.0 mL) was stirred for 16 h at 105° C. under nitrogen. The mixture was poured into water and extracted with EtOAc (60 mL×2). The combined organic layers were washed with brine, dried over anhydrous sodium sulfate, filtered and concentrated. The residue was purified by column chromatography ($SiO_2$, 0-35% EtOAc in PE) to give 6-(benzyloxy)-8,8-difluoro-6-(methoxymethyl)-2-(1-((2-(trimethylsilyl)ethoxy)methyl)-1H-pyrazol-4-yl)-6,7,8,9-tetrahydro-4H-thieno[2,3-c]chromen-4-one (360 mg, 69%). MS obsd. ($ESI^+$): 589.5 [$(M+H)^+$].

Step H: 6-(benzyloxy)-8,8-difluoro-6-(methoxymethyl)-2-(1-((2-(trimethylsilyl)ethoxy)methyl)-1H-pyrazol-4-yl)-6,7,8,9-tetrahydrothieno[2,3-c]quinolin-4(5H)-one

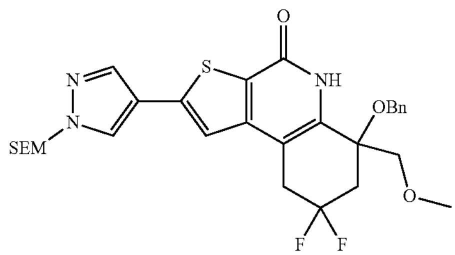 [SMILES: COCC1(OCc2ccccc2)CC(F)(F)Cc2c1[nH]c(=O)c1sc(-c3cnn(COCC[Si](C)(C)C)c3)cc21]

A mixture of 6-(benz yloxy)-8,8-difluoro-6-(methoxymethyl)-2-(1-((2-(trimethylsilyl)ethoxy)methyl)-1H-pyrazol-4-yl)-6,7,8,9-tetrahydro-4H-thieno[2,3-c]chromen-4-one (180 mg, 305 μmol, 1.0 eq.), ammonium hydroxide (8.0 mL) and 2-propylalcohol (8.0 mL) was stirred for 4 h at 100° C. in a microwave reactor. The mixture was concentrated in vacuo, and the residue was purified by column chromatography ($SiO_2$, 0-1% MeOH in DCM) to afford 6-(benzyloxy)-8,8-difluoro-6-(methoxymethyl)-2-(1-((2-(trimethylsilyl)ethoxy)methyl)-1H-pyrazol-4-yl)-6,7,8,9-tetrahydrothieno[2,3-c]quinolin-4(5H)-one (80 mg, 44%). MS obsd. ($ESI^+$): 588.5 [$(M+H)^+$].

Step I: (S)-8,8-difluoro-6-hydroxy-6-(methoxymethyl)-2-(1H-pyrazol-4-yl)-6,7,8,9-tetrahydrothieno[2,3-c]quinolin-4(5H)-one (Compound 48) & (R)-8,8-difluoro-6-hydroxy-6-(methoxymethyl)-2-(1H-pyrazol-4-yl)-6,7,8,9-tetrahydrothieno[2,3-c]quinolin-4(5H)-one (Compound 49)

Compound 48

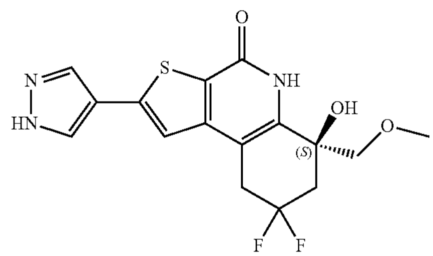

Compound 49

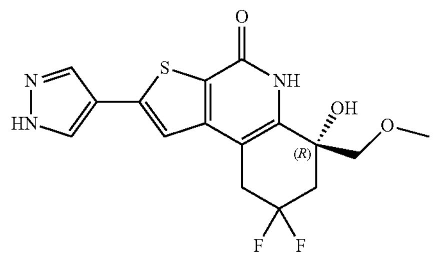

Boron trichloride (1 M, 4.7 mL, 15 eq.) was added to a solution of 6-(benzyloxy)-8,8-difluoro-6-(methoxymethyl)-2-(1-((2-(trimethylsilyl)ethoxy)methyl)-1H-pyrazol-4-yl)-6,7,8,9-tetrahydrothieno[2,3-c]quinolin-4(5H)-one (190 mg, 320 μmol, 1.0 eq.) in DCM (25.0 mL) at 0° C. The mixture was stirred for 2 h at room temperature then quenched with MeOH, concentrated and neutralized with $NH_3$/MeOH (7 M). The residue was purified by column chromatography ($SiO_2$, 0-4% MeOH in DCM) to give racemic 8,8-difluoro-6-hydroxy-6-(methoxymethyl)-2-(1H-pyrazol-4-yl)-6,7,8,9-tetrahydrothieno[2,3-c]quinolin-4(5H)-one (64 mg, 53%). MS obsd. ($ESI^+$): 368.0 [$(M+H)^+$].

Separation via SFC afforded each enantiomer. (S)-8,8-difluoro-6-hydroxy-6-(methoxymethyl)-2-(1H-pyrazol-4-yl)-6,7,8,9-tetrahydrothieno[2,3-c]quinolin-4(5H)-one (Compound 48): MS obsd. ($ESI^+$): 368.0 [$(M+H)^+$]. (R)-8,8-difluoro-6-hydroxy-6-(methoxymethyl)-2-(1H-pyrazol-4-yl)-6,7,8,9-tetrahydrothieno[2,3-c]quinolin-4(5H)-one (Compound 49): MS obsd. ($ESI^+$): 368.0 [$(M+H)^+$]; $^1H$ NMR (400 MHz, DMSO-d6) δ ppm: 13.23 (s, 1H), 10.70 (s, 1H), 8.30 (s, 1H), 7.97 (s, 1H), 7.58 (s, 1H), 5.69 (s, 1H), 3.60 (dd, J=45.2, 10.0 Hz, 2H), 3.29 (s, 3H), 3.21-3.10 (m, 2H), 2.77-2.61 (m, 1H), 2.38-2.19 (m, 1H).

Examples 50 and 51—Compounds 50 and 51: (S)-6-ethyl-8,8-difluoro-6-hydroxy-2-(1H-pyrazol-4-yl)-6,7,8,9-tetrahydrothieno[2,3-c]quinolin-4(5H)-one (Compound 50) and (R)-6-ethyl-8,8-difluoro-6-hydroxy-2-(1H-pyrazol-4-yl)-6,7,8,9-tetrahydrothieno[2,3-c]quinolin-4(5H)-one (Compound 51)

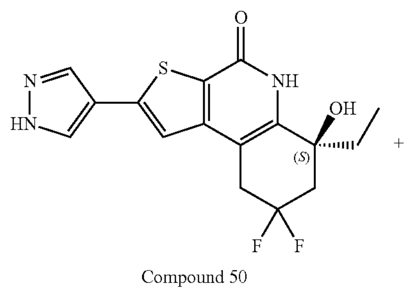

+

Compound 50

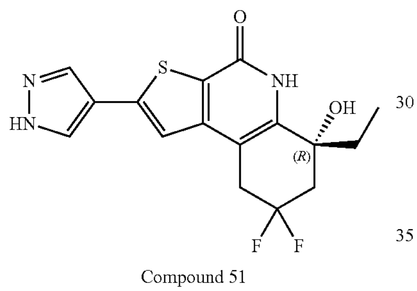

Compound 51

Step A: 1-ethyl-5,5-difluoro-2,2-dimethoxycyclohexan-1-ol

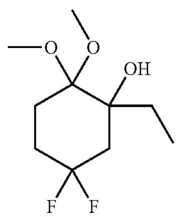

To a solution of 5,5-difluoro-2,2-dimethoxy-1-vinylcyclohexan-1-ol (1.8 g, 8.1 mmol, 1.0 eq.) in MeOH (90 mL) and $H_2O$ (2.0 mL) was added wetted Pd/C (10%, 540 mg). The mixture was purged with nitrogen then stirred at 50° C. for 16 h under a hydrogen atmosphere. The reaction mixture was cooled to room temperature, filtered through celite, and the filter cake was washed with MeOH (100 mL). The filtrate was concentrated in vacuo, and purified by flash column chromatography ($SiO_2$, 10-50% EtOAc in PE) to give 1-ethyl-5,5-difluoro-2,2-dimethoxycyclohexan-1-ol (1.5 g, 82%). $^1H$ NMR (400 MHz, $CDCl_3$) δ ppm: 3.39 (s, 3H), 3.33 (s, 3H), 1.99-1.62 (m, 8H), 0.99 (t, J=7.6 Hz, 3H).

Step B: 2-ethyl-4,4-difluoro-2-hydroxycyclohexan-1-one

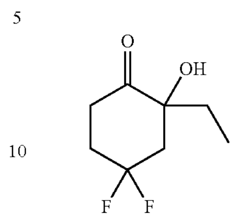

To a solution of 1-ethyl-5,5-difluoro-2,2-dimethoxycyclohexan-1-ol (1.8 g, 8.03 mmol, 1.0 eq.) in DCM (28.0 mL) was added water (7.0 mL) and trifluoroacetic acid (7.0 mL). The mixture was stirred for 1 h at room temperature then concentrated. Purification by column chromatography ($SiO_2$, 10-50% EtOAc in PE) afforded 2-ethyl-4,4-difluoro-2-hydroxycyclohexan-1-one (1.2 g, 85%). $^1H$ NMR (400 MHz, $CDCl_3$) δ ppm: 2.84-2.70 (m, 2H), 2.59-2.46 (m, 2H), 2.29-2.11 (m, 2H), 1.97-1.87 (m, 1H), 1.84-1.74 (m, 1H), 0.84 (t, J=7.2 Hz, 3H).

Step C: 6-ethyl-8,8-difluoro-6-hydroxy-2-(1-((2-(trimethylsilyl)ethoxy)methyl)-1H-pyrazol-4-yl)-6,7,8,9-tetrahydro-4H-thieno[2,3-c]chromen-4-one

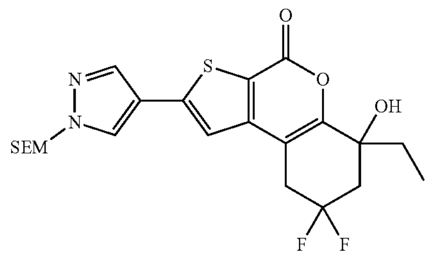 [SMILES: CCC1(O)CC(F)(F)Cc2c1oc(=O)c1sc(-c3cnn(COCC[Si](C)(C)C)c3)cc21]

To a solution of 2-ethyl-4,4-difluoro-2-hydroxycyclohexan-1-one (205 mg, 1.15 mmol, 2.0 eq.) and methyl 3-bromo-5-[1-(2-trimethylsilylethoxymethyl)pyrazol-4-yl]thiophene-2-carboxylate (240 mg, 0.58 mmol, 1.0 eq.) in toluene (15.0 mL) was added sodium metabisulfite (22 mg, 0.12 mmol, 0.2 eq.), $Cs_2CO_3$ (374 mg, 1.15 mmol, 2.0 eq.) and $Pd_2(dba)_3$ (105 mg, 0.12 mmol, 0.2 eq.), Xantphos (100 mg, 0.17 mmol, 0.3 eq.) under a $N_2$ atmosphere. The mixture was stirred at 105° C. for 16 h. then filtered and concentrated in vacuo. The residue was purified by column chromatography ($SiO_2$, 0-100% EtOAc in PE) to give 6-ethyl-8,8-difluoro-6-hydroxy-2-(1-((2-(trimethylsilyl)ethoxy)methyl)-1H-pyrazol-4-yl)-6,7,8,9-tetrahydro-4H-thieno[2,3-c]chromen-4-one (224 mg, 80%). MS obsd. ($ESI^+$): 483.7 $[(M+H)^+]$.

Step D: 6-ethyl-8,8-difluoro-6-hydroxy-2-(1-((2-(trimethylsilyl)ethoxy)methyl)-1H-pyrazol-4-yl)-6,7,8,9-tetrahydrothieno[2,3-c]quinolin-4(5H)-one

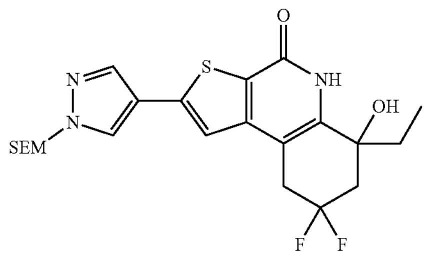 [SMILES: CCC1(O)CC(F)(F)Cc2c1[nH]c(=O)c1sc(-c3cnn(COCC[Si](C)(C)C)c3)cc21]

A solution of 6-ethyl-8,8-difluoro-6-hydroxy-2-(1-((2-(trimethylsilyl)ethoxy)methyl)-1H-pyrazol-4-yl)-6,7,8,9-tetrahydro-4H-thieno[2,3-c]chromen-4-one (595 mg, 1.23 mmol, 1.0 eq.) in a mixture of MeOH (9 mL) and $NH_4OH$ (9.0 mL) was heated in a microwave reactor at 100° C. for 3 h. The mixture was concentrated, and the residue was purified by column chromatography ($SiO_2$, 0-10% MeOH in DCM) to give 6-ethyl-8,8-difluoro-6-hydroxy-2-(1-((2-(trimethylsilyl)ethoxy)methyl)-1H-pyrazol-4-yl)-6,7,8,9-tetrahydrothieno[2,3-c]quinolin-4(5H)-one (360 mg, 60%). MS obsd. ($ESI^+$): 482.7 [$(M+H)^+$].

Step E: (S)-6-ethyl-8,8-difluoro-6-hydroxy-2-(1H-pyrazol-4-yl)-6,7,8,9-tetrahydrothieno[2,3-c]quinolin-4(5H)-one (Compound 50) and (R)-6-ethyl-8,8-difluoro-6-hydroxy-2-(1H-pyrazol-4-yl)-6,7,8,9-tetrahydrothieno[2,3-c]quinolin-4(5H)-one (Compound 51)

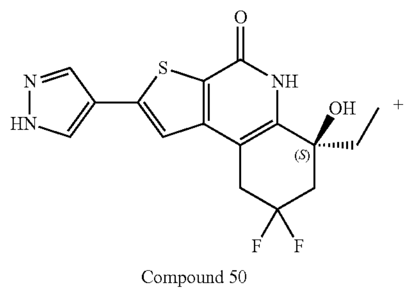

Compound 50

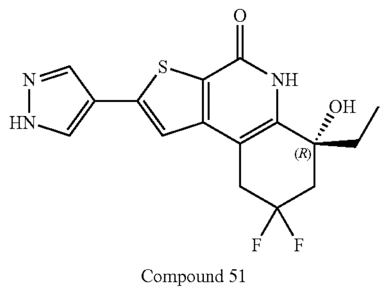

Compound 51

To a solution of 6-ethyl-8,8-difluoro-6-hydroxy-2-(1-((2-(trimethylsilyl)ethoxy)methyl)-1H-pyrazol-4-yl)-6,7,8,9-tetrahydrothieno[2,3-c]quinolin-4(5H)-one (357 mg, 0.74 mmol, 1.0 eq.) in DCM (5.0 mL) was added trifluoroacetic acid (5.0 mL). The mixture was stirred at room temperature for 1 h. then concentrated in vacuo, and the residue was purified by column chromatography ($SiO_2$, 0-10% MeOH in DCM) to give racemic 6-ethyl-8,8-difluoro-6-hydroxy-2-(1H-pyrazol-4-yl)-6,7,8,9-tetrahydrothieno[2,3-c]quinolin-4(5H)-one (140 mg, 54%). MS obsd. ($ESI^+$): 352.4 [$(M+H)^+$].

The individual isomers were separated by chiral SFC. (S)-6-ethyl-8,8-difluoro-6-hydroxy-2-(1H-pyrazol-4-yl)-6,7,8,9-tetrahydrothieno[2,3-c]quinolin-4(5H)-one (Compound 50): MS obsd. ($ESI^+$): 352.2 [$(M+H)^+$]. (R)-6-ethyl-8,8-difluoro-6-hydroxy-2-(1H-pyrazol-4-yl)-6,7,8,9-tetrahydrothieno[2,3-c]quinolin-4(5H)-one (Compound 51): MS obsd. ($ESI^+$): 352.0 [$(M+H)^+$]; $^1H$ NMR (400 MHz, DMSO-$d_6$) δ ppm: 13.23 (s, 1H), 10.74 (s, 1H), 8.30 (s, 1H), 8.00 (s, 1H), 7.57 (s, 1H), 5.33 (s, 1H), 3.30-3.27 (m, 2H), 2.68-2.54 (m, 1H), 2.33-2.20 (m, 1H), 1.96-1.87 (m, 1H), 1.83-1.74 (m, 1H), 0.89-0.84 (m, 3H).

Examples 52 & 53—Compounds 52 & 53: (S)-8,8-difluoro-6-methoxy-6-methyl-2-(1H-pyrazol-4-yl)-6,7,8,9-tetrahydrothieno[2,3-c]quinolin-4(5H)-one (Compound 52) & (R)-8,8-difluoro-6-methoxy-6-methyl-2-(1H-pyrazol-4-yl)-6,7,8,9-tetrahydrothieno[2,3-c]quinolin-4(5H)-one (Compound 53) (Stereoisomers are Arbitrarily Assigned)

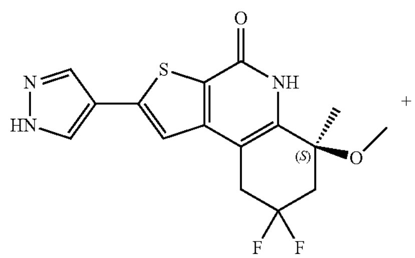

Compound 52

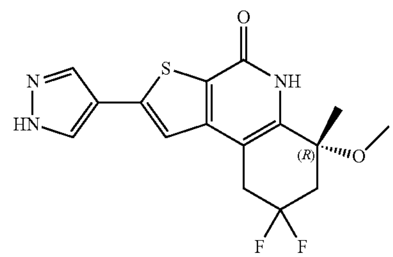

Compound 53

Step A: 5,5-difluoro-2,2-dimethoxy-1-methylcyclohexan-1-ol

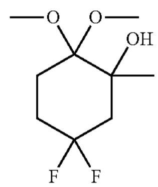

To a dried three-necked flask containing of 5,5-difluoro-2,2-dimethoxycyclohexan-1-one (5.65 g, 29.1 mmol, 1.0 eq.) in anhydrous THF (270.0 mL) was added methylmagnesium bromide (3 M in diethyl ether, 29.1 mL, 87.4 mmol, 3.0 eq.) at 0° C. The mixture was stirred at room temperature for 2 h under $N_2$ atmosphere and monitored by TLC to completion. The mixture was quenched with sat'd $NH_4Cl$ (aq.) at 0° C., diluted with water (125 mL) and extracted with EtOAc (90 mL×3). The combined organic layers were dried over anhydrous sodium sulfate, filtered, concentrated in vacuo, and the residue was purified by column chromatography ($SiO_2$, 0-20% EtOAc in PE) to give 5,5-difluoro-2,2-dimethoxy-1-methylcyclohexan-1-ol (5.98 g, 97%). $^1H$ NMR (400 MHz, $CDCl_3$) δ ppm: 3.41 (s, 3H), 3.32 (s, 3H), 2.69 (s, 1H), 2.20-2.06 (m, 2H), 2.03-1.90 (m, 2H), 1.85-1.68 (m, 2H), 1.32 (s, 3H).

Step B: 4,4-difluoro-1,1,2-trimethoxy-2-methylcyclohexane

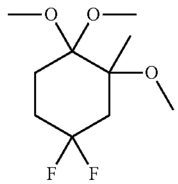

To a dried three-necked round bottom flask containing sodium hydride (2.28 g, 56.7 mmol, 60% in mineral oil, 2.0 eq) was added anhydrous THF (170.0 mL) at 0° C., followed by a mixture of 5,5-difluoro-2,2-dimethoxy-1-methylcyclohexan-1-ol (5.98 g, 28.5 mmol, 1.0 eq) in THF (3.0 mL). The mixture was stirred at 0° C. for 30 min, then iodomethane (40.4 g, 285 mmol, 10.0 eq) was added, and the mixture was stirred for another 1.5 h. Additional iodomethane (40.4 g, 285 mmol, 10.0 eq) was added to the reaction mixture at 0° C. The mixture was stirred for another 1.5 h., then water at 0° C. was added. The mixture was extracted with EtOAc (160 mL×2), and the combined organic layers were washed with brine (150 mL×2), dried over anhydrous sodium sulfate, filtered and concentrated in vacuo. Purification by column chromatography ($SiO_2$, 0-10% EtOAc in PE) afforded 4,4-difluoro-1,1,2-trimethoxy-2-methylcyclohexane (5.1 g, 80%). $^1H$ NMR (400 MHz, $CDCl_3$) δ ppm: 3.37 (s, 3H), 3.33 (s, 3H), 3.27 (s, 3H), 2.27-2.20 (m, 1H), 2.18-2.05 (m, 2H), 2.00-1.86 (m, 2H), 1.80-1.69 (m, 1H), 1.29 (s, 3H).

Step C: 4,4-difluoro-2-methoxy-2-methylcyclohexan-1-one

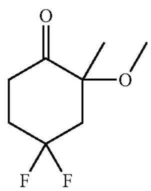

To a flask containing of 4,4-difluoro-1,1,2-trimethoxy-2-methylcyclohexane (2.58 g, 11.51 mmol) in DCM (28 mL) was added water (7 mL) and trifluoroacetic acid (7 mL) at 0° C. The mixture was stirred at room temperature for 5 h. then extracted with DCM (30 mL×2). The combined organic layers were concentrated in vacuo. The residue was diluted with DCM (20 mL), washed with aqueous NaHCO3 (10 mL×2), and the organic phase was dried over anhydrous sodium sulfate. The mixture was filtered and concentrated in vacuo give 4,4-difluoro-2-methoxy-2-methylcyclohexan-1-one (1.9 g, 10.1 mmol, 88%). $^1H$ NMR (400 MHz, CDCl3) δ ppm: 3.21 (s, 3H), 2.91-2.85 (m, 1H), 2.65-2.57 (m, 1H), 2.48-2.41 (m, 2H), 2.23-2.09 (m, 2H), 1.30 (s, 3H).

Step D: 8,8-difluoro-6-methoxy-6-methyl-2-(1-((2-(trimethylsilyl)ethoxy)methyl)-1H-pyrazol-4-yl)-6,7,8,9-tetrahydro-4H-thieno[2,3-c]chromen-4-one

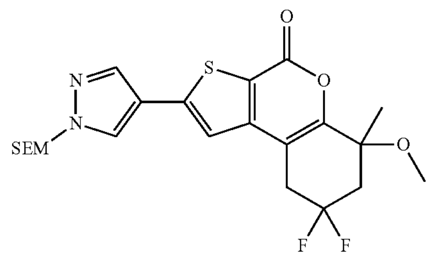 [SMILES: COC1(C)CC(F)(F)Cc2c1oc(=O)c1sc(-c3cnn(COCC[Si](C)(C)C)c3)cc21]

To a solution of methyl 3-bromo-5-(1-((2-(trimethylsilyl)ethoxy)methyl)-1H-pyrazol-4-yl)thiophene-2-carboxylate (1.0 g, 2.4 mmol) and 4,4-difluoro-2-methoxy-2-methylcyclohexan-1-one (598 mg, 3.35 mmol) in toluene (30.0 mL) was added $Cs_2CO_3$ (2.34 g, 7.19 mmol), $Pd_2(dba)_3$ (439 mg, 479 μmol), and $Na_2S_2O_5$ (91.1 mg, 479 μmol). The mixture was stirred under nitrogen for 12 h at 105° C. The mixture was cooled to 0° C., $H_2O$ (40 mL) was added, and the resulting mixture was extracted with EtOAc (30 mL×3). The combined organic layers were dried over anhydrous sodium sulfate, filtered and concentrated. Purification by column chromatography ($SiO_2$, 0-10% EtOAc in PE) gave 8,8-difluoro-6-methoxy-6-methyl-2-(1-((2-(trimethylsilyl)ethoxy)methyl)-1H-pyrazol-4-yl)-6,7,8,9-tetrahydro-4H-thieno[2,3-c]chromen-4-one (385 mg, 33%). MS obsd. ($ESI^+$): 483.4 $[(M+H)^+]$.

Step E: 8,8-difluoro-6-methoxy-6-methyl-2-(1-((2-(trimethylsilyl)ethoxy)methyl)-1H-pyrazol-4-yl)-6,7,8,9-tetrahydrothieno[2,3-c]quinolin-4(5H)-one

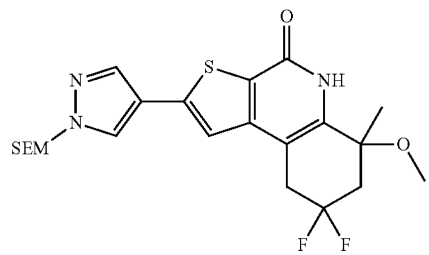 [SMILES: COC1(C)CC(F)(F)Cc2c1[nH]c(=O)c1sc(-c3cnn(COCC[Si](C)(C)C)c3)cc21]

To a solution of 8,8-difluoro-6-methoxy-6-methyl-2-(1-((2-(trimethylsilyl)ethoxy)methyl)-1H-pyrazol-4-yl)-6,7,8,9-tetrahydro-4H-thieno[2,3-c]chromen-4-one (0.70 g, 1.45 mmol) in MeOH (6.0 mL) was added ammonium hydroxide (6.0 mL). The mixture was stirred at 95° C. for 2 h in a microwave reactor. The mixture was cooled to 0° C., and $H_2O$ (20 mL) was added. The resulting mixture was extracted with EtOAc (50 mL×3). The combined organic layers were dried over anhydrous sodium sulfate, filtered and concentrated. The crude product was purified by flash column chromatography ($SiO_2$, 0-30% EtOAc in PE) to afford 8,8-difluoro-6-methoxy-6-methyl-2-(1-((2-(trimethylsilyl)ethoxy)methyl)-1H-pyrazol-4-yl)-6,7,8,9-tetrahydrothieno[2,3-c]quinolin-4(5H)-one (170 mg, 24%). MS obsd. ($ESI^+$): 482.5 [$(M+H)^+$].

Step F: (S)-8,8-difluoro-6-methoxy-6-methyl-2-(1H-pyrazol-4-yl)-6,7,8,9-tetrahydrothieno[2,3-c]quinolin-4(5H)-one (Compound 52) & (R)-8,8-difluoro-6-methoxy-6-methyl-2-(1H-pyrazol-4-yl)-6,7,8,9-tetrahydrothieno[2,3-c]quinolin-4(5H)-one (Compound 53)

Compound 52

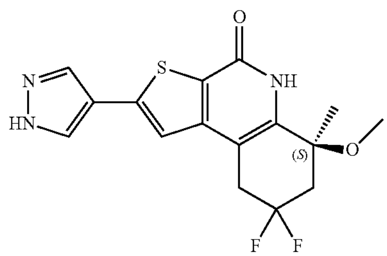

Compound 53

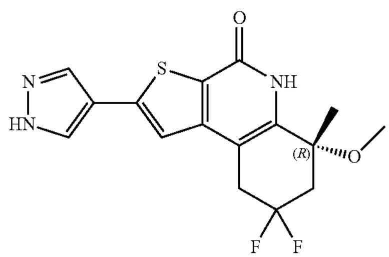

To a solution of 8,8-difluoro-6-methoxy-6-methyl-2-[1-(2-trimethylsilylethoxymethyl)pyrazol-4-yl]-7,9-dihydro-5H-thieno[2,3-c]quinolin-4-one (170 mg, 353 μmol, 1.0 eq.) in DCM (5.0 mL) was added trifluoroacetic acid (402 mg, 3.53 mmol, 272 μL, 10.0 eq.) at 0° C. The mixture was stirred at 25° C. for 15 h. The mixture was then cooled to 0° C. and saturated aqueous $NaHCO_3$ (20 mL) was added dropwise at 0° C. The resulting mixture was extracted with EtOAc (20 mL×3). The combined organic phase was dried over anhydrous sodium sulfate, filtered and concentrated. The crude product was purified by flash column chromatography ($SiO_2$, 0-10% MeOH in DCM) to give racemic 8,8-difluoro-6-methoxy-6-methyl-2-(1H-pyrazol-4-yl)-6,7,8,9-tetrahydrothieno[2,3-c]quinolin-4(5H)-one (100 mg, 80%).

The individual enantiomers were isolated via chiral SFC. (S)-8,8-difluoro-6-methoxy-6-methyl-2-(1H-pyrazol-4-yl)-6,7,8,9-tetrahydrothieno[2,3-c]quinolin-4(5H)-one (Compound 52): MS obsd. ($ESI^+$): 352.1 $[M+H]^+$. (R)-8,8-difluoro-6-methoxy-6-methyl-2-(1H-pyrazol-4-yl)-6,7,8,9-tetrahydrothieno[2,3-c]quinolin-4(5H)-one (Compound 53): MS obsd. ($ESI^+$): 352.1 $[M+H]^+$; $^1H$ NMR (400 MHz, DMSO-d6) δ ppm: 13.23 (s, 1H), 11.02 (s, 1H), 8.28 (s, 1H), 8.01 (s, 1H), 7.59 (s, 1H), 3.44-3.37 (m, 2H), 3.07 (s, 3H) 2.82-2.61 (m, 1H), 2.40-2.26 (m, 1H), 1.56 (s, 3H).

Examples 54 & 55—Compounds 54 & 55: (R)-8,8-difluoro-6-hydroxy-6-methyl-2-(1H-pyrazol-4-yl)-6,7,8,9-tetrahydrothieno[2,3-c]quinolin-4(5H)-one (Compound 54) & (S)-8,8-difluoro-6-hydroxy-6-methyl-2-(1H-pyrazol-4-yl)-6,7,8,9-tetrahydrothieno[2,3-c]quinolin-4(5H)-one (Compound 55) (Stereoisomers are Arbitrarily Assigned)

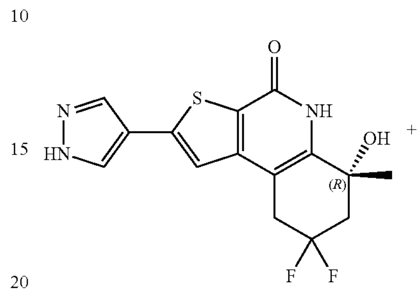

Compound 54

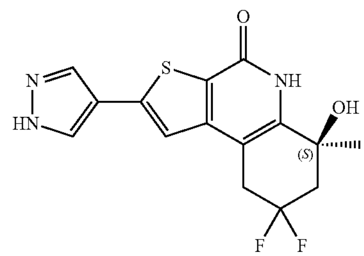

Compound 55

Step A: (((5,5-difluoro-2,2-dimethoxy-1-methylcyclohexyl)oxy)methyl)benzene

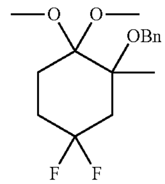

To a solution of 5,5-difluoro-2,2-dimethoxy-1-methylcyclohexan-1-ol (300 mg, 1.43 mmol, 1.0 eq.) in anhydrous DMF (3.0 mL) was added NaH (109 mg, 2.85 mmol, 60% in mineral oil, 2.0 eq.) at 0° C. The mixture was stirred at 0° C. for 10 min. then benzyl bromide (488.16 mg, 2.85 mmol, 339 μL, 2.0 eq.) was added dropwise. The mixture was stirred at room temperature for 1 h. then quenched by saturated aqueous $NH_4Cl$ solution and diluted with water (60 mL). The mixture was extracted with EtOAc (40 mL×3) and the combined organic layers were dried over anhydrous sodium sulfate, filtered and concentrated. The residue was purified by flash column chromatography ($SiO_2$, 0-4% EtOAc in PE) to give (((5,5-difluoro-2,2-dimethoxy-1-methylcyclohexyl)oxy)methyl)benzene (370 mg, 86%). $^1H$ NMR (400 MHz, $CDCl_3$) δ ppm: 7.36-7.24 (m, 5H), 4.60-4.52 (m, 2H), 3.39 (s, 3H), 3.33 (s, 3H), 2.50-2.35 (m, 1H), 2.26-2.22 (m, 1H), 2.15-2.07 (m, 1H), 2.05-1.89 (m, 2H), 1.83-1.77 (m, 1H), 1.38 (s, 3H).

Step B: 2-(benzyloxy)-4,4-difluoro-2-methylcyclohexan-1-one

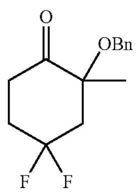 [SMILES: CC1(OCc2ccccc2)CC(F)(F)CCC1=O]

To a solution of (((5,5-difluoro-2,2-dimethoxy-1-methylcyclohexyl)oxy)methyl)benzene (370 mg, 1.23 mmol, 1.0 eq.) in acetone (15.0 mL) was added iodine (31.7 mg, 125 μmol, 0.10 eq.). The mixture was stirred at room temperature for 10 min. then quenched by saturated $Na_2SO_3$ (aq.) (20 mL) and extracted with DCM (30 mL×3). The combined organic layers were dried over anhydrous sodium sulfate, filtered and concentrated. The residue was purified by flash column chromatography ($SiO_2$, 0-10% EtOAc in PE) to give 2-(benzyloxy)-4,4-difluoro-2-methylcyclohexan-1-one (280 mg, 88%). $^1H$ NMR (400 MHz, $CDCl_3$) δ ppm: 7.35-7.26 (m, 5H), 4.56 (d, J=11.6 Hz, 1H), 4.26 (d, J=11.6 Hz, 1H), 2.94-2.91 (m, 1H), 2.79-2.74 (m, 1H), 2.48-2.42 (m, 2H), 2.25-2.18 (m, 2H), 1.41 (s, 3H).

Step C: 6-(benzyloxy)-8,8-difluoro-6-methyl-2-(1-((2-(trimethylsilyl)ethoxy)methyl)-1H-pyrazol-4-yl)-6,7,8,9-tetrahydro-4H-thieno[2,3-c]chromen-4-one

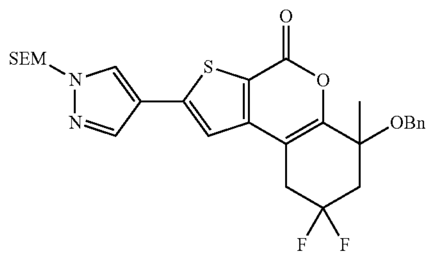 [SMILES: CC1(OCc2ccccc2)CC(F)(F)Cc2c1oc(=O)c1sc(-c3cnn(COCC[Si](C)(C)C)c3)cc21]

To a solution of methyl 3-bromo-5-(1-((2-(trimethylsilyl) ethoxy)methyl)-1H-pyrazol-4-yl)thiophene-2-carboxylate (240 mg, 575 μmol, 1.0 eq.) and 2-(benzyloxy)-4,4-difluoro-2-methylcyclohexan-1-one (292 mg, 1.15 mmol, 2.0 eq.) in toluene (18.0 mL) was added $Pd_2(dba)_3$ (105 mg, 115 μmol, 0.20 eq.), Xantphos (133 mg, 230 μmol, 0.40 eq.) and cesium carbonate (562 mg, 1.72 mmol, 3.0 eq.). The mixture was stirred at 105° C. for 16 h under nitrogen then cooled and filtered. The filtrate was concentrated in vacuo, and the residue was purified by column chromatography ($SiO_2$, 0-16% EtOAc in PE) to give 6-(benzyloxy)-8,8-difluoro-6-methyl-2-(1-((2-(trimethylsilyl)ethoxy)methyl)-1H-pyrazol-4-yl)-6,7,8,9-tetrahydro-4H-thieno[2,3-c]chromen-4-one (220 mg, 68%). MS obsd. (ESI$^+$): 559.5 [(M+H)$^+$].

Step D: 6-(benzyloxy)-8,8-difluoro-6-methyl-2-(1-((2-(trimethylsilyl)ethoxy)methyl)-1H-pyrazol-4-yl)-6,7,8,9-tetrahydrothieno[2,3-c]quinolin-4(5H)-one

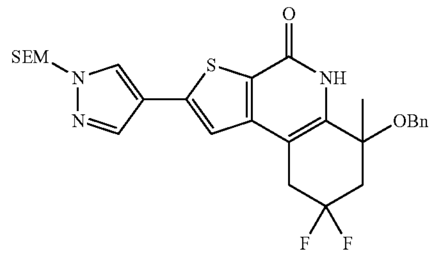 [SMILES: CC1(OCc2ccccc2)CC(F)(F)Cc2c1[nH]c(=O)c1sc(-c3cnn(COCC[Si](C)(C)C)c3)cc21]

To a solution of 6-(benzyloxy)-8,8-difluoro-6-methyl-2-(1-((2-(trimethylsilyl)ethoxy)methyl)-1H-pyrazol-4-yl)-6,7,8,9-tetrahydro-4H-thieno[2,3-c]chromen-4-one (220 mg, 394 μmol) in MeOH (7 mL) was added ammonia (7 M in MeOH, 7.0 mL). The mixture was stirred at 95° C. for 16 h. then cooled and concentrated in vacuo. The residue was purified by column chromatography ($SiO_2$, 0-5% MeOH in DCM) to give 6-(benzyloxy)-8,8-difluoro-6-methyl-2-(1-((2-(trimethylsilyl)ethoxy)methyl)-1H-pyrazol-4-yl)-6,7,8,9-tetrahydrothieno[2,3-c]quinolin-4(5H)-one (180 mg, 77%). MS obsd. (ESI$^+$): 558.6 [(M+H)$^+$].

Step E: (R)-8,8-difluoro-6-hydroxy-6-methyl-2-(1H-pyrazol-4-yl)-6,7,8,9-tetrahydrothieno[2,3-c]quinolin-4(5H)-one (Compound 54) & (S)-8,8-difluoro-6-hydroxy-6-methyl-2-(1H-pyrazol-4-yl)-6,7,8,9-tetrahydrothieno[2,3-c]quinolin-4(5H)-one (Compound 55) (Stereoisomers are Arbitrarily Assigned)

Compound 54

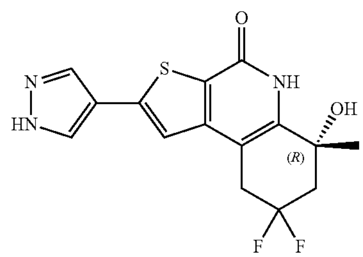

Compound 55

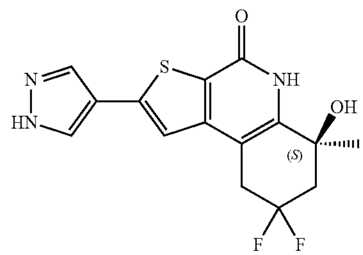

To a solution of 6-(benzyloxy)-8,8-difluoro-6-methyl-2-(1-((2-(trimethylsilyl) ethoxy)methyl)-1H-pyrazol-4-yl)-6,7,8,9-tetrahydrothieno[2,3-c]quinolin-4(5H)-one (90 mg, 161 μmol, 1.0 eq.) in DCM (10.0 mL) was added boron trichloride (1 M, 2.0 mL, 12 eq.) at −5° C. The mixture was stirred for 1.5 h at −5° C., quenched with MeOH then concentrated under a stream of nitrogen. The pH was adjusted to around 9 by progressively adding $NH_3$/MeOH (7 M). Then the mixture was concentrated in vacuo, and the residue was purified by flash column chromatography ($SiO_2$, 0-10% MeOH in DCM) to give racemic 8,8-difluoro-6-hydroxy-6-methyl-2-(1H-pyrazol-4-yl)-6,7,8,9-tetrahydrothieno[2,3-c]quinolin-4(5H)-one (23 mg, 42%). MS obsd. ($ESI^+$): 338.3 [$(M+H)^+$].

The individual enantiomers were separated via chiral SFC. (R)-8,8-difluoro-6-hydroxy-6-methyl-2-(1H-pyrazol-4-yl)-6,7,8,9-tetrahydrothieno[2,3-c]quinolin-4(5H)-one (Compound 54): MS obsd. ($ESI^+$): 338.0 [$(M+H)^+$]; $^1H$ NMR (400 MHz, DMSO-d6) δ ppm: 13.24 (s, 1H), 10.88 (s, 1H), 8.13 (s, 2H), 7.56 (s, 1H), 5.57 (s, 1H), 3.33-3.24 (m, 2H), 2.50-2.42 (m, 2H), 1.54 (s, 3H). (S)-8,8-difluoro-6-hydroxy-6-methyl-2-(1H-pyrazol-4-yl)-6,7,8,9-tetrahydrothieno[2,3-c]quinolin-4(5H)-one (Compound 55): MS obsd. ($ESI^+$): 338.0 [$(M+H)^+$].

Examples 56 and 57—Compounds 56 and 57: (S)-4-(2-hydroxypropan-2-yl)-4-methyl-8-(1H-pyrazol-4-yl)-1,5-dihydro-2H-pyrano[3,4-b]thieno[3,2-d]pyridin-6(4H)-one (Compound 56) & (R)-4-(2-hydroxypropan-2-yl)-4-methyl-8-(1H-pyrazol-4-yl)-1,5-dihydro-2H-pyrano[3,4-b]thieno[3,2-d]pyridin-6(4H)-one (Compound 57)

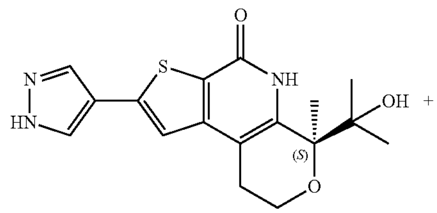

+

Compound 56

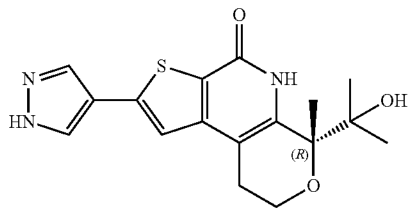

Compound 57

Step A: 4-methyl-6-oxo-8-(1-((2-(trimethylsilyl)ethoxy)methyl)-1H-pyrazol-4-yl)-1,4,5,6-tetrahydro-2H-pyrano[3,4-b]thieno[3,2-d]pyridine-4-carbaldehyde

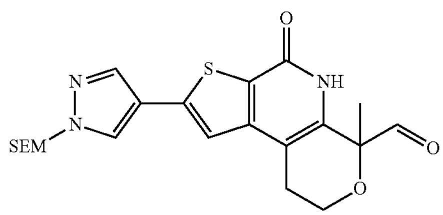 [SMILES: CC1(C=O)OCCc2c1[nH]c(=O)c1sc(-c3cnn(COCC[Si](C)(C)C)c3)cc21]

A mixture of 4-(hydroxymethyl)-4-methyl-8-(1-((2-(trimethylsilyl)ethoxy)methyl)-1H-pyrazol-4-yl)-1,5-dihydro-2H-pyrano[3,4-b]thieno[3,2-d]pyridin-6(4H)-one (100 mg, 223 μmol, 1.0 eq., synthesized according to the procedures for Compounds 34 & 35), IBX (626 mg, 2.23 mmol, 10.0 eq.) and DCM (12 mL) was stirred for 24 h at 45° C. The mixture was quenched with saturated aqueous $Na_2SO_3$ solution, extracted with DCM (30 mL×3). The combined organic phases were dried over anhydrous sodium sulfate, filtered and concentrated. The residue was purified by column chromatography ($SiO_2$, 0-4% MeOH in DCM) to give 4-methyl-6-oxo-8-(1-((2-(trimethylsilyl)ethoxy)methyl)-1H-pyrazol-4-yl)-1,4,5,6-tetrahydro-2H-pyrano[3,4-b]thieno[3,2-d]pyridine-4-carbaldehyde (80 mg, 80%). MS obsd. ($ESI^+$): 464.3 [$(M+H_2O+H)^+$].

Step B: 4-(1-hydroxyethyl)-4-methyl-8-(1-((2-(trimethylsilyl)ethoxy)methyl)-1H-pyrazol-4-yl)-1,5-dihydro-2H-pyrano[3,4-b]thieno[3,2-d]pyridin-6(4H)-one

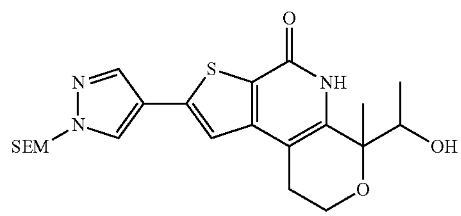 [SMILES: CC(O)C1(C)OCCc2c1[nH]c(=O)c1sc(-c3cnn(COCC[Si](C)(C)C)c3)cc21]

To a solution of 4-methyl-6-oxo-8-(1-((2-(trimethylsilyl)ethoxy)methyl)-1H-pyrazol-4-yl)-1,4,5,6-tetrahydro-2H-pyrano[3,4-b]thieno[3,2-d]pyridine-4-carbaldehyde (160 mg, 360 μmol, 1.0 eq.) in THF (7.5 mL) was added methylmagnesium bromide (3 M in diethyl ether, 23.3 mL, 195 eq.). The mixture was stirred at rt for 1.5 h., quenched with saturated $NH_4Cl$ (aq.), then poured into water and extracted with DCM (50 mL×3). The combined organic layers were dried over anhydrous sodium sulfate, filtered and concentrated. The residue was purified by column chromatography ($SiO_2$, 0-4% MeOH in DCM) to give 4-(1-hydroxyethyl)-4-methyl-8-(1-((2-(trimethylsilyl)ethoxy)methyl)-1H-pyrazol-4-yl)-1,5-dihydro-2H-pyrano[3,4-b]thieno[3,2-d]pyridin-6(4H)-one (152 mg, 82%). MS obsd. ($ESI^+$): 462.3 [$(M+H)^+$].

Step C: 4-acetyl-4-methyl-8-(1-((2-(trimethylsilyl)ethoxy)methyl)-1H-pyrazol-4-yl)-1,5-dihydro-2H-pyrano[3,4-b]thieno[3,2-d]pyridin-6(4H)-one

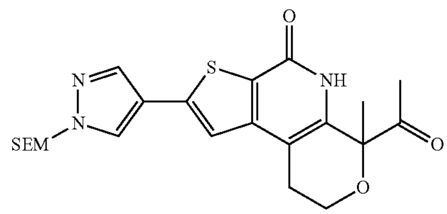 [SMILES: CC(=O)C1(C)OCCc2c1[nH]c(=O)c1sc(-c3cnn(COCC[Si](C)(C)C)c3)cc21]

To a solution of 4-(1-hydroxyethyl)-4-methyl-8-(1-((2-(trimethylsilyl)ethoxy)methyl)-1H-pyrazol-4-yl)-1,5-dihydro-2H-pyrano[3,4-b]thieno[3,2-d]pyridin-6(4H)-one (126 mg, 273 μmol, 1.0 eq.) in DCM (40.0 mL) was added Dess-Martin Periodinane (694 mg, 1.64 mmol, 6.0 eq.) in small portions at 0° C. The mixture was stirred at room temperature for 1.5 hr., then quenched with saturated $Na_2SO_3$ (aq.) and extracted with DCM (30 mL×3). The combined organic layers were dried over anhydrous sodium sulfate, filtered and concentrated. The residue was purified by flash column chromatography ($SiO_2$, 0-3% MeOH in DCM) to give 4-acetyl-4-methyl-8-(1-((2-(trimethylsilyl)ethoxy)methyl)-1H-pyrazol-4-yl)-1,5-dihydro-2H-pyrano[3,4-b]thieno[3,2-d]pyridin-6(4H)-one (85 mg, 67%). MS obsd. ($ESI^+$): 460.3 $[(M+H)^+]$.

Step D: 4-(2-hydroxypropan-2-yl)-4-methyl-8-(1-((2-(trimethylsilyl)ethoxy)methyl)-1H-pyrazol-4-yl)-1,5-dihydro-2H-pyrano[3,4-b]thieno[3,2-d]pyridin-6(4H)-one

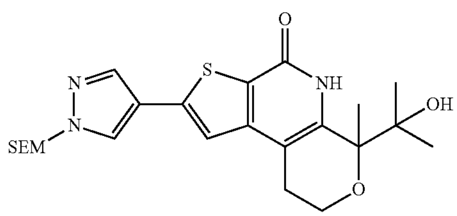 [SMILES: CC(C)(O)C1(C)OCCc2c1[nH]c(=O)c1sc(-c3cnn(COCC[Si](C)(C)C)c3)cc21]

To a solution of 4-acetyl-4-methyl-8-(1-((2-(trimethylsilyl)ethoxy)methyl)-1H-pyrazol-4-yl)-1,5-dihydro-2H-pyrano[3,4-b]thieno[3,2-d]pyridin-6(4H)-one (85 mg, 185 μmol, 1.0 eq.) in THF (2.0 mL) was added methylmagnesium bromide (3 M in diethyl ether, 2.0 mL, 32.4 eq.). The mixture was stirred at room temperature for 2 hr., quenched with saturated $NH_4Cl$ (aq.), then poured into water and extracted with DCM (30 mL×3). The combined organic layers were dried over anhydrous sodium sulfate, filtered, and concentrated. The residue was purified by flash column chromatography ($SiO_2$, 0-4% MeOH in DCM) to give 4-(2-hydroxypropan-2-yl)-4-methyl-8-(1-((2-(trimethyl silyl)ethoxy)methyl)-1H-pyrazol-4-yl)-1,5-dihydro-2H-pyrano[3,4-b]thieno[3,2-d]pyridin-6(4H)-one (50 mg, 56%). MS obsd. ($ESI^+$): 476.3 $[(M+H)^+]$.

Step E: (S)-4-(2-hydroxypropan-2-yl)-4-methyl-8-(1H-pyrazol-4-yl)-1,5-dihydro-2H-pyrano[3,4-b]thieno[3,2-d]pyridin-6(4H)-one (Compound 56) & (R)-4-(2-hydroxypropan-2-yl)-4-methyl-8-(1H-pyrazol-4-yl)-1,5-dihydro-2H-pyrano[3,4-b]thieno[3,2-d]pyridin-6(4H)-one (Compound 57)

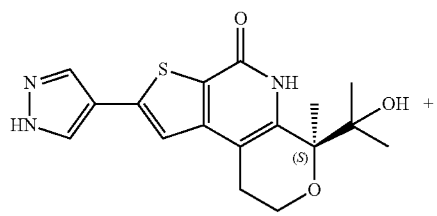

Compound 56

-continued

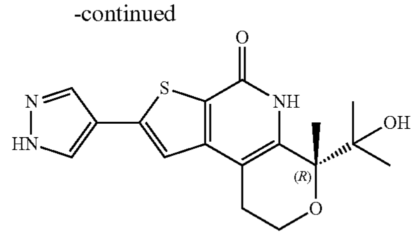

Compound 57

To a solution of 4-(2-hydroxypropan-2-yl)-4-methyl-8-(1-((2-(trimethylsilyl)ethoxy) methyl)-1H-pyrazol-4-yl)-1,5-dihydro-2H-pyrano[3,4-b]thieno[3,2-d]pyridin-6(4H)-one (75 mg, 160 μmol, 1.0 eq.) in DCM (6.0 mL) was added trifluoroacetic acid (2.0 mL) at 0° C. The mixture was allowed to warm to room temperature and stirred for 4 hr. The mixture was concentrated under a stream of nitrogen, and the pH was adjusted to around 9 by progressively adding $NH_3$/MeOH (7 M) at 0° C. The mixture was concentrated to afford a residue, which was purified by column chromatography ($SiO_2$, 0-7% MeOH in DCM) to give racemic 4-(2-hydroxypropan-2-yl)-4-methyl-8-(1H-pyrazol-4-yl)-1,5-dihydro-2H-pyrano[3,4-b]thieno[3,2-d]pyridin-6(4H)-one (48 mg, 85%). MS obsd. ($ESI^+$): 346.0 $[(M+H)^+]$.

The individual enantiomers were separated via chiral SFC. (S)-4-(2-hydroxypropan-2-yl)-4-methyl-8-(1H-pyrazol-4-yl)-1,5-dihydro-2H-pyrano[3,4-b]thieno[3,2-d]pyridin-6(4H)-one (Compound 56): MS obsd. ($ESI^+$): 346.2 $[(M+H)^+]$; $^1H$ NMR (400 MHz, DMSO-d6) δ ppm: 13.22 (s, 1H), 10.21 (s, 1H), 8.31 (s, 1H), 7.97 (s, 1H), 7.51 (s, 1H), 5.98 (s, 1H), 4.02-3.89 (m, 2H), 2.76-2.60 (m, 2H), 1.53 (s, 3H), 1.27 (s, 3H), 1.00 (s, 3H). (R)-4-(2-hydroxypropan-2-yl)-4-methyl-8-(1H-pyrazol-4-yl)-1,5-dihydro-2H-pyrano[3,4-b]thieno[3,2-d]pyridin-6(4H)-one (Compound 57): MS obsd. ($ESI^+$): 346.2 $[(M+H)^+]$.

Example 58—Compound 58: 4,4-dimethyl-8-(1H-pyrazol-4-yl)-1,3,4,5-tetrahydro-6H-pyrano[4,3-b]thieno[3,2-d]pyridin-6-one Compound 58

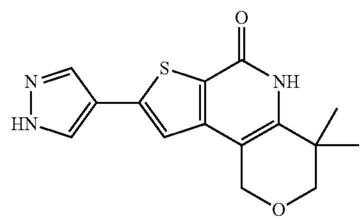

Step A: 4,4-dimethyl-8-(1-((2-(trimethylsilyl)ethoxy)methyl)-1H-pyrazol-4-yl)-3,4-dihydro-1H,6H-pyrano[4,3-b]thieno[3,2-d]pyran-6-one

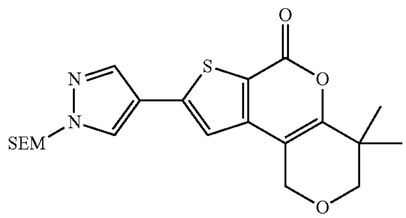 [SMILES: CC1(C)COCc2c1oc(=O)c1sc(-c3cnn(COCC[Si](C)(C)C)c3)cc21]

Methyl 3-bromo-5-(1-((2-(trimethylsilyl)ethoxy)methyl)-1H-pyrazol-4-yl)thiophene-2-carboxylic acid (100 mg, 240 μmol, 1.0 eq.) was dissolved in DMF (10.0 mL) before 3,3-dimethyltetrahydropyran-4-one (61 mg, 480 μmol, 2.0 eq.), $Na_2S_2O_5$ (9.0 mg, 48 μmol, 0.20 eq.), $Cs_2CO_3$ (230 mg, 720 μmol, 3.0 eq.) and BINAP-Pd-G3 (24 mg, 24 μmol, 0.10 eq.) were added. The mixture was stirred at 105° C. for 16 h, cooled, filtered, and concentrated. Purification by column chromatography ($SiO_2$ 0-4% MeOH in DCM) afforded 4,4-dimethyl-8-(1-((2-(trimethylsilyl)ethoxy)methyl)-1H-pyrazol-4-yl)-3,4-dihydro-1H,6H-pyrano[4,3-b]thieno[3,2-d]pyran-6-one (20 mg, 19%). MS obsd. ($ESI^+$): 433.4 [$(M+H)^+$].

Step B: 4,4-dimethyl-8-(1H-pyrazol-4-yl)-3,4-dihydro-1H,6H-pyrano[4,3-b]thieno[3,2-d]pyran-6-one

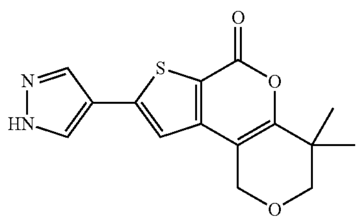 [SMILES: CC1(C)COCc2c1oc(=O)c1sc(-c3cn[nH]c3)cc21]

A mixture of 4,4-dimethyl-8-(1-((2-(trimethylsilyl)ethoxy)methyl)-1H-pyrazol-4-yl)-3,4-dihydro-1H,6H-pyrano[4,3-b]thieno[3,2-d]pyran-6-one (45 mg, 100 μmol), DCM (5.0 mL) and trifluoroacetic acid (1.5 mL) was stirred at rt for 2 h. The mixture was concentrated in vacuo to give 4,4-dimethyl-8-(1H-pyrazol-4-yl)-3,4-dihydro-1H,6H-pyrano[4,3-b]thieno[3,2-d]pyran-6-one (40 mg) which was used without further purification. MS obsd. ($ESI^+$): 303.2 [$(M+H)^+$].

Step C: 4,4-dimethyl-8-(1H-pyrazol-4-yl)-1,3,4,5-tetrahydro-6H-pyrano[4,3-b]thieno[3,2-d]pyridin-6-one Compound 58

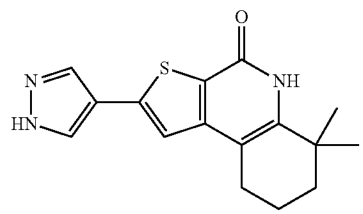

A mixture of 4,4-dimethyl-8-(1H-pyrazol-4-yl)-3,4-dihydro-1H,6H-pyrano[4,3-b]thieno[3,2-d]pyran-6-one (40 mg, crude), $NH_4OH$ (5.0 mL) and MeOH (5.0 mL) was heated to 100° C. for 4 h in a microwave reactor. The mixture was concentrated in vacuo, and the residue was purified by column chromatography ($SiO_2$, 0-5% MeOH in DCM) to afford 4,4-dimethyl-8-(1H-pyrazol-4-yl)-1,3,4,5-tetrahydro-6H-pyrano[4,3-b]thieno[3,2-d]pyridin-6-one (9.0 mg, 36%). MS obsd. ($ESI^+$): 302.2 [$(M+H)^+$]; $^1H$ NMR (400 MHz, DMSO-d6) δ ppm: 13.21 (brs, 1H), 11.20 (s, 1H), 8.29 (s, 1H), 7.94 (s, 1H), 7.37 (s, 1H), 4.69 (s, 2H), 3.57 (s, 2H), 1.26 (s, 6H).

Examples 59 and 60—Compounds 59 and 60: (S)-4-(tert-butyl)-8-(3-fluoropyridin-4-yl)-4-hydroxy-1,3,4,5-tetrahydro-6H-pyrano[4,3-b]thieno[3,2-d]pyridin-6-one (Compound 59) and (R)-4-(tert-butyl)-8-(3-fluoropyridin-4-yl)-4-hydroxy-1,3,4,5-tetrahydro-6H-pyrano[4,3-b]thieno[3,2-d]pyridin-6-one (Compound 60) (Stereochemistry for Compounds 59 and 60 is Arbitrarily Assigned)

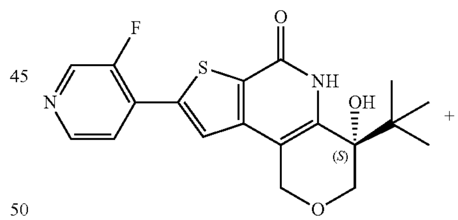

Compound 59

+

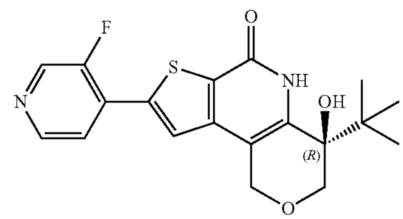

Compound 60

Step A: 4,4-dimethoxytetrahydro-2H-pyran-3-ol

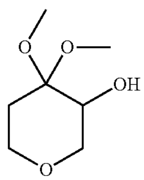

A solution of tetrahydropyran-4-one (40.0 g, 400 mmol, 1.0 eq.) and potassium hydroxide (67.3 g, 1.20 mol, 3.0 eq.) in MeOH (1.7 L) was cooled to 0° C. and 12 (117 g, 459 mmol, 1.15 eq.) was added slowly. The reaction mixture was allowed to warm to rt and after 4 h the mixture was concentrated. The crude product was triturated with EtOAc (300 mL) to afford 4,4-dimethoxytetrahydro-2H-pyran-3-ol (50 g, used without further purification). $^1$H NMR (400 MHz, DMSO-d6) δ 4.75 (s, 1H), 3.68-3.54 (m, 2H), 3.52-3.41 (m, 2H), 3.32-3.25 (m, 1H), 3.12 (s, 3H), 3.11 (s, 3H), 1.84-1.76 (m, 1H), 1.62-1.57 (m, 1H).

Step B: 4,4-dimethoxydihydro-2H-pyran-3(4H)-one

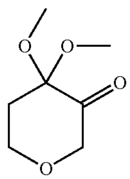

A solution of 4,4-dimethoxytetrahydropyran-3-ol (40.0 g, 247 mmol, 1.0 eq.) in DCM (900 mL) was cooled to 0° C. and DMP (157 g, 370 mmol, 1.5 eq.) was added. The mixture was heated to 30° C. for 16 h before addition of a mixture of petroleum ether and EtOAc (8:1, 400 mL). The filtrate was concentrated and purified ($SiO_2$, 5% petroleum ether in EtOAc) to give 4,4-dimethoxydihydro-2H-pyran-3(4H)-one (23 g, 45%, 2 steps) as a light-yellow solid.

$^1$H NMR (400 MHz, DMSO-d6) δ 3.99 (s, 2H), 3.87-3.80 (m, 2H), 3.14 (s, 6H), 2.16-2.10 (m, 2H).

Step C: 3-(tert-butyl)-3-hydroxytetrahydro-4H-pyran-4-one

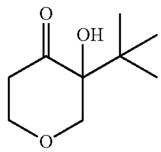

A solution of 4,4-dimethoxytetrahydropyran-3-one (10.0 g, 62.4 mmol, 1.0 eq.) in anhydrous THF (100 mL) was cooled to −78° C. and t-BuLi (1.3 M in THF, 62 mL, 1.3 eq.) was added dropwise over 30 min. The mixture was stirred at −78° C. for 2 h before HCl (2 M aq., 94 mL) was added dropwise over 15 min. After addition, the mixture was stirred at 0° C. for 2 h. The mixture was extracted with EtOAc (3×100 mL), washed with brine (2×100 mL) and the combined organic layers were concentrated and purified ($SiO_2$, 0-10% EtOAc in PE) to give 3-(tert-butyl)-3-hydroxytetrahydro-4H-pyran-4-one (3.6 g, 33%). $^1$H NMR (400 MHz, DMSO-d6) δ 5.05 (s, 1H), 4.06 (dd, J=12.0, 1.2 Hz, 1H), 4.03-3.95 (m, 1H), 3.75-3.64 (m, 1H), 3.35 (d, J=12.0 Hz, 1H), 2.60-2.52 (m, 2H), 0.95 (s, 9H).

Step D: 4-(tert-butyl)-4-hydroxy-3,4-dihydro-1H,6H-pyrano[4,3-b]thieno[3,2-d]pyran-6-one

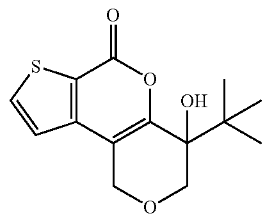 [SMILES: CC(C)(C)C1(O)COCc2c1oc(=O)c1sccc21]

To a dried three-necked flask containing of methyl 3-bromothiophene-2-carboxylate (2 g, 9.05 mmol, 1.0 eq.) and 3-tert-butyl-3-hydroxy-tetrahydropyran-4-one (1.56 g, 9.05 mmol, 1.0 eq.) was added anhydrous toluene (50 mL). The mixture was degassed and purged with $N_2$ (3×) before $Pd_2(dba)_3$ (414 mg, 452 μmol, 0.050 eq.), Xantphos (524 mg, 905 μmol, 0.10 eq.), $K_3PO_4$ (3.84 g, 18.1 mmol, 2.0 eq.) were added. It was degassed and purged with $N_2$ (3×) again and stirred at 105° C. for 16 h. The mixture was cooled to rt filtered, and the filtrate was concentrated. Purification by column chromatography ($SiO_2$, 0-30% EtOAc in PE) and further purification by reverse phase column chromatography (C18 $SiO_2$, 0-30% MeCN in water (0.1% $NH_4OH$) afforded 4-(tert-butyl)-4-hydroxy-3,4-dihydro-1H,6H-pyrano[4,3-b]thieno[3,2-d]pyran-6-one (600 mg, 2.14 mmol, 24%) as a white solid. MS obsd. ($ESI^+$): 281.2 $[(M+H)^+]$.

Step E: (4-(tert-butyl)-4-hydroxy-6-oxo-4,6-dihydro-1H,3H-pyrano[4,3-b]thieno[3,2-d]pyran-8-yl) boronic Acid

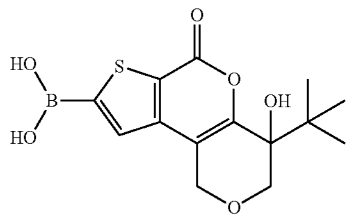 [SMILES: CC(C)(C)C1(O)COCc2c1oc(=O)c1sc(B(O)O)cc21]

A mixture of 4-(tert-butyl)-4-hydroxy-3,4-dihydro-1H,6H-pyrano[4,3-b]thieno[3,2-d]pyran-6-one (500 mg, 1.78 mmol, 1.0 eq.), 4,4,5,5-tetramethyl-1,3,2-dioxaborolane (1.37 g, 10.7 mmol, 1.55 mL, 6.0 eq.), (1,5-Cyclooctadiene)(methoxy)iridium dimer (59.1 mg, 89.2 μmol, 0.050 eq.), 2,6-diisopropyl-N-(pyridin-2-ylmethylene)aniline (47.5 mg, 178 μmol, 0.10 eq.) and anhydrous DME (10 mL) was stirred at 85° C. for 24 h. The mixture was cooled and concentrated in vacuo to give (4-(tert-butyl)-4-hydroxy-6-oxo-4,6-dihydro-1H,3H-pyrano[4,3-b]thieno[3,2-d]pyran-8-yl)boronic acid (2 g, crude) which was used without further purification. MS obsd. ($ESI^+$): 325.5 $[(M+H)^+]$.

Step F: 10-tert-butyl-4-(3-fluoro-4-pyridyl)-10-hydroxy-8,12-dioxa-5-thiatricyclo[7.4.0.0$^{2,6}$]trideca-1(9),2(6),3-trien-7-one

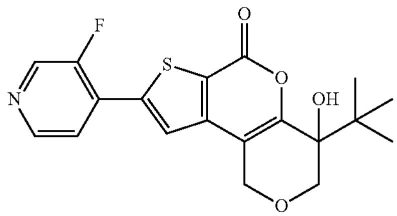 [SMILES: CC(C)(C)C1(O)COCc2c1oc(=O)c1sc(-c3ccncc3F)cc21]

To the mixture of (10-tert-butyl-10-hydroxy-7-oxo-8,12-dioxa-5-thiatricyclo[7.4.0.0$^{2,6}$]trideca-1(9),2(6),3-trien-4-yl)boronic acid (130 mg, 401 μmol, 1.0 eq.), $Na_2CO_3$ (128 mg, 1.20 mmol, 3.0 eq.) in THF (12 mL) and $H_2O$ (1.2 mL) was added 3-fluoro-4-iodo-pyridine (99 mg, 441 μmol, 1.1 eq.) and Sphos-Pd-G3 (32 mg, 40.1 μmol, 0.10 eq.). The mixture was degassed and purged with $N_2$ (2×) before stirring at 50° C. for 6 h. The reaction mixture was concentrated and the residue was diluted with DCM/MeOH=10/1 (300 mL). The mixture was filtered and the filtrate was concentrated in vacuo. The crude residue was purified by flash column chromatography ($SiO_2$ 0-5% MeOH in DCM) to give 10-tert-butyl-4-(3-fluoro-4-pyridyl)-10-hydroxy-8,12-dioxa-5-thiatricyclo[7.4.0.0$^{2,6}$]trideca-1(9),2(6),3-trien-7-one (280 mg, 23%) as a yellow solid. MS obsd. (ESI$^+$): 376.4 [(M+H)$^+$].

Step G: (S)-4-(tert-butyl)-8-(3-fluoropyridin-4-yl)-4-hydroxy-1,3,4,5-tetrahydro-6H-pyrano[4,3-b]thieno[3,2-d]pyridin-6-one (Compound 59) and (R)-4-(tert-butyl)-8-(3-fluoropyridin-4-yl)-4-hydroxy-1,3,4,5-tetrahydro-6H-pyrano[4,3-b]thieno[3,2-d]pyridin-6-one (Compound 60)

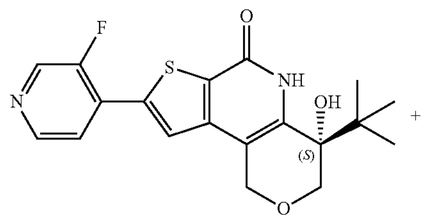

Compound 59

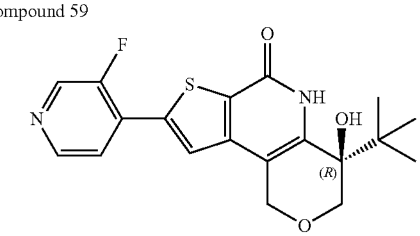

Compound 60

A solution of 10-tert-butyl-4-(3-fluoro-4-pyridyl)-10-hydroxy-8,12-dioxa-5-thiatricyclo[7.4.0.0$^{2,6}$]trideca-1(9),2(6),3-trien-7-one (140 mg, 373 μmol, 1.0 eq.) in $NH_3$/MeOH (7.0 M, 10 mL) was stirred at 95° C. for 3 h. The reaction mixture was cooled, concentrated in vacuo to give the residue, which was purified by flash column chromatography (SiO2 0-5% MeOH in DCM) to give 4-(tert-butyl)-8-(3-fluoropyridin-4-yl)-4-hydroxy-1,3,4,5-tetrahydro-6H-pyrano[4,3-b]thieno[3,2-d]pyridin-6-one (123 mg, 44%) MS obsd. (ESI$^+$): 375.0 [(M+H)$^+$].

The enantiomers were separated via chiral SFC. (S)-4-(tert-butyl)-8-(3-fluoropyridin-4-yl)-4-hydroxy-1,3,4,5-tetrahydro-6H-pyrano[4,3-b]thieno[3,2-d]pyridin-6-one (Compound 59): MS obsd. (ESI$^+$): 375.0 [(M+H)$^+$]; $^1$H NMR (400 MHz, DMSO-d6) δ ppm: 10.41 (s, 1H), 8.78 (d, J=2.8 Hz, 1H), 8.57 (dd, J=5.2, 0.8 Hz, 1H), 8.08-7.99 (m, 2H), 5.36 (s, 1H), 4.82 (dd, J=44.0, 15.2 Hz, 2H), 4.14 (d, J=11.2 Hz, 1H), 3.46 (d, J=11.2 Hz, 1H), 1.04 (s, 10H). (R)-4-(tert-butyl)-8-(3-fluoropyridin-4-yl)-4-hydroxy-1,3,4,5-tetrahydro-6H-pyrano[4,3-b]thieno[3,2-d]pyridin-6-one (Compound 60): MS obsd. (ESI$^+$): 375.0 [(M+H)$^+$].

Examples 61 and 62—Compounds 61 and 62: (S)-4-(tert-butyl)-4-hydroxy-8-(2-methylpyridin-4-yl)-1,3,4,5-tetrahydro-6H-pyrano[4,3-b]thieno[3,2-d]pyridin-6-one (Compound 61) and (R)-4-(tert-butyl)-4-hydroxy-8-(2-methylpyridin-4-yl)-1,3,4,5-tetrahydro-6H-pyrano[4,3-b]thieno[3,2-d]pyridin-6-one (Compound 62) (Stereochemistry for Compounds 61 and 62 is Arbitrarily Assigned)

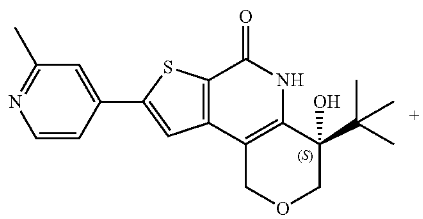

Compound 61

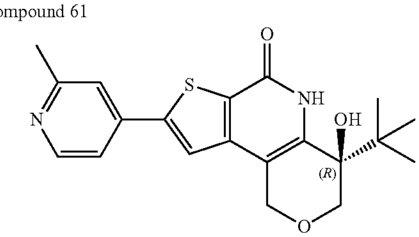

Compound 62

Step A: 10-tert-butyl-10-hydroxy-4-(2-methyl-4-pyridyl)-8,12-dioxa-5-thiatricyclo[7.4.0.0$^{2,6}$]trideca-1(9),2(6),3-trien-7-one

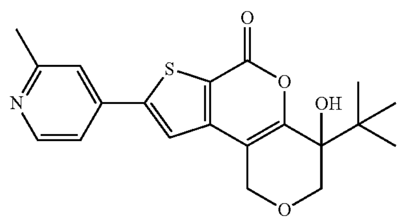 [SMILES: Cc1cc(-c2cc3c4c(oc(=O)c3s2)C(O)(C(C)(C)C)COC4)ccn1]

4-Iodo-2-methyl-pyridine was subjected to similar conditions as described for Compound 59, Step F, to afford 10-tert-butyl-10-hydroxy-4-(2-methyl-4-pyridyl)-8,12-dioxa-5-thiatricyclo[7.4.0.0$^{2,6}$]trideca-1(9),2(6),3-trien-7-one (169 mg, 29%). MS obsd. (ESI$^+$): 372.2 [M+H]$^+$.

Step B: (S)-4-(tert-butyl)-4-hydroxy-8-(2-methylpyridin-4-yl)-1,3,4,5-tetrahydro-6H-pyrano[4,3-b]thieno[3,2-d]pyridin-6-one (Compound 61) and (R)-4-(tert-butyl)-4-hydroxy-8-(2-methylpyridin-4-yl)-1,3,4,5-tetrahydro-6H-pyrano[4,3-b]thieno[3,2-d]pyridin-6-one (Compound 62)

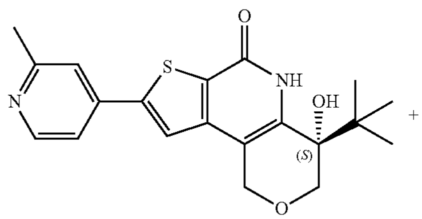

+

Compound 61

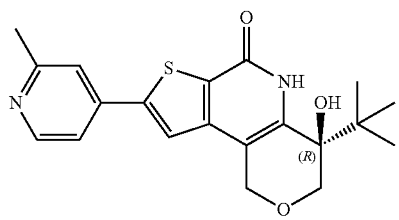

Compound 62

10-Tert-butyl-10-hydroxy-4-(2-methyl-4-pyridyl)-8,12-dioxa-5-thiatricyclo[7.4.0.0$^{2,6}$]trideca-1(9),2(6),3-trien-7-one was subjected to similar conditions as described for Compound 59, Step G, to afford 4-(tert-butyl)-4-hydroxy-8-(2-methylpyridin-4-yl)-1,3,4,5-tetrahydro-6H-pyrano[4,3-b]thieno[3,2-d]pyridin-6-one (200 mg, 78%). MS obsd. (ESI$^+$): 371.1 [M+H]$^+$.

The enantiomers were separated via chiral SFC. (S)-4-(tert-butyl)-4-hydroxy-8-(2-methylpyridin-4-yl)-1,3,4,5-tetrahydro-6H-pyrano[4,3-b]thieno[3,2-d]pyridin-6-one (Compound 61): MS obsd. (ESI$^+$): 371.0 [(M+H)$^+$]; $^1$H NMR (400 MHz, DMSO-d6) δ 10.32 (s, 1H), 8.55 (d, J=5.2 Hz, 1H), 7.99 (s, 1H), 7.70 (s, 1H), 7.61 (dd, J=5.2, 1.6 Hz, 1H), 5.35 (s, 1H), 4.80 (dd, J=38.8, 14.8 Hz, 2H), 4.14 (d, J=11.2 Hz, 1H), 3.45 (d, J=11.2 Hz, 1H), 2.55 (s, 3H), 1.03 (s, 9H). (R)-4-(tert-butyl)-4-hydroxy-8-(2-methylpyridin-4-yl)-1,3,4,5-tetrahydro-6H-pyrano[4,3-b]thieno[3,2-d]pyridin-6-one (Compound 62): MS obsd. (ESI$^+$): 371.0 [(M+H)$^+$].

Examples 63 and 64—Compounds 63 and 64: (S)-4-(tert-butyl)-8-(5-chloropyrimidin-4-yl)-4-hydroxy-1,3,4,5-tetrahydro-6H-pyrano[4,3-b]thieno[3,2-d]pyridin-6-one (Compound 63) and (R)-4-(tert-butyl)-8-(5-chloropyrimidin-4-yl)-4-hydroxy-1,3,4,5-tetrahydro-6H-pyrano[4,3-b]thieno[3,2-d]pyridin-6-one (Compound 64) (Stereochemistry for Compounds 63 and 64 is Arbitrarily Assigned)

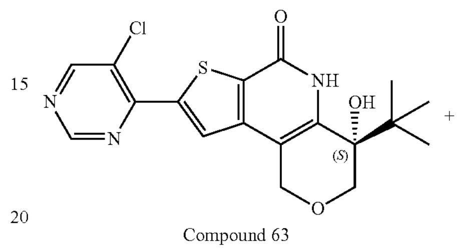

+

Compound 63

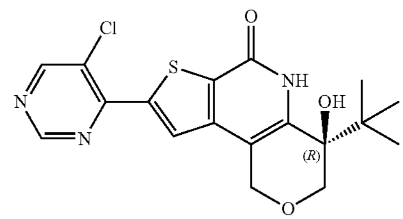

Compound 64

Step A: 5-chloro-4-iodopyrimidine

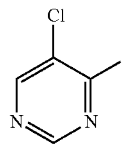

To the solution of 5-chloropyrimidin-4-amine (500 mg, 3.86 mmol, 1.0 eq.) and diiodomethane (2.07 g, 7.72 mmol, 622 μL, 2.0 eq.) in $CH_3CN$ (20 mL) was added isopentyl nitrite (995 mg, 8.49 mmol, 1.14 mL, 2.2 eq.) in $CH_3CN$ (1 mL) dropwise at 0° C. The mixture was stirred at 0° C. for 30 min before heating to 70° C. for 16 h. The reaction mixture was concentrated in vacuo and the crude residue was purified by flash column chromatography ($SiO_2$, 0-3% EtOAc in PE) to give 5-chloro-4-iodopyrimidine (410 mg, 44% yield). MS obsd. (ESI$^+$): 241.1 [(M+H)$^+$].

Step B: 4-(tert-butyl)-8-(5-chloropyrimidin-4-yl)-4-hydroxy-3,4-dihydro-1H,6H-pyrano[4,3-b]thieno[3,2-d]pyran-6-one

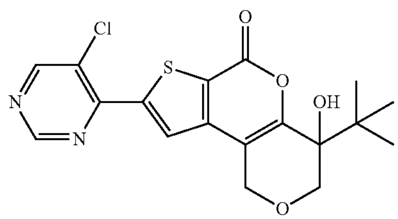 [SMILES: CC(C)(C)C1(O)COCc2c1oc(=O)c1sc(-c3ncncc3Cl)cc21]

Similar conditions described in Compound 59, Step F were utilized for (4-(tert-butyl)-4-hydroxy-6-oxo-4,6-dihydro-1H,3H-pyrano[4,3-b]thieno[3,2-d]pyran-8-yl)boronic acid and 5-chloro-4-iodopyrimidine to afford 4-(tert-butyl)-8-(5-chloropyrimidin-4-yl)-4-hydroxy-3,4-dihydro-1H,6H-pyrano[4,3-b]thieno[3,2-d]pyran-6-one (76 mg, 31%). MS obsd. ($ESI^+$): 393.4 $[(M+H)^+]$.

Step C: (S)-4-(tert-butyl)-8-(5-chloropyrimidin-4-yl)-4-hydroxy-1,3,4,5-tetrahydro-6H-pyrano[4,3-b]thieno[3,2-d]pyridin-6-one (Compound 63) and (R)-4-(tert-butyl)-8-(5-chloropyrimidin-4-yl)-4-hydroxy-1,3,4,5-tetrahydro-6H-pyrano[4,3-b]thieno[3,2-d]pyridin-6-one (Compound 64)

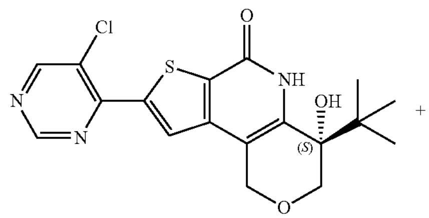

+

Compound 63

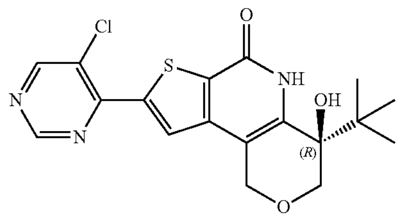

Compound 64

Similar conditions described in Compound 59, Step G were utilized for 4-(tert-butyl)-8-(5-chloropyrimidin-4-yl)-4-hydroxy-3,4-dihydro-1H,6H-pyrano[4,3-b]thieno[3,2-d]pyran-6-one to give 4-(tert-butyl)-8-(5-chloropyrimidin-4-yl)-4-hydroxy-1,3,4,5-tetrahydro-6H-pyrano[4,3-b]thieno[3,2-d]pyridin-6-one (53 mg, 70%) as yellow solid. MS obsd. ($ESI^+$): 392.4 $[(M+H)^+]$.

Chiral SFC was used to separate the enantiomers. (S)-4-(tert-butyl)-8-(5-chloropyrimidin-4-yl)-4-hydroxy-1,3,4,5-tetrahydro-6H-pyrano[4,3-b]thieno[3,2-d]pyridin-6-one (Compound 63): MS obsd. ($ESI^+$): 392.0 $[(M+H)^+]$; $^1H$ NMR (400 MHz, DMSO-d6) δ ppm: 10.46 (s, 1H), 9.22 (s, 1H), 9.10 (s, 1H), 8.33 (s, 1H), 5.36 (s, 1H), 4.93-4.76 (m, 2H), 4.14 (d, J=11.2 Hz, 1H), 3.46 (d, J=11.6 Hz, 1H), 1.04 (s, 9H). (R)-4-(tert-butyl)-8-(5-chloropyrimidin-4-yl)-4-hydroxy-1,3,4,5-tetrahydro-6H-pyrano[4,3-b]thieno[3,2-d]pyridin-6-one (Compound 64): MS obsd. ($ESI^+$): 392.0 $[(M+H)^+]$.

Examples 65 and 66—Compounds 65 and 66: (R)-4-(tert-butyl)-8-(3-fluoro-1H-pyrazol-4-yl)-4-hydroxy-1,3,4,5-tetrahydro-6H-pyrano[4,3-b]thieno[3,2-d]pyridin-6-one (Compound 65) and (S)-4-(tert-butyl)-8-(3-fluoro-1H-pyrazol-4-yl)-4-hydroxy-1,3,4,5-tetrahydro-6H-pyrano[4,3-b]thieno[3,2-d]pyridin-6-one (Compound 66) (Stereochemistry for Compounds 65 and 66 is Arbitrarily Assigned)

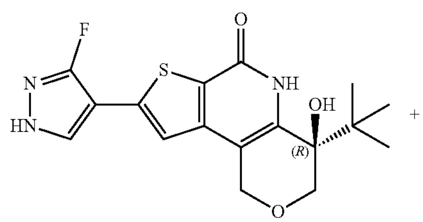

+

Compound 65

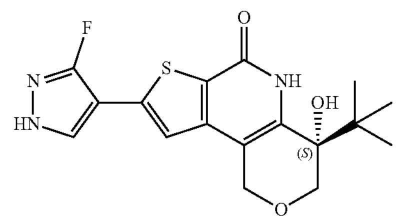

Compound 66

Step A: 4-(tert-butyl)-8-(3-fluoro-1-((2-(trimethylsilyl)ethoxy)methyl)-1H-pyrazol-4-yl)-4-hydroxy-3,4-dihydro-1H,6H-pyrano[4,3-b]thieno[3,2-d]pyran-6-one

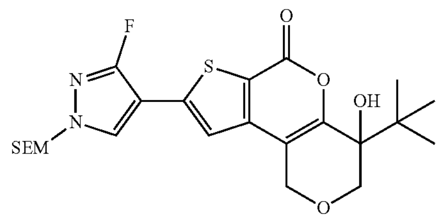 [SMILES: CC(C)(C)C1(O)COCc2c1oc(=O)c1sc(-c3cn(COCC[Si](C)(C)C)nc3F)cc21]

4-Bromo-3-fluoro-1-((2-(trimethylsilyl)ethoxy)methyl)-1H-pyrazole was subjected to similar conditions as described for Compound 59, Step D, to afford 4-(tert-butyl)-8-(3-fluoro-1-((2-(trimethylsilyl)ethoxy)methyl)-1H-pyrazol-4-yl)-4-hydroxy-3,4-dihydro-1H,6H-pyrano[4,3-b]thieno[3,2-d]pyran-6-one (10 mg, 13%). MS obsd. ($ESI^+$): 495.5 $[(M+H)^+]$.

Step B: 4-(tert-butyl)-8-(3-fluoro-1H-pyrazol-4-yl)-4-hydroxy-3,4-dihydro-1H,6H-pyrano[4,3-b]thieno[3,2-d]pyran-6-one

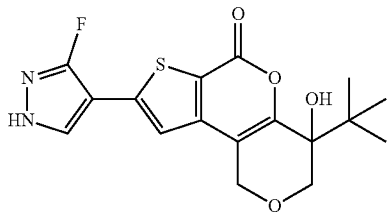 [SMILES: CC(C)(C)C1(O)COCc2c1oc(=O)c1sc(-c3c[nH]nc3F)cc21]

To a solution of 4-(tert-butyl)-8-(3-fluoro-1-((2-(trimethylsilyl)ethoxy)methyl)-1H-pyrazol-4-yl)-4-hydroxy-3,4-dihydro-1H,6H-pyrano[4,3-b]thieno[3,2-d]pyran-6-one (100 mg, 202 μmol, 1.0 eq.) in DCM (5 mL) was added boron trichloride (1.0 M, 1.0 mL, 5.0 eq.) at −78° C. The mixture was stirred at −78° C. for 2 h before MeOH was added. The mixture was concentrated in vacuo to give 4-(tert-butyl)-8-(3-fluoro-1H-pyrazol-4-yl)-4-hydroxy-3,4-dihydro-1H,6H-pyrano[4,3-b]thieno[3,2-d]pyran-6-one (75 mg, used without further purification). MS obsd. ($ESI^+$): 365.5 [$(M+H)^+$].

Step C: (R)-4-(tert-butyl)-8-(3-fluoro-1H-pyrazol-4-yl)-4-hydroxy-1,3,4,5-tetrahydro-6H-pyrano[4,3-b]thieno[3,2-d]pyridin-6-one (Compound 65) and (S)-4-(tert-butyl)-8-(3-fluoro-1H-pyrazol-4-yl)-4-hydroxy-1,3,4,5-tetrahydro-6H-pyrano[4,3-b]thieno[3,2-d]pyridin-6-one (Compound 66)

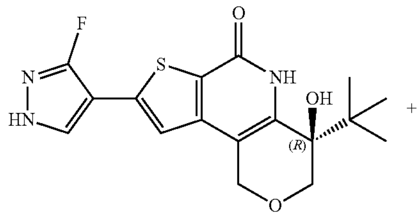

+

Compound 65

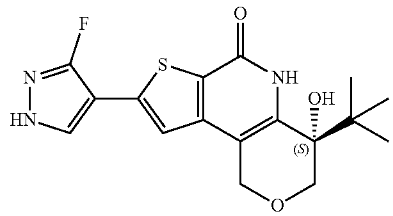

Compound 66

4-(Tert-butyl)-8-(3-fluoro-1H-pyrazol-4-yl)-4-hydroxy-3,4-dihydro-1H,6H-pyrano[4,3-b]thieno[3,2-d]pyran-6-one was subjected to similar conditions as described for Compound 59, Step G, to afford 4-(tert-butyl)-8-(3-fluoro-1H-pyrazol-4-yl)-4-hydroxy-1,3,4,5-tetrahydro-6H-pyrano[4,3-b]thieno[3,2-d]pyridin-6-one (40 mg, 110 μmol, 45%, 2 steps). MS obsd. ($ESI^+$): 364.4 [$(M+H)^+$].

The isomers were separated by chiral HPLC. (R)-4-(tert-butyl)-8-(3-fluoro-1H-pyrazol-4-yl)-4-hydroxy-1,3,4,5-tetrahydro-6H-pyrano[4,3-b]thieno[3,2-d]pyridin-6-one (Compound 65): MS obsd. ($ESI^+$): 364.0 [$(M+H)^+$]. $^1$H NMR (400 MHz, DMSO-d6) δ ppm: 12.83 (brs, 1H), 10.16 (brs, 1H), 8.32 (d, J=1.8 Hz, 1H), 7.33 (s, 1H), 5.33 (s, 1H), 4.75 (dd, J=34.2, 14.8 Hz, 2H), 4.12 (d, J=11.2 Hz, 1H), 3.44 (d, J=11.2 Hz, 1H), 1.03 (s, 9H). (S)-4-(tert-butyl)-8-(3-fluoro-1H-pyrazol-4-yl)-4-hydroxy-1,3,4,5-tetrahydro-6H-pyrano[4,3-b]thieno[3,2-d]pyridin-6-one (Compound 66): MS obsd. ($ESI^+$): 364.0 [$(M+H)^+$].

Examples 67 and 68—Compounds 67 and 68: (S)-4-(tert-butyl)-4-hydroxy-8-(pyridazin-4-yl)-1,3,4,5-tetrahydro-6H-pyrano[4,3-b]thieno[3,2-d]pyridin-6-one (Compound 67) and (R)-4-(tert-butyl)-4-hydroxy-8-(pyridazin-4-yl)-1,3,4,5-tetrahydro-6H-pyrano[4,3-b]thieno[3,2-d]pyridin-6-one (Compound 68) (Stereochemistry for Compounds 67 and 68 is Arbitrarily Assigned)

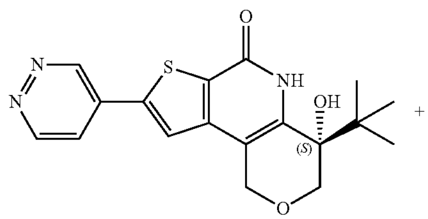

+

Compound 67

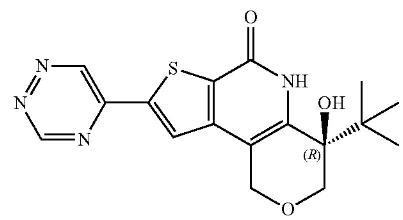

Compound 68

Step A: 4-(tert-butyl)-4-hydroxy-8-(pyridazin-4-yl)-3,4-dihydro-1H,6H-pyrano[4,3-b]thieno[3,2-d]pyran-6-one

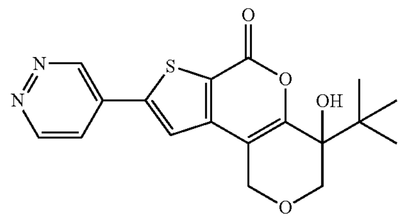 [SMILES: CC(C)(C)C1(O)COCc2c1oc(=O)c1sc(-c3ccnnc3)cc21]

Similar conditions described in Compound 59, Step F were utilized for 4-bromopyridazine hydrobromide to give 4-(tert-butyl)-4-hydroxy-8-(pyridazin-4-yl)-3,4-dihydro-1H,6H-pyrano[4,3-b]thieno[3,2-d]pyran-6-one (53 mg, 40%). MS obsd. ($ESI^+$): 359.4 [$(M+H)^+$].

Step B: (S)-4-(tert-butyl)-4-hydroxy-8-(pyridazin-4-yl)-1,3,4,5-tetrahydro-6H-pyrano[4,3-b]thieno[3,2-d]pyridin-6-one (Compound 67) and (R)-4-(tert-butyl)-4-hydroxy-8-(pyridazin-4-yl)-1,3,4,5-tetrahydro-6H-pyrano[4,3-b]thieno[3,2-d]pyridin-6-one (Compound 68)

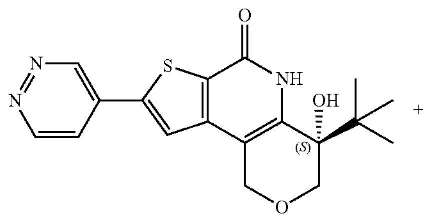

+

Compound 67

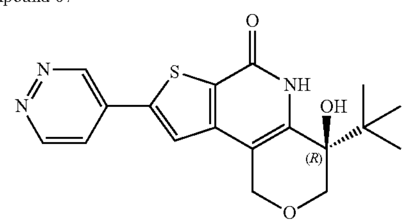

Compound 68

Similar conditions described in Compound 59, Step G were utilized for 4-(tert-butyl)-4-hydroxy-8-(pyridazin-4-yl)-3,4-dihydro-1H,6H-pyrano[4,3-b]thieno[3,2-d]pyran-6-one to give 4-(tert-butyl)-4-hydroxy-8-(pyridazin-4-yl)-1,3,4,5-tetrahydro-6H-pyrano[4,3-b]thieno[3,2-d]pyridin-6-one (37 mg, 66%). MS obsd. ($ESI^+$): 358.4 [$(M+H)^+$].

The enantiomers were separated by chiral SFC. (S)-4-(tert-butyl)-4-hydroxy-8-(pyridazin-4-yl)-1,3,4,5-tetrahydro-6H-pyrano[4,3-b]thieno[3,2-d]pyridin-6-one (Compound 67): MS obsd. ($ESI^+$): 358.0 [$(M+H)^+$]; $^1H$ NMR (400 MHz, DMSO-d6) δ ppm: 10.45 (s, 1H), 9.76-9.75 (m, 1H), 9.35-9.33 (m, 1H), 8.22 (s, 1H), 8.08-8.06 (m, 1H), 5.37 (s, 1H), 4.87-4.75 (m, 2H), 4.14 (d, J=11.6 Hz, 1H), 3.46 (d, J=11.2 Hz, 1H), 1.03 (s, 9H). (R)-4-(tert-butyl)-4-hydroxy-8-(pyridazin-4-yl)-1,3,4,5-tetrahydro-6H-pyrano[4,3-b]thieno[3,2-d]pyridin-6-one (Compound 68): MS obsd. ($ESI^+$): 358.0 [$(M+H)^+$].

Examples 69 and 70—Compounds 69 and 70: (S)-4-(tert-butyl)-4-hydroxy-8-(3-methylpyridin-4-yl)-1,3,4,5-tetrahydro-6H-pyrano[4,3-b]thieno[3,2-d]pyridin-6-one (Compound 69) and (R)-4-(tert-butyl)-4-hydroxy-8-(3-methylpyridin-4-yl)-1,3,4,5-tetrahydro-6H-pyrano[4,3-b]thieno[3,2-d]pyridin-6-one (Compound 70) (Stereochemistry for Compounds 69 and 70 is Arbitrarily Assigned)

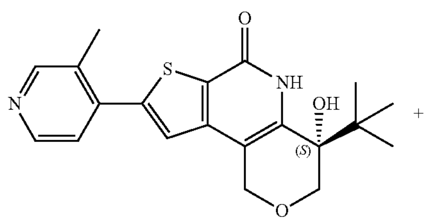

+

Compound 69

-continued

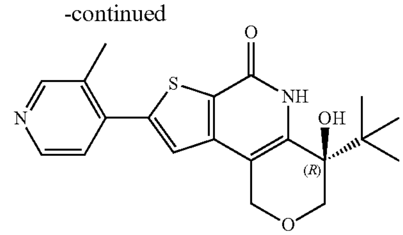

Compound 70

Step A: 4-(tert-butyl)-4-hydroxy-8-(3-methylpyridin-4-yl)-3,4-dihydro-1H,6H-pyrano[4,3-b]thieno[3,2-d]pyran-6-one

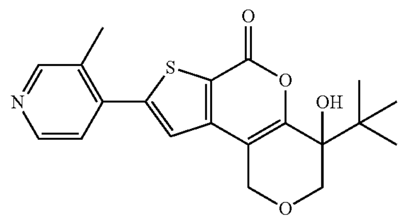 [SMILES: Cc1cnccc1-c1cc2c3c(oc(=O)c2s1)C(O)(C(C)(C)C)COC3]

Similar conditions described in Compound 59, Step F were utilized for 4-bromo-3-methyl-pyridine hydrochloride to afford 4-(tert-butyl)-4-hydroxy-8-(3-methylpyridin-4-yl)-3,4-dihydro-1H,6H-pyrano[4,3-b]thieno[3,2-d]pyran-6-one (87 mg, 63%) as yellow solid. MS obsd. ($ESI^+$): 372.4 [$(M+H)^+$].

Step B: (S)-4-(tert-butyl)-4-hydroxy-8-(3-methylpyridin-4-yl)-1,3,4,5-tetrahydro-6H-pyrano[4,3-b]thieno[3,2-d]pyridin-6-one (Compound 69) and (R)-4-(tert-butyl)-4-hydroxy-8-(3-methylpyridin-4-yl)-1,3,4,5-tetrahydro-6H-pyrano[4,3-b]thieno[3,2-d]pyridin-6-one (Compound 70)

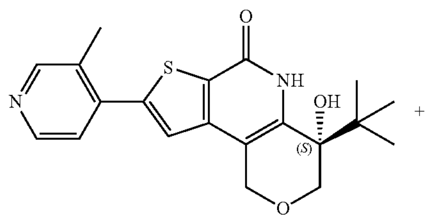

+

Compound 69

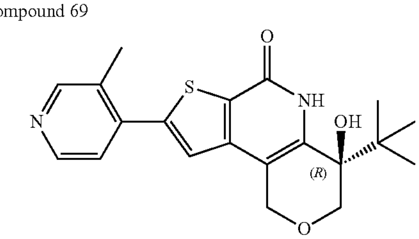

Compound 70

Similar conditions described in Compound 59, Step G were utilized for 4-(tert-butyl)-4-hydroxy-8-(3-methylpyridin-4-yl)-3,4-dihydro-1H,6H-pyrano[4,3-b]thieno[3,2-d]pyran-6-one to give 4-(tert-butyl)-4-hydroxy-8-(3-methylpyridin-4-yl)-1,3,4,5-tetrahydro-6H-pyrano[4,3-b]thieno[3,2-d]pyridin-6-one (36 mg, 41%). MS obsd. (ESI$^+$): 371.4 [(M+H)$^+$].

The enantiomers were separated by chiral SFC. (S)-4-(tert-butyl)-4-hydroxy-8-(3-methylpyridin-4-yl)-1,3,4,5-tetrahydro-6H-pyrano[4,3-b]thieno[3,2-d]pyridin-6-one (Compound 69): MS obsd. (ESI$^+$): 371.0 [(M+H)$^+$]. $^1$H NMR (400 MHz, DMSO-d6) δ ppm: 10.30 (s, 1H), 8.60 (s, 1H), 8.52 (d, J=4.8 Hz, 1H), 7.60 (s, 1H), 7.55 (d, J=4.8 Hz, 1H), 5.35 (s, 1H), 4.87-4.72 (m, 2H), 4.14 (d, J=11.2 Hz, 1H), 3.45 (d, J=11.2 Hz, 1H), 1.04 (s, 9H). (R)-4-(tert-butyl)-4-hydroxy-8-(3-methylpyridin-4-yl)-1,3,4,5-tetrahydro-6H-pyrano[4,3-b]thieno[3,2-d]pyridin-6-one (Compound 70) (27.2 mg 29%). MS obsd. (ESI$^+$): 371.0 [(M+H)$^+$].

Examples 71—Compound 71: 4-methyl-8-(1H-pyrazol-4-yl)-4-(pyrrolidin-1-yl)-1,3,4,5-tetrahydro-6H-pyrano[4,3-b]thieno[3,2-d]pyridin-6-one Compound 71

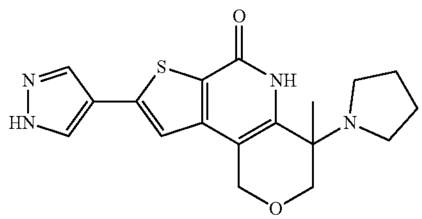

Step A: 4-hydroxy-4-methyl-8-(1H-pyrazol-4-yl)-1,3,4,5-tetrahydro-6H-pyrano[4,3-b]thieno[3,2-d]pyridin-6-one

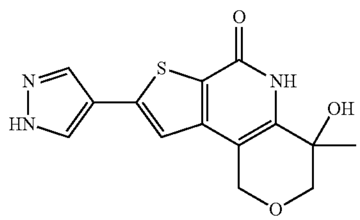 [SMILES: CC1(O)COCc2c1[nH]c(=O)c1sc(-c3cn[nH]c3)cc21]

To a dried three-necked flask containing of tert-butyl 4-(4-hydroxy-4-methyl-6-oxo-3,4,5,6-tetrahydro-1H-pyrano[4,3-b]thieno[3,2-d]pyridin-8-yl)-1H-pyrazole-1-carboxylate (500 mg, 1.29 mmol, 1.0 eq.) was added THF (50 mL) and the mixture was degassed and purged with $N_2$ (3×). Methyl magnesium bromide (1 M, 25.8 mL, 20.0 eq.) was added at 0° C. before warming to rt. After 2 h $NH_4Cl$ solution (13 mL) was added and the mixture was extracted with EtOAc (3×50 mL). The combined organic layers were dried ($MgSO_4$), filtered and concentrated to give the residue which was purified by flash column chromatography ($SiO_2$, 0-8% MeOH in DCM) to give 4-hydroxy-4-methyl-8-(1H-pyrazol-4-yl)-1,3,4,5-tetrahydro-6H-pyrano[4,3-b]thieno[3,2-d]pyridin-6-one (340 mg, 69%). MS obsd. (ESI$^+$): 304.1 [(M+H)$^+$].

Step B: 4-chloro-4-methyl-8-(1H-pyrazol-4-yl)-1,3,4,5-tetrahydro-6H-pyrano[4,3-b]thieno[3,2-d]pyridin-6-one

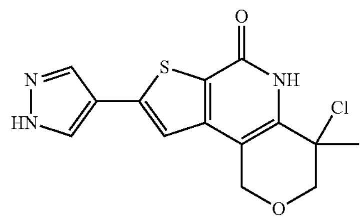 [SMILES: CC1(Cl)COCc2c1[nH]c(=O)c1sc(-c3cn[nH]c3)cc21]

Oxalyl chloride (15 mL) and N, N-dimethylformamide (0.1 mL) were added to a solution of 4-hydroxy-4-methyl-8-(1H-pyrazol-4-yl)-1,3,4,5-tetrahydro-6H-pyrano[4,3-b]thieno[3,2-d]pyridin-6-one (340 mg, 1.12 mmol, 1.0 eq.) in DCM (50 mL. The reaction mixture was heated to 40° C. and stirred for 16 h. The mixture was concentrated in vacuo to give 4-chloro-4-methyl-8-(1H-pyrazol-4-yl)-1,3,4,5-tetrahydro-6H-pyrano[4,3-b]thieno[3,2-d]pyridin-6-one (280 mg, used without further purification).

Step C: 4-methyl-8-(1H-pyrazol-4-yl)-4-(pyrrolidin-1-yl)-1,3,4,5-tetrahydro-6H-pyrano[4,3-b]thieno[3,2-d]pyridin-6-one (Compound 71)

Compound 71

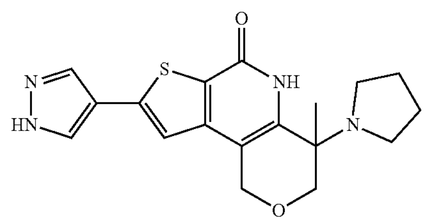

A solution of 4-chloro-4-methyl-8-(1H-pyrazol-4-yl)-1,3,4,5-tetrahydro-6H-pyrano[4,3-b]thieno[3,2-d]pyridin-6-one (280 mg, crude) in acetonitrile (40 mL) was cooled to 0° C. before pyrrolidine (15 mL) was added in a dropwise manner. The reaction mixture was allowed to warm to rt and for 16 h before being concentrated and purified by reverse phase column chromatography (0-20% MeCN in water (0.1% FA). Further purification by prep-TLC ($SiO_2$, 0-10% MeOH in DCM) afforded 4-methyl-8-(1H-pyrazol-4-yl)-4-(pyrrolidin-1-yl)-1,3,4,5-tetrahydro-6H-pyrano[4,3-b]thieno[3,2-d]pyridin-6-one (Compound 71) (2.2 mg, 17%). MS obsd. (ESI$^+$): 357.2 [(M+H)$^+$]. $^1$H NMR (400 MHz, DMSO-d6) δ ppm: 8.11 (s, 2H), 7.40 (s, 1H), 4.74 (d, J=14.2 Hz, 1H), 4.61 (d, J=14.2 Hz, 1H), 4.12 (d, J=11.6 Hz, 1H), 3.58 (d, J=11.8 Hz, 1H), 2.80 (d, J=6.4 Hz, 2H), 2.44-2.38 (m, 1H), 2.06-1.92 (m, 1H), 1.65 (s, 4H), 1.42 (s, 3H).

Examples 72 and 73—Compounds 72 and 73: (S)-4-hydroxy-4-(prop-1-yn-1-yl)-8-(1H-pyrazol-4-yl)-1,3,4,5-tetrahydro-6H-pyrano[4,3-b]thieno[3,2-d]pyridin-6-one (Compound 72) and (R)-4-hydroxy-4-(prop-1-yn-1-yl)-8-(1H-pyrazol-4-yl)-1,3,4,5-tetrahydro-6H-pyrano[4,3-b]thieno[3,2-d]pyridin-6-one (Compound 73) (Stereochemistry for Compounds 72 and 73 is Arbitrarily Assigned)

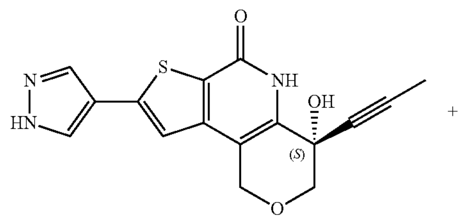

+

Compound 72

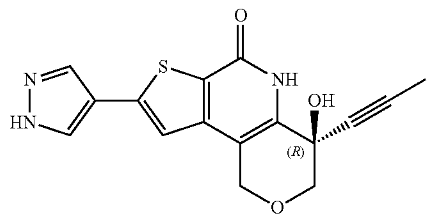

Compound 73

To a solution of tert-butyl 4-(7,10-dioxo-12-oxa-5-thia-8-azatricyclo[7.4.0.0$^{2,6}$]trideca-1(9),2(6),3-trien-4-yl)pyrazole-1-carboxylate (100 mg, 258 μmol, 1.0 eq.) in 1,4-dioxane (20 mL) was added prop-1-yn-1-ylmagnesium bromide (0.5 M, 10 mL, 20 eq.) at 0° C. The mixture was stirred at 0° C. for 1 h before $H_2O$ (20 mL) were added slowly at 0° C. The resulting mixture was extracted with EtOAc (3×350 mL) and the combined organic phase were dried ($Na_2SO_4$), filtered and concentrated in vacuo. The crude product was purified by flash silica gel column chromatography ($SiO_2$, 0-10% MeOH in DCM) to give 4-hydroxy-4-(prop-1-yn-1-yl)-8-(1H-pyrazol-4-yl)-1,3,4,5-tetrahydro-6H-pyrano[4,3-b]thieno[3,2-d]pyridin-6-one (110 mg, 43%). MS obsd. ($ESI^+$): 328.0 [$(M+H)^+$].

The enantiomers were separated by chiral SFC. (S)-4-hydroxy-4-(prop-1-yn-1-yl)-8-(1H-pyrazol-4-yl)-1,3,4,5-tetrahydro-6H-pyrano[4,3-b]thieno[3,2-d]pyridin-6-one (Compound 72): MS obsd. ($ESI^+$): 328.1 [$(M+H)^+$]; $^1H$ NMR (400 MHz, DMSO-$d_6$) δ ppm: 13.23 (s, 1H), 10.90 (s, 1H), 8.29 (s, 1H), 7.97 (s, 1H), 7.43 (s, 1H), 6.20 (s, 1H), 4.74 (s, 2H), 3.94 (d, J=11.2 Hz, 1H), 3.76 (d, J=11.2 Hz, 1H), 1.86 (s, 3H). (R)-4-hydroxy-4-(prop-1-yn-1-yl)-8-(1H-pyrazol-4-yl)-1,3,4,5-tetrahydro-6H-pyrano[4,3-b]thieno[3,2-d]pyridin-6-one (Compound 73): MS obsd. ($ESI^+$): 327.8 [$(M+H)^+$].

Examples 74, 75, 76 and 77—Compounds 74, 75, 76, and 77: (S)-4-((S)-sec-butyl)-4-hydroxy-8-(1H-pyrazol-4-yl)-1,3,4,5-tetrahydro-6H-pyrano[4,3-b]thieno[3,2-d]pyridin-6-one (Compound 74), (R)-4-((R)-sec-butyl)-4-hydroxy-8-(1H-pyrazol-4-yl)-1,3,4,5-tetrahydro-6H-pyrano[4,3-b]thieno[3,2-d]pyridin-6-one (Compound 75), (S)-4-((R)-sec-butyl)-4-hydroxy-8-(1H-pyrazol-4-yl)-1,3,4,5-tetrahydro-6H-pyrano[4,3-b]thieno[3,2-d]pyridin-6-one (Compound 76) and (R)-4-((S)-sec-butyl)-4-hydroxy-8-(1H-pyrazol-4-yl)-1,3,4,5-tetrahydro-6H-pyrano[4,3-b]thieno[3,2-d]pyridin-6-one (Compound 77) (Stereochemistry for Compounds 74, 75, 76, and 77 is Arbitrarily Assigned)

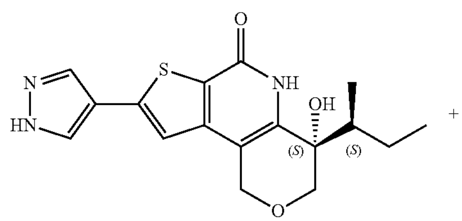

+

Compound 74

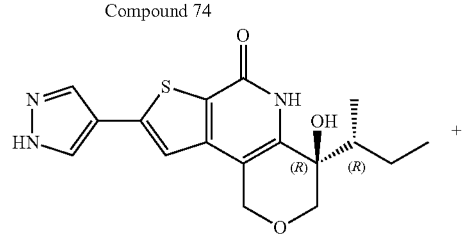

+

Compound 75

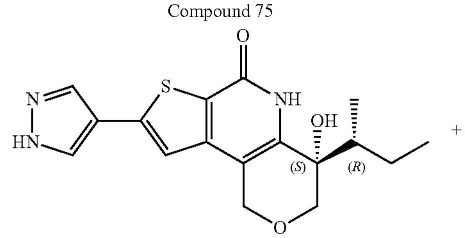

+

Compound 76

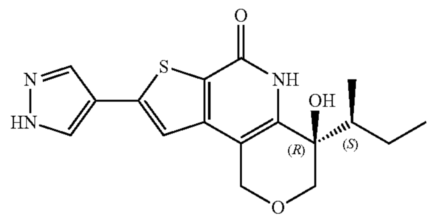

Compound 77

A procedure similar to Compound 72, Step A was performed with tert-pentylmagnesium chloride (1 M in THF, 7.74 mL, 30 eq.) to give 4-(sec-butyl)-4-hydroxy-8-(1H-pyrazol-4-yl)-1,3,4,5-tetrahydro-6H-pyrano[4,3-b]thieno[3,2-d]pyridin-6-one (35.2 mg, 39%). MS obsd. ($ESI^+$): 346.2 [$(M+H)^+$].

The four diastereomers were separated by chiral SFC. (S)-4-((S)-sec-butyl)-4-hydroxy-8-(1H-pyrazol-4-yl)-1,3,4,5-tetrahydro-6H-pyrano[4,3-b]thieno[3,2-d]pyridin-6-one (Compound 74): MS obsd. ($ESI^+$): 346.2 [$(M+H)^+$]. $^1H$ NMR (400 MHz, DMSO-d6) δ ppm: 13.22 (s, 1H), 10.80 (s, 1H), 8.28 (brs, 1H), 7.96 (brs, 1H), 7.42 (s, 1H), 5.27 (s, 1H), 4.77-4.53 (m, 2H), 3.92 (d, J=11.6 Hz, 1H), 3.56 (d, J=11.6 Hz, 1H), 2.12-2.07 (m, 1H), 1.87-1.80 (m, 1H), 1.09-0.97 (m, 1H), 0.92 (t, J=7.2 Hz, 3H), 0.72 (d, J=7.2 Hz, 3H). (R)-4-((R)-sec-butyl)-4-hydroxy-8-(1H-pyrazol-4-yl)-1,3,4,5-tetrahydro-6H-pyrano[4,3-b]thieno[3,2-d]pyridin-6-one (Compound 75): MS obsd. ($ESI^+$): 346.0 [$(M+H)^+$]. $^1H$ NMR (400 MHz, DMSO-d6) δ ppm: 13.22 (s, 1H), 10.82 (s, 1H), 8.28 (brs, 1H), 7.96 (brs, 1H), 7.41 (s, 1H), 5.24 (s, 1H), 4.73-4.53 (m, 2H), 3.93 (d, J=11.6 Hz, 1H), 3.54 (d, J=11.6 Hz, 1H), 2.13-2.02 (m, 1H), 1.15-1.05 (m, 2H), 0.98 (d, J=7.2 Hz, 3H), 0.77 (t, J=7.2 Hz, 3H). (S)-4-((R)-sec-butyl)-4-hydroxy-8-(1H-pyrazol-4-yl)-1,3,4,5-tetrahydro-6H-pyrano[4,3-b]thieno[3,2-d]pyridin-6-one (Compound 76): MS obsd. ($ESI^+$): 346.0 [$(M+H)^+$]. $^1H$ NMR (400 MHz, DMSO-d6) δ ppm: 13.22 (s, 1H), 10.82 (s, 1H), 8.09 (brs, 2H), 7.41 (s, 1H), 5.25 (s, 1H), 4.72-4.62 (m, 2H), 3.93 (d, J=11.6 Hz, 1H), 3.54 (d, J=11.6 Hz, 1H), 2.13-2.02 (m, 1H), 1.13-1.09 (m, 2H), 0.98 (d, J=7.2 Hz, 3H), 0.76 (d, J=7.2 Hz, 3H). (R)-4-((S)-sec-butyl)-4-hydroxy-8-(1H-pyrazol-4-yl)-1,3,4,5-tetrahydro-6H-pyrano[4,3-b]thieno[3,2-d]pyridin-6-one (Compound 77): MS obsd. ($ESI^+$): 346.0 [$(M+H)^+$]. $^1H$ NMR (400 MHz, DMSO-d6) δ ppm: 13.22 (s, 1H), 10.81 (s, 1H), 8.27 (brs, 1H), 7.96 (brs, 1H), 7.42 (s, 1H), 5.27 (s, 1H), 4.65 (t, J=9.2 Hz, 2H), 3.92 (d, J=11.6 Hz, 1H), 3.56 (d, J=11.6 Hz, 1H), 2.14-2.03 (m, 1H), 1.91-1.82 (m, 1H), 0.97-1.10 (m, 1H), 0.92 (t, J=7.2 Hz, 3H), 0.72 (d, J=7.2 Hz, 3H).

Examples 78 and 79—Compounds 78 and 79: (S)-4-cyclopentyl-4-hydroxy-8-(1H-pyrazol-4-yl)-1,3,4,5-tetrahydro-6H-pyrano[4,3-b]thieno[3,2-d]pyridin-6-one (Compound 78) and (R)-4-cyclopentyl-4-hydroxy-8-(1H-pyrazol-4-yl)-1,3,4,5-tetrahydro-6H-pyrano[4,3-b]thieno[3,2-d]pyridin-6-one (Compound 79) (Stereochemistry for Compounds 78 and 79 is Arbitrarily Assigned)

Compound 78

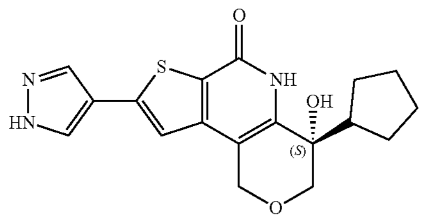

Compound 79

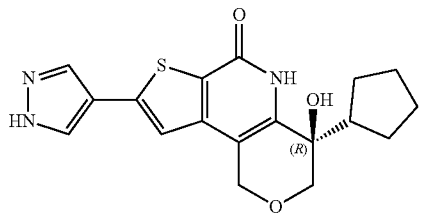

Cyclopentyl magnesium bromide (17 mmol, 17 mL, 10 eq.) was added rapidly to a solution of tert-butyl 4-(4,6-dioxo-3,4,5,6-tetrahydro-1H-pyrano[4,3-b]thieno[3,2-d]pyridin-8-yl)-1H-pyrazole-1-carboxylate (1.0 g, 1.73 mmol, 1.0 eq.) in THF (100 mL) at rt. The reaction mixture was degassed and purged with $N_2$ and stirred for 2 h at rt. A solution of $NH_4Cl$ (160 mL) was added and the mixture was extracted with EtOAc (3×40 mL). The combined organic layer were dried ($Na_2SO_4$), filtered, and concentrated. Column chromatography ($SiO_2$, 0-5% MeOH in DCM) followed by reverse phase column chromatography (C18-$SiO_2$, 0-20% MeCN in water (0.1% FA)) gave 4-cyclopentyl-4-hydroxy-8-(1H-pyrazol-4-yl)-1,3,4,5-tetrahydro-6H-pyrano[4,3-b]thieno[3,2-d]pyridin-6-one (130 mg, 14%). MS obsd. ($ESI^+$): 358.1 [$(M+H)^+$].

The enantiomers were separated by chiral SFC. (S)-4-cyclopentyl-4-hydroxy-8-(1H-pyrazol-4-yl)-1,3,4,5-tetrahydro-6H-pyrano[4,3-b]thieno[3,2-d]pyridin-6-one (Compound 78): MS obsd. ($ESI^+$): 357.8 [$(M+H)^+$]. $^1H$ NMR (400 MHz, DMSO-d6) δ ppm: 13.23 (s, 1H), 10.62 (s, 1H), 8.11 (brs, 2H), 7.40 (s, 1H), 5.29 (s, 1H), 4.71 (q, J=14.4 Hz, 2H), 3.90 (d, J=11.2 Hz, 1H), 3.57 (d, J=11.2 Hz, 1H), 1.69-1.37 (m, 9H). (R)-4-cyclopentyl-4-hydroxy-8-(1H-pyrazol-4-yl)-1,3,4,5-tetrahydro-6H-pyrano[4,3-b]thieno[3,2-d]pyridin-6-one (Compound 79): MS obsd. ($ESI^+$): 357.8 [$(M+H)^+$].

Examples 80 and 81—Compounds 80 and 81: (S)-4-hydroxy-4-(tert-pentyl)-8-(1H-pyrazol-4-yl)-1,3,4,5-tetrahydro-6H-pyrano[4,3-b]thieno[3,2-d]pyridin-6-one (Compound 80) and (R)-4-hydroxy-4-(tert-pentyl)-8-(1H-pyrazol-4-yl)-1,3,4,5-tetrahydro-6H-pyrano[4,3-b]thieno[3,2-d]pyridin-6-one (Compound 81) (Stereochemistry for Compounds 80 and 81 is Arbitrarily Assigned)

Compound 80

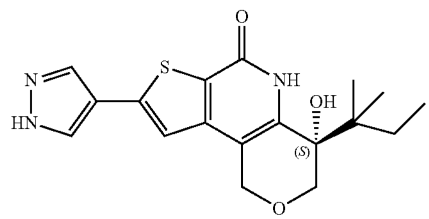

Compound 81

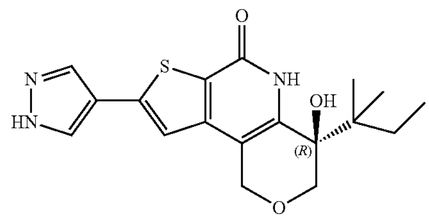

A procedure similar to Compound 72, Step A was performed with chloro(1,1-dimethylpropyl)magnesium to give 4-(sec-butyl)-4-hydroxy-8-(1H-pyrazol-4-yl)-1,3,4,5-tetrahydro-6H-pyrano[4,3-b]thieno[3,2-d]pyridin-6-one (30 mg, 32%). MS obsd. ($ESI^+$): 360.2 [$(M+H)^+$].

The enantiomers were separated by chiral SFC. (S)-4-hydroxy-4-(tert-pentyl)-8-(1H-pyrazol-4-yl)-1,3,4,5-tetrahydro-6H-pyrano[4,3-b]thieno[3,2-d]pyridin-6-one (Compound 80): MS obsd. ($ESI^+$): 360.2 [$(M+H)^+$]; $^1H$ NMR (400 MHz, DMSO) δ 13.23 (s, 1H), 9.99 (s, 1H), 8.29 (brs, 1H), 7.96 (brs, 1H), 7.40 (s, 1H), 5.31 (s, 1H), 4.74 (q, J=14.8 Hz, 2H), 4.17 (d, J=11.4 Hz, 1H), 3.44 (d, J=11.4 Hz, 1H), 1.63-1.56 (m, 1H), 1.33-1.38 (m, 1H), 0.96 (d, J=6.0 Hz, 7H), 0.76 (s, 2H). (R)-4-hydroxy-4-(tert-pentyl)-8-(1H- pyrazol-4-yl)-1,3,4,5-tetrahydro-6H-pyrano[4,3-b]thieno[3,2-d]pyridin-6-one (Compound 81): MS obsd. ($ESI^+$): 360.2 $[(M+H)^+]$.

Examples 82 and 83—Compounds 82 and 83: (S)-4-(dimethylamino)-4-methyl-8-(1H-pyrazol-4-yl)-1,3,4,5-tetrahydro-6H-pyrano[4,3-b]thieno[3,2-d]pyridin-6-one (Compound 82) & (R)-4-(dimethylamino)-4-methyl-8-(1H-pyrazol-4-yl)-1,3,4,5-tetrahydro-6H-pyrano[4,3-b]thieno[3,2-d]pyridin-6-one (Compound 83) (Stereochemistry for Compound 82 and 83 is Arbitrarily Assigned)

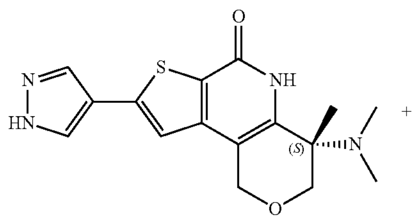

+

Compound 82

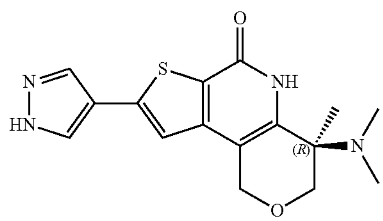

Compound 83

Step A: N-(4,4-dimethoxydihydro-2H-pyran-3(4H)-ylidene)-2-methylpropane-2-sulfinamide

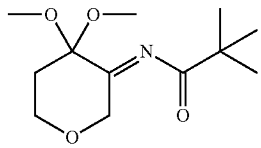 [SMILES: COC1(OC)CCOC/C1=N\C(=O)C(C)(C)C]

To a solution of 2-methylpropane-2-sulfinamide (15.2 g, 125 mmol, 2.0 eq.) and 4,4-dimethoxytetrahydropyran-3-one (10 g, 62 mmol, 1.0 eq.) in THF (150 mL) was added $Ti(EtO)_4$ (28.6 g, 125 mmol, 2.0 eq.). The mixture was stirred at 70° C. for 16 h before being cooled. Water (100 mL) was added and the biphasic mixture and the biphasic mixture was extracted with EtOAc (100 mL×3). The collected organic phases were washed with brine (100 mL), dried ($Na_2SO_4$), and concentrated. The residue was purified by flash silica gel column chromatography ($SiO_2$, 0-60% EtOAc in PE) to give N-(4,4-dimethoxytetrahydropyran-3-ylidene)-2-methyl-propane-2-sulfinamide (8.4 g, 51%) as a colorless oil. MS obsd. ($ESI^+$): 264.1 $[(M+H)^+]$.

Step B: N-(4,4-dimethoxy-3-methyltetrahydro-2H-pyran-3-yl)-2-methylpropane-2-sulfinamide

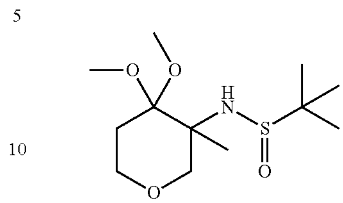

A solution of N-(4,4-dimethoxytetrahydropyran-3-ylidene)-2-methyl-propane-2-sulfinamide (8.4 g, 32 mmol, 1.0 eq.) in THF (150 mL) was cooled to 0° C. and MeMgBr (1.0 M, 96 mL, 96 mmol, 3.0 eq.) was added dropwise. The mixture was stirred at 0° C. for 0.5 h and rt for 3 h. Saturated $NH_4Cl$ solution (100 mL) was added and the biphasic mixture was extracted with EtOAc (100 mL×3) and combined organic layers were concentrated. The residue was purified by flash silica gel column chromatography ($SiO_2$, 0-70% EtOAc in PE) to afford N-(4,4-dimethoxy-3-methyl-tetrahydropyran-3-yl)-2-methyl-propane-2-sulfinamide (5.4 g, 61%).

$^1H$ NMR (400 MHz, $CDCl_3$) δ ppm: 4.10 (s, 1H), 3.82-3.74 (m, 2H), 3.51-3.36 (m, 2H), 3.35 (s, 3H), 3.27 (s, 3H), 1.91-1.77 (m, 2H), 1.46 (s, 3H), 1.21 (s, 9H).

Step C: tert-butyl N-(3-methyl-4-oxo-tetrahydropyran-3-yl)carbamate

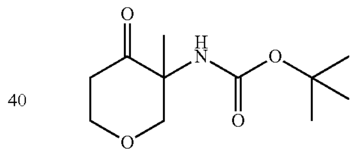

To a solution of N-(4,4-dimethoxy-3-methyl-tetrahydro-pyran-3-yl)-2-methyl-propane-2-sulfinamide (660 mg, 2.36 mmol, 1.0 eq.) in 1,4-dioxane (10 mL) was added HCl/1,4-dioxane (10 mL), the mixture was stirred at rt for 4 h. The solvent was removed to afford 3-amino-3-methyl-tetrahydropyran-4-one HCl salt (477 mg, crude). The crude residue was dissolved in THF in THF (5 mL) and $(Boc)_2O$ (1.03 g, 4.72 mmol, 2.0 eq.) and triethylamine (955 mg, 9.44 mmol, 1.32 mL, 4.0 eq.) were added. The mixture was stirred at rt for 16 h, the solvent was removed, and the residue was purified by flash silica gel column chromatography ($SiO_2$, 0-70% EtOAc in PE) to afford tert-butyl N-(3-methyl-4-oxo-tetrahydropyran-3-yl)carbamate (350 mg, 1.53 mmol, 64%). $^1H$ NMR (400 MHz, $CDCl_3$) δ ppm: 5.56 (brs, 1H), 4.30-4.29 (m, 1H), 4.19-4.15 (m, 1H), 3.81-3.75 (m, 1H), 3.66 (d, J=11.2 Hz, 1H), 2.80-2.79 (m, 1H), 2.54-2.50 (m, 1H), 1.55 (s, 3H), 1.43 (s, 9H).

Step D: Tert-butyl (4-methyl-6-oxo-8-(1-((2-(trimethylsilyl)ethoxy)methyl)-1H-pyrazol-4-yl)-4,6-dihydro-1H,3H-pyrano[4,3-b]thieno[3,2-d]pyran-4-yl) carbamate

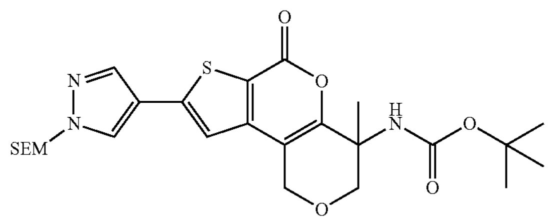 [SMILES: CC(C)(C)OC(=O)NC1(C)COCc2c1oc(=O)c1sc(-c3cnn(COCC[Si](C)(C)C)c3)cc21]

A solution of methyl 3-bromo-5-[1-(2-trimethylsilylethoxymethyl)pyrazol-4-yl]thiophene-2-carboxylate (1.60 g, 3.84 mmol, 2.0 eq.) and tert-butyl N-(3-methyl-4-oxo-tetrahydropyran-3-yl)carbamate (440 mg, 1.92 mmol, 1.0 eq.) in toluene (10 mL) was degassed and purged with $N_2$ before $Pd_2(dba)_3$ (352 mg, 384 μmol, 0.20 eq.), xantphos (444 mg, 768 μmol, 0.40 eq.), $Cs_2CO_3$ (1.25 g, 3.84 mmol, 2.0 eq.) and $Na_2S_2O_5$ (73 mg, 380 μmol, 2.0 eq.) was added. The mixture was degassed and purged with $N_2$ and stirred for 16 h at 105° C. The suspension was cooled to rt, filtered, and concentrated in vacuo. The residue was purified by flash silica gel column chromatography ($SiO_2$, 0-50% EtOAc in PE) to give test-butyl N-[10-methyl-7-oxo-4-[1-(2-trimethylsilylethoxymethyl)pyrazol-4-yl]-8,12-dioxa-5-thiatricyclo [$7.4.0.0^{2,6}$]trideca-1(9),2(6),3--trien-10-yl]carbamate (412 mg, 40%). MS obsd. ($ESI^+$): 478.2 [$(M-55)^+$].

Step E: 4-amino-4-methyl-8-(1H-pyrazol-4-yl)-3,4-dihydro-1H,6H-pyrano[4,3-b]thieno[3,2-d]pyran-6-one

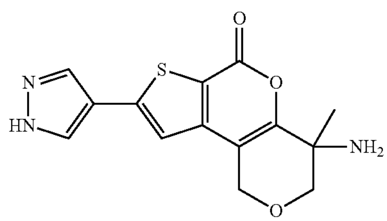 [SMILES: CC1(N)COCc2c1oc(=O)c1sc(-c3cn[nH]c3)cc21]

To a suspension of 2,2-dimethyl-N-[10-methyl-7-oxo-4-[1-(2-trimethylsilylethoxymethyl)pyrazol-4-yl]-12-oxa-5-thia-8-azatricyclo[$7.4.0.0^{2,6}$]trideca-1(9),2(6),3-trien-10-yl] propanamide (400 mg, 770 μmol) in DCM (15 mL) was added TFA (5 mL) and the mixture was stirred at rt for 5 h. The solvent was removed and the residue was purified by reverse phase column chromatography (0-20% MeCN in water (0.1% $NH_4OH$)] to give 10-amino-10-methyl-4-(1H-pyrazol-4-yl)-12-oxa-5-thia-8-azatricyclo[$7.4.0.0^{2,6}$]trideca-1(9),2(6),3-trien-7-one (130 mg, 57%). MS obsd. ($ESI^+$): 287.0 [$(M-16)^+$].

Step F: 4-amino-4-methyl-8-(1H-pyrazol-4-yl)-1,3,4,5-tetrahydro-6H-pyrano[4,3-b]thieno[3,2-d]-pyridin-6-one

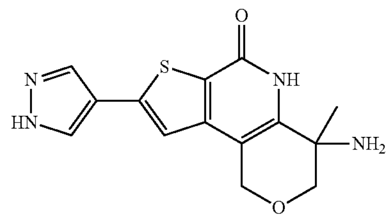 [SMILES: CC1(N)COCc2c1[nH]c(=O)c1sc(-c3cn[nH]c3)cc21]

A suspension of 10-amino-10-methyl-4-(1H-pyrazol-4-yl)-8,12-dioxa-5-thiatricyclo[$7.4.0.0^{2,6}$]trideca-1(9),2(6),3-trien-7-one (130 mg, 428.57 umol) in $NH_4OH$ (8 mL) and IPA (8 mL) was stirred at 100° C. under microwave for 5 h. The solvent was removed in vacuo to afford crude 10-amino-10-methyl-4-(1H-pyrazol-4-yl)-12-oxa-5-thia-8-azatricyclo [$7.4.0.0^{2,6}$]trideca-1(9),2(6),3-trien-7-one (110 mg, crude). MS obsd. ($ESI^+$): 303.0 [$(M+H)^+$].

Step G: (S)-4-(dimethylamino)-4-methyl-8-(1H-pyrazol-4-yl)-1,3,4,5-tetrahydro-6H-pyrano[4,3-b] thieno[3,2-d]pyridin-6-one (Compound 82) and (R)-4-(dimethylamino)-4-methyl-8-(1H-pyrazol-4-yl)-1,3,4,5-tetrahydro-6H-pyrano[4,3-b]thieno[3,2-d] pyridin-6-one (Compound 83)

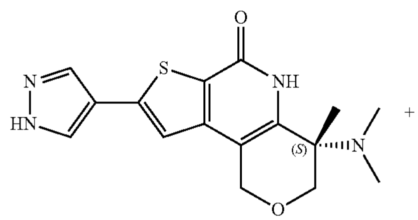

+

Compound 82

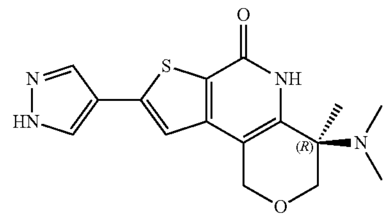

Compound 83

To a suspension of 10-amino-10-methyl-4-(1H-pyrazol-4-yl)-12-oxa-5-thia-8-azatricyclo[$7.4.0.0^{2,6}$]trideca-1(9),2(6),3-trien-7-one (70 mg, 231 μmol) in methanol (20 mL) was added paraformaldehyde (42 mg, 1.4 mmol, 39 μL), $NaBH_3CN$ (116 mg, 1.85 mmol), and AcOH (70 mg, 1.16 mmol). The mixture was stirred at 60° C. for 2 h, concentrated and purified by reverse phase column chromatography (C18 $SiO_2$, 0-20% MeCN in water (0.1% $NH_4OH$)) to afford 10-(dimethylamino)-10-methyl-4-(1H-pyrazol-4-yl)-12-oxa-5-thia-8-azatricyclo[$7.4.0.0^{2,6}$]trideca-1(9),2(6),3-trien-7-one (60 mg, 78%). MS obsd. ($ESI^+$): 330.9 [$(M+H)^+$].

The enantiomers were separated by SFC. (S)-4-(dimethylamino)-4-methyl-8-(1H-pyrazol-4-yl)-1,3,4,5-tetrahydro- 6H-pyrano[4,3-b]thieno[3,2-d]pyridin-6-one (Compound 82): MS obsd. (ESI$^+$): 330.9 [(M+H)$^+$]; $^1$H NMR (400 MHz, DMSO-d6) δ ppm: 13.22 (s, 1H), 10.62 (s, 1H), 8.28 (brs, 1H), 7.96 (brs, 1H), 7.25 (s, 1H), 4.74 (d, J=14.0 Hz, 1H), 4.60 (d, J=14.0 Hz, 1H), 4.16 (d, J=12.0 Hz, 1H), 3.50 (d, J=12.0 Hz, 1H), 2.25 (s, 6H), 1.38 (s, 3H). ((R)-4-(dimethylamino)-4-methyl-8-(1H-pyrazol-4-yl)-1,3,4,5-tetrahydro-6H-pyrano[4,3-b]thieno[3,2-d]pyridin-6-one (Compound 83): MS obsd. (ESI$^+$): 331.0 [(M+H)$^+$].

Example 84—Compound 84: 4-methyl-4-(methylamino)-8-(1H-pyrazol-4-yl)-1,3,4,5-tetrahydro-6H-pyrano[4,3-b]thieno[3,2-d]pyridin-6-one Compound 84

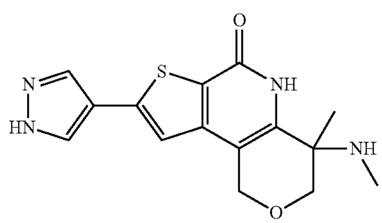

Step A: 3-methyl-3-(methylamino)tetrahydro-2H-pyran-4-ol

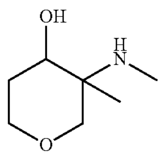

Tert-butyl (3-methyl-4-oxotetrahydro-2H-pyran-3-yl)carbamate (2.0 g, 8.7 mmol, 1.0 eq.) was dissolved in THF (40.0 mL) and $LiAlH_4$ (1.0 M, 35 mmol, 35 mL, 4.0 eq.) was added. The mixture was heated to 65° C. for 6 h before water (1.0 mL) was added. The resulting suspension was filtered and the filtrate was concentrated to afford 3-methyl-3-(methylamino)tetrahydro-2H-pyran-4-ol (700 mg, used without further purification). $^1$H NMR (400 MHz, $CDCl_3$) δ ppm: 3.92-3.90 (m, 1H), 3.87-3.83 (m, 1H), 3.64-3.60 (m, 3H), 3.55-3.52 (m, 1H), 3.42-3.30 (m, 2H), 3.12 (d, J=12 Hz, 1H), 2.29 (s, 3H), 1.04 (s, 3H).

Step B: tert-butyl (4-hydroxy-3-methyltetrahydro-2H-pyran-3-yl)(methyl)carbamate

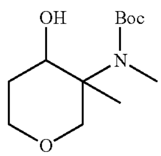 [SMILES: CN(C(=O)OC(C)(C)C)C1(C)COCCC1O]

To a solution of 3-methyl-3-(methylamino)tetrahydro-2H-pyran-4-ol (700 mg, crude) in THF (30 mL) was added $(Boc)_2O$ (3.2 g, 14 mmol, 3.0 eq.) and triethylamine (2.4 g, 24 mmol, 5.0 eq.). After 16 h at rt the mixture was concentrated and purified ($SiO_2$, 0-40% EtOAc in PE) to afford tert-butyl (4-hydroxy-3-methyltetrahydro-2H-pyran-3-yl)(methyl)carbamate (700 mg, 32%). $^1$H NMR (400 MHz, $CDCl_3$) δ ppm: 4.49-4.02 (m, 1H), 3.96-3.85 (m, 1H), 3.78-3.55 (m, 1H), 3.51-3.35 (m, 2H), 2.92-2.87 (m, 3H), 2.03-1.68 (m, 2H), 1.48-1.45 (m, 9H), 1.27-1.24 (m, 3H).

Step C: tert-butyl methyl(3-methyl-4-oxotetrahydro-2H-pyran-3-yl)carbamate

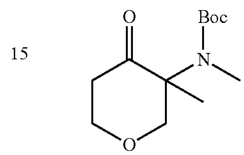

Tert-butyl (4-hydroxy-3-methyltetrahydro-2H-pyran-3-yl)(methyl)carbamate (620 mg, 2.53 mmol, 1.0 eq.) was dissolved in DCM (24 mL) and DMP (2.14 g, 5.05 mmol, 2.0 eq.) was added. After 16 h at rt $NaHCO_3$ (sat. aq.) was added and the mixture was extracted with EtOAc. The organic layers was dried ($Na_2SO_4$), filtered, and concentrated. Purification ($SiO_2$, 0-30% EtOAc in PE) afforded tert-butyl methyl(3-methyl-4-oxotetrahydro-2H-pyran-3-yl) carbamate (530 mg, 86%). $^1$H NMR (400 MHz, MeOD) δ ppm: 4.20-4.17 (m, 2H), 3.72-3.66 (m, 1H), 3.24 (d, J=8, 1 Hz), 2.99 (s, 3H), 2.92-2.82 (m, 1H), 2.33-2.29 (m, 1H), 1.42 (s, 9H), 1.15 (s, 3H).

Step D: tert-butyl methyl(4-methyl-6-oxo-8-(1-((2-(trimethylsilyl)ethoxy)methyl)-1H-pyrazol-4-yl)-1,3,4,6-tetrahydropyrano[4,3-b]thieno[3,2-d]pyran-4-yl) carbamate

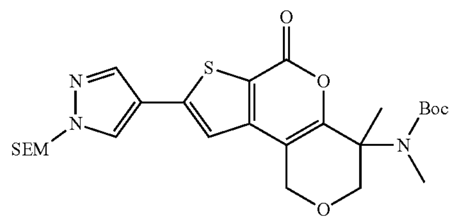 [SMILES: CN(C(=O)OC(C)(C)C)C1(C)COCc2c1oc(=O)c1sc(-c3cnn(COCC[Si](C)(C)C)c3)cc21]

A mixture of tert-butyl methyl(3-methyl-4-oxotetrahydro-2H-pyran-3-yl)carbamate (210 mg, 0.86 mmol, 1.0 eq.), methyl 3-bromo-5-(1-((2-(trimethylsilyl)ethoxy)methyl)-1H-pyrazol-4-yl)thiophene-2-carboxylate (200 mg, 0.48, 1.8 eq.), Sphos-Pd-G3 (75 mg, 0.10 mmol, 0.20 eq.), and $Cs_2CO_3$ (470 mg, 1.4 mmol, 3.0 eq.) in toluene (10 mL) was heated to 105° C. for 16 h. The reaction mixture was diluted with EtOAc and filtered. The filtrate was concentrated and purified ($SiO_2$, 0-30% EtOAc in PE) to afford tert-butyl methyl(4-methyl-6-oxo-8-(1-((2-(trimethylsilyl)ethoxy) methyl)-1H-pyrazol-4-yl)-1,3,4,6-tetrahydropyrano[4,3-b] thieno[3,2-d]pyran-4-yl)carbamate (120 mg, 45%). MS Obsd. (ESI$^+$): 492.6 [(M−56(t-Bu)+H)$^+$].

Step E: 4-methyl-4-(methylamino)-8-(1H-pyrazol-4-yl)-1,3,4,5-tetrahydro-6H-pyrano[4,3-b]thieno[3,2-d]pyridin-6-one (Compound 84)

Compound 84

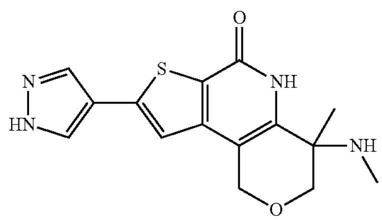

Tert-butyl methyl(4-methyl-6-oxo-8-(1-((2-(trimethylsilyl)ethoxy)methyl)-1H-pyrazol-4-yl)-1,3,4,6-tetrahydropyrano[4,3-b]thieno[3,2-d]pyran-4-yl)carbamate (120 mg) was dissolved in TFA and DCM (1:1, 5 mL). After 2 h at rt the mixture was concentrated and subject to conditions similar to those described in Compound 82, Step G to give 4-methyl-4-(methylamino)-8-(1H-pyrazol-4-yl)-1,3,4,5-tetrahydro-6H-pyrano[4,3-b]thieno[3,2-d]pyridin-6-one (Compound 84) (27 mg, 32%). MS obsd. ($ESI^+$): 317.1 $[(M+H)^+]$. $^1H$ NMR (400 MHz, DMSO-$d_6$) δ ppm: 13.22 (s, 1H), 11.08 (brs, 1H), 8.27 (brs, 1H), 7.97 (brs, 1H), 8.00-7.92 (m, 1H), 7.40 (s, 1H), 4.68 (s, 2H), 3.82 (d, J=11.2 Hz, 1H), 3.51 (d, J=11.2 Hz, 1H), 2.07 (s, 3H), 1.31 (s, 3H).

Examples 85—Compound 85: (S)-4-(tert-butyl)-4-hydroxy-8-morpholino-1,3,4,5-tetrahydro-6H-pyrano[4,3-b]thieno[3,2-d]pyridin-6-one Compound 85

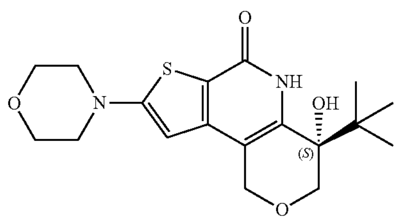

Step A: methyl 3-bromo-5-morpholinothiophene-2-carboxylate

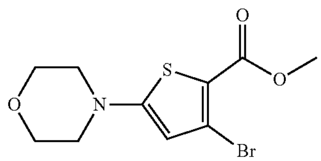 [SMILES: COC(=O)c1sc(N2CCOCC2)cc1Br]

A mixture of methyl 3,5-dibromothiophene-2-carboxylate (200 mg, 670 μmol, 1.0 eq.), morpholine (87 mg, 1.0 mmol, 1.5 eq.), $Cs_2CO_3$ (430 mg, 1.3 mmol, 2.0 eq.) in toluene (5 mL), (1E,4E)-1,5-diphenylpenta-1,4-dien-3-one palladium (30 mg, 33 μmol, 0.050 eq.), (5-diphenylphosphanyl-9,9-dimethyl-xanthen-4-yl)-diphenyl-phosphane (39 mg, 67 μmol, 0.10 eq.) was degassed and purged with $N_2$. The mixture was stirred for 16 h at 80° C. before being cooled and filtered. The filtrate was concentrated in vacuo and the residue was purified by column chromatography ($SiO_2$, 15% EtOAc in PE) to give methyl 3-bromo-5-morpholinothiophene-2-carboxylate (110 mg, 54%). MS obsd. ($ESI^+$): 306.1, 308.1 $[(M+H)^+]$.

Step B: (R)-3-(tert-butyl)-3-hydroxytetrahydro-4H-pyran-4-one

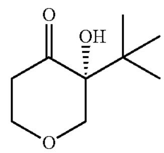

3-(tert-butyl)-3-hydroxytetrahydro-4H-pyran-4-one (1.0 g, 5.8 mmol) was separated by chiral HPLC using the condition as below (Column: IG-3, Column size: 0.46 cm*100 mm 3 um, Injection: 2.0 mL. Co-Solvent: $CO_2$: EtOH (0.1% DEA), Flow rate: 3 mL/min, Run time: 6.0 Minutes, Temperature: 25° C.) to give (R)-3-(tert-butyl)-3-hydroxytetrahydro-4H-pyran-4-one (370 mg, 37%), first eluting peak. Stereochemistry is assigned arbitrarily. $^1H$ NMR (400 MHz, DMSO-d6) δ 5.05 (s, 1H), 4.06 (dd, J=12.0, 1.2 Hz, 1H), 4.03-3.95 (m, 1H), 3.75-3.64 (m, 1H), 3.35 (d, J=12.0 Hz, 1H), 2.60-2.52 (m, 2H), 0.95 (s, 9H).

Step C: (R)-4-(tert-butyl)-4-hydroxy-8-morpholino-3,4-dihydro-1H,6H-pyrano[4,3-b]thieno[3,2-d]pyran-6-one

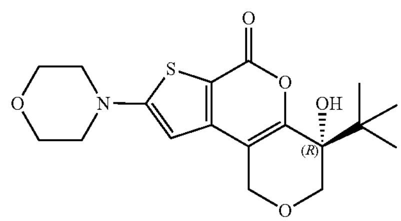

A solution of methyl 3-bromo-5-morpholinothiophene-2-carboxylate (110 mg, 360 μmol, 1.0 eq.), (R)-3-(tert-butyl)-3-hydroxytetrahydro-4H-pyran-4-one (74 mg, 430 μmol, 1.2 eq.), $Cs_2CO_3$ (350 mg, 1.1 mmol, 3.0 eq.) in toluene (5 mL), (1E,4E)-1,5-diphenylpenta-1,4-dien-3-one palladium (33 mg, 36 μmol, 0.1 eq.), (5-diphenylphosphanyl-9,9-dimethyl-xanthen-4-yl)-diphenyl-phosphane (41 mg, 72 μmol, 0.20 eq.) was degassed and purged with $N_2$ before heating to 100° C. for 16 h. The mixture was poured into water and extracted with DCM (20 mL×3). The organic layers was combined, washed (NaCl), dried ($MgSO_4$), filtered and concentrated in vacuo. The residue was purified by column chromatography ($SiO_2$, 3% MeOH in DCM) to give (R)-4-(tert-butyl)-4-hydroxy-8-morpholino-3,4-dihydro-1H,6H-pyrano[4,3-b]thieno[3,2-d]pyran-6-one (75 mg, 57%). MS obsd. ($ESI^+$): 366.4 $[(M+H)^+]$.

Step D: (S)-4-(tert-butyl)-4-hydroxy-8-morpholino-1,3,4,5-tetrahydro-6H-pyrano[4,3-b]thieno[3,2-d]pyridin-6-one (Compound 85)

Compound 85

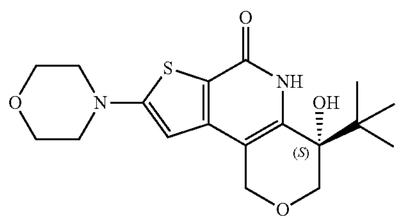

A mixture of (R)-4-(tert-butyl)-4-hydroxy-8-morpholino-3,4-dihydro-1H,6H-pyrano[4,3-b]thieno[3,2-d]pyran-6-one (70 mg, 191.55 μmol, 1.0 eq.), aq. $NH_4OH$ solution (8 mL) and isopropanol (8 mL) was stirred for 48 h at 120° C. The mixture was concentrated in vacuo, the residue was purified by column chromatography ($SiO_2$, 3% MeOH in DCM) to give (S)-4-(tert-butyl)-4-hydroxy-8-morpholino-1,3,4,5-tetrahydro-6H-pyrano[4,3-b]thieno[3,2-d]pyridin-6-one (Compound 85) (30 mg, 43%) as a yellow solid. MS obsd. ($ESI^+$): 365.0 $[(M+H)^+]$. $^1H$ NMR (400 MHz, DMSO-d6) δ ppm: 9.62 (s, 1H), 6.20 (s, 1H), 5.27 (s, 1H), 4.60 (q, J=14.8 Hz, 2H), 4.09 (d, J=11.2 Hz, 1H), 3.83-3.68 (m, 4H), 3.40 (d, J=11.2 Hz, 1H), 3.28-3.19 (m, 4H), 1.00 (s, 9H).

Example 86—Compound 86: 4-(2,2-difluoropropyl)-4-hydroxy-8-(1H-pyrazol-4-yl)-1,3,4,5-tetrahydro-6H-pyrano[4,3-b]thieno[3,2-d]pyridin-6-one Compound 86

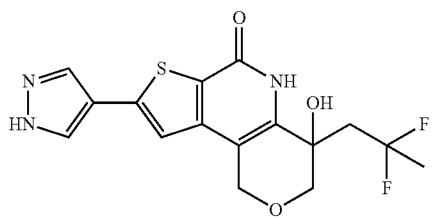

Step A: 4,4-dimethoxy-3-(2-methylallyl)tetrahydro-2H-pyran-3-ol

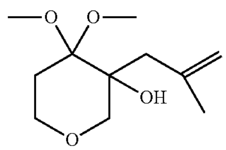

To a solution of 4,4-dimethoxydihydro-2H-pyran-3(4H)-one (5.0 g, 31 mmol, 1.0 eq.) in THF (5 mL) was added chloro(2-methylallyl)magnesium (0.5 M in THF, 125 mL, 2.0 eq.) at rt. After 1 h $NH_4Cl$ (sat. aq., 40 mL) was added. The biphasic mixture was extracted with EtOAc (100 mL×3) and the organic layers were dried, filtered and concentrated. Purification by flash column chromatography ($SiO_2$, 0-30% EtOAc in PE) to give 4,4-dimethoxy-3-(2-methylallyl)tetrahydro-2H-pyran-3-ol (1.5 g, 55%) as a colorless oil. $^1H$ NMR (400 MHz, $CDCl_3$) δ ppm: 4.96 (dd, J=2.4, 1.6 Hz, 1H), 4.82 (dd, J=2.4, 1.6 Hz, 1H), 3.82-3.72 (m, 1H), 3.68 (dd, J=11.4, 1.2 Hz, 1H), 3.43 (s, 4H), 3.31 (s, 3H), 3.10 (dd, J=11.4, 1.2 Hz, 1H), 2.53 (d, J=13.8 Hz, 1H), 2.36 (d, J=13.8 Hz, 1H), 1.96-1.87 (m, 4H), 1.80-1.67 (m, 2H).

Step B: 3-(benzyloxy)-4,4-dimethoxy-3-(2-methylallyl)tetrahydro-2H-pyran

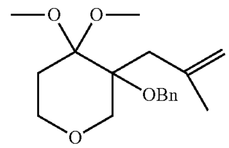 [SMILES: C=C(C)CC1(OCc2ccccc2)COCCC1(OC)OC]

A mixture of 4,4-dimethoxy-3-(2-methylallyl)tetrahydro-2H-pyran-3-ol (4.2 g, 19 mmol, 10 eq.), BnBr (3.14 g, 29.1 mmol, 1.5 eq.) and NaH (893 mg, 38.8 mmol, 2.0 eq.) in DMF (50 mL) was stirred at 0° C. for 2 h. Ice was added and the biphasic mixture was extracted with DCM (60 mL×3). The organic layers were concentrated and the residue was purified by flash column chromatography ($SiO_2$, 0-30% EtOAc in PE) to give 3-(benzyloxy)-4,4-dimethoxy-3-(2-methylallyl)tetrahydro-2H-pyran (5.6 g, 94%). $^1H$ NMR (400 MHz, $CDCl_3$) δ ppm: 7.35-7.21 (m, 5H), 4.95 (dd, J=4.0, 2.0 Hz, 1H), 4.84 (dd, J=2.4, 1.6 Hz, 1H), 4.76-4.70 (m, 2H), 4.53 (d, J=11.8 Hz, 1H), 4.32 (dd, J=14.8, 4.0 Hz, 1H), 4.14 (dd, J=14.8, 1.9 Hz, 1H), 4.00 (d, J=12.4 Hz, 1H), 3.79 (d, J=12.4 Hz, 1H), 3.56 (s, 3H), 3.48 (s, 3H), 2.84-2.42 (m, 3H), 1.80 (s, 3H).

Step C: 3-(benzyloxy)-3-(2-methylallyl)tetrahydro-4H-pyran-4-one

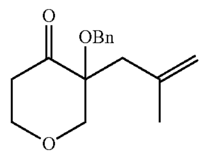 [SMILES: C=C(C)CC1(OCc2ccccc2)COCCC1=O]

To a solution of 3-(benzyloxy)-4,4-dimethoxy-3-(2-methylallyl)tetrahydro-2H-pyran (980 mg, 3.33 mmol, 1.0 eq.) in acetone (15 mL) was added 12 (84 mg, 0.33 mmol, 0.10 eq.). The reaction mixture stirred at rt for 16 h before addition of aq. $Na_2SO_3$ (20 mL) and the biphasic mixture was extracted with DCM (30 mL×3). The organic layers were dried ($Na_2SO_4$), filtered and concentrated. Column chromatography ($SiO_2$, 0-10% EtOAc in PE) afforded 3-(benzyloxy)-3-(2-methylallyl)tetrahydro-4H-pyran-4-one (310 mg, 37%). $^1H$ NMR (400 MHz, $CDCl_3$) δ 7.42-7.20 (m, 5H), 4.95-4.84 (m, 1H), 4.81 (d, J=0.8 Hz, 1H), 4.70 (d, J=11.2 Hz, 1H), 4.30 (d, J=11.2 Hz, 1H), 4.10-3.85 (m, 3H), 3.68 (d, J=12.0 Hz, 1H), 2.83-2.83 (m, 2H), 2.56-2.41 (m, 2H), 1.81 (s, 3H).

Step D: 4-(benzyloxy)-4-(2-methylallyl)-8-(1-(tetrahydro-2H-pyran-2-yl)-1H-pyrazol-4-yl)-3,4-dihydro-1H,6H-pyrano[4,3-b]thieno[3,2-d]pyran-6-one

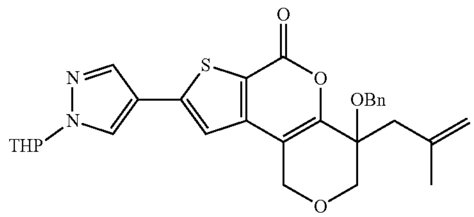

To a solution of 3-(benzyloxy)-3-(2-methylallyl)tetrahydro-4H-pyran-4-one (210 mg, 0.81 mmol, 1.5 eq.) and methyl 3-bromo-5-(1-(tetrahydro-2H-pyran-2-yl)-1H-pyrazol-4-yl)thiophene-2-carboxylate (200 mg, 0.56 mmol, 1.0 eq.) in dioxane (10 mL) was added $Cs_2CO_3$ (439 mg, 1.35 mmol, 2.0 eq.) and sphos Pd G3 (93 mg, 0.11 mmol, 0.20 eq.). The mixture was degassed and purged with $N_2$ before heating to 105° C. for 16 h. The mixture was purified by flash column chromatography ($SiO_2$, 0-50% EtOAc in PE) to give 4-(benzyloxy)-4-(2-methylallyl)-8-(1-(tetrahydro-2H-pyran-2-yl)-1H-pyrazol-4-yl)-3,4-dihydro-1H,6H-pyrano[4,3-b]thieno[3,2-d]pyran-6-one (60 mg, 21%) as a yellow solid. MS obsd. ($ESI^+$): 519.3 [$(M+H)^+$].

Step E: 4-(benzyloxy)-4-(2-oxopropyl)-8-(1-(tetrahydro-2H-pyran-2-yl)-1H-pyrazol-4-yl)-3,4-dihydro-1H,6H-pyrano[4,3-b]thieno[3,2-d]pyran-6-one

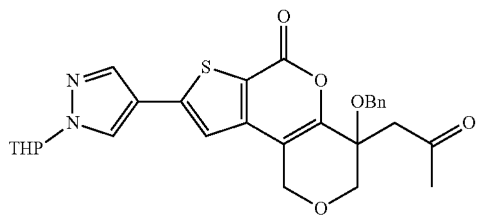

A solution of 4-(benzyloxy)-4-(2-methylallyl)-8-(1-(tetrahydro-2H-pyran-2-yl)-1H-pyrazol-4-yl)-3,4-dihydro-1H,6H-pyrano[4,3-b]thieno[3,2-d]pyran-6-one (80 mg, 0.15 mmol) in DCM (5 mL) in MeOH (5 mL) was cooled to −75° C. before ozone was bubbled into the solution for 20 min. Dimethylsulfide (8 drops) was added at −75° C., the mixture was stirred at −75° C. for 30 min before warming to rt. The mixture was concentrated and purified by flash column chromatography ($SiO_2$, 0-50% EtOAc in PE) to give 4-(benzyloxy)-4-(2-oxopropyl)-8-(1-(tetrahydro-2H-pyran-2-yl)-1H-pyrazol-4-yl)-3,4-dihydro-1H,6H-pyrano[4,3-b]thieno[3,2-d]pyran-6-one (52 mg, 65%). MS obsd. ($ESI^+$): 413.2 [$(M-OBn)^+$].

Step F: 4-(benzyloxy)-4-(2,2-difluoropropyl)-8-(1-(tetrahydro-2H-pyran-2-yl)-1H-pyrazol-4-yl)-3,4-dihydro-1H,6H-pyrano[4,3-b]thieno[3,2-d]pyran-6-one

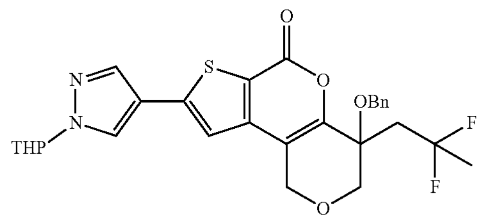

A mixture of 4-(benzyloxy)-4-(2-oxopropyl)-8-(1-(tetrahydro-2H-pyran-2-yl)-1H-pyrazol-4-yl)-3,4-dihydro-1H,6H-pyrano[4,3-b]thieno[3,2-d]pyran-6-one (50 mg, 0.10 mmol, 1.0 eq.) in $CHCl_3$ (0.20 mL) and DAST (10 mL) was stirred at 35° C. for 16 h. The mixture was cooled to 0° C. and diluted with EtOAc (20 mL) and aqueous $NaHCO_3$ (20 mL). The organic layer was concentrated and the residue was purified by flash column chromatography ($SiO_2$, 0-50% EtOAc in PE) to give 4-(benzyloxy)-4-(2,2-difluoropropyl)-8-(1-(tetrahydro-2H-pyran-2-yl)-1H-pyrazol-4-yl)-3,4-dihydro-1H,6H-pyrano[4,3-b]thieno[3,2-d]pyran-6-one (21 mg, 40%). MS obsd. ($ESI^+$): 543.2 [$(M+H)^+$].

Step G: 4-(2,2-difluoropropyl)-4-hydroxy-8-(1H-pyrazol-4-yl)-3,4-dihydro-1H,6H-pyrano[4,3-b]thieno[3,2-d]pyran-6-one

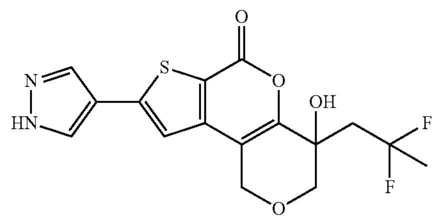 [SMILES: CC(F)(F)CC1(O)COCc2c1oc(=O)c1sc(-c3cn[nH]c3)cc21]

A solution of 4-(benzyloxy)-4-(2,2-difluoropropyl)-8-(1-(tetrahydro-2H-pyran-2-yl)-1H-pyrazol-4-yl)-3,4-dihydro-1H,6H-pyrano[4,3-b]thieno[3,2-d]pyran-6-one (40 mg, 0.070 mmol, 1.0 eq.) in DCE (4 mL) and TFA (1 mL) was stirred at 35° C. for 3 h. $NH_4OH$ was added at rt, and the mixture was concentrated to give 4-(2,2-difluoropropyl)-4-hydroxy-8-(1H-pyrazol-4-yl)-3,4-dihydro-1H,6H-pyrano[4,3-b]thieno[3,2-d]pyran-6-one (25 mg, crude) which was used for the next step. MS obsd. ($ESI^+$): 369.4 [$(M+H)^+$].

Step H: 4-(2,2-difluoropropyl)-4-hydroxy-8-(1H-pyrazol-4-yl)-1,3,4,5-tetrahydro-6H-pyrano[4,3-b]thieno[3,2-d]pyridin-6-one (Compound 86)

Compound 86

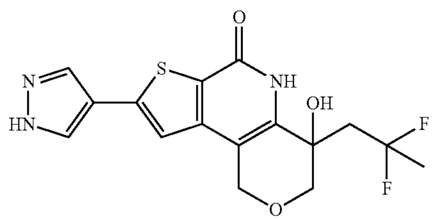

A mixture of 4-(2,2-difluoropropyl)-4-hydroxy-8-(1H-pyrazol-4-yl)-3,4-dihydro-1H,6H-pyrano[4,3-b]thieno[3,2-d]pyran-6-one (25 mg, crude), i-PrOH (2.5 mL) and $NH_4OH$ (2.5 mL) was stirred at 95° C. for 16 h. The mixture was concentrated and purified by reverse phase column chromatography (C18 $SiO_2$, 0-40% MeCN in water (0.1% $NH_4OH$)) to give 4-(2,2-difluoroprop yl)-4-hydroxy-8-(1H-pyrazol-4-yl)-1,3,4,5-tetrahydro-6H-pyrano[4,3-b]thieno[3,2-d]pyridin-6-one (Compound 86) (2.6 mg, 10%). MS obsd. ($ESI^+$): 368.0 [$(M+H)^+$]; $^1$H NMR (400 MHz, DMSO-d6) δ ppm: 13.23 (s, 1H), 11.00 (s, 1H), 8.32 (brs, 1H), 8.26 (brs, 1H), 7.42 (s, 1H), 5.76 (s, 1H), 4.90-4.55 (m, 2H), 4.04 (d, J=11.6 Hz, 1H), 3.65 (d, J=11.6 Hz, 1H), 2.65-2.52 (m, 2H), 1.70 (t, J=19.6 Hz, 3H).

Examples 87 and 88—Compounds 87 and 88: (S)-6-hydroxy-6-isopropyl-2-(1H-pyrazol-4-yl)-6,7,8,9-tetrahydrothieno[2,3-c]quinolin-4(5H)-one (Compound 87) and (R)-6-hydroxy-6-isopropyl-2-(1H-pyrazol-4-yl)-6,7,8,9-tetrahydrothieno[2,3-c]quinolin-4(5H)-one (Compound 88) (Stereochemistry for Compounds 87 and 88 is Arbitrarily Assigned)

Compound 87

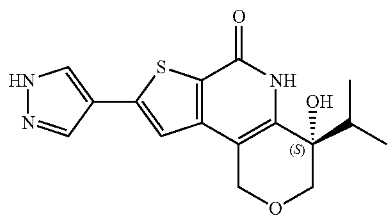

Compound 88

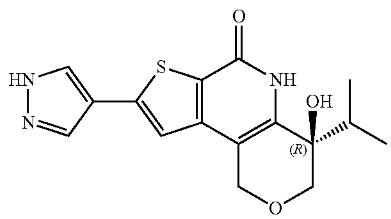

To a solution of 6-hydroxy-6-isopropyl-2-(1-((2-(trimethylsilyl)ethoxy)methyl)-1H-pyrazol-4-yl)-6,7,8,9-tetrahydrothieno[2,3-c]quinolin-4(5H)-one (100 mg, 220 μmol, 1.0 eq.) in DCM (7 mL) was added $BCl_3$ (1.0 M, 650 μL, 3.0 eq.). The mixture was stirred at −70° C. for 10 min. The reaction mixture was bubbled with $N_2$ for 2 min before NH 4 OH (25% aq., 1 mL) was added. The mixture was stirred at 0° C. for 15 min before MeOH (2 mL) was added. After another 10 min at 0° C. the mixture was concentrated in vacuo to give 6-hydroxy-6-isopropyl-2-(1H-pyrazol-4-yl)-6,7,8,9-tetrahydrothieno[2,3-c]quinolin-4(5H)-one (20 mg), MS obsd. ($ESI^+$): 330.1 [$(M+H)^+$].

The enantiomers were separated by chiral SFC. (6S)-6-hydroxy-6-isopropyl-2-(1H-pyrazol-4-yl)-5,7,8,9-tetrahydrothieno[2,3-c]quinolin-4-one (Compound 87): MS obsd. ($ESI^+$): 311.9 [$(M-17)^+$];

$^1$H NMR (400 MHz, DMSO-$d_6$) δ ppm: 13.20 (s, 1H), 10.36 (s, 1H), 8.30 (s, 1H), 7.96 (s, 1H), 7.49 (s, 1H), 5.00 (s, 1H), 2.78-2.65 (m, 1H), 2.54-2.32 (m, 2H), 1.76-1.69 (m, 4H), 0.97 (d, J=6.8 Hz, 3H), 0.59 (d, J=6.8 Hz, 3H). (6R)-6-hydroxy-6-isopropyl-2-(1H-pyrazol-4-yl)-5,7,8,9-tetrahydrothieno[2,3-c]quinolin-4-one (Compound 88): MS obsd. ($ESI^+$): 329.9 [$(M+H)^+$].

Examples 89 and 90—Compounds 89 and 90: (S)-4-(tert-butyl)-4-hydroxy-8-(1-methyl-1H-pyrazol-5-yl)-1,3,4,5-tetrahydro-6H-pyrano[4,3-b]thieno[3,2-d]pyridin-6-one (Compound 89) and (R)-4-(tert-butyl)-4-hydroxy-8-(1-methyl-1H-pyrazol-5-yl)-1,3,4,5-tetrahydro-6H-pyrano[4,3-b]thieno[3,2-d]pyridin-6-one (Compound 90) (Stereochemistry for Compounds 89 and 90 is Arbitrarily Assigned)

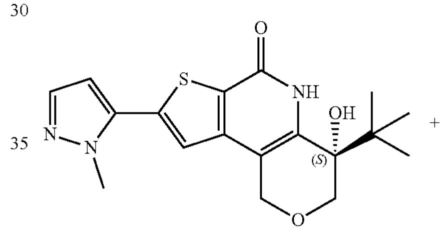

+

Compound 89

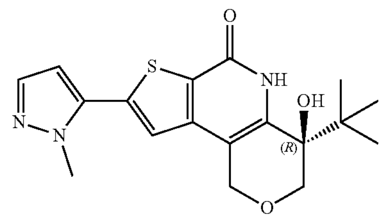

Compound 90

Step A: 4-(benzyloxy)-8-(1-methyl-1H-pyrazol-5-yl)-3,4-dihydro-1H,6H-pyrano[4,3-b]thieno[3,2-d]pyran-6-one

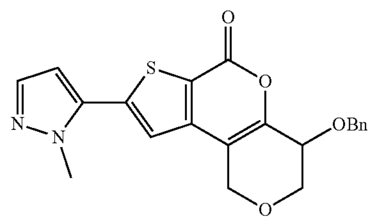 [SMILES: Cn1nccc1-c1cc2c3c(oc(=O)c2s1)C(OCc1ccccc1)COC3]

Similar conditions described in Compound 16, Step A were performed with methyl 3-bromo-5-(1-methyl-1H-pyrazol-5-yl)thiophene-2-carboxylate to give 4-(benzyloxy)-8-(1-methyl-1H-pyrazol-5-yl)-3,4-dihydro-1H,6H-pyrano[4,3-b]thieno[3,2-d]pyran-6-one (1.3 g, 50%). MS obsd. ($ESI^+$): 395.1 [$(M+H)^+$].

Step B: 4-(benzyloxy)-8-(1-methyl-1H-pyrazol-5-yl)-1,3,4,5-tetrahydro-6H-pyrano[4,3-b]thieno[3,2-d]pyridin-6-one

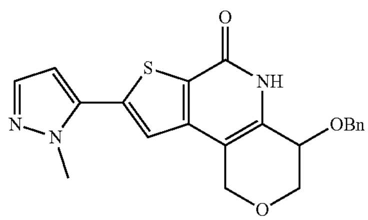 [SMILES: Cn1nccc1-c1cc2c3c([nH]c(=O)c2s1)C(OCc1ccccc1)COC3]

Similar conditions as described in Compound 16, Step B were used to afford 4-(benzyloxy)-8-(1-methyl-1H-pyrazol-5-yl)-1,3,4,5-tetrahydro-6H-pyrano[4,3-b]thieno[3,2-d]pyridin-6-one (870 mg, 55%). MS obsd. ($ESI^+$): 394.3 [$(M+H)^+$].

Step C: 4-hydroxy-8-(1-methyl-1H-pyrazol-5-yl)-1,3,4,5-tetrahydro-6H-pyrano[4,3-b]thieno[3,2-d]pyridin-6-one

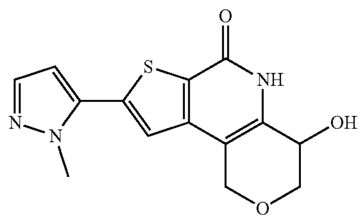 [SMILES: Cn1nccc1-c1cc2c3c([nH]c(=O)c2s1)C(O)COC3]

A solution of 4-(benzyloxy)-8-(1-methyl-1H-pyrazol-5-yl)-1,3,4,5-tetrahydro-6H-pyrano[4,3-b]thieno[3,2-d]pyridin-6-one (680 mg, 1.73 mmol, 1.0 eq.) in TFA (7 mL) was stirred at 80° C. for 3 h. The mixture was concentrated in vacuo and $NH_3$/MeOH (7 M) was added at 0° C. to achieve a pH of −0.9. The mixture was concentrated in vacuo and purified by flash column chromatography ($SiO_2$, 0-9% MeOH in DCM) to give 4-hydroxy-8-(1-methyl-1H-pyrazol-5-yl)-1,3,4,5-tetrahydro-6H-pyrano[4,3-b]thieno[3,2-d]pyridin-6-one (455 mg, 87%). MS obsd. ($ESI^+$): 304.2 [$(M+H)^+$].

Step D: 8-(1-methyl-1H-pyrazol-5-yl)-1,5-dihydro-6H-pyrano[4,3-b]thieno[3,2-d]pyridine-4,6(3H)-dione

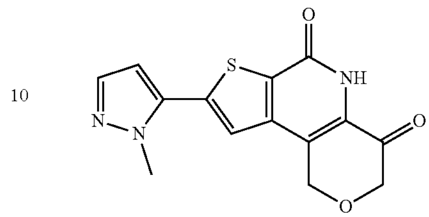

The reaction conditions described in Compound 16, Step E were employed to afford 8-(1-methyl-1H-pyrazol-5-yl)-1,5-dihydro-6H-pyrano[4,3-b]thieno[3,2-d]pyridine-4,6(3H)-dione (330 mg, 73%). MS obsd. ($ESI^+$): 302.1 [$(M+H)^+$].

Step E: (S)-4-(tert-butyl)-4-hydroxy-8-(1-methyl-1H-pyrazol-5-yl)-1,3,4,5-tetrahydro-6H-pyrano[4,3-b]thieno[3,2-d]pyridin-6-one (Compound 89) and (R)-4-(tert-butyl)-4-hydroxy-8-(1-methyl-1H-pyrazol-5-yl)-1,3,4,5-tetrahydro-6H-pyrano[4,3-b]thieno[3,2-d]pyridin-6-one (Compound 90)

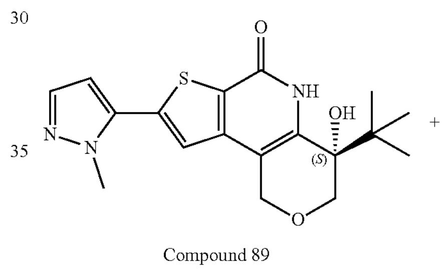

+

Compound 89

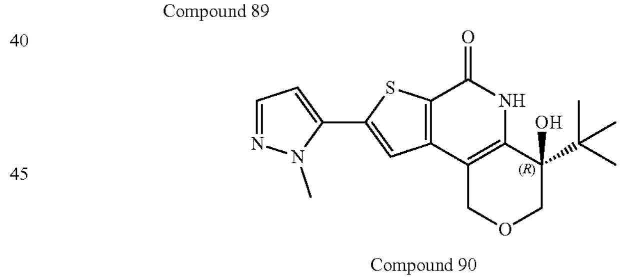

Compound 90

A solution of 8-(1-methyl-1H-pyrazol-5-yl)-1,5-dihydro-6H-pyrano[4,3-b]thieno[3,2-d]pyridine-4,6(3H)-dione (110 mg, 370 μmol, 1.0 eq.) in THF (6 mL) was cooled to 0° C. before t-BuMgCl (1.0 M, 6 mL, 16.5 eq.) was added. The reaction mixture was stirred at 0° C. for 2 h before aqueous $NH_4Cl$ solution was added. The mixture was poured into water (20 mL) and extracted with DCM/MeOH (10:1, v/v) (40 mL×3). The organic layers were combined, washed with brine, dried ($MgSO_4$), filtered, and concentrated in vacuo. Purification ($SiO_2$, 0-6% MeOH in DCM) gave 4-(tert-butyl)-4-hydroxy-8-(1-methyl-1H-pyrazol-5-yl)-1,3,4,5-tetrahydro-6H-pyrano[4,3-b]thieno[3,2-d]pyridin-6-one (56 mg, 43%). MS obsd. ($ESI^+$): 360.3 [$(M+H)^+$].

The enantiomers were separated via chiral SFC. (S)-4-(tert-butyl)-4-hydroxy-8-(1-methyl-1H-pyrazol-5-yl)-1,3,4,5-tetrahydro-6H-pyrano[4,3-b]thieno[3,2-d]pyridin-6-one (Compound 89): MS obsd. ($ESI^+$): 360.2 [$(M+H)^+$]; $^1H$ NMR (400 MHz, DMSO-d6) δ ppm: 10.31 (s, 1H), 7.56 (s, 1H), 7.53 (d, J=2.0 Hz, 1H), 6.70 (d, J=2.0 Hz, 1H), 5.35 (s, 1H), 4.87-4.72 (m, 2H), 4.14 (d, J=11.6 Hz, 1H), 4.04 (s, 3H), 3.45 (d, J=11.2 Hz, 1H), 1.03 (s, 9H). (R)-4-(tert-butyl)-4-hydroxy-8-(1-methyl-1H-pyrazol-5-yl)-1,3,4,5-tetrahydro-6H-pyrano[4,3-b]thieno[3,2-d]pyridin-6-one (Compound 90): MS obsd. ($ESI^+$): 360.2 [$(M+H)^+$].

Examples 91 and 92—Compounds 91 and 92: (S)-4-(tert-butyl)-4-hydroxy-8-(3-methyl-1H-pyrazol-4-yl)-1,3,4,5-tetrahydro-6H-pyrano[4,3-b]thieno[3,2-d]pyridin-6-one (Compound 91) and (R)-4-(tert-butyl)-4-hydroxy-8-(3-methyl-1H-pyrazol-4-yl)-1,3,4,5-tetrahydro-6H-pyrano[4,3-b]thieno[3,2-d]pyridin-6-one (Compound 92) (Stereochemistry for Compounds 91 and 92 is Assigned Arbitrarily)

Compound 91

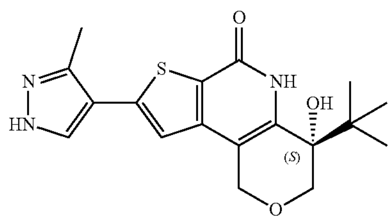

Compound 92

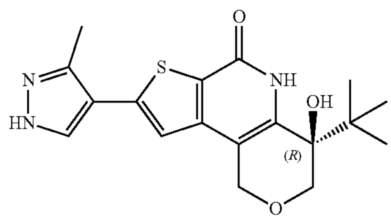

Step A: methyl 3-bromo-5-(3-methyl-1-((2-(trimethylsilyl)ethoxy)methyl)-1H-pyrazol-4-yl)thiophene-2-carboxylate and methyl 3-bromo-5-(5-methyl-1-((2-(trimethylsilyl)ethoxy)methyl)-1H-pyrazol-4-yl)thiophene-2-carboxylate

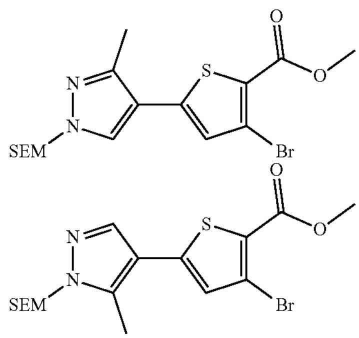

To a solution of 3-methyl-4-(4,4,5,5-tetramethyl-1,3,2-dioxaborolan-2-yl)-1H-pyrazole (10 g, 48.1 mmol, 1 eq.) in DMF (150 mL) was added NaH (2.39 g, 59.9 mmol, 60% purity, 1.25 eq.) at 0° C. The mixture was stirred at 0° C. for 1 hr before 2-(chloromethoxy)ethyl-trimethyl-silane (12.0 g, 72.1 mmol, 12.76 mL, 1.5 eq.) was added. The reaction was stirred at rt for 3 h before being diluted with water. The biphasic mixture was extracted with EtOAc (80 mL×3) and washed by brine. The organic layer was dried, filtered and concentrated to give the mixture of 3-methyl-4-(4,4,5,5-tetramethyl-1,3,2-dioxaborolan-2-yl)-1-((2-(trimethylsilyl)ethoxy)methyl)-1H-pyrazole and 5-methyl-4-(4,4,5,5-tetramethyl-1,3,2-dioxaborolan-2-yl)-1-((2-(trimethylsilyl)ethoxy)methyl)-1H-pyrazole (16 g, crude). The crude mixture was dissolved in 1,4-dioxane (160 mL) and $Pd(dppf)Cl_2$ (3.46 g, 4.73 mmol, 0.1 eq.), $K_3PO_4$ (30.1 g, 141.88 mmol, 3 eq.), water (160 mL) and $CH_3CN$ (160 mL) were added. The reaction mixture was heated to 90° C. for 8 h, cooled, and filtered. The filtrate was concentrated in vacuo and purified by silica gel column ($SiO_2$, 0-10% EtOAc in PE) to give the mixture of 3-bromo-5-(3-methyl-1-((2-(trimethylsilyl)ethoxy)methyl)-1H-pyrazol-4-yl)thiophene-2-carboxylate and methyl 3-bromo-5-(5-methyl-1-((2-(trimethylsilyl)ethoxy)methyl)-1H-pyrazol-4-yl)thiophene-2-carboxylate (12 g, 59%, 2 steps). $^1H$ NMR (400 MHz, $CDCl_3$) δ ppm: 7.66 (s, 1H), 7.05 (s, 1H), 5.47 (s, 2H), 3.92 (s, 3H), 3.64-3.58 (m, 2H), 2.55 (s, 3H), 0.97-0.90 (m, 2H), 0.01 (s, 9H).

$^1H$ NMR (400 MHz, $CDCl_3$) δ ppm: 7.75 (s, 1H), 7.05 (s, 1H), 5.38 (s, 2H), 3.91 (s, 3H), 3.64-3.58 (m, 2H), 2.47 (s, 3H), 0.97-0.90 (m, 2H), 0.02 (s, 9H).

Step B: 4-(benzyloxy)-8-(3-methyl-1-((2-(trimethylsilyl)ethoxy)methyl)-1H-pyrazol-4-yl)-3,4-dihydro-1H,6H-pyrano[4,3-b]thieno[3,2-d]pyran-6-one and 4-(benzyloxy)-8-(5-methyl-1-((2-(trimethylsilyl)ethoxy)methyl)-1H-pyrazol-4-yl)-3,4-dihydro-1H,6H-pyrano[4,3-b]thieno[3,2-d]pyran-6-one

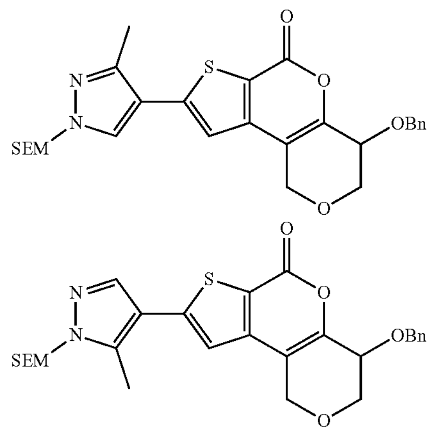

A mixture of 3-bromo-5-(3-methyl-1-((2-(trimethylsilyl)ethoxy)methyl)-1H-pyrazol-4-yl)thiophene-2-carboxylate and methyl 3-bromo-5-(5-methyl-1-((2-(trimethylsilyl)ethoxy)methyl)-1H-pyrazol-4-yl)thiophene-2-carboxylate (20 g, 46 mmol, 1.0 eq.) was dissolved in 1,4-dioxane (600 mL) and 3-benzyloxytetrahydropyran-4-one (19.1 g, 92.7 mmol, 2.0 eq.), $Cs_2CO_3$ (45.3 g, 139 mmol, 3.0 eq.), $Pd_2(dba)_3$ (2.12 g, 2.32 mmol, 0.050 eq.), $Na_2S_2O_5$ (881 mg, 4.64 mmol. 0.10 eq.) and Xantphos (2.68 g, 4.64 mmol, 0.1 eq.) were added. The reaction mixture was heated to 105° C. for 16 h, cooled, filtered, and concentrated. The crude residue was triturated with MeOH to give the mixture of 4-(benzyloxy)-8-(3-methyl-1-((2-(trimethylsilyl)ethoxy)methyl)-1H-pyrazol-4-yl)-3,4-dihydro-1H,6H-pyrano[4,3- b]thieno[3,2-d]pyran-6-one and 4-(benzyloxy)-8-(5-methyl-1-((2-(trimethylsilyl)ethoxy)methyl)-1H-pyrazol-4-yl)-3,4-dihydro-1H,6H-pyrano[4,3-b]thieno[3,2-d]pyran-6-one (11.5 g, 46%). MS. Obsd. ($ESI^+$): 525.5 $[M+H]^+$.

Step C: 4-(benzyloxy)-8-(3-methyl-1-((2-(trimethylsilyl)ethoxy)methyl)-1H-pyrazol-4-yl)-1,3,4,5-tetrahydro-6H-pyrano[4,3-b]thieno[3,2-d]pyridin-6-one and 4-(benzyloxy)-8-(5-methyl-1-((2-(trimethylsilyl)ethoxy)methyl)-1H-pyrazol-4-yl)-1,3,4,5-tetrahydro-6H-pyrano[4,3-b]thieno[3,2-d]pyridin-6-one

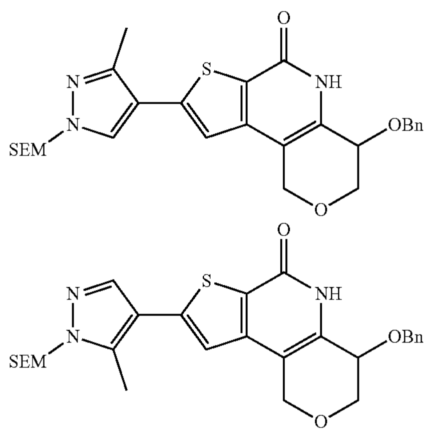

To a solution of 4-(benzyloxy)-8-(3-methyl-1-((2-(trimethylsilyl)ethoxy)methyl)-1H-pyrazol-4-yl)-3,4-dihydro-1H,6H-pyrano[4,3-b]thieno[3,2-d]pyran-6-one and 4-(benzyloxy)-8-(5-methyl-1-((2-(trimethylsilyl)ethoxy)methyl)-1H-pyrazol-4-yl)-3,4-dihydro-1H,6H-pyrano[4,3-b]thieno[3,2-d]pyran-6-one (3.0 g, 11 mmol, 1 eq.) in i-PrOH (30 mL) was added $NH_4OH$ (30 mL). The reaction was stirred at 100° C. for 20 h, cooled, concentrated and filtered. Trituration with MeOH afforded 4-(benzyloxy)-8-(3-methyl-1-((2-(trimethylsilyl)ethoxy)methyl)-1H-pyrazol-4-yl)-1,3,4,5-tetrahydro-6H-pyrano[4,3-b]thieno[3,2-d]pyridin-6-one and 4-(benzyloxy)-8-(5-methyl-1-((2-(trimethylsilyl)ethoxy)methyl)-1H-pyrazol-4-yl)-1,3,4,5-tetrahydro-6H-pyrano[4,3-b]thieno[3,2-d]pyridin-6-one (3.8 g, 63%). MS. Obsd. ($ESI^+$): 524.5 $[M+H]^+$.

Step D: tert-butyl 4-(4-hydroxy-6-oxo-3,4,5,6-tetrahydro-1H-pyrano[4,3-b]thieno[3,2-d]pyridin-8-yl)-3-methyl-1H-pyrazole-1-carboxylate

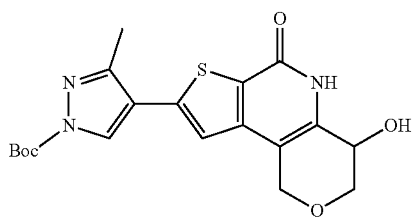 [SMILES: Cc1nn(C(=O)OC(C)(C)C)cc1-c1cc2c3c([nH]c(=O)c2s1)C(O)COC3]

A mixture of 4-(benzyloxy)-8-(3-methyl-1-((2-(trimethylsilyl)ethoxy)methyl)-1H-pyrazol-4-yl)-1,3,4,5-tetrahydro-6H-pyrano[4,3-b]thieno[3,2-d]pyridin-6-one and 4-(benzyloxy)-8-(5-methyl-1-((2-(trimethylsilyl)ethoxy)methyl)-1H-pyrazol-4-yl)-1,3,4,5-tetrahydro-6H-pyrano[4,3-b]thieno[3,2-d]pyridin-6-one (5.4 g, 10. mmol, 1.0 eq.) was dissolved in DCM (150 mL) and cooled to 0° C. and $BCl_3$ (1.0 M, 50 mL, 5 eq.) was added. The reaction was stirred at 0° C. for 1 h before adding MeOH. The mixture was concentrated to give 4-hydroxy-8-(3-methyl-1H-pyrazol-4-yl)-1,3,4,5-tetrahydro-6H-pyrano[4,3-b]thieno[3,2-d]pyridin-6-one (3.2 g, crude). MS. Obsd. ($ESI^+$): 304.0 $[M+H]^+$. The crude residue was dissolved in DMF (90 mL) and $Et_3N$ (4.20 g, 41.5 mmol), DMAP (169 mg, 1.38 mmol), and $(Boc)_2O$ (3.63 g, 16.6 mmol) were added. The mixture was stirred at rt for 6 h before being concentrated in vacuo. The residue was triturated with DCM to give tert-butyl 4-(4-hydroxy-6-oxo-3,4,5,6-tetrahydro-1H-pyrano[4,3-b]thieno[3,2-d]pyridin-8-yl)-3-methyl-1H-pyrazole-1-carboxylate (4.8 g, crude). MS obsd. ($ESI^+$): 404.2 $[(M+H)^+]$.

Step E: Tert-butyl 4-(4,6-dioxo-3,4,5,6-tetrahydro-1H-pyrano[4,3-b]thieno[3,2-d]pyridin-8-yl)-3-methyl-1H-pyrazole-1-carboxylate

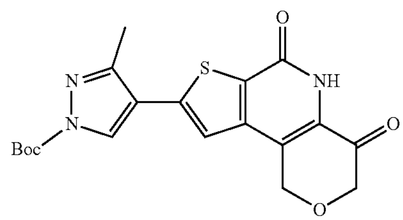 [SMILES: Cc1nn(C(=O)OC(C)(C)C)cc1-c1cc2c3c([nH]c(=O)c2s1)C(=O)COC3]

The reaction conditions described in Compound 16, Step E afforded tert-butyl 4-(4,6-dioxo-3,4,5,6-tetrahydro-1H-pyrano[4,3-b]thieno[3,2-d]pyridin-8-yl)-3-methyl-1H-pyrazole-1-carboxylate (750 mg, 50%). MS. Obsd. ($ESI^+$): 402.0 $[(M+H)^+]$.

Step F: (S)-4-(tert-butyl)-4-hydroxy-8-(3-methyl-1H-pyrazol-4-yl)-1,3,4,5-tetrahydro-6H-pyrano[4,3-b]thieno[3,2-d]pyridin-6-one (Compound 91) and (R)-4-(tert-butyl)-4-hydroxy-8-(3-methyl-1H-pyrazol-4-yl)-1,3,4,5-tetrahydro-6H-pyrano[4,3-b]thieno[3,2-d]pyridin-6-one (Compound 92)

Compound 91

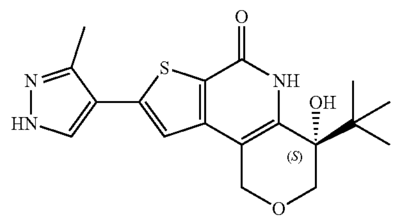

Compound 92

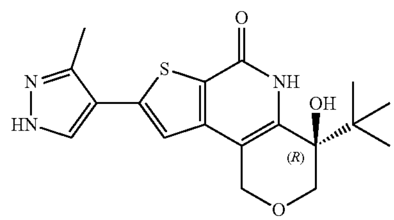

Reaction conditions similar to those described in Compound 89, Step E to afford 4-(tert-butyl)-4-hydroxy-8-(3-methyl-1H-pyrazol-4-yl)-1,3,4,5-tetrahydro-6H-pyrano[4,3-b]thieno[3,2-d]pyridin-6-one (30 mg, 32%). MS. Obsd. ($ESI^+$): 360.2 $[M+H]^+$.

The enantiomers were separated by SFC. (S)-4-(tert-butyl)-4-hydroxy-8-(3-methyl-1H-pyrazol-4-yl)-1,3,4,5-tetrahydro-6H-pyrano[4,3-b]thieno[3,2-d]pyridin-6-one (Compound 91): MS. Obsd. ($ESI^+$): 360.2 $[(M+H)^+]$; $^1H$ NMR (400 MHz, DMSO-d6) ppm: 12.96 (s, 1H), 10.02 (s, 1H), 8.17-7.87 (m, 1H), 7.27 (s, 1H), 5.32 (s, 1H), 4.80 (d, J=15.2 Hz, 1H), 4.71 (d, J=15.2 Hz, 1H), 4.13 (d, J=11.6 Hz, 1H), 3.45 (d, J=11.6 Hz, 1H), 2.45 (s, 3H), 1.03 (s, 9H). (R)-4-(tert-butyl)-4-hydroxy-8-(3-methyl-1H-pyrazol-4-yl)-1,3,4,5-tetrahydro-6H-pyrano[4,3-b]thieno[3,2-d]pyridin-6-one (Compound 92): MS. Obsd. ($ESI^+$): 360.0 $[(M+H)^+]$.

Example 93—Compound 93: 4-(tert-butyl)-4-hydroxy-8-(1H-pyrazol-4-yl)-1,3,4,5-tetrahydrothieno[2,3-c][1,6]naphthyridin-6(2H)-one Compound 93

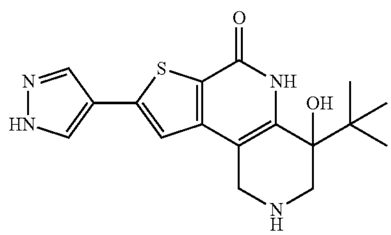

Step A: Benzyl 3-(benzoyloxy)-4,4-dimethoxypiperidine-1-carboxylate

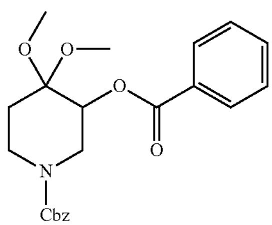 [SMILES: COC1(OC)CCN(C(=O)OCc2ccccc2)CC1OC(=O)c1ccccc1]

A solution of potassium hydroxide (7.22 g, 129 mmol, 3.0 eq.) in MeOH (450 mL) was added benzyl 4-oxopiperidine-1-carboxylate (10 g, 43 mmol, 8.5 mL, 1.0 eq.) at 0° C. before 12 (15.2 g, 60.0 mmol, 1.4 eq.) was added slowly under $N_2$ atmosphere. After addition, the reaction mixture was allowed to warm to rt and stirred for 2 h. The reaction mixture was concentrated in vacuo. The crude product was stirred in 150 mL of DCM and the precipitate was filtered. The filtrate was concentrated in vacuo to give Benzyl 3-hydroxy-4,4-dimethoxypiperidine-1-carboxylate (14.2 g, crude). The crude residue was dissolved in pyridine (140 mL) and cooled to 0° C. before benzoyl chloride (16.9 g, 120 mmol, 13.8 mL, 2.5 eq.) was added. After addition, the reaction mixture was stirred at rt for 4 h. The mixture was concentrated in vacuo and purified ($SiO_2$, 0-9% EtOAc in PE) to give Benzyl 3-(benzoyloxy)-4,4-dimethoxypiperidine-1-carboxylate (9.8 g, 57%). $^1H$ NMR (400 MHz, DMSO-d6) δ ppm: 7.96-7.86 (m, 2H), 7.72-7.69 (m, 1H), 7.63-7.50 (m, 2H), 7.49-7.33 (m, 2H), 7.17-7.07 (m, 2H), 7.02-6.93 (m, 1H), 5.07-4.99 (m, 2H), 4.88-4.57 (m, 1H), 4.24-4.18 (m, 1H), 4.07-4.02 (m, 1H), 3.30-3.32 (m, 1H), 3.26 (s, 3H), 3.07 (s, 3H), 2.97-2.82 (m, 1H), 2.02-1.99 (m, 1H), 1.85-1.82 (m, 1H).

Step B: Benzyl 3-(benzoyloxy)-4-oxopiperidine-1-carboxylate

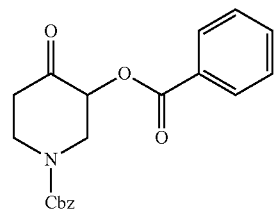 [SMILES: O=C(OC1CN(C(=O)OCc2ccccc2)CCC1=O)c1ccccc1]

To the solution of benzyl 3-(benzoyloxy)-4,4-dimethoxypiperidine-1-carboxylate (9.8 g, 24 mmol, 1.0 eq.) in acetone (100 mL) was added molecular iodine (1.25 g, 4.91 mmol, 0.1 eq.). After 16 h at rt $Na_2SO_3$ (100 mL, sat. aq.) was added and the mixture was extracted with DCM (120 mL×3). The combined organic phases were dried ($Na_2SO_4$), filtered, and concentrated. Purification by flash column chromatography ($SiO_2$, 0-11% EtOAc in PE) gave benzyl 3-(benzoyloxy)-4-oxopiperidine-1-carboxylate (4.7 g, 54%). $^1H$ NMR (400 MHz, $CDCl_3$) δ ppm: 8.06 (d, J=7.2 Hz, 2H), 7.61-7.57 (m, 1H), 7.47-7.43 (m, 2H), 7.37 (s, 5H), 5.41-5.37 (m, 1H), 5.20 (s, 2H), 4.73-4.57 (m, 1H), 4.43-4.40 (m, 1H), 3.44-3.26 (m, 2H), 2.65 (s, 2H).

Step C: Benzyl 4-(benzoyloxy)-6-oxo-8-(1-(tetrahydro-2H-pyran-2-yl)-1H-pyrazol-4-yl)-4,6-dihydro-1H-thieno[3',2':4,5]pyrano[3,2-c]pyridine-2 (3H)-carboxylate

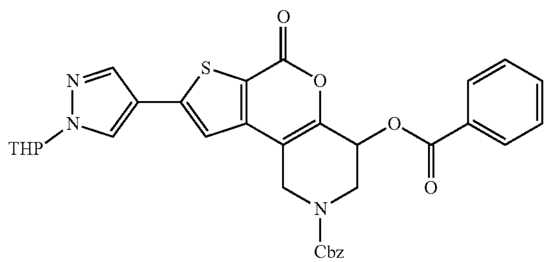

A mixture of methyl 3-bromo-5-(1-tetrahydropyran-2-ylpyrazol-4-yl)thiophene-2-carboxylate (500 mg, 1.35 mmol, 1.0 eq.), benzyl 3-(benzoyloxy)-4-oxopiperidine-1-carboxylate (714 mg, 2.02 mmol, 1.5 eq.), $Cs_2CO_3$, (1.32 g, 4.04 mmol, 3.0 eq.), $Pd_2(dba)_3$ (123 mg, 135 μmol, 0.10 eq.) and Xantphos (156 mg, 269 μmol, 0.20 eq.) in toluene (18 mL) was heated to 105° C. for 2 h. The reaction mixture was filtered, concentrated in vacuo and purified by flash column chromatography ($SiO_2$, 0-36% EtOAc in PE) to give benzyl 4-(benzoyloxy)-6-oxo-8-(1-(tetrahydro-2H-pyran-2-yl)-1H-pyrazol-4-yl)-4,6-dihydro-1H-thieno[3',2':4,5]pyrano[3,2-c]pyridine-2(3H)-carboxylate (450 mg, 55%). MS obsd. ($ESI^+$): 612.4 $[(M+H)^+]$.

Step D: Benzyl 4-hydroxy-6-oxo-8-(1-(tetrahydro-2H-pyran-2-yl)-1H-pyrazol-4-yl)-3,4,5,6-tetrahydrothieno[2,3-c][1,6]naphthyridine-2(1H)-carboxylate

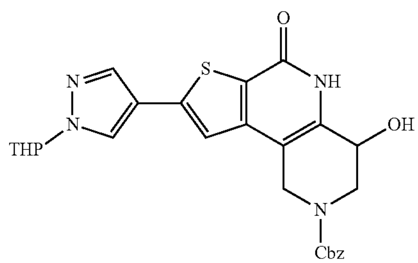

A solution of benzyl 4-(benzoyloxy)-6-oxo-8-(1-(tetrahydro-2H-pyran-2-yl)-1H-pyrazol-4-yl)-4,6-dihydro-1H-thieno[3',2':4,5]pyrano[3,2-c]pyridine-2 (3H)-carboxylate (900 mg, 1.47 mmol, 1.0 eq.) in $NH_3$/MeOH (7 M, 10 mL, 10 mL) was stirred at 95° C. for 2 h. The reaction mixture was concentrated in vacuo and purified by flash column chromatography ($SiO_2$, 0-4% MeOH in DCM) to give benzyl 4-hydroxy-6-oxo-8-(1-(tetrahydro-2H-pyran-2-yl)-1H-pyrazol-4-yl)-3,4,5,6-tetrahydrothieno[2,3-c][1,6]naphthyridine-2(1H)-carboxylate (500 mg, 67%). MS obsd. ($ESI^+$): 507.4 [$(M+H)^+$].

Step E: Benzyl 4,6-dioxo-8-(1-(tetrahydro-2H-pyran-2-yl)-1H-pyrazol-4-yl)-3,4,5,6-tetrahydrothieno[2,3-c][1,6]naphthyridine-2(1H)-carboxylate

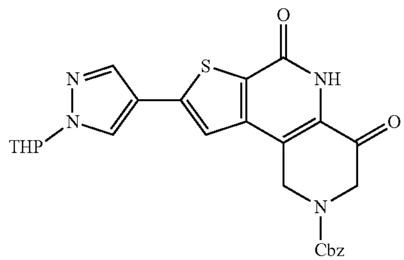

The reaction conditions described in Compound 16, Step E were used to give benzyl 4,6-dioxo-8-(1-(tetrahydro-2H-pyran-2-yl)-1H-pyrazol-4-yl)-3,4,5,6-tetrahydrothieno[2,3-c][1,6]naphthyridine-2(1H)-carboxylate (395 mg, 79%). MS obsd. ($ESI^+$): 505.4 [$(M+H)^+$].

Step F: Benzyl 4-(tert-butyl)-4-hydroxy-6-oxo-8-(1-(tetrahydro-2H-pyran-2-yl)-1H-pyrazol-4-yl)-3,4,5,6-tetrahydrothieno[2,3-c][1,6]naphthyridine-2(1H)-carboxylate

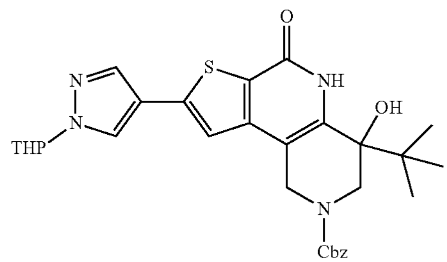

To the solution of benzyl 4,6-dioxo-8-(1-(tetrahydro-2H-pyran-2-yl)-1H-pyrazol-4-yl)-3,4,5,6-tetrahydrothieno[2,3-c][1,6]naphthyridine-2(1H)-carboxylate (200 mg, 396 μmol, 1.0 eq.) in THF (12 mL) was added $ZnCl_2$ (0.50 M, 1.19 mL, 1.5 eq.). The mixture was stirred at 0° C. for 10 min before t-BuMgCl (1.0 M, 3.96 mL, 10.0 eq.) was added. After 1 h at 0° C. saturated $NH_4Cl$ (aq.) was added and the biphasic mixture was extracted with DCM/MeOH (35 mL×3, 20:1 v/v). The organic layers were dried ($Na_2SO_4$), filtered, concentrated, and purified by flash column chromatography ($SiO_2$, 0-3% MeOH in DCM) to give benzyl 4-(tert-butyl)-4-hydroxy-6-oxo-8-(1-(tetrahydro-2H-pyran-2-yl)-1H-pyrazol-4-yl)-3,4,5,6-tetrahydrothieno[2,3-c][1,6]naphthyridine-2(1H)-carboxylate (57 mg, 26%). MS obsd. ($ESI^+$): 563.5 [$(M+H)^+$].

Step G: 4-(tert-butyl)-4-hydroxy-8-(1H-pyrazol-4-yl)-1,3,4,5-tetrahydrothieno[2,3-c][1,6]naphthyridin-6(2H)-one (Compound 93)

Compound 93

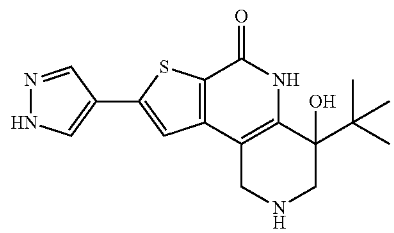

A solution of Benzyl 4-(tert-butyl)-4-hydroxy-6-oxo-8-(1-(tetrahydro-2H-pyran-2-yl)-1H-pyrazol-4-yl)-3,4,5,6-tetrahydrothieno[2,3-c][1,6]naphthyridine-2(1H)-carboxylate (15 mg, 27 μmol, 1.0 eq.) in TFA (3.00 mL) was heated to 80° C. for 1 h. The resulting mixture was concentrated in vacuo and cooled to 0° C. before $NH_3$/MeOH was added to adjust the pH to ~9. The mixture was concentrated in vacuo and purified by reverse phase column chromatography ($SiO_2$, 0-30% MeCN in water (0.1% FA)) to give 4-(tert-butyl)-4-hydroxy-8-(1H-pyrazol-4-yl)-1,3,4,5-tetrahydrothieno[2,3-c][1,6]naphthyridin-6(2H)-one (Compound 93) (4.7 mg, 51%). $^1H$ NMR (400 MHz, DMSO-d6) δ ppm: 13.23 (s, 1H), 9.51 (s, 1H), 8.15 (brs, 2H), 7.46 (s, 1H), 5.22 (s, 1H), 3.95-3.80 (m, 2H), 3.32 (s, 1H), 2.78 (d, J=12.8 Hz, 1H), 1.03 (s, 9H).

Example 94—Compound 94: 2-acetyl-4-tert-butyl-4-hydroxy-8-(1H-pyrazol-4-yl)-3,5-dihydro-1H-thieno[2,3-c][1,6]naphthyridin-6-one Compound 94

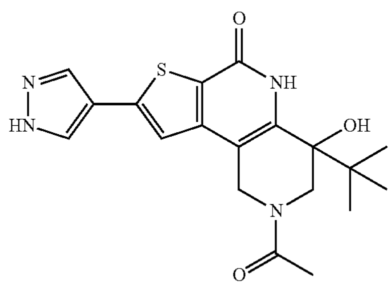

Step A: 4-(tert-butyl)-4-hydroxy-8-(1-(tetrahydro-2H-pyran-2-yl)-1H-pyrazol-4-yl)-1,3,4,5-tetrahydrothieno[2,3-c][1,6]naphthyridin-6(2H)-one

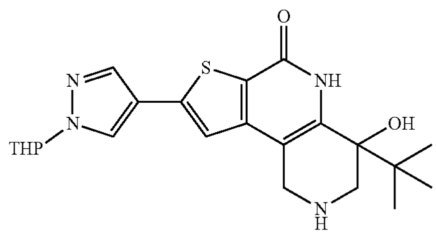

To the solution of benzyl 4-(tert-butyl)-4-hydroxy-6-oxo-8-(1-(tetrahydro-2H-pyran-2-yl)-1H-pyrazol-4-yl)-3,4,5,6-tetrahydrothieno[2,3-c][1,6]naphthyridine-2(1H)-carboxylate (57 mg, 100 μmol, 1.0 eq.) in IPA (6 mL) was added Pd/C (13 mg, 10.1 μmol, 10% Pd, 0.1 eq.). The mixture was degassed, purged with $H_2$ and stirred at rt for 1.5 h. The reaction mixture was filtered and concentrated in vacuo to give the 4-(tert-butyl)-4-hydroxy-8-(1-(tetrahydro-2H-pyran-2-yl)-1H-pyrazol-4-yl)-1,3,4,5-tetrahydrothieno[2,3-c][1,6]naphthyridin-6(2H)-one (42 mg, crude) as a yellow solid, which was directly used for next step without further purification. MS obsd. ($ESI^+$): 429.5 [$(M+H)^+$].

Step B: 2-acetyl-4-tert-butyl-4-hydroxy-8-(1-tetrahydropyran-2-ylpyrazol-4-yl)-3,5-dihydro-1H-thieno[2,3-c][1,6]naphthyridin-6-one

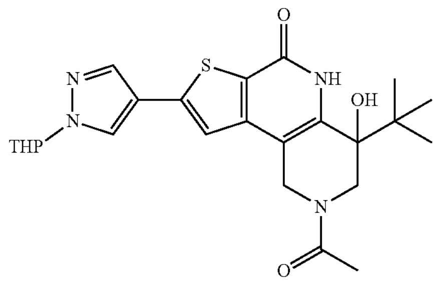

A solution of 4-tert-butyl-4-hydroxy-8-(1-tetrahydropyran-2-ylpyrazol-4-yl)-1,2,3,5-tetrahydrothieno[2,3-c][1,6]naphthyridin-6-one (47 mg, 110 μmol, 1.0 eq.) and triethylamine (33 mg, 330 μmol, 3.0 eq.) in DCM (3 mL) was cooled to 0° C. Acetyl chloride (8.61 mg, 110 μmol, 1.0 eq.) was added dropwise and the reaction mixture was warmed to rt. After 2 h saturated aq. $Na_2CO_3$ (2 mL) and MeCN (3 mL) were added. The mixture was stirred at rt for 3 h, diluted with brine (30 mL), extracted with DCM (30 mL×3), and washed with brine (30 mL×2). The combined organic layers were concentrated and purified by flash column chromatography ($SiO_2$, 0-6% MeOH in DCM) to give 2-acetyl-4-tert-butyl-4-hydroxy-8-(1-tetrahydropyran-2-ylpyrazol-4-yl)-3,5-dihydro-1H-thieno[2,3-c][1,6]naphthyridin-6-one (20 mg, 39%). MS obsd. ($ESI^+$): 471.4 [$(M+1)^+$].

Step C: 2-acetyl-4-tert-butyl-4-hydroxy-8-(1H-pyrazol-4-yl)-3,5-dihydro-1H-thieno[2,3-c][1,6]naphthyridin-6-one (Compound 94)

Compound 94

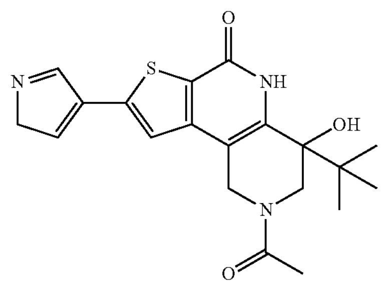

A solution of 2-acetyl-4-tert-butyl-4-hydroxy-8-(1-tetrahydropyran-2-ylpyrazol-4-yl)-3,5-dihydro-1H-thieno[2,3-c][1,6]naphthyridin-6-one (20 mg, 42 μmol, 1.0 eq.) in HCl/MeOH (4 M, 2 mL) was stirred at 0° C. for 1 h. The mixture was concentrated in vacuo and the pH was adjusted to ~9 by adding $NH_3$/MeOH at 0° C. The mixture was concentrated in vacuo and purified by Prep-HPLC (ACN/water/0.1% FA) to give 2-acetyl-4-tert-butyl-4-hydroxy-8-(1H-pyrazol-4-yl)-3,5-dihydro-1H-thieno[2,3-c][1,6]naphthyridin-6-one (Compound 94) (9.6 mg, 58%). MS obsd. ($ESI^+$): 386.1 [$(M+1)^+$]; $^1H$ NMR (400 MHz, DMSO-$d_6$) δ 13.25 (s, 1H), 10.03 (d, J=37.6 Hz, 1H), 8.32 (s, 1H), 7.98 (s, 1H), 7.58 (d, J=1.2 Hz, 1H), 5.61 (d, J=55.2 Hz, 1H), 4.96-4.05 (m, 3H), 2.68 (d, J=13.2 Hz, 1H), 2.16 (d, J=18.8 Hz, 3H), 0.95 (d, J=12.8 Hz, 9H).

Examples 95 and 96—Compounds 95 and 96: (S)-4-(1,1-difluoroethyl)-4-hydroxy-8-(1H-pyrazol-4-yl)-1,3,4,5-tetrahydro-6H-pyrano[4,3-b]thieno[3,2-d]pyridin-6-one (Compound 95) and (R)-4-(1,1-difluoroethyl)-4-hydroxy-8-(1H-pyrazol-4-yl)-1,3,4,5-tetrahydro-6H-pyrano[4,3-b]thieno[3,2-d]pyridin-6-one (Compound 96) (Stereochemistry for Compounds 95 and 96 is Assigned Arbitrarily)

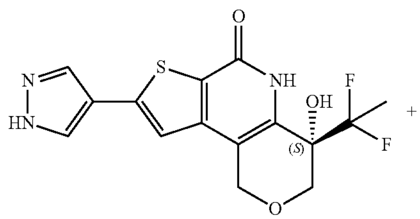

+

Compound 95

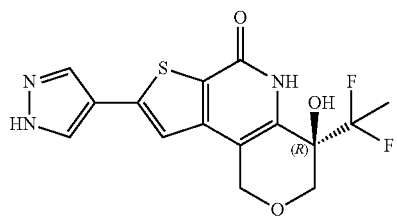

Compound 96

Step A: 3-(benzyloxy)-3-(prop-1-en-2-yl)tetrahydro-2H-pyran-4-ol

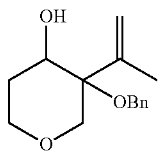 [SMILES: C=C(C)C1(OCc2ccccc2)COCCC1O]

A solution of 3-(benzyloxy)-3-(prop-1-en-2-yl)tetrahydro-4H-pyran-4-one (5.0 g, 20.3 mmol, 1.0 eq.) in methanol (50 mL) was cooled to 0° C. before $NaBH_4$ (922 mg, 24.4 mmol, 1.2 eq.) was added in portions. The mixture was allowed to warm to rt for 1 h and $NH_4Cl$ (sat. aq.) was added. The biphasic mixture was extracted with DCM (50 mL mL×3) and the combined organic phases were washed with brine, dried $Na_2SO_4$, filtered, and concentrated in vacuo. Purification by flash column chromatography ($SiO_2$, 0-12% EtOAc in PE) gave trans and cis diastereomers, assigned arbitrarily: (3R,4S)-3-benz yloxy-3-isopropenyl-tetrahydropyran-4-ol and (3S,4S)-3-benzyloxy-3-isopropenyl-tetrahydropyran-4-ol (2.4 g, 48%); $^1$H NMR (400 MHz, DMSO-d6) δ ppm: 7.39-7.31 (m, 4H), 7.27-7.25 (m, 1H), 5.12 (s, 1H), 5.09 (s, 1H), 4.55 (d, J=6.0 Hz, 1H), 4.41 (d, J=3.2 Hz, 2H), 3.86-3.77 (m, 3H), 3.51 (d, J=12.0 Hz, 1H), 3.47-3.40 (m, 1H), 1.89-1.81 (m, 1H), 1.78 (s, 3H), 1.64-1.60 (m, 1H). (3S,4R)-3-benzyloxy-3-isopropenyl-tetrahydropyran-4-ol and (3R,4R)-3-benzyloxy-3-isopropenyl-tetrahydropyran-4-ol (2.3 g, 46%); $^1$H NMR (400 MHz, DMSO-d6) δ ppm: 7.33-7.27 (m, 4H), 7.26-7.24 (m, 1H), 5.09 (s, 1H), 4.82 (d, J=4.4 Hz, 1H), 4.78 (s, 1H), 4.39 (d, J=11.2 Hz, 1H), 4.09 (d, J=11.2 Hz, 1H), 3.99 (d, J=12.4 Hz, 1H), 3.78-3.72 (m, 2H), 3.63-3.59 (m, 2H), 2.15-2.12 (m, 1H), 1.71 (s, 3H), 1.40-1.36 (m, 1H).

Step B: 3-(benzyloxy)-3-(prop-1-en-2-yl)tetrahydro-2H-pyran-4-yl benzoate

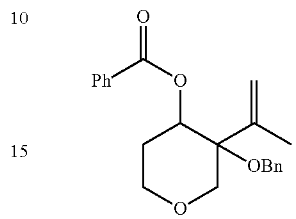

A mixture of (3R,4S)-3-benzyloxy-3-isopropenyl-tetrahydropyran-4-ol and (3S,4S)-3-benzyloxy-3-isopropenyl-tetrahydropyran-4-ol (2.4 g, 9.67 mmol, 1.0 eq., arbitrarily assigned) in pyridine (24 mL) was cooled to 0° C. before benzoyl chloride (5.43 g, 38.7 mmol, 4.45 mL, 4.0 eq.) was added and the reaction mixture was warmed to rt. The mixture was concentrated in vacuo and the residue diluted with EtOAc (100 mL). The organic layers were washed with HCl (5×60 mL, 1.0 M aq.) and brine, dried over $Na_2SO_4$, filtered, and concentrated in vacuo. Purification by flash column chromatography ($SiO_2$, 0-5% EtOAc in PE) gave 3-(benzyloxy)-3-(prop-1-en-2-yl)tetrahydro-2H-pyran-4-yl benzoate (3.0 g, 88%). $^1$H NMR (400 MHz, DMSO-d6) δ ppm: 8.00-7.94 (m, 2H), 7.68-7.64 (m, 1H), 7.56-7.50 (m, 2H), 7.36-7.30 (m, 4H), 7.27-7.25 (m, 1H), 5.50-5.47 (m, 1H), 5.17 (s, 1H), 5.13 (s, 1H), 4.51-4.39 (m, 2H), 4.04-4.01 (m, 1H), 3.92-3.88 (m, 1H), 3.80 (d, J=12.4 Hz, 1H), 3.69-3.64 (m, 1H), 2.16-2.07 (m, 1H), 1.88-1.83 (m, 1H), 1.76 (s, 3H).

Step C: 3-acetyl-3-(benzyloxy)tetrahydro-2H-pyran-4-yl benzoate

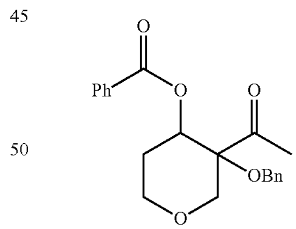

A solution of 3-(benzyloxy)-3-(prop-1-en-2-yl)tetrahydro-2H-pyran-4-yl benzoate (3.0 g, 8.51 mmol, 1.0 eq.) in DCM (60 mL) was cooled to −78° C. Ozone was gently bubbled through the stirring solution at −78° C. about 1.5 h before $N_2$ was passed through the solution for 10 min. Five drops of dimethylsulfide was added and the reaction mixture was slowly warmed to rt. The reaction mixture was concentrated in vacuo and purified by flash column chromatography ($SiO_2$, 0-6% EtOAc in PE) to give 3-acetyl-3-(benzyloxy)tetrahydro-2H-pyran-4-yl benzoate (2.5 g, 83%). $^1$H NMR (400 MHz, DMSO-d6) δ ppm: 7.99-7.97 (m, 2H), 7.70-7.66 (m, 1H), 7.57-7.53 (m, 2H), 7.39-7.27 (m, 5H), 5.57-5.54 (m, 1H), 4.57 (s, 2H), 4.14 (d, J=12.8 Hz, 1H), 3.89-3.85 (m, 2H), 3.70-3.67 (m, 1H), 2.27 (s, 3H), 2.08-2.05 (m, 1H), 1.95-1.92 (m, 1H).

Step D: 3-(benzyloxy)-3-(1,1-difluoroethyl)tetrahydro-2H-pyran-4-yl benzoate

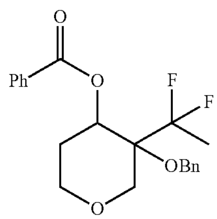 [SMILES: CC(F)(F)C1(OCc2ccccc2)COCCC1OC(=O)c1ccccc1]

To a mixture of 3-acetyl-3-(benzyloxy)tetrahydro-2H-pyran-4-yl benzoate (1.5 g, 4.23 mmol, 1.0 eq.) in chloroform (1.5 mL) was added DAST (18.3 g, 114 mmol, 15 mL, 26.8 eq.) and the mixture was stirred at 75° C. for 16 h. The reaction mixture was diluted with DCM (50 mL) and ice water (150 mL), and extracted with DCM (70 mL×3). The organic phase was washed with brine, dried ($Na_2SO_4$), filtered, and concentrated in vacuo. Column chromatography ($SiO_2$, 0-5% EtOAc in PE) gave 3-(benzyloxy)-3-(1,1-difluoroethyl)tetrahydro-2H-pyran-4-yl benzoate (470 mg, 29%). $^1$H NMR (400 MHz, DMSO-d6) δ ppm: 7.97-7.95 (m, 2H), 7.70-7.66 (m, 1H), 7.57-7.53 (m, 2H), 7.47 (d, J=7.6 Hz, 2H), 7.42-7.38 (m, 2H), 7.34-7.32 (m, 1H), 5.46-5.43 (m, 1H), 4.92 (d, J=11.2 Hz, 1H), 4.70 (d, J=10.8 Hz, 1H), 4.47 (d, J=13.2 Hz, 1H), 3.98-3.95 (m, 1H), 3.66-3.61 (m, 2H), 2.13-2.09 (m, 1H), 1.91-1.89 (m, 1H), 1.68 (t, J=20.4 Hz, 3H).

Step E: 3-(benzyloxy)-3-(1,1-difluoroethyl)tetrahydro-2H-pyran-4-ol

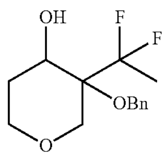 [SMILES: CC(F)(F)C1(OCc2ccccc2)COCCC1O]

A mixture of 3-(benzyloxy)-3-(1,1-difluoroethyl)tetrahydro-2H-pyran-4-yl benzoate (470 mg, 1.25 mmol, 1.0 eq.) in THF (5 mL), $H_2O$ (5 mL), MeOH (5 mL) and $LiOH·H_2O$ (157 mg, 3.75 mmol, 3.0 eq.) was stirred at rt for 2 h. The mixture was extracted with DCM (30 mL×3), the organic phases were combined, washed with brine, dried ($Na_2SO_4$), filtered, and concentrated. Purification by flash column chromatography ($SiO_2$, 0-9% EtOAc in PE) gave 3-(benzyloxy)-3-(1,1-difluoroethyl)tetrahydro-2H-pyran-4-ol (305 mg, 89%). $^1$H NMR (400 MHz, DMSO-d6) δ ppm: 7.43 (d, J=7.2 Hz, 2H), 7.37-7.34 (m, 2H), 7.30-7.26 (m, 1H), 4.84 (d, J=8.0 Hz, 1H), 4.77 (d, J=11.2 Hz, 1H), 4.54-4.51 (m, 1H), 4.35 (d, J=13.2 Hz, 1H), 3.89-3.85 (m, 1H), 3.80-3.77 (m, 1H), 3.43-3.39 (m, 1H), 3.36-3.31 (m, 1H), 1.99-1.90 (m, 1H), 1.81 (t, J=20.4 Hz, 3H), 1.60-1.56 (m, 1H).

Step F: 3-(benzyloxy)-3-(1,1-difluoroethyl)tetrahydro-4H-pyran-4-one

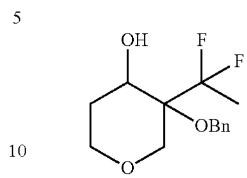

To the mixture of 3-benzyloxy-3-(1,1-difluoroethyl)tetrahydropyran-4-ol (525 mg, 1.93 mmol, 1.0 eq.) in DCM (6 mL) and DMF (6 mL) was added DMP (1.64 g, 1.93 mmol, 2.0 eq.) and the mixture was stirred at 50° C. for 2 h. Aqueous $Na_2SO_3$ solution and water (70 mL) were added and the biphasic mixture was extracted with EtOAc (35 mL×3). The organic phase was washed with brine, dried ($Na_2SO_4$), filtered and concentrated. Column chromatography ($SiO_2$, 0-6% EtOAc in PE) gave 3-(benzyloxy)-3-(1,1-difluoroethyl)tetrahydro-4H-pyran-4-one (505 mg, 96%). $^1$H NMR (400 MHz, DMSO-d6) δ ppm: 7.38-7.34 (m, 4H), 7.33-7.30 (m, 1H), 4.75 (d, J=11.2 Hz, 1H), 4.57 (d, J=11.2 Hz, 1H), 4.31 (d, J=12.8 Hz, 1H), 4.11-4.04 (m, 2H), 3.97-3.94 (m, 1H), 2.84-2.80 (m, 1H), 2.53-2.52 (m, 1H), 1.70 (t, J=20.4 Hz, 3H).

Step G: 4-(benzyloxy)-4-(1,1-difluoroethyl)-8-(1-(tetrahydro-2H-pyran-2-yl)-1H-pyrazol-4-yl)-3,4-dihydro-1H,6H-pyrano[4,3-b]thieno[3,2-d]pyran-6-one

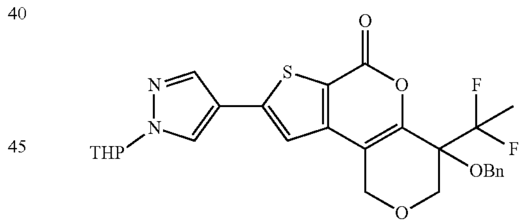

To a solution of 3-(benzyloxy)-3-(1,1-difluoroethyl)tetrahydro-4H-pyran-4-one (505 mg, 1.87 mmol, 1.5 eq.) and methyl 3-bromo-5-(1-tetrahydropyran-2-ylpyrazol-4-yl)thiophene-2-carboxylate (460 mg, 1.24 mmol, 1.0 eq.) in toluene (18 mL) was added $Cs_2CO_3$ (1.21 g, 3.72 mmol, 3.0 eq.), Sphos-Pd-$G_3$ (107 mg, 124 μmol, 0.10 eq.). The mixture was heated to 105° C. for 2 h, cooled, and filtered. The filtrate was concentrated in vacuo and purified by flash column chromatography ($SiO_2$, 0-27% EtOAc in PE) to give 4-(benzyloxy)-4-(1,1-difluoroethyl)-8-(1-(tetrahydro-2H-pyran-2-yl)-1H-pyrazol-4-yl)-3,4-dihydro-1H,6H-pyrano[4,3-b]thieno[3,2-d]pyran-6-one (260 mg, 39%). MS obsd. ($ESI^+$): 529.2 [$(M+H)^+$].

Step H: (S)-4-(1,1-difluoroethyl)-4-hydroxy-8-(1H-pyrazol-4-yl)-1,3,4,5-tetrahydro-6H-pyrano[4,3-b]thieno[3,2-d]pyridin-6-one (Compound 95) and (R)-4-(1,1-difluoroethyl)-4-hydroxy-8-(1H-pyrazol-4-yl)-1,3,4,5-tetrahydro-6H-pyrano[4,3-b]thieno[3,2-d]pyridin-6-one (Compound 96)

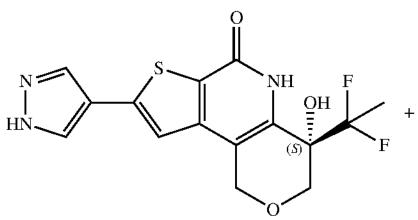

+

Compound 95

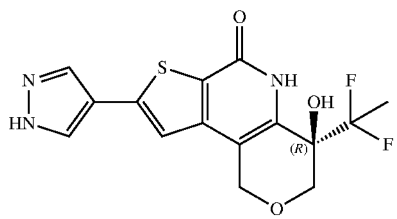

Compound 96

A solution of 4-(benzyloxy)-4-(1,1-difluoroethyl)-8-(1-(tetrahydro-2H-pyran-2-yl)-1H-pyrazol-4-yl)-3,4-dihydro-1H,6H-pyrano[4,3-b]thieno[3,2-d]pyran-6-one (260 mg, 492 μmol) in TFA (6 mL) was stirred at 50° C. for 1 h. The reaction mixture was concentrated in vacuo to give 4-(1,1-difluoroethyl)-4-hydroxy-8-(1H-pyrazol-4-yl)-3,4-dihydro-1H,6H-pyrano[4,3-b]thieno[3,2-d]pyran-6-one (305 mg, crude). The crude residue was dissolved in isopropanol (8 mL) and ammonia (sat. aq. 8 mL) was added. The mixture was stirred at 95° C. for 16 h before being cooled, concentrated in vacuo, and purified by flash column chromatography ($SiO_2$, 0-5% MeOH in DCM) to give 4-(1,1-difluoroethyl)-4-hydroxy-8-(1H-pyrazol-4-yl)-1,3,4,5-tetrahydro-6H-pyrano[4,3-b]thieno[3,2-d]pyridin-6-one (138 mg, 45%). MS obsd. ($ESI^+$): 354.0 [$(M+H)^+$].

The enantiomers were separated by chiral SFC. (S)-4-(1,1-difluoroethyl)-4-hydroxy-8-(1H-pyrazol-4-yl)-1,3,4,5-tetrahydro-6H-pyrano[4,3-b]thieno[3,2-d]pyridin-6-one (Compound 95): MS obsd. ($ESI^+$): 354.0 [$(M+H)^+$]. $^1H$ NMR (400 MHz, DMSO-d6) δ ppm: 13.26 (s, 1H), 10.36 (s, 1H), 8.31 (s, 1H), 7.99 (s, 1H), 7.47 (s, 1H), 6.44 (s, 1H), 4.85-4.74 (m, 2H), 4.13 (d, J=12.0 Hz, 1H), 3.62 (d, J=12.0 Hz, 1H), 1.67 (t, J=19.6 Hz, 3H). (R)-4-(1,1-difluoroethyl)-4-hydroxy-8-(1H-pyrazol-4-yl)-1,3,4,5-tetrahydro-6H-pyrano[4,3-b]thieno[3,2-d]pyridin-6-one (Compound 96): MS obsd. ($ESI^+$): 354.0 [$(M+H)^+$].

Biological Assays

CDC7 Kinase Biochemical Assay Protocol:

Full length human CDC7 protein co-expressed with DBF4 was purchased from SignalChem (China). CDC7 kinase activity was determined with PDKtide (SignalChem) as a substrate and by measuring ADP production using the ADP-Glo™ Kinase Assay kit (Promega) following the manufacturer's instructions. The kinase reaction was performed using the following conditions: Buffer: 40 mM Tris pH 7.5, 20 mM $MgCl_2$, 0.1 mg/mL BSA and 50 μM DTT. Final reaction mix contained 0.1 nM CDC7/DBF4, 1 μM ATP and 10 μM PDKtide. The kinase reaction time was 4 h. The ADP-Glo signal was measured using an EnVision plate reader (PerkinELmer).

Percent inhibition of CDC7 kinase activity was calculated based on the following formula:

$$\text{Inhibition (\%)} = 100\% \times \left(1 - \frac{S_{Sample} - S_{Low\ Ctrl}}{S_{High\ Ctrl} - S_{Low\ Ctrl}}\right)$$

$S_{Sample}$: the signal of compounds $S_{High\ Ctrl}$: the signal of high control (DMSO)

$S_{Low\ Ctrl}$: the signal of low control (positive control CDC7 inhibitor)

Phosphorylated MCM2 MSD Electrochemiluminescence Assay

The effect of CDC7 inhibitors on cellular phosphorylation of the CDC7 substrate MCM2 was determined using the following protocol:

A total of 40,000 colo205 cells in 100 μL culture medium (1640 medium+10% Fetal bovine serum+1% Penicillin-Streptomycin) were plated in 96-well cell culture plates and allowed to attach for 6 hours. 3-fold serial dilutions of test compounds were prepared in completed PBS at 25× final concentration and 4 μL of each were added to the cells and incubated for 20 hours at 37° C., 5% $CO_2$. Each concentration was tested in duplicate. After the 20 h incubation, cells were washed with 150 μL PBS and lysed with 40 μL MSD lysis buffer (obtained from Meso Scale Diagnostics) supplied with 1× complete ULTRA cocktail inhibitor (obtained from Roche). To detect phosphorylation of MCM2 S53, 30 μL of capture antibody solution (obtained from Abnova, catalog number H00004171-M01, 1:500) was added to each well of MULTI-ARRAY 96-well High Bind Plate, and incubated overnight. The antibody solution was removed, wells blocked with BSA solution and plates washed, followed by addition of 30 μl of cell lysate per well. After 2 h incubation, plates were washed. 30 μL of 1× detection antibody solution (obtained from Abcam, catalog number ab109133, 1:1000) was then added to each well and incubate for 1 hour. Plates were washed and 30 μL of 1× secondary antibody solution (obtained from MSD, catalog number R32AB-1, 1:5000) was added to each well and incubate for 1 hour. Plates were washed and 150 μL of 1× Read Buffer T was added to each well of the MSD plate. The electrochemiluminescence signal was measured on a MESO SECTOR 5600 plate reader. The percentage of remaining phosphorylated MCM2 signal was calculated following the equation below.

$$\text{\% Inhibition} = 100 \times \frac{R_{HC} - R_{cpds}}{R_{HC} - R_{LC}}$$

HC (high control): Cells treated with DMSO

Cpds: Cells treated with test compounds

LC (low control): Cells treated with positive control CDC7 inhibitor

TABLE 2

| Biological Data | |
|---|---|
| Cpmd. No. | CDC7 ADP-Glo PDKtide $IC_{50}$ * |
| 1 | A |
| 2 | A |

TABLE 2-continued

| Biological Data | |
|---|---|
| Cpmd. No. | CDC7 ADP-Glo PDKtide $IC_{50}$ * |
| 3 | B |
| 4 | A |
| 5 | A |
| 6 | C |
| 7 | A |
| 8 | A |
| 9 | A |
| 10 | A |
| 11 | C |
| 12 | B |
| 13 | A |
| 14 | B |
| 15 | A |
| 16 | A |
| 17 | B |
| 18 | A |
| 19 | C |
| 20 | A |
| 21 | B |
| 22 | A |
| 23 | C |
| 24 | A |
| 25 | B |
| 26 | B |
| 27 | A |
| 28 | A |
| 29 | B |
| 30 | A |
| 31 | B |
| 32 | A |
| 33 | B |
| 34 | C |
| 35 | A |
| 36 | C |
| 37 | A |
| 38 | B |
| 39 | A |
| 40 | ND |
| 41 | B |
| 42 | A |
| 43 | B |
| 44 | A |
| 45 | C |
| 46 | A |
| 47 | C |
| 48 | C |
| 49 | A |
| 50 | B |
| 51 | A |
| 52 | B |
| 53 | A |
| 54 | A |
| 55 | B |
| 56 | C |
| 57 | B |
| 58 | B |
| 59 | A |
| 60 | B |
| 61 | A |
| 62 | C |
| 63 | A |
| 64 | B |
| 65 | C |
| 66 | A |
| 67 | A |
| 68 | C |
| 69 | A |
| 70 | C |
| 71 | C |
| 72 | B |
| 73 | C |
| 74 | C |
| 75 | C |
| 76 | A |
| 77 | A |

TABLE 2-continued

| Biological Data | |
|---|---|
| Cpmd. No. | CDC7 ADP-Glo PDKtide $IC_{50}$ * |
| 78 | A |
| 79 | B |
| 80 | C |
| 81 | A |
| 82 | B |
| 83 | B |
| 84 | A |
| 85 | A |
| 86 | A |
| 87 | A |
| 88 | B |
| 89 | A |
| 90 | C |
| 91 | C |
| 92 | A |
| 93 | A |
| 94 | A |
| 95 | B |
| 96 | A |

* A denotes $IC_{50} \leq 1$ nM; B denotes 1 nM < $IC_{50} \leq 10$ nM; C denotes $IC_{50} > 10$ nM

TABLE 3

| Electrochemiluminescence assay | |
|---|---|
| Cmpd. No. | pMCM2-S53 MSD Colo205 $IC_{50}$ (nM) ** |
| 7 | C |
| 8 | C |
| 16 | A |
| 18 | B |
| 20 | A |
| 22 | A |
| 27 | A |
| 30 | D |
| 32 | B |
| 37 | B |
| 41 | D |
| 42 | C |
| 44 | B |
| 46 | B |
| 51 | A |
| 58 | D |
| 59 | A |
| 69 | B |
| 85 | D |
| 89 | B |
| 91 | A |
| 93 | C |

** A denotes $IC_{50} \leq 5$ nM; B Denotes 5 nM < $IC_{50} \leq 20$ nM; C denotes 20 nM < $IC_{50} \leq 50$ nM; D denotes $IC_{50} > 50$ nM

What is claimed is:

1. A compound of Formula (I):

Formula (I)

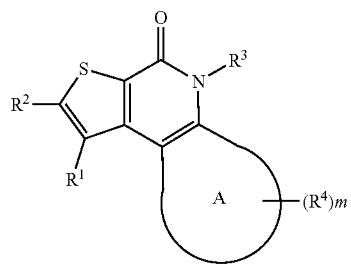

or a pharmaceutically acceptable salt thereof;

wherein:

$R^1$ is hydrogen or halogen;

$R^2$ is a 5-6 membered heteroaryl optionally substituted with 1 or 2 substituents independently selected from the group consisting of halogen and C1-C6 alkyl; or a 5-6 membered heterocyclyl optionally substituted with 1 or 2 substituents independently selected from the group consisting of halogen and C1-C6 alkyl;

$R^3$ is hydrogen or C1-C6 alkyl;

Ring A is a C6-C10 cycloalkyl or a 6-10 membered heterocyclyl;

each $R^4$ is independently selected from the group consisting of halogen, hydroxyl, C1-C6 alkyl, C1-C6 alkoxy, C1-C6 hydroxyalkyl, C1-C6 haloalkyl, C1-C6 alkoxy (C1-C6 alkyl)-, —C(═O) C1-C6 alkyl, C2-C6 alkynyl, C3-C6 cycloalkyl, —$NR^AR^B$, and 4-6 membered heterocyclyl optionally substituted with 1 or 2 independently selected halogen;

each $R^A$ and $R^B$ is independently hydrogen or C1-C6 alkyl; and m is 0, 1, 2, 3, or 4.

2. The compound of claim 1, wherein m is 1, 2, 3, or 4.

3. The compound of claim 1, wherein $R^2$ is a 5 membered heteroaryl optionally substituted with 1 or 2 substituents independently selected from the group consisting of halogen and C1-C6 alkyl.

4. The compound of claim 3, wherein the 5 membered heteroaryl of $R^2$ is pyrazolyl or isothiazolyl.

5. The compound of claim 1, wherein $R^2$ is a 6 membered heteroaryl optionally substituted with 1 or 2 substituents independently selected from the group consisting of halogen and C1-C6 alkyl.

6. The compound of claim 5, wherein the 6 membered heteroaryl of $R^2$ is pyridyl, pyrimidinyl, or pyridazinyl.

7. The compound claim 1, wherein $R^2$ is an unsubstituted 5-6 membered heteroaryl.

8. The compound of claim 7, wherein $R^2$ is selected from the group consisting of pyrazolyl, isothiazolyl, pyridyl, and pyridazinyl.

9. The compound of claim 1, wherein $R^2$ is a 5-6 membered heterocyclyl optionally substituted with 1 or 2 substituents independently selected from the group consisting of halogen and C1-C6 alkyl.

10. The compound of claim 1, wherein Ring A is C6-C10 cycloalkyl.

11. The compound of claim 10, wherein Ring A is cyclohexyl or bicyclo[2.2.2]octanyl.

12. The compound of claim 1, wherein Ring A is 6-10 membered heterocyclyl.

13. The compound of claim 12, wherein Ring A is tetrahydropyranyl or piperidinyl.

14. The compound of claim 1, wherein one $R^4$ is halogen.

15. The compound of claim 1, wherein one $R^4$ is hydroxyl.

16. The compound of claim 1, wherein one $R^4$ is C1-C6 alkyl.

17. The compound of claim 16, wherein one $R^4$ is selected from the group consisting of $—CH_3$, $—CH_2CH_3$, $—CH(CH_3)_2$, $—CH(CH_3)CH_2CH_3$, $—C(CH_3)_2CH_2CH_3$, and $—C(CH_3)_3$.

18. The compound of claim 1, wherein m is 2; and wherein the two $R^4$ groups are geminal; wherein one $R^4$ is hydroxyl; and the other $R^4$ is C1-C6 alkyl.

19. The compound of claim 1, wherein m is 2; and wherein the two $R^4$ groups are geminal; wherein each $R^4$ is fluoro.

20. The compound of claim 1, wherein $R^1$ is hydrogen.

21. The compound of claim 1, wherein $R^3$ is hydrogen.

22. The compound of claim 1, wherein the compound of Formula (I) is a compound of Formula (I-A), (I-B), (I-C), (I-D), (I-E), (I-F), (I-G), (I-H), (I-I), (I-J), (I-K), (I-L), (I-M), (I-N), (I-O), or (I-P):

Formula (I-A)

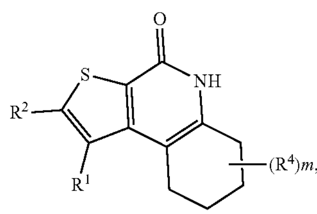

Formula (I-B)

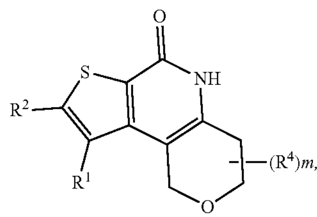

Formula (I-C)

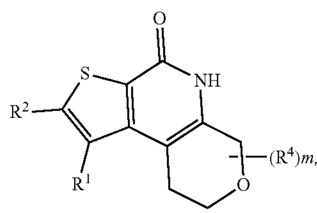

Formula (I-D)

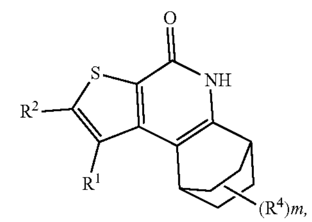

-continued
Formula (I-E)
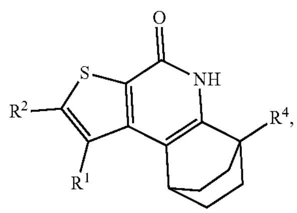
Formula (I-F)
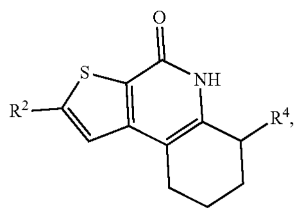
Formula (I-G)
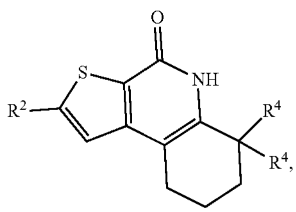
Formula (I-H)
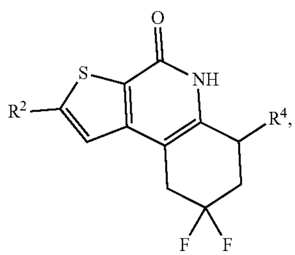
Formula (I-I)
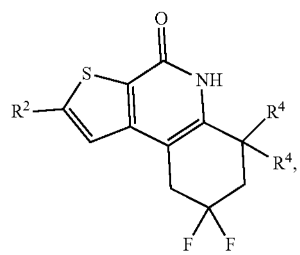
Formula (I-J)
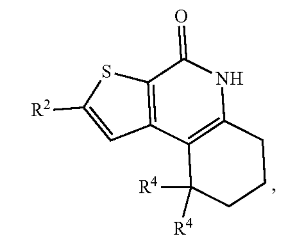
Formula (I-K)
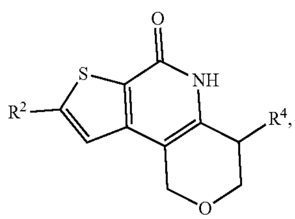
-continued
Formula (I-L)
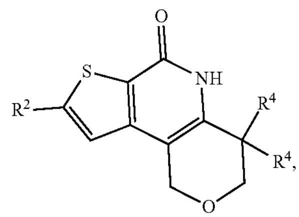
Formula (I-M)
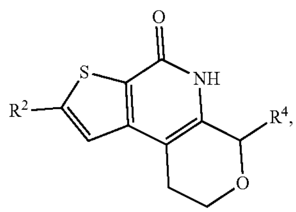
Formula (I-N)
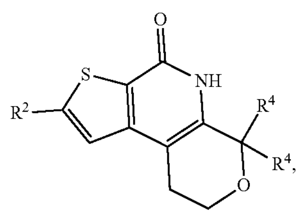
Formula (I-O)
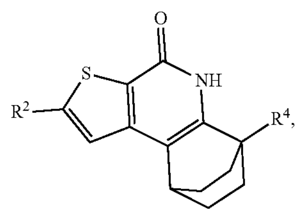
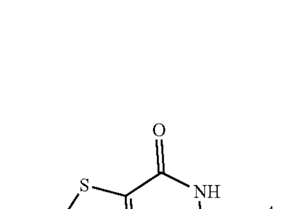
Formula (I-P)
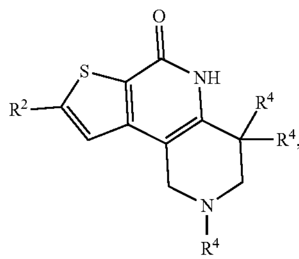
or a pharmaceutically acceptable salt thereof.
23. The compound of claim 1, wherein the compound is selected from the group consisting of:
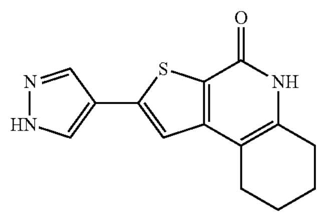

-continued
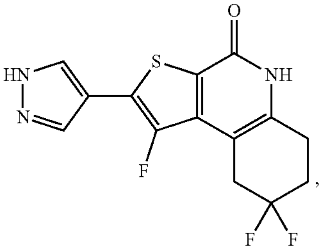
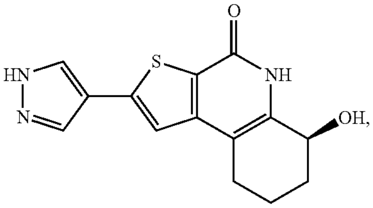
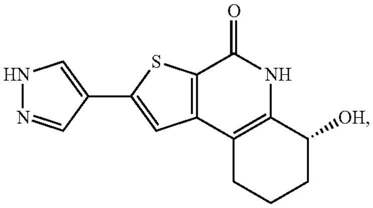
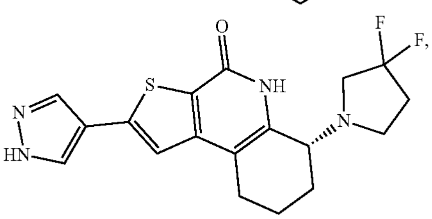
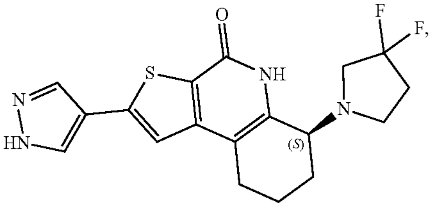
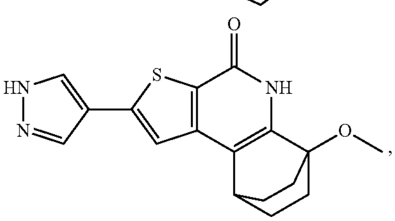
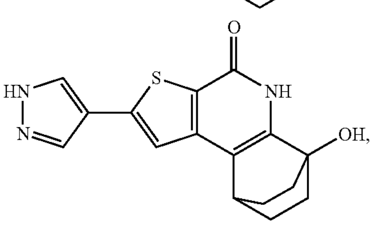
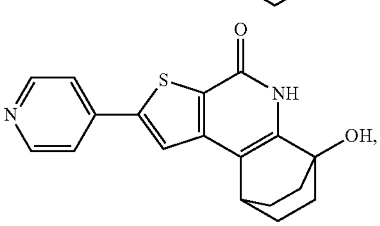
-continued
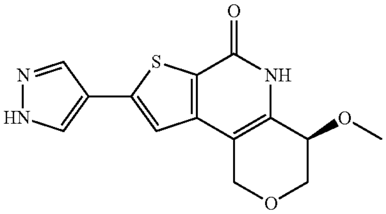
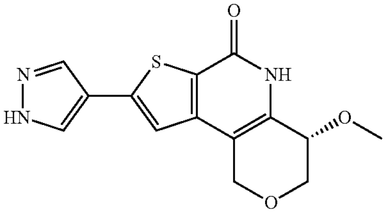
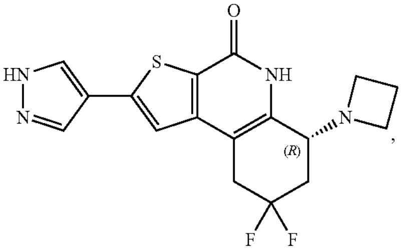
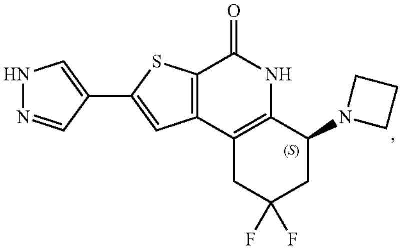
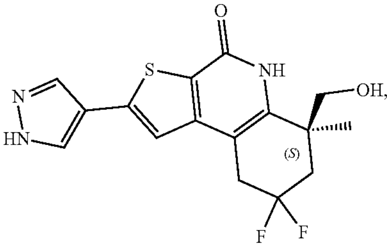
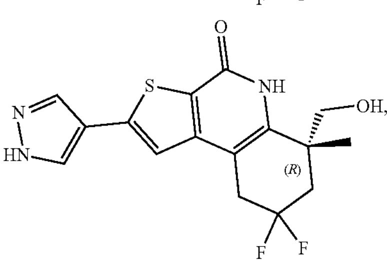
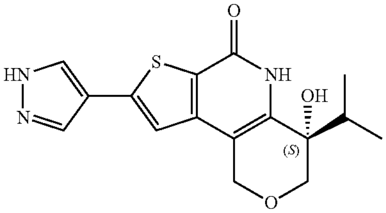

-continued
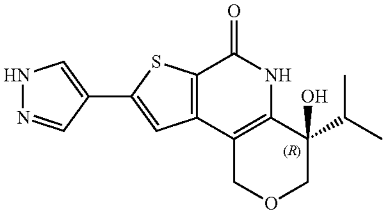,
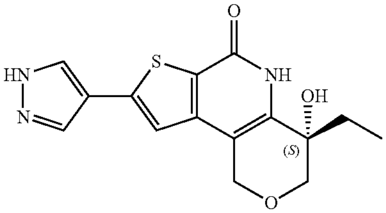,
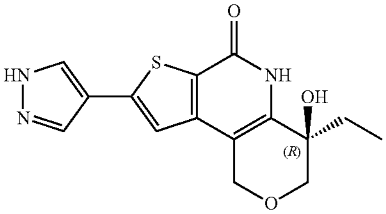,
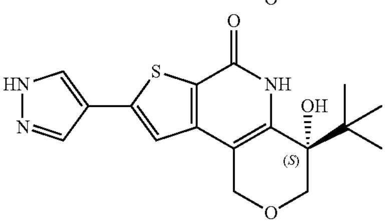,
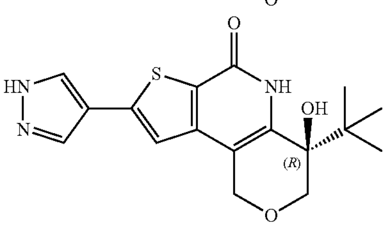,
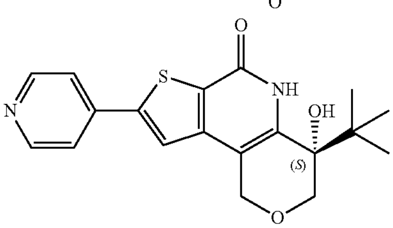,
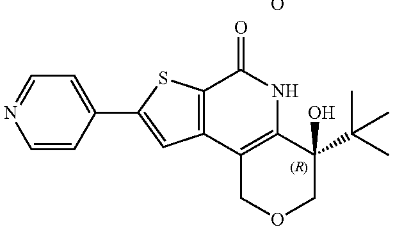,
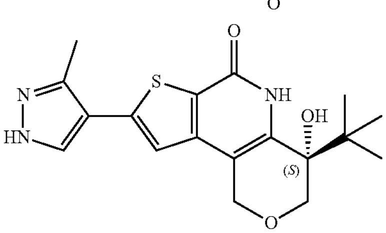,
-continued
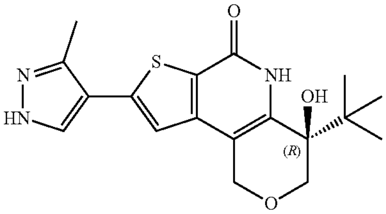,
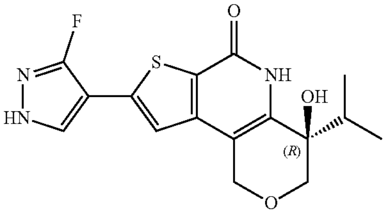,
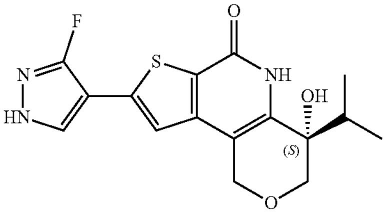,
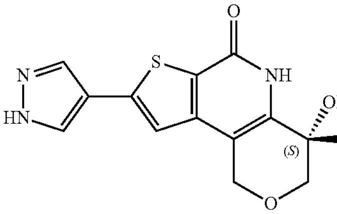,
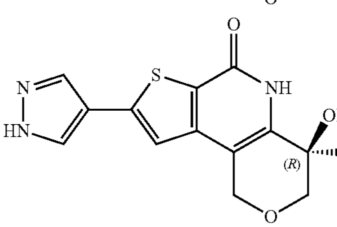,
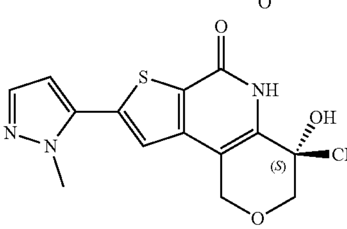,
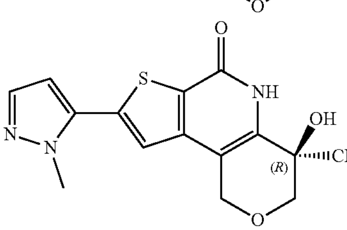,
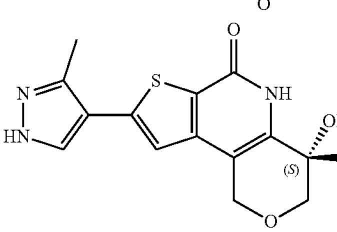, -continued
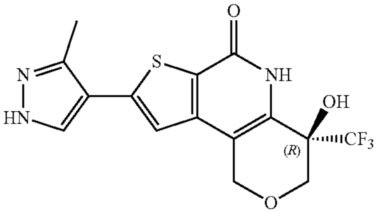
,
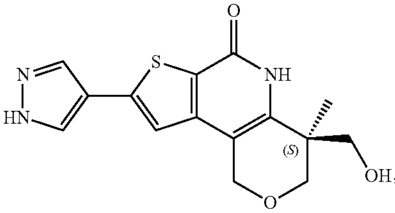
,
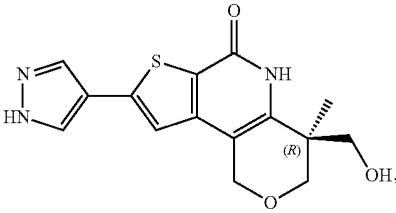
,
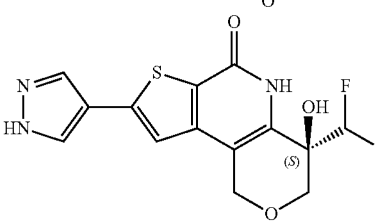
,
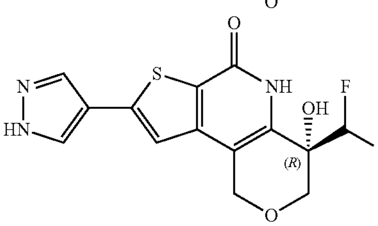
,
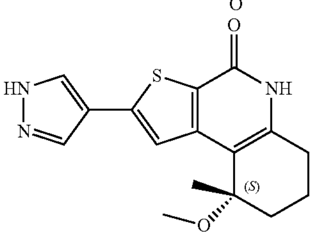
,
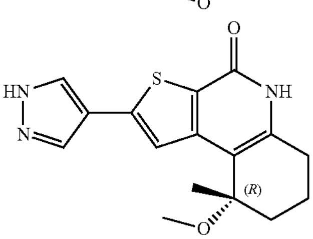
,
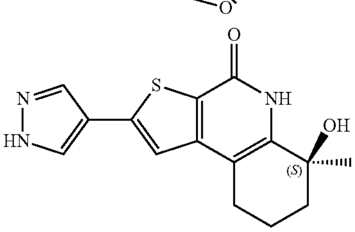
,
-continued
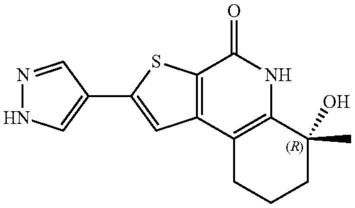
,
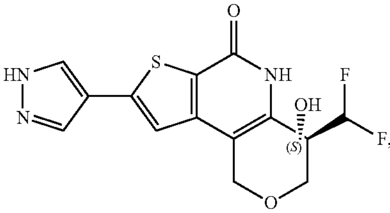
,
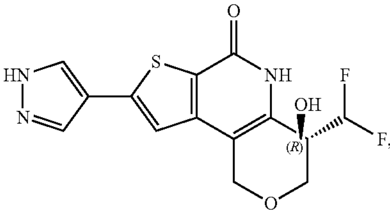
,
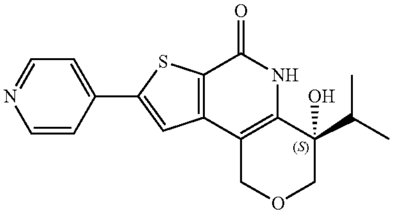
,
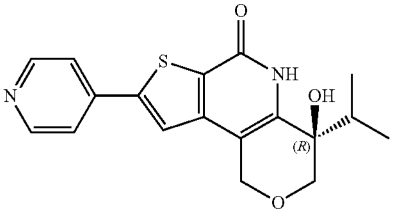
,
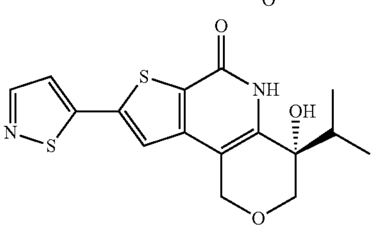
,
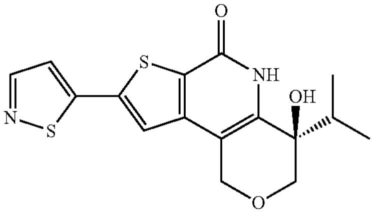
, -continued
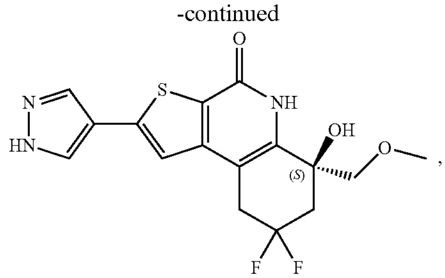
,
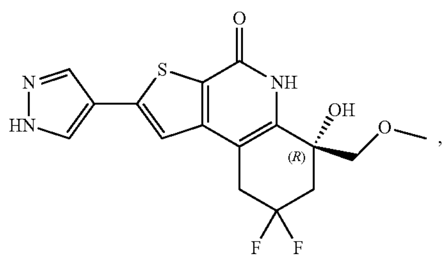
,
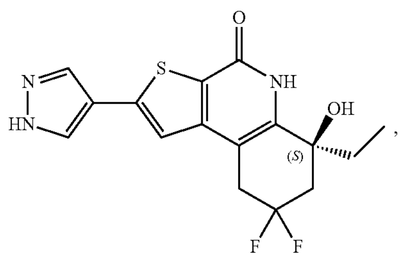
,
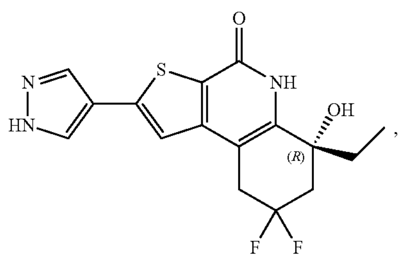
,
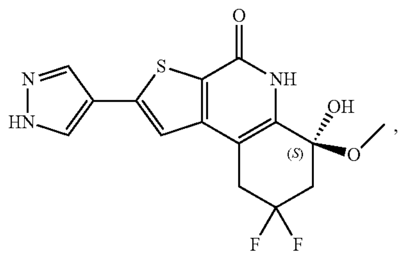
,
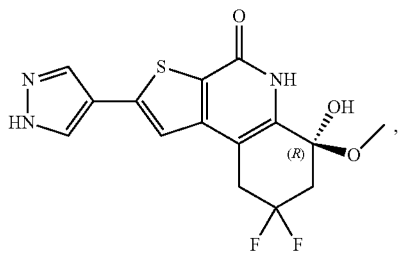
,
-continued
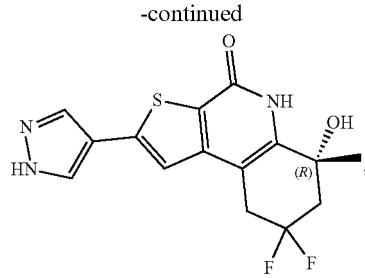
,
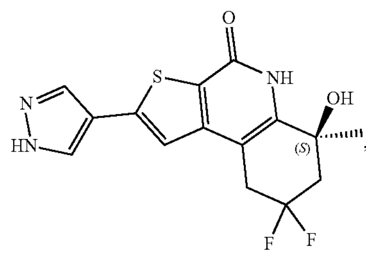
,
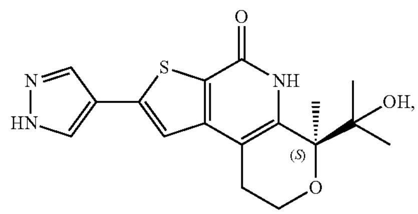
,
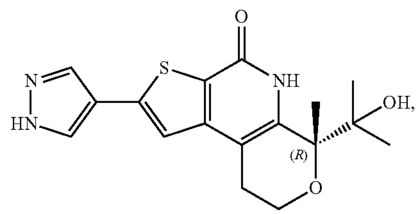
,
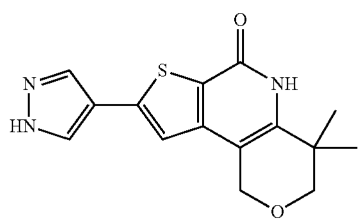
,
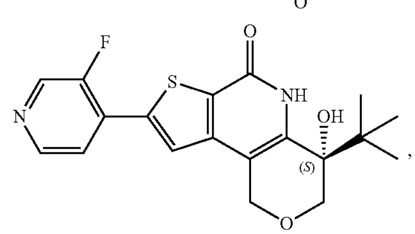
,
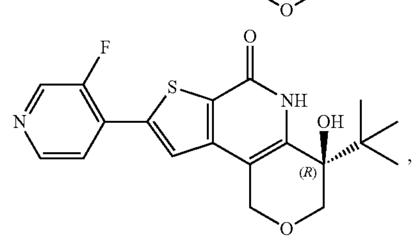
, -continued
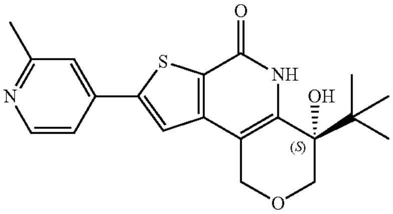,
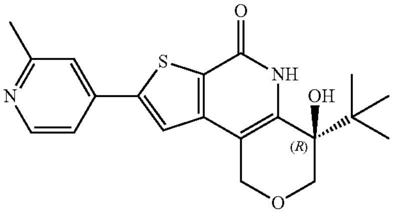,
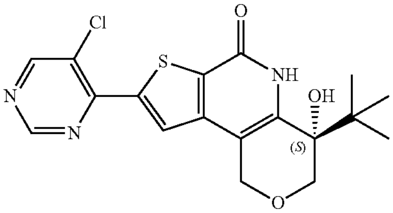,
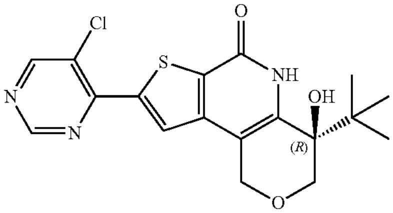,
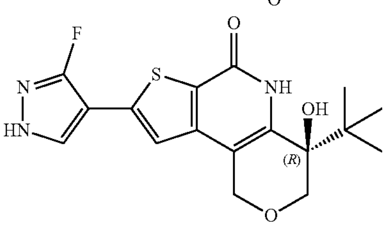,
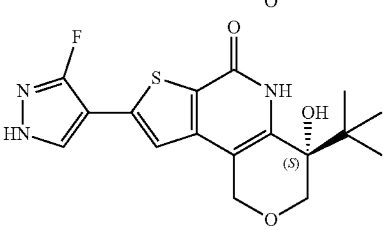,
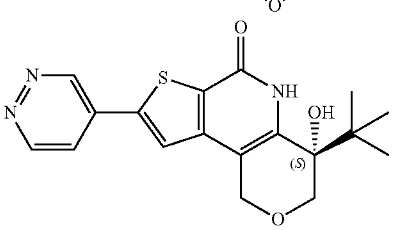,
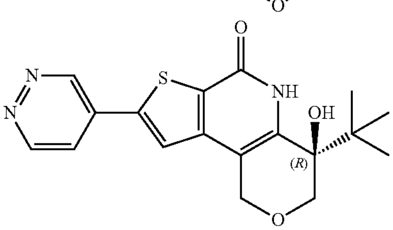,
-continued
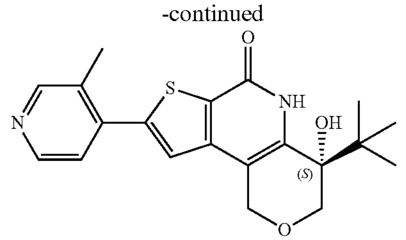,
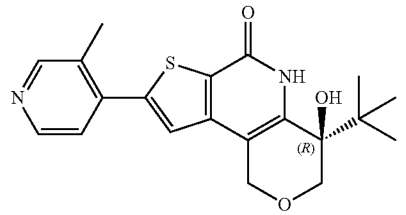,
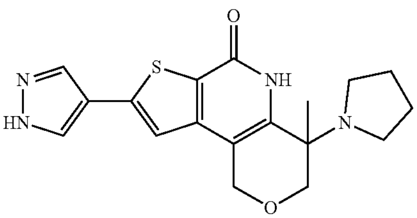,
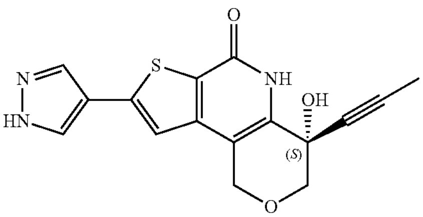,
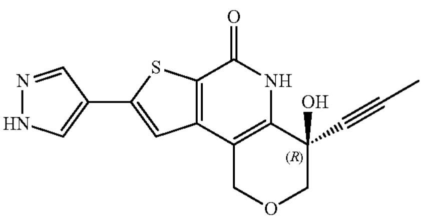,
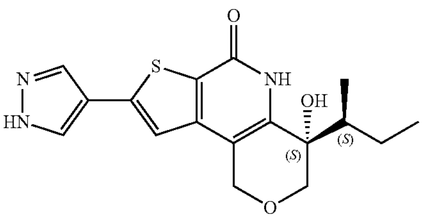,
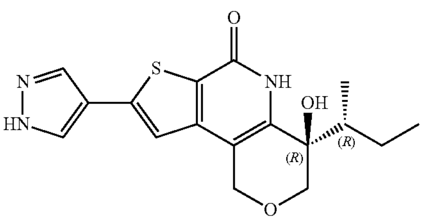,
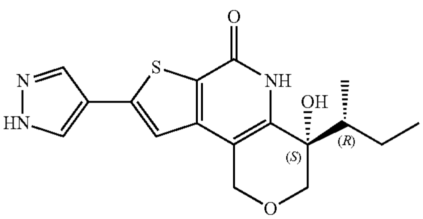, -continued
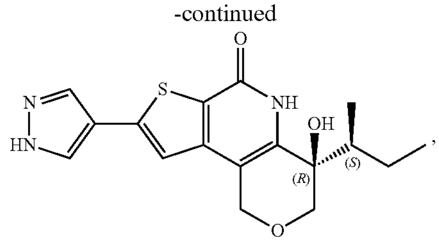
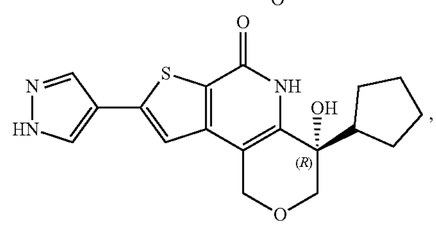
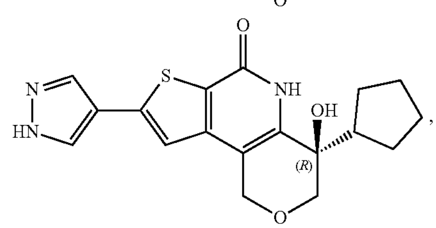
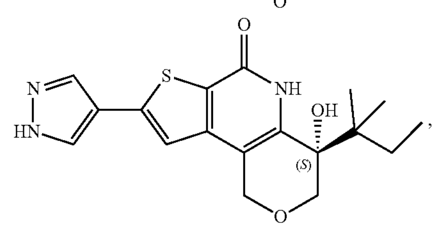
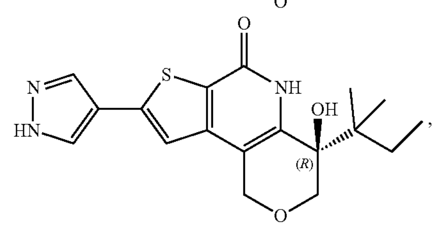
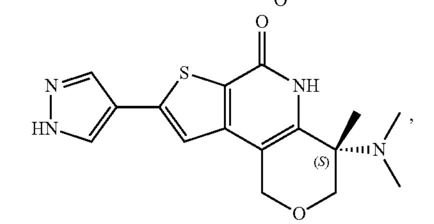
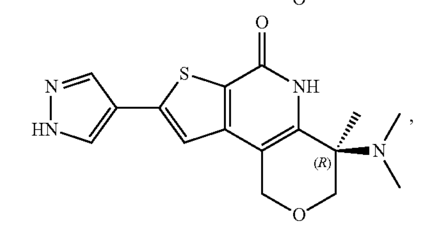
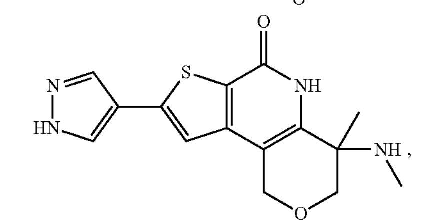
-continued
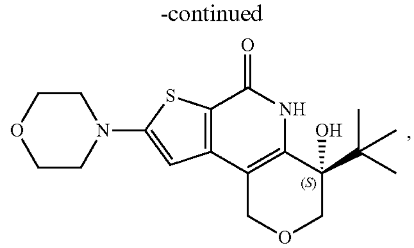
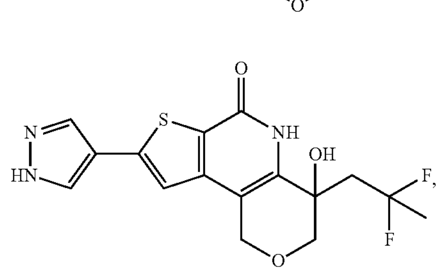
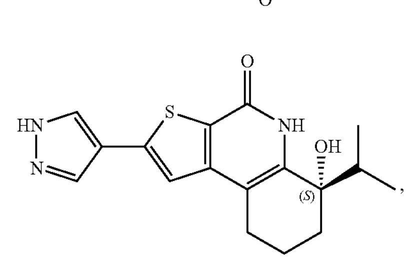
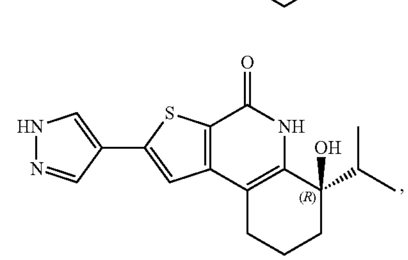
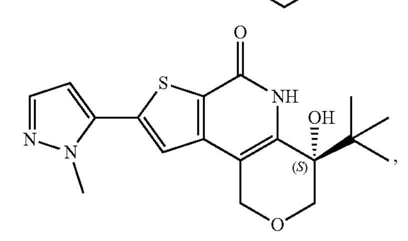
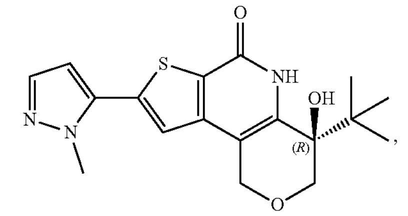
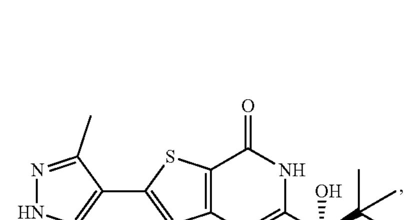
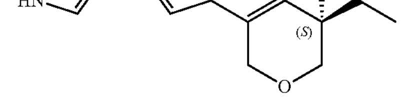

-continued

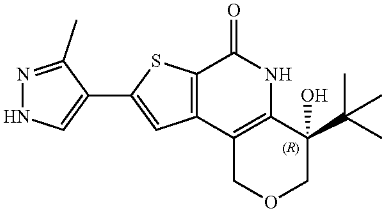

,

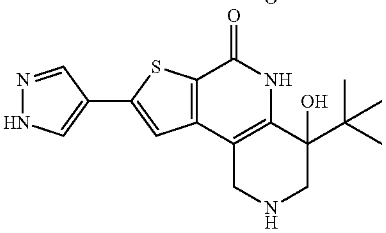

,

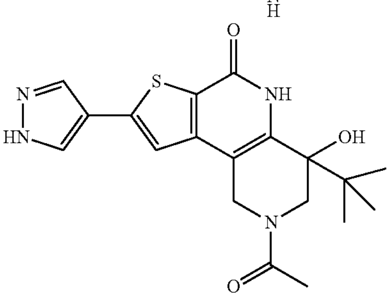

,

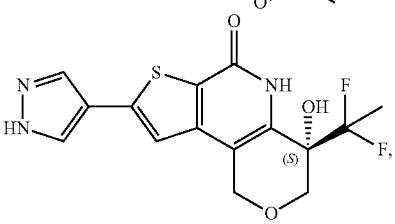

and

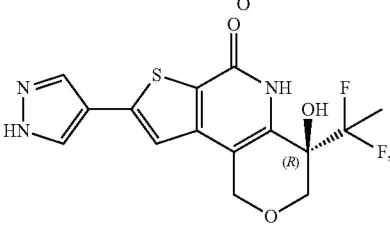

or a pharmaceutically acceptable salt thereof.

24. A pharmaceutical composition comprising a compound of claim 1, or a pharmaceutically acceptable salt thereof, and at least one pharmaceutically acceptable excipient.

25. A method for treating cancer in a subject in need thereof, comprising administering to the subject an effective amount of a compound of claim 1 or a pharmaceutically acceptable salt thereof.

26. The method of claim 25, further comprising administering an additional therapy or therapeutic agent to the subject.

27. The method of claim 25, wherein the cancer is acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, or uterine sarcoma.

28. The method of claim 27, wherein the cancer is a myelodysplastic syndrome (MDS), acute myeloid leukemia (AML) or acute lymphocytic leukemia (ALL).

29. The method of claim 27, wherein the cancer is prostate cancer or small cell lung cancer.

30. The compound of claim 1, wherein the compound is selected from the group consisting of:

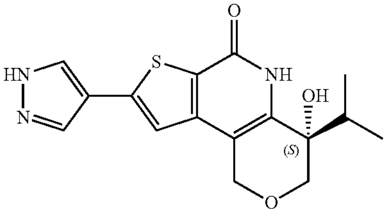

,

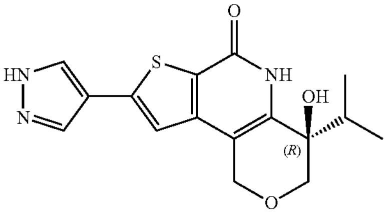

,

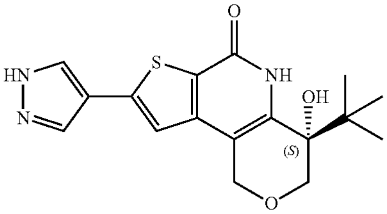

,

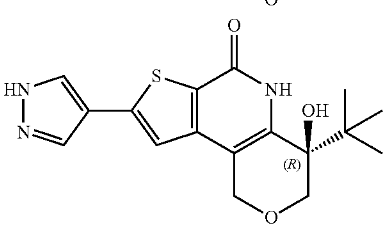

,

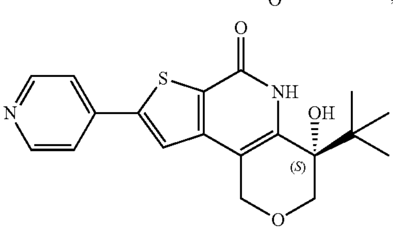

,

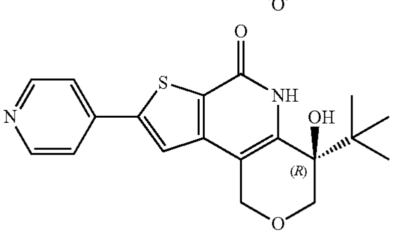

,

-continued

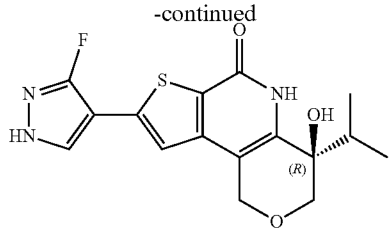

,

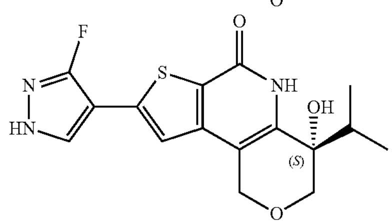

,

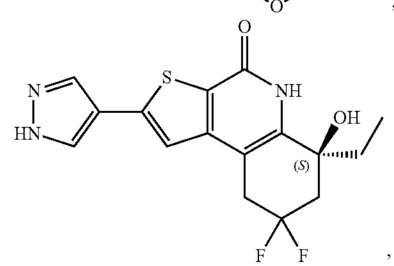

,

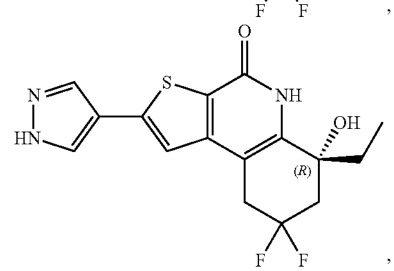

,

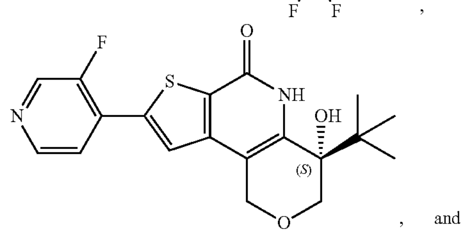

, and

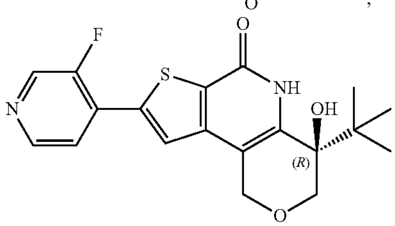

, or a pharmaceutically acceptable salt thereof.

31. A pharmaceutical composition comprising the compound of claim 30, or a pharmaceutically acceptable salt thereof, and at least one pharmaceutically acceptable excipient.

32. A method for treating cancer in a subject in need thereof, comprising administering to the subject an effective amount of a compound of claim 30, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

33. The method of claim 32, wherein the cancer is a myelodysplastic syndrome (MDS), acute myeloid leukemia (AML) or acute lymphocytic leukemia (ALL).

34. The method of claim 32, wherein the cancer is prostate cancer or small cell lung cancer.

35. A compound, wherein the compound is:

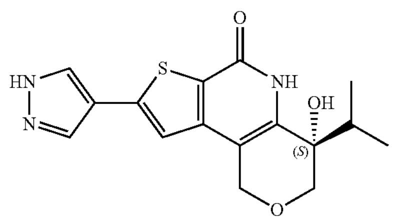

, or a pharmaceutically acceptable salt thereof.

36. A pharmaceutical composition comprising the compound of claim 35, or a pharmaceutically acceptable salt thereof, and at least one pharmaceutically acceptable excipient.

37. A method for treating cancer in a subject in need thereof, comprising administering to the subject an effective amount of a compound of claim 35, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

38. The method of claim 37, wherein the cancer is a myelodysplastic syndrome (MDS), acute myeloid leukemia (AML) or acute lymphocytic leukemia (ALL).

39. The method of claim 37, wherein the cancer is prostate cancer or small cell lung cancer.

40. A compound, wherein the compound is:

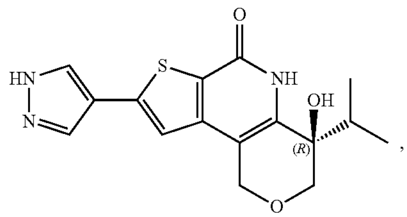

or a pharmaceutically acceptable salt thereof.

41. A pharmaceutical composition comprising the compound of claim 40, or a pharmaceutically acceptable salt thereof, and at least one pharmaceutically acceptable excipient.

42. A method for treating cancer in a subject in need thereof, comprising administering to the subject an effective amount of a compound of claim 40, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

43. The method of claim 42, wherein the cancer is a myelodysplastic syndrome (MDS), acute myeloid leukemia (AML) or acute lymphocytic leukemia (ALL).

44. The method of claim 42, wherein the cancer is prostate cancer or small cell lung cancer.

45. A compound, wherein the compound is:

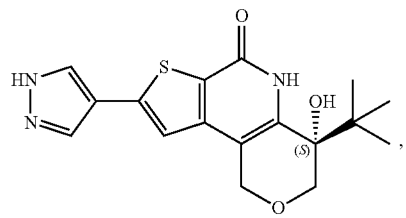

or a pharmaceutically acceptable salt thereof.

46. A pharmaceutical composition comprising the compound of claim 45, or a pharmaceutically acceptable salt thereof, and at least one pharmaceutically acceptable excipient.

47. A method for treating cancer in a subject in need thereof, comprising administering to the subject an effective amount of a compound of claim 45, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

48. The method of claim 47, wherein the cancer is a myelodysplastic syndrome (MDS), acute myeloid leukemia (AML) or acute lymphocytic leukemia (ALL).

49. The method of claim 47, wherein the cancer is prostate cancer or small cell lung cancer.

50. A compound, wherein the compound is:

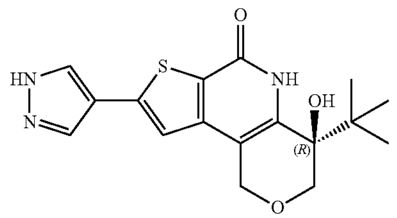

or a pharmaceutically acceptable salt thereof.

51. A pharmaceutical composition comprising the compound of claim 50, or a pharmaceutically acceptable salt thereof, and at least one pharmaceutically acceptable excipient.

52. A method for treating cancer in a subject in need thereof, comprising administering to the subject an effective amount of a compound of claim 50, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

53. The method of claim 52, wherein the cancer is a myelodysplastic syndrome (MDS), acute myeloid leukemia (AML) or acute lymphocytic leukemia (ALL).

54. The method of claim 52, wherein the cancer is prostate cancer or small cell lung cancer.

55. A compound, wherein the compound is:

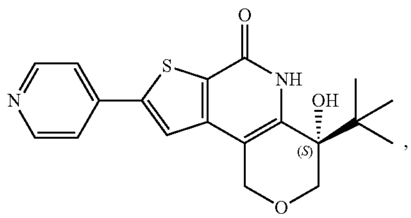

or a pharmaceutically acceptable salt thereof.

56. A pharmaceutical composition comprising the compound of claim 55, or a pharmaceutically acceptable salt thereof, and at least one pharmaceutically acceptable excipient.

57. A method for treating cancer in a subject in need thereof, comprising administering to the subject an effective amount of a compound of claim 55, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

58. The method of claim 57, wherein the cancer is a myelodysplastic syndrome (MDS), acute myeloid leukemia (AML) or acute lymphocytic leukemia (ALL).

59. The method of claim 57, wherein the cancer is prostate cancer or small cell lung cancer.

60. A compound, wherein the compound is:

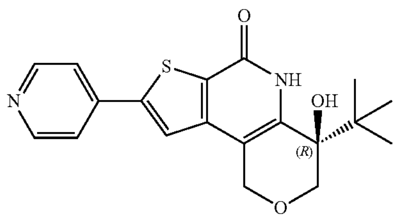

or a pharmaceutically acceptable salt thereof.

61. A pharmaceutical composition comprising the compound of claim 60, or a pharmaceutically acceptable salt thereof, and at least one pharmaceutically acceptable excipient.

62. A method for treating cancer in a subject in need thereof, comprising administering to the subject an effective amount of a compound of claim 60, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

63. The method of claim 62, wherein the cancer is a myelodysplastic syndrome (MDS), acute myeloid leukemia (AML) or acute lymphocytic leukemia (ALL).

64. The method of claim 62, wherein the cancer is prostate cancer or small cell lung cancer.

65. A compound, wherein the compound is:

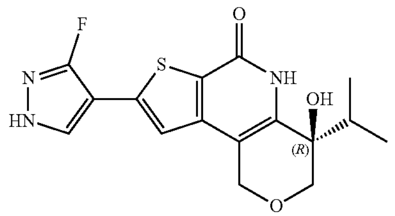

or a pharmaceutically acceptable salt thereof.

66. A pharmaceutical composition comprising the compound of claim 65, or a pharmaceutically acceptable salt thereof, and at least one pharmaceutically acceptable excipient.

67. A method for treating cancer in a subject in need thereof, comprising administering to the subject an effective amount of a compound of claim 65, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, colorectal cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

68. The method of claim 67, wherein the cancer is a myelodysplastic syndrome (MDS), acute myeloid leukemia (AML) or acute lymphocytic leukemia (ALL).

69. The method of claim 67, wherein the cancer is prostate cancer or small cell lung cancer.

70. A compound, wherein the compound is:

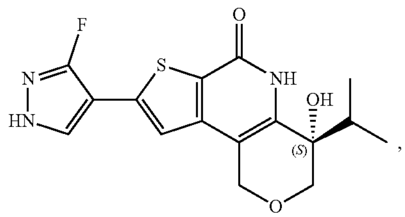

or a pharmaceutically acceptable salt thereof.

71. A pharmaceutical composition comprising the compound of claim 70, or a pharmaceutically acceptable salt thereof, and at least one pharmaceutically acceptable excipient.

72. A method for treating cancer in a subject in need thereof, comprising administering to the subject an effective amount of a compound of claim 70, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

73. The method of claim 72, wherein the cancer is a myelodysplastic syndrome (MDS), acute myeloid leukemia (AML) or acute lymphocytic leukemia (ALL).

74. The method of claim 72, wherein the cancer is prostate cancer or small cell lung cancer.

75. A compound, wherein the compound is:

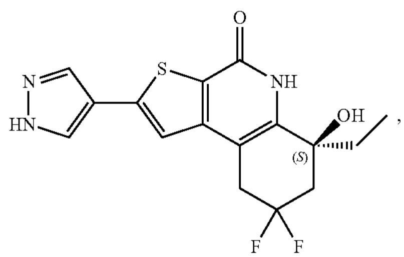

or a pharmaceutically acceptable salt thereof.

76. A pharmaceutical composition comprising the compound of claim 75, or a pharmaceutically acceptable salt thereof, and at least one pharmaceutically acceptable excipient.

77. A method for treating cancer in a subject in need thereof, comprising administering to the subject an effective amount of a compound of claim 75, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, colorectal cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

78. The method of claim 77, wherein the cancer is a myelodysplastic syndrome (MDS), acute myeloid leukemia (AML) or acute lymphocytic leukemia (ALL).

79. The method of claim 77, wherein the cancer is prostate cancer or small cell lung cancer.

80. A compound, wherein the compound is:

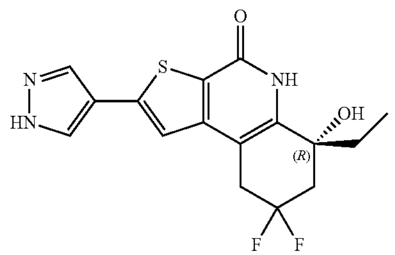

or a pharmaceutically acceptable salt thereof.

81. A pharmaceutical composition comprising the compound of claim 80, or a pharmaceutically acceptable salt thereof, and at least one pharmaceutically acceptable excipient.

82. A method for treating cancer in a subject in need thereof, comprising administering to the subject an effective amount of a compound of claim 80, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

83. The method of claim 82, wherein the cancer is a myelodysplastic syndrome (MDS), acute myeloid leukemia (AML) or acute lymphocytic leukemia (ALL).

84. The method of claim 82, wherein the cancer is prostate cancer or small cell lung cancer.

85. A compound, wherein the compound is:

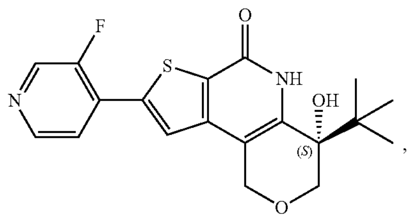

or a pharmaceutically acceptable salt thereof.

86. A pharmaceutical composition comprising the compound of claim 85, or a pharmaceutically acceptable salt thereof, and at least one pharmaceutically acceptable excipient.

87. A method for treating cancer in a subject in need thereof, comprising administering to the subject an effective amount of a compound of claim 85, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

88. The method of claim 87, wherein the cancer is a myelodysplastic syndrome (MDS), acute myeloid leukemia (AML) or acute lymphocytic leukemia (ALL).

89. The method of claim 87, wherein the cancer is prostate cancer or small cell lung cancer.

90. A compound, wherein the compound is:

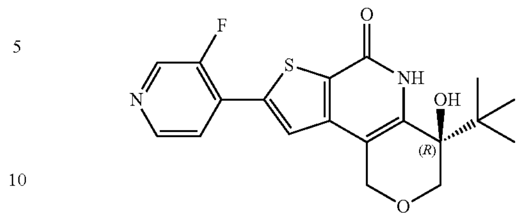

or a pharmaceutically acceptable salt thereof.

91. A pharmaceutical composition comprising the compound of claim 90, or a pharmaceutically acceptable salt thereof, and at least one pharmaceutically acceptable excipient.

92. A method for treating cancer in a subject in need thereof, comprising administering to the subject an effective amount of a compound of claim 90, or a pharmaceutically acceptable salt thereof, wherein the cancer is selected from acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), myelodysplastic syndromes (MDSs), bladder cancer, breast cancer, cervical cancer, colon cancer, endometrial cancer, esophageal cancer, Ewing sarcoma, gastrointestinal carcinoid tumor, gastrointestinal stromal tumors (GIST), head and neck cancer, hepatocellular cancer, pancreatic neuroendocrine tumors, melanoma, non-small cell lung cancer, osteosarcoma, ovarian cancer, pancreatic cancer, prostate cancer, rectal cancer, small cell lung cancer, small intestine cancer, soft tissue sarcoma, squamous cell carcinoma, stomach cancer, and uterine sarcoma.

93. The method of claim 92, wherein the cancer is a myelodysplastic syndrome (MDS), acute myeloid leukemia (AML) or acute lymphocytic leukemia (ALL).

94. The method of claim 92, wherein the cancer is prostate cancer or small cell lung cancer.

* * * * *